(12) United States Patent
Cottam et al.

(10) Patent No.: US 10,751,598 B2
(45) Date of Patent: Aug. 25, 2020

(54) SYSTEMS, METHODS, AND ARTICLES OF MANUFACTURE TO MEASURE, ANALYZE AND SHARE GOLF SWING AND BALL MOTION CHARACTERISTICS

(71) Applicant: KARSTEN MANUFACTURING CORPORATION, Phoenix, AZ (US)

(72) Inventors: Roger J. Cottam, New River, AZ (US); Paul D. Wood, Phoenix, AZ (US); Erik M. Henrikson, Phoenix, AZ (US); Alex J. Hope, Phoenix, AZ (US)

(73) Assignee: Karsten Manufacturing Corporation, Phoenix, AZ (US)

( * ) Notice: Subject to any disclaimer, the term of this patent is extended or adjusted under 35 U.S.C. 154(b) by 474 days.

(21) Appl. No.: 15/275,038

(22) Filed: Sep. 23, 2016

(65) Prior Publication Data
US 2017/0007902 A1    Jan. 12, 2017

Related U.S. Application Data

(63) Continuation-in-part of application No. 14/836,552, filed on Aug. 26, 2015, now abandoned, which is a
(Continued)

(51) Int. Cl.
*A63F 9/24* (2006.01)
*A63F 13/00* (2014.01)
(Continued)

(52) U.S. Cl.
CPC ........ *A63B 69/3632* (2013.01); *A63F 13/211* (2014.09); *A63F 13/428* (2014.09); *A63F 13/46* (2014.09); *A63F 13/812* (2014.09); *G16H 20/30* (2018.01); *G16H 40/63* (2018.01); *G16H 40/67* (2018.01); *G16H 50/30* (2018.01); *H04M 1/04* (2013.01); *H04W 4/80* (2018.02); *A63B 69/3685* (2013.01); *A63B 71/0669* (2013.01); *A63B 2071/065* (2013.01); *A63B 2071/0625* (2013.01); *A63B 2071/0647* (2013.01); *A63B 2071/0694* (2013.01); *A63B 2209/10* (2013.01); *A63B 2220/12* (2013.01); *A63B 2220/17* (2013.01); *A63B 2220/36* (2013.01); *A63B 2220/40* (2013.01); *A63B 2220/44* (2013.01); *A63B 2220/52* (2013.01); *A63B 2220/801* (2013.01); *A63B 2220/805* (2013.01);
(Continued)

(58) Field of Classification Search
CPC .............. A63F 17/3239; A63F 17/3225; A63F 17/3234
See application file for complete search history.

(56) References Cited

U.S. PATENT DOCUMENTS 5,911,635 A    6/1999   Ogden
6,238,198 B1   5/2001   Chen
(Continued)

FOREIGN PATENT DOCUMENTS

JP    2010068947    4/2010

*Primary Examiner* — Kang Hu
*Assistant Examiner* — Jason Pinheiro

(57) ABSTRACT

Embodiments of systems, methods, computer-readable media and article of manufacture related to measuring, analyzing, and sharing golf swing and ball motion characteristics are generally described herein. Other embodiments may be described and claimed.

19 Claims, 89 Drawing Sheets

Related U.S. Application Data continuation-in-part of application No. 13/524,257, filed on Jun. 15, 2012, now Pat. No. 9,821,210, which is a continuation-in-part of application No. 13/246,663, filed on Sep. 27, 2011, now abandoned, which is a continuation-in-part of application No. 29/391,657, filed on May 11, 2011, now Pat. No. Des. 648,119, and a continuation-in-part of application No. 29/391,647, filed on May 11, 2011, now Pat. No. Des. 663,947.

(60) Provisional application No. 62/395,519, filed on Sep. 16, 2016, provisional application No. 62/222,893, filed on Sep. 24, 2015, provisional application No. 62/043,705, filed on Aug. 29, 2014, provisional application No. 61/532,503, filed on Sep. 8, 2011, provisional application No. 61/522,165, filed on Aug. 10, 2011, provisional application No. 61/506,583, filed on Jul. 11, 2011, provisional application No. 61/497,891, filed on Jun. 16, 2011, provisional application No. 61/485,549, filed on May 12, 2011.

(51) Int. Cl.

| | | |
|---|---|---|
| *G06F 17/00* | (2019.01) | |
| *A63B 69/36* | (2006.01) | |
| *H04W 4/80* | (2018.01) | |
| *H04M 1/04* | (2006.01) | |
| *A63F 13/812* | (2014.01) | |
| *A63F 13/428* | (2014.01) | |
| *A63F 13/211* | (2014.01) | |
| *A63F 13/46* | (2014.01) | |
| *G16H 50/30* | (2018.01) | |
| *G16H 40/63* | (2018.01) | |
| *G16H 40/67* | (2018.01) | |
| *G16H 20/30* | (2018.01) | |
| *A63B 71/06* | (2006.01) | |
| *H04M 1/725* | (2006.01) | |
| *G06K 9/00* | (2006.01) | |

(52) U.S. Cl.
CPC ... *A63B 2220/806* (2013.01); *A63B 2220/807* (2013.01); *A63B 2220/833* (2013.01); *A63B 2225/02* (2013.01); *A63B 2225/50* (2013.01); *A63B 2225/54* (2013.01); *A63B 2225/685* (2013.01); *G06K 9/00335* (2013.01); *H04M 1/72522* (2013.01)

(56) References Cited

U.S. PATENT DOCUMENTS

| | | |
|---|---|---|
| 6,398,670 B1 | 6/2002 | Engelhardt et al. |
| 6,607,450 B1 | 8/2003 | Hackman |
| 6,884,180 B2 | 4/2005 | Corzilius et al. |
| 7,040,998 B2 | 5/2006 | Jolliffe et al. |
| 7,160,200 B2 | 1/2007 | Grober |
| 2005/0085309 A1 | 4/2005 | McGann et al. |
| 2005/0215340 A1 | 9/2005 | Stites et al. |
| 2007/0135225 A1* | 6/2007 | Nieminen .......... A63B 24/0006 473/212 |
| 2008/0085775 A1 | 4/2008 | Dugan |
| 2008/0119298 A1 | 5/2008 | Buckley et al. |
| 2009/0017944 A1 | 1/2009 | Savarese et al. |
| 2009/0088276 A1 | 4/2009 | Solheim et al. |
| 2009/0326688 A1 | 12/2009 | Thomas et al. |
| 2010/0009780 A1 | 1/2010 | Doherty et al. |
| 2010/0130298 A1 | 5/2010 | Dugan et al. |
| 2010/0222152 A1 | 9/2010 | Jaekel et al. |
| 2011/0183780 A1 | 7/2011 | Leech et al. |
| 2011/0224012 A1 | 9/2011 | Hashimoto et al. |

\* cited by examiner

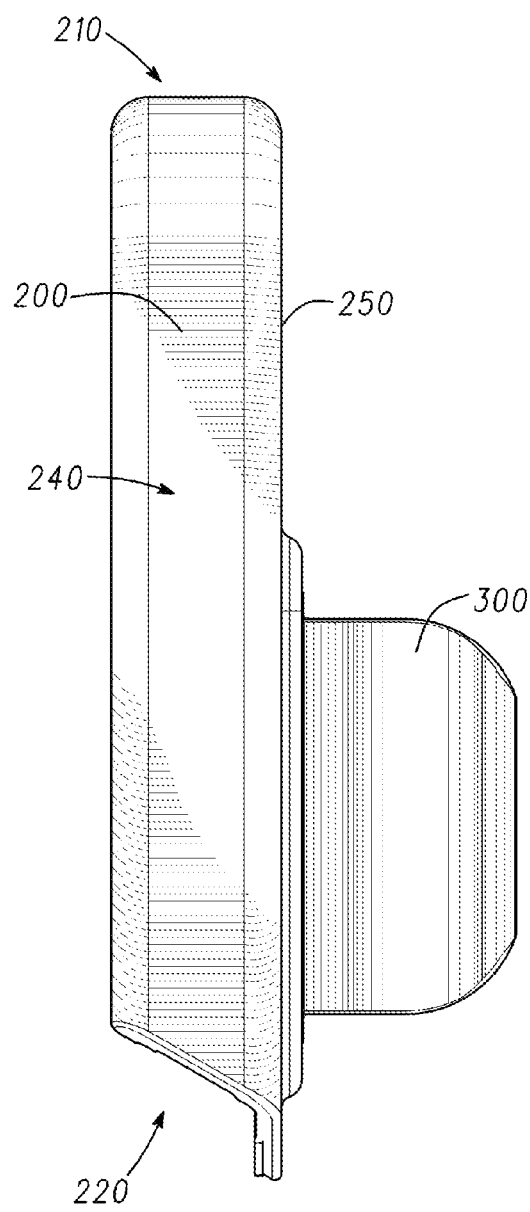
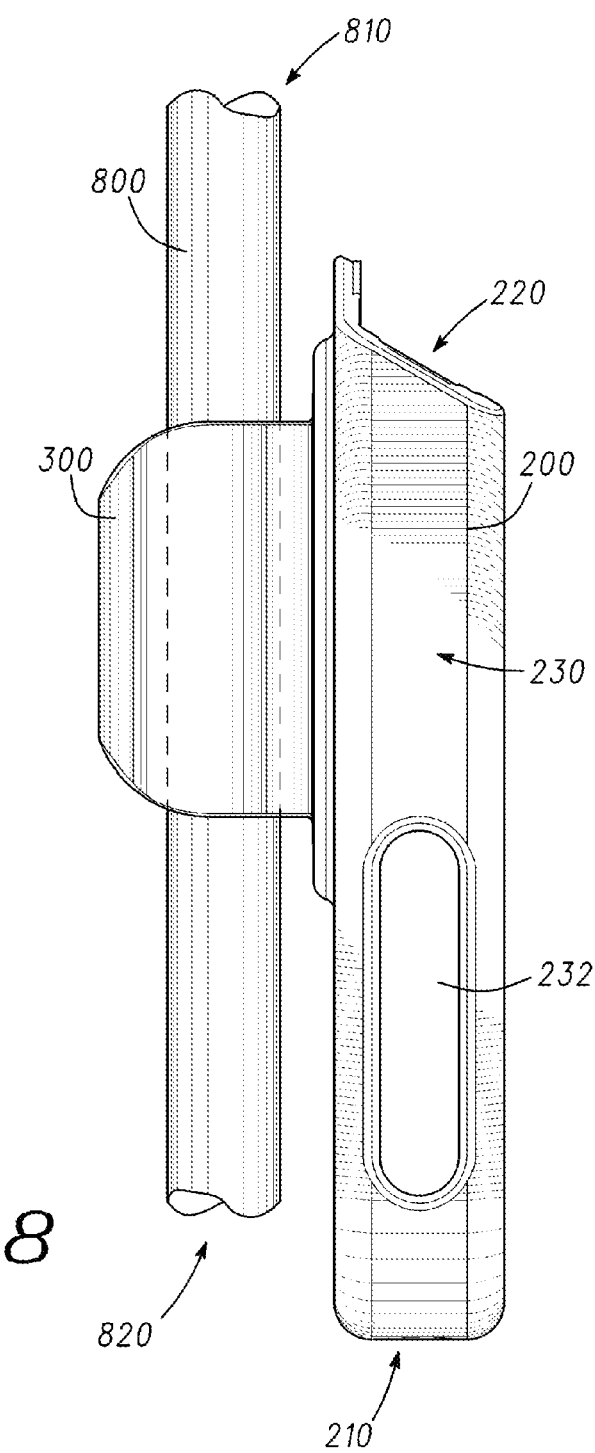
Fig. 7
Fig. 8

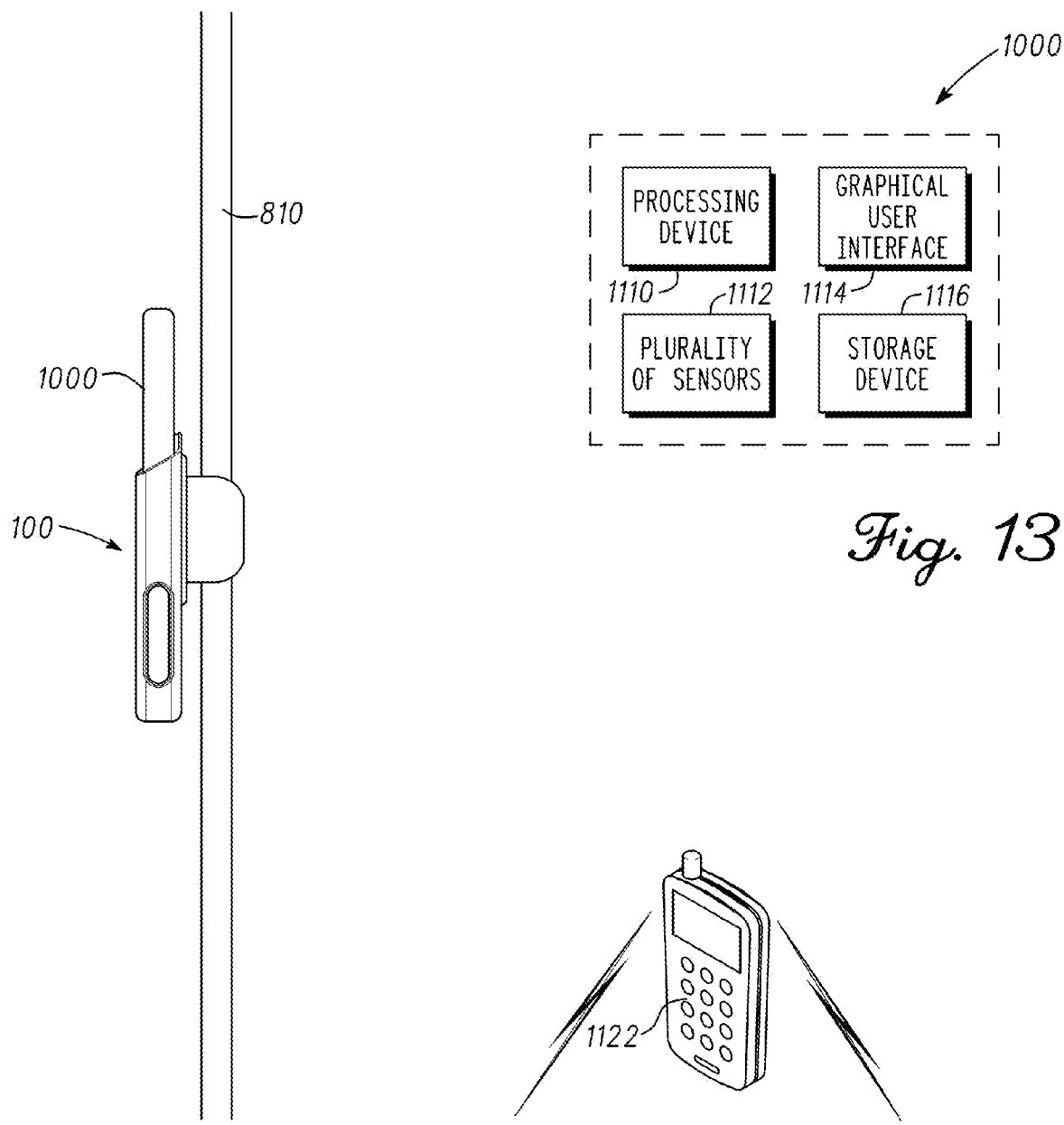
*Fig. 12*
*Fig. 13*
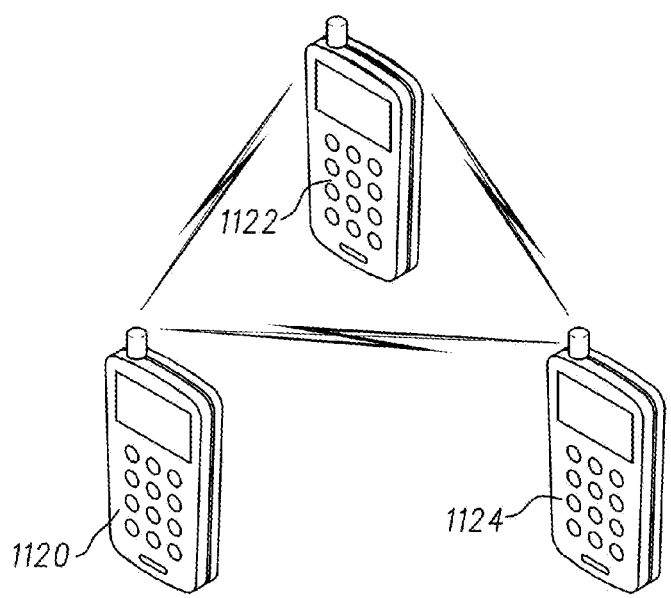
*Fig. 14*

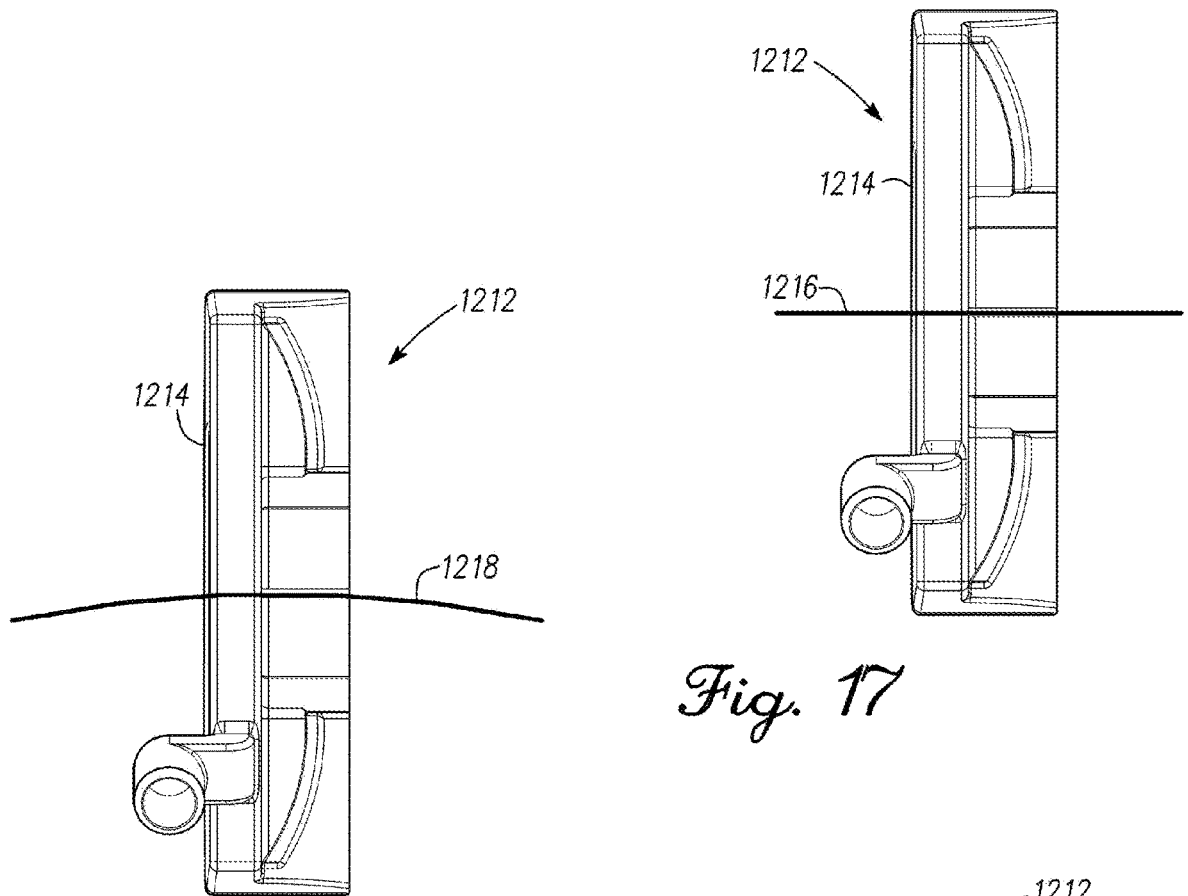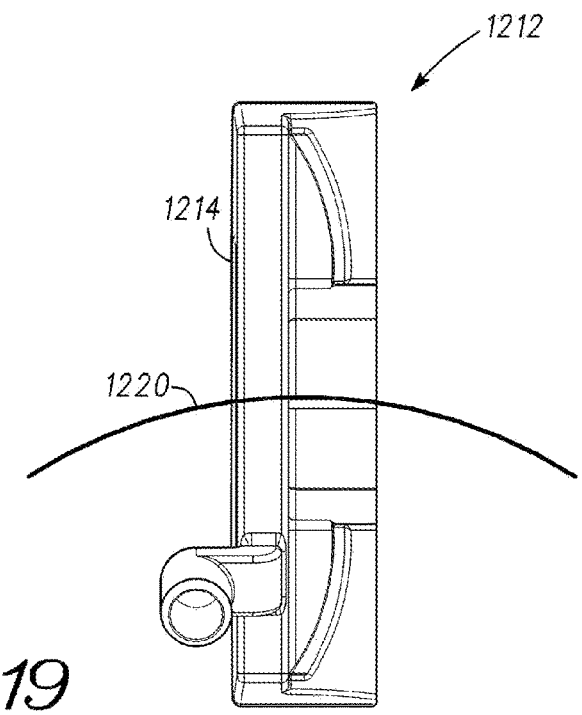

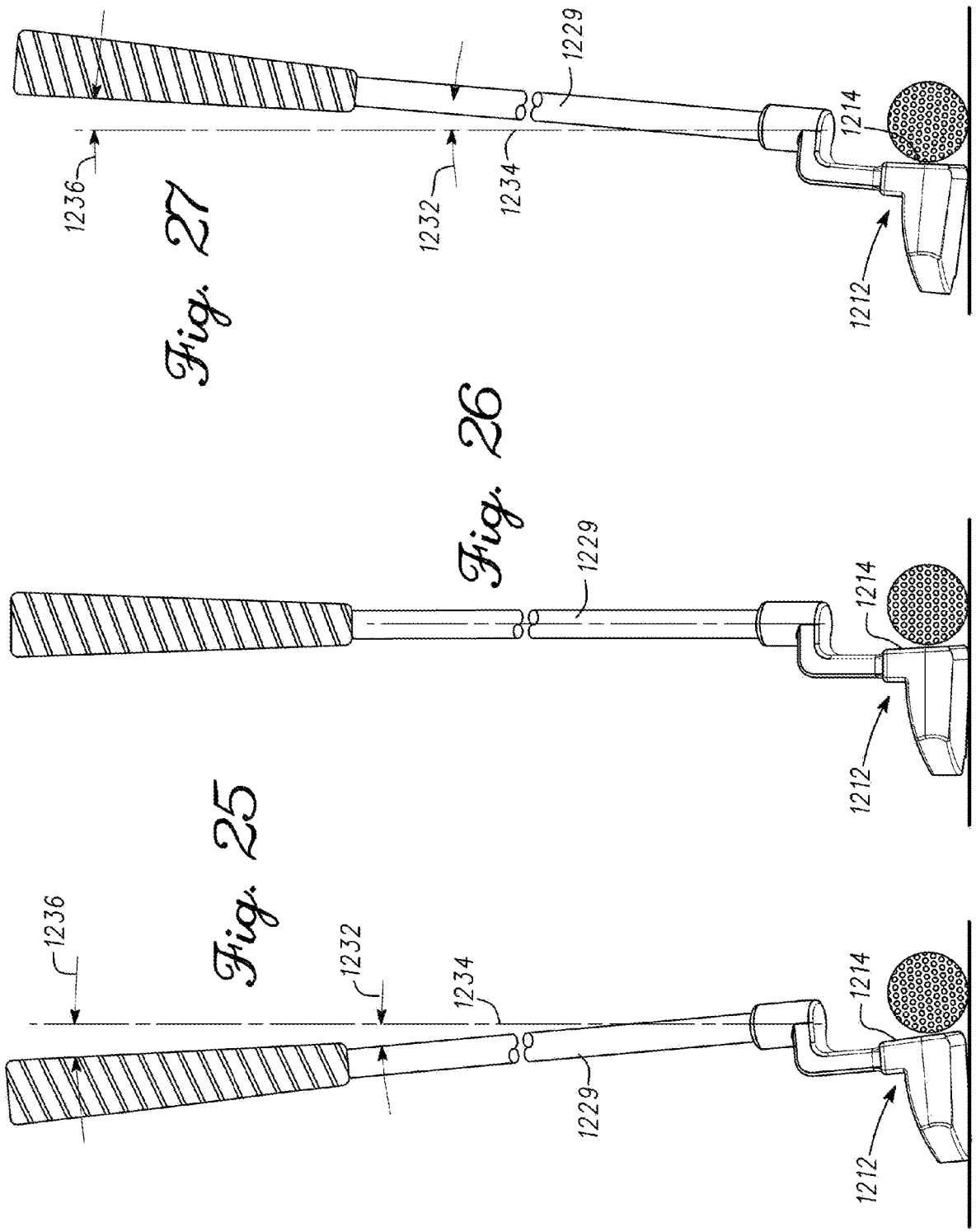

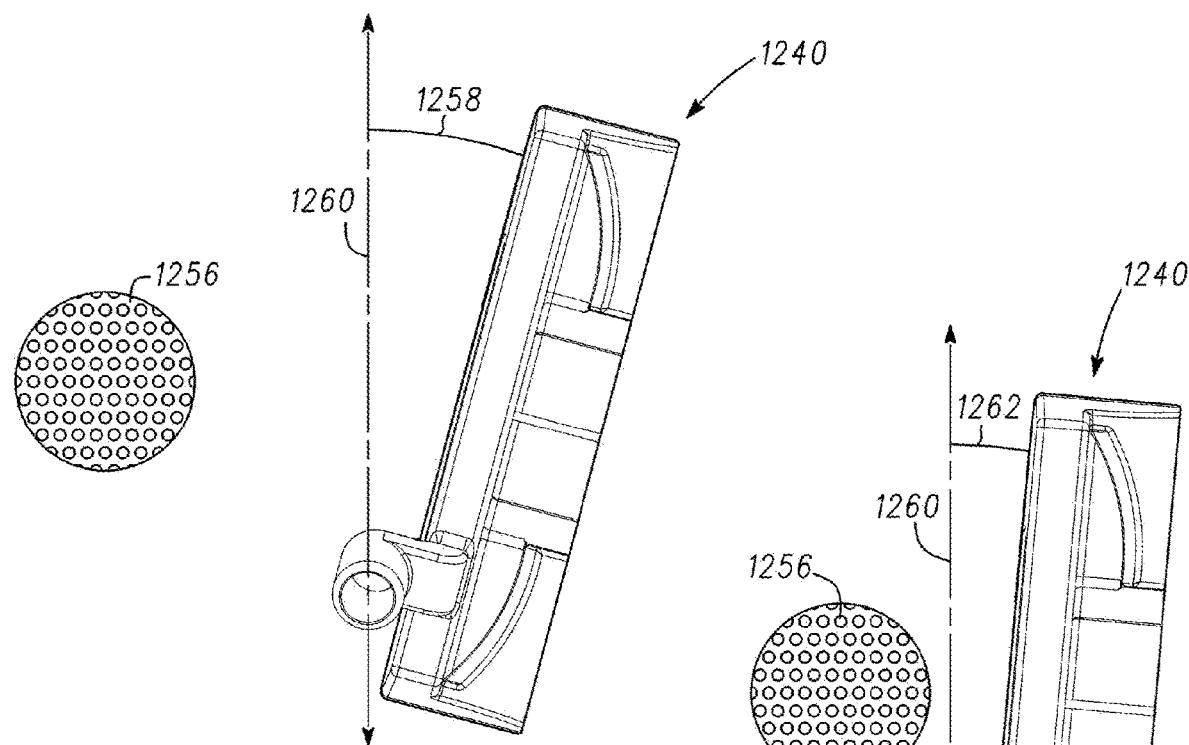
*Fig. 31*
*Fig. 30*
*Fig. 32*
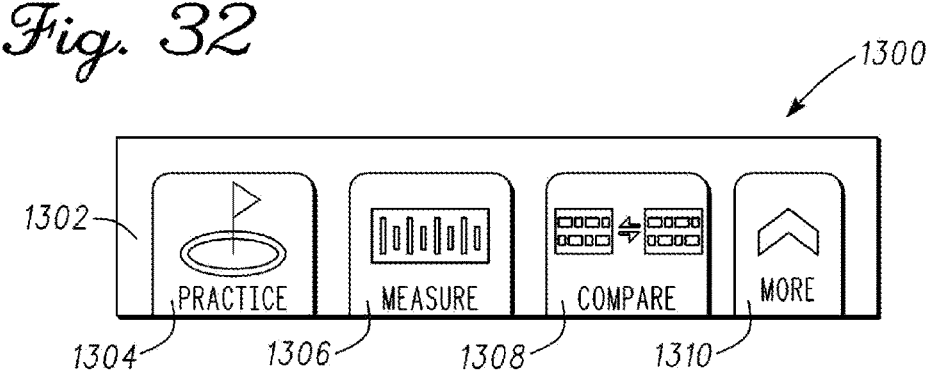

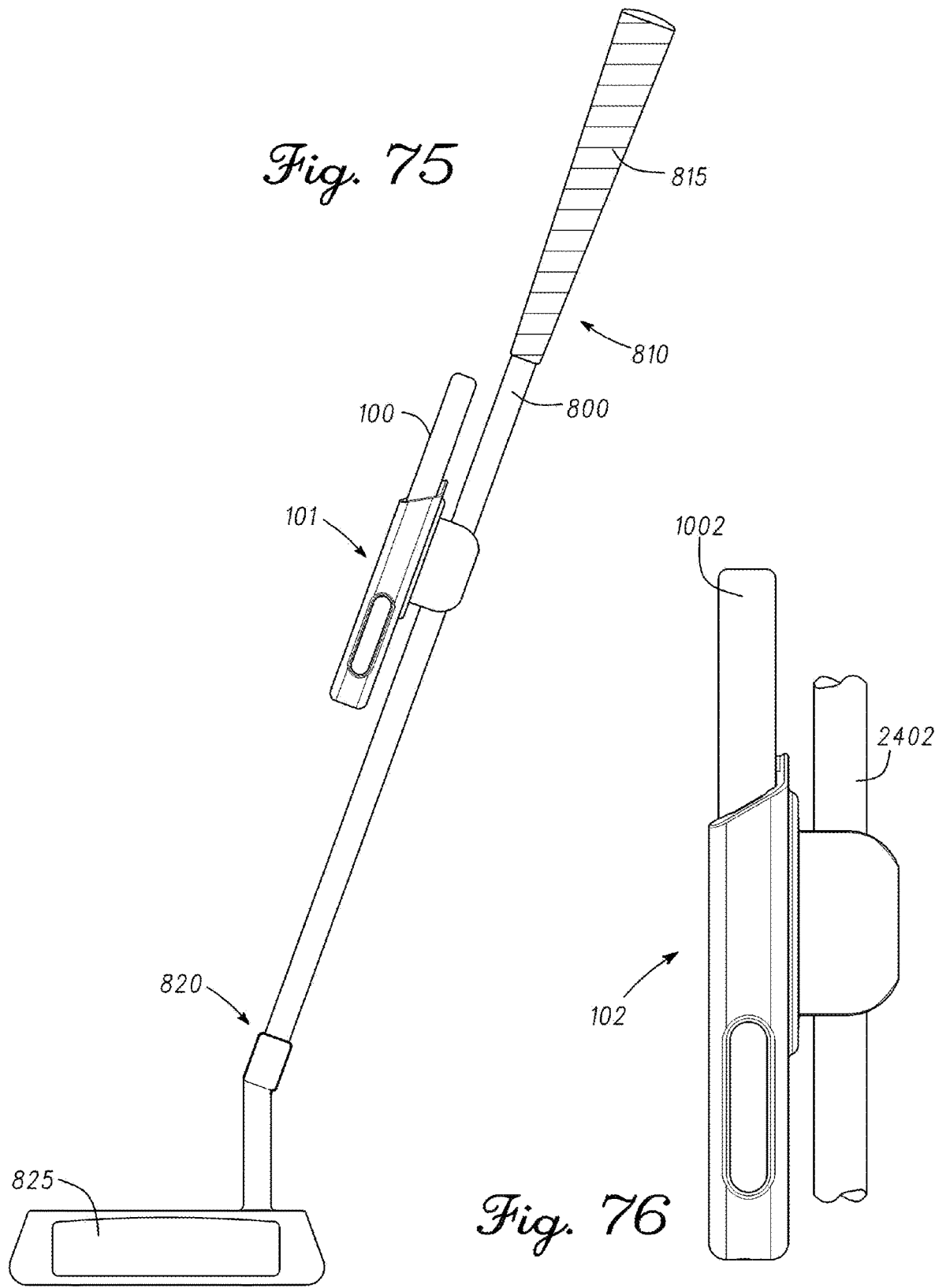

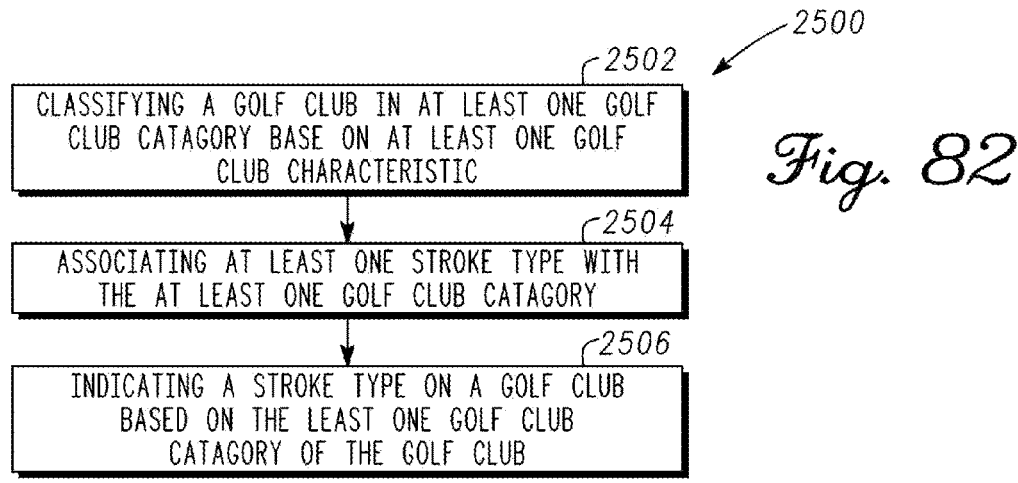
Fig. 82
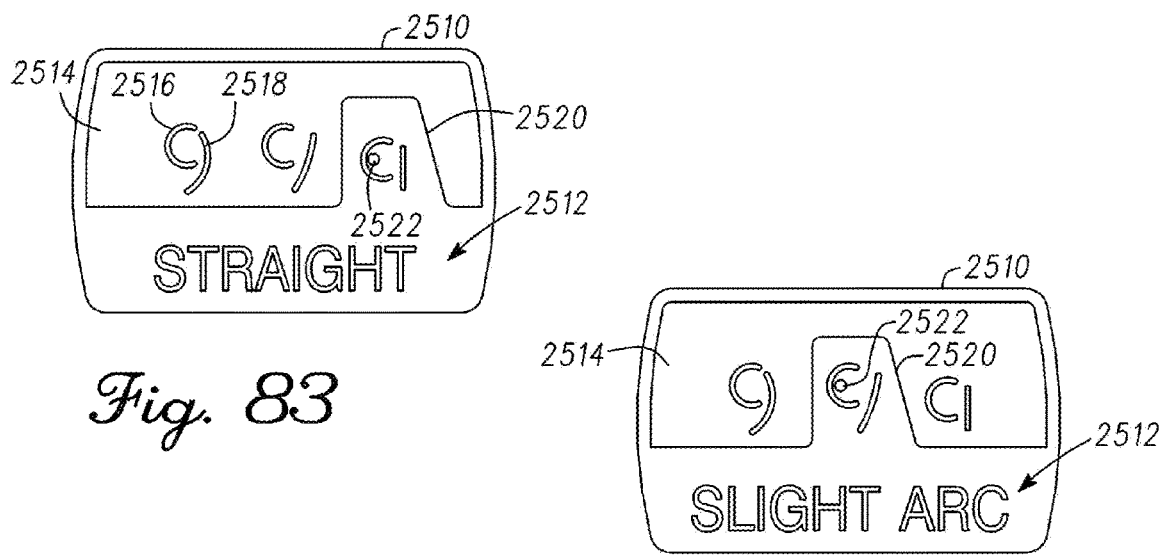
Fig. 83
Fig. 84
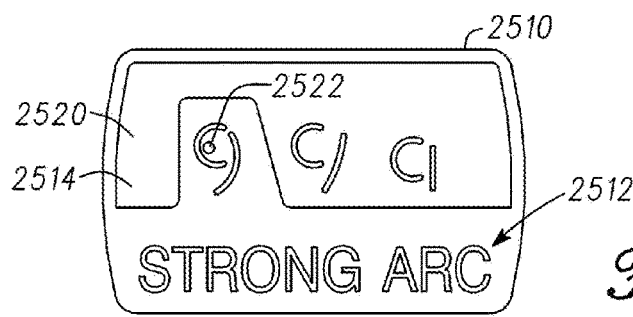
Fig. 85

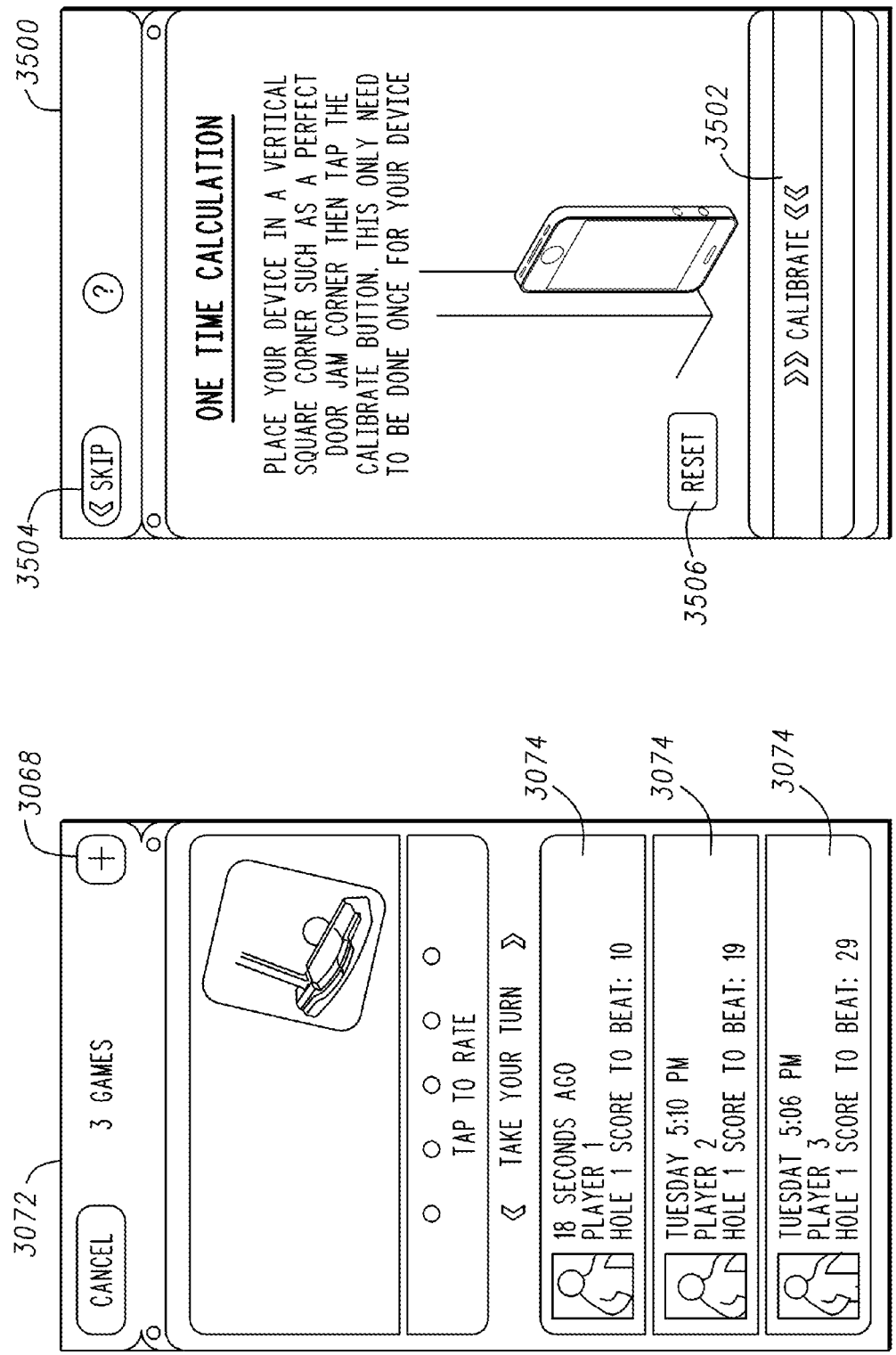

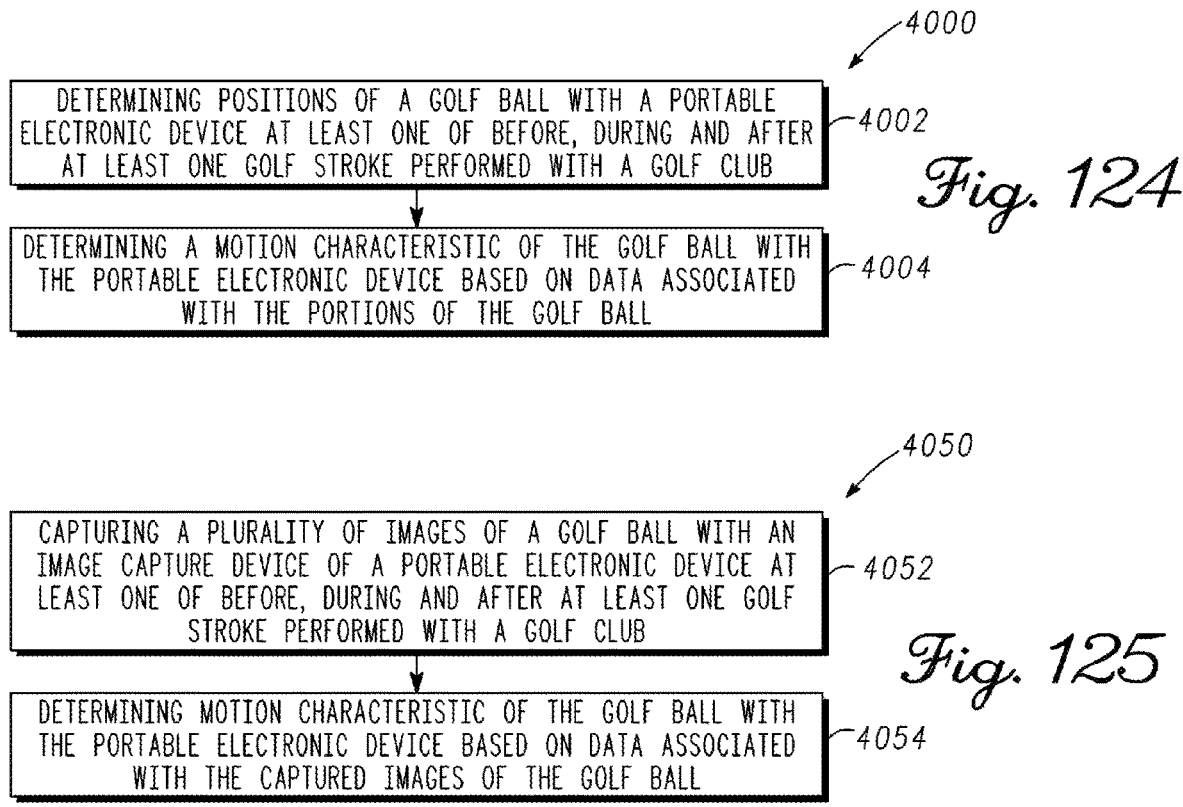
Fig. 124
Fig. 125
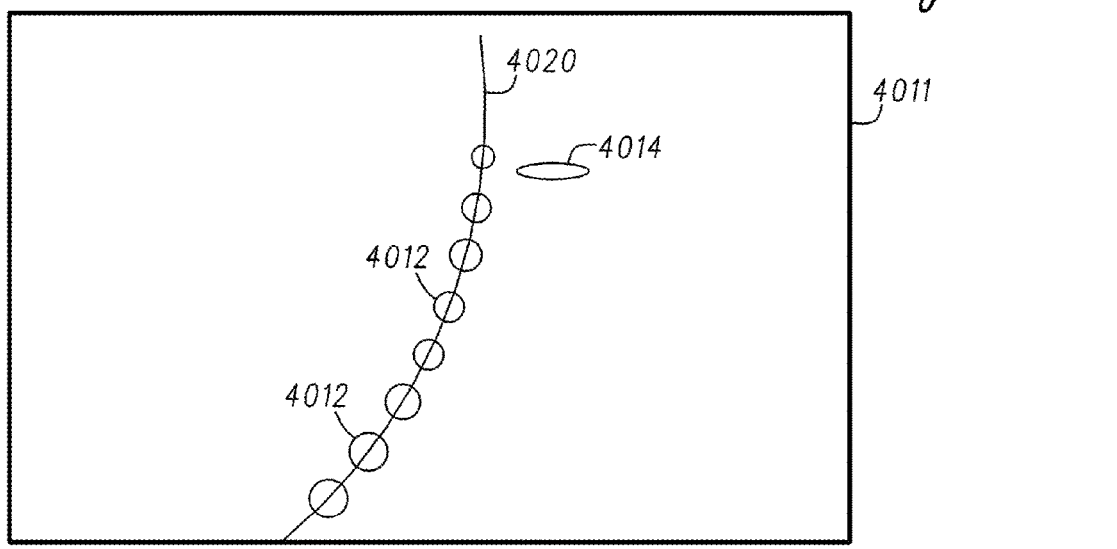
Fig. 127

SYSTEMS, METHODS, AND ARTICLES OF MANUFACTURE TO MEASURE, ANALYZE AND SHARE GOLF SWING AND BALL MOTION CHARACTERISTICS

CROSS-REFERENCE TO RELATED APPLICATIONS

This claims the benefit of U.S. Provisional Patent Appl. No. 62/222,893, filed on Sep. 24, 2015 and U.S. Provisional Patent Appl. No. 62/395,519, filed Sep. 16, 2016, and is a continuation in part of U.S. Non-Provisional patent application Ser. No. 14/836,552, filed on Aug. 26, 2015, which claims the benefit of U.S. Provisional Patent Appl. No. 62/043,705, filed on Aug. 29, 2014, and is a continuation in part of U.S. Non-Provisional patent application Ser. No. 13/524,257, filed on Jun. 15, 2012, which is a continuation in part of U.S. Non-Provisional patent application Ser. No. 13/246,663, filed on Sep. 27, 2011 which claims the benefit of U.S. Provisional Patent Application No. 61/485,549, filed on May 12, 2011, and is a continuation in part of U.S. Design patent application Ser. No. 29/391,647, filed on May 11, 2011, and U.S. Design patent application Ser. No. 29/391,657, filed on May 11, 2011. U.S. Non-Provisional patent application Ser. No. 13/524,257 further claims the benefit of U.S. Provisional Patent Appl. No. 61/497,891, filed on Jun. 16, 2011, U.S. Provisional Patent Appl. No. 61/506,583, filed on Jul. 11, 2011, U.S. Provisional Patent Appl. No. 61/522,165, filed on Aug. 10, 2011, and U.S. Provisional Patent Appl. No. 61/532,503, filed on Sep. 8, 2011. The contents of all disclosures above are incorporated fully herein by reference.

TECHNICAL FIELD

The present disclosure relates generally to golf, and more particularly, to measure, analyze and share golf swing characteristics.

BACKGROUND

In golf, some training devices may be an integral part of a golf club (i.e., built-in). That is, the golf club may not be readily used for play in a round of golf. Alternatively, other training devices may only function as a golf training device such that the training device may not be used for other purposes. Instead of the types of training device for golf mentioned above, individuals may want use already-owned and/or everyday-used portable electronic devices as a training device for golf.

SUMMARY

A need exists for convenient and accurate swing tempo detection. Accordingly, one implementation of the present disclosure may take the form of a method, comprising the steps of generating swing data by a wearable device as the wearable device moves during a predetermined period of time associated with a swing of a golf club, the swing data comprising accelerometer data generated from an accelerometer component of the wearable device and gyroscope data generated from a gyroscope component of the wearable device, utilizing a processor for: determining an impact data point of the swing data as an acceleration rate of change of the accelerometer data that exceeds a predetermined maximum threshold within the predetermined period of time, the impact data point associated with a first time interval; determining a backswing-end data point of the swing data as a minimum value of the gyroscope data associated with a second time interval before the first time interval; determining a swing-start data point of the swing data associated with a third time interval before the second time interval, by identifying a maximum value of the gyroscope data before the second time interval, and selecting the swing-start data point of the swing data as a value of the gyroscope data that drops below a predetermined minimum threshold before the second time interval; generating a backswing time and a downswing time associated with the swing of the golf club by analyzing time differences between the first time interval, the second time interval, and the third time interval; and generating a swing tempo using the backswing time and the downswing time.

Another implementation of the present disclosure may take the form of a method comprising determining a first time interval associated with a swing of a golf club when the golf club impacts a golf ball using an accelerometer of a wearable device; determining a second time interval associated with a backswing of the swing of the golf club using a gyroscope of the wearable device; determining a third time interval associated with a start of the swing of the golf club using the gyroscope of the wearable device; and generating a tempo of the swing of the golf club by a calculating a difference between at least two of the first time interval, the second time interval or the third time interval.

Another implementation of the present disclosure may take the form of a swing aid apparatus, comprising: a golf club; and a wearable device that assists with computation of a swing tempo from a swing of the golf club by detecting a first time interval associated with an impact of the golf club against a golf ball using an accelerometer of the wearable device, determining a second time interval associated with a backswing of the swing of the golf club using a gyroscope of the wearable device, and determining a third time interval associated with a start of the swing of the golf club using the gyroscope of the wearable device.

BRIEF DESCRIPTION OF THE DRAWINGS

FIG. 7 depicts a first side view of the example portable electronic device holder of FIG. 1.

FIG. 8 depicts a second side view of the example portable electronic device holder of FIG. 1 engaging a golf club shaft.

FIG. 12 depicts a visual representation of the example portable electronic device holder of FIG. 1 engaging a golf flagstick.

FIG. 13 depicts a schematic diagram of a typical portable electronic device.

FIG. 14 depicts a schematic diagram of communication between typical portable electronic devices.

FIGS. 17-27 depict visual diagram representations of example stroke characteristics according to the disclosure.

FIGS. 28-31 show an example golf club head.

FIG. 32 depicts a visual diagram representation of an example display according to the disclosure.

FIG. 75 depicts a side view of a portable electronic device mounted to a golf club shaft with a device holder according to the disclosure.

FIG. 76 depicts a side view of a portable electronic device mounted to a flagstick with a device holder according to the disclosure.

FIG. 82 depicts a block diagram representation of a process associated with the systems, methods, and articles of manufacture according to the disclosure.

FIGS. 83-85 depict three example stroke type indicators according to the disclosure.

FIGS. 114-123 depict visual diagram representations of example displays according to the disclosure.

FIG. 124 depicts a method of determining motion characteristics of a golf ball according to one example.

FIG. 125 depicts a method of determining motion characteristics of a golf ball according to one example.

FIG. 127 depicts an image displayed on a display screen of a portable electronic device according to one embodiment.

DETAILED DESCRIPTION

In general, apparatus, methods, and articles of manufacture associated with a portable electronic device holder are described herein. The methods, apparatus, and articles of manufacture described herein are not limited in this regard.

Figure 1:
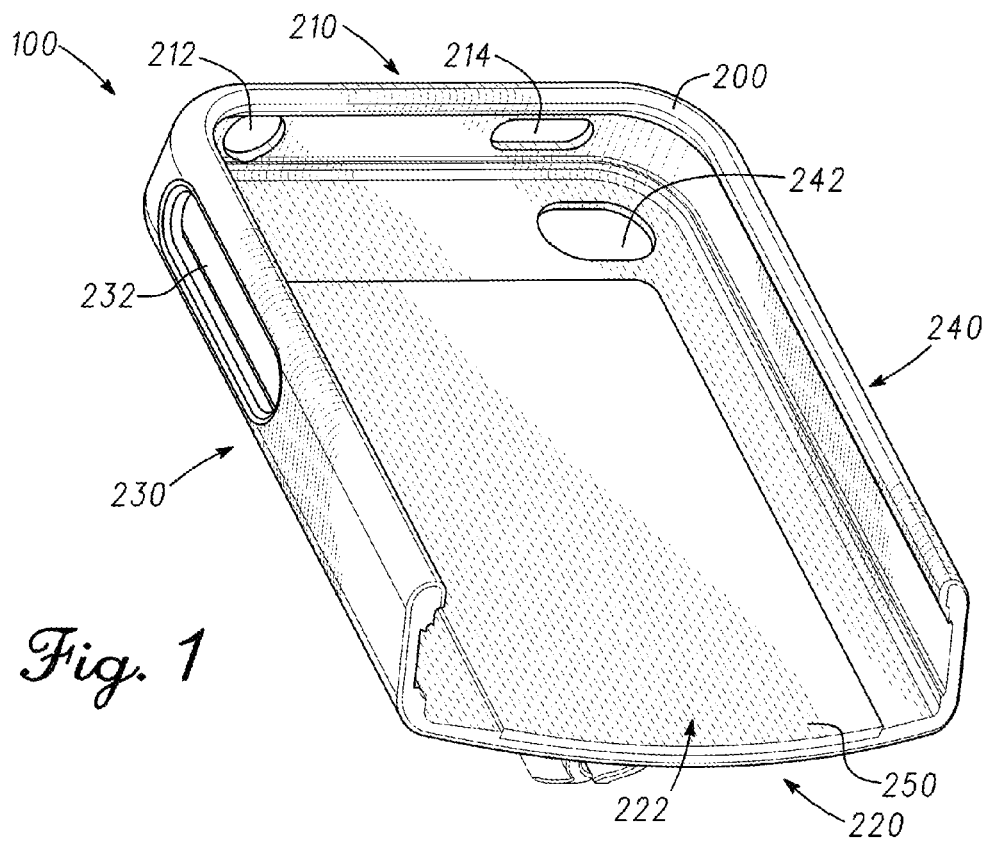
FIG. 1 depicts a front perspective view of an example portable electronic device holder according to an embodiment of the methods and articles of manufacture described herein.
Figure 2:
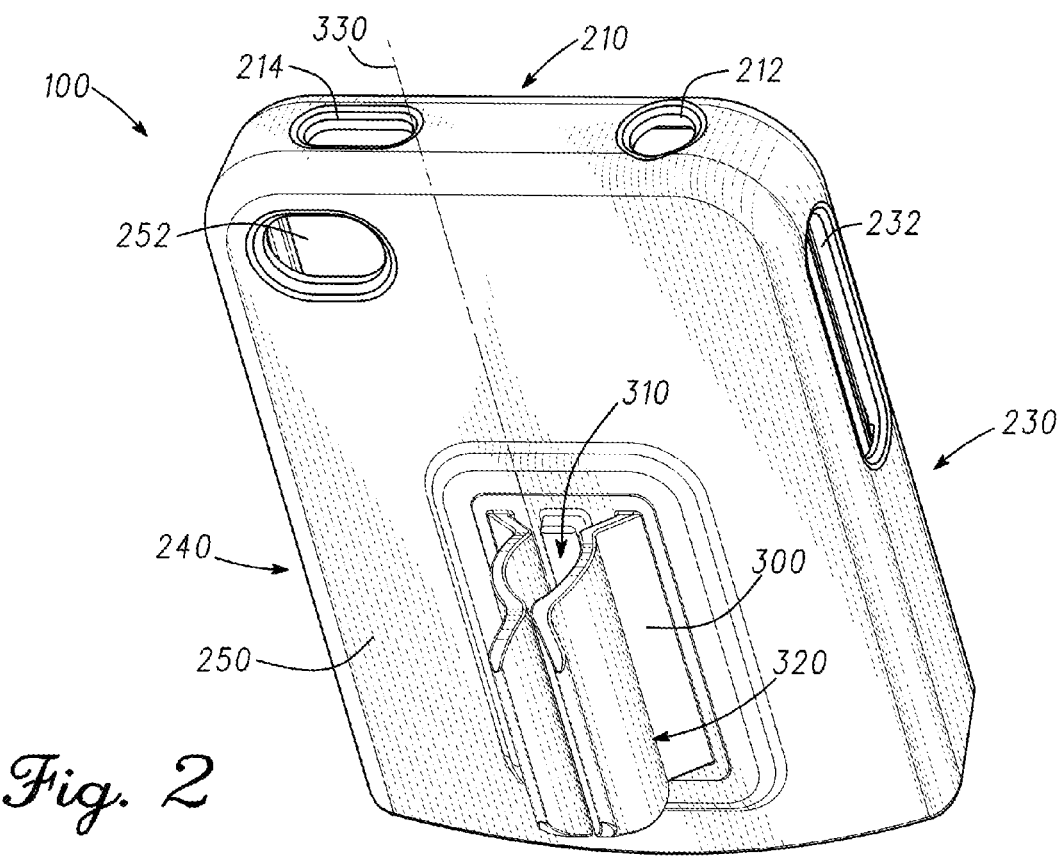
FIG. 2 depicts a back perspective view of an example portable electronic device holder of FIG. 1.
Figure 3:
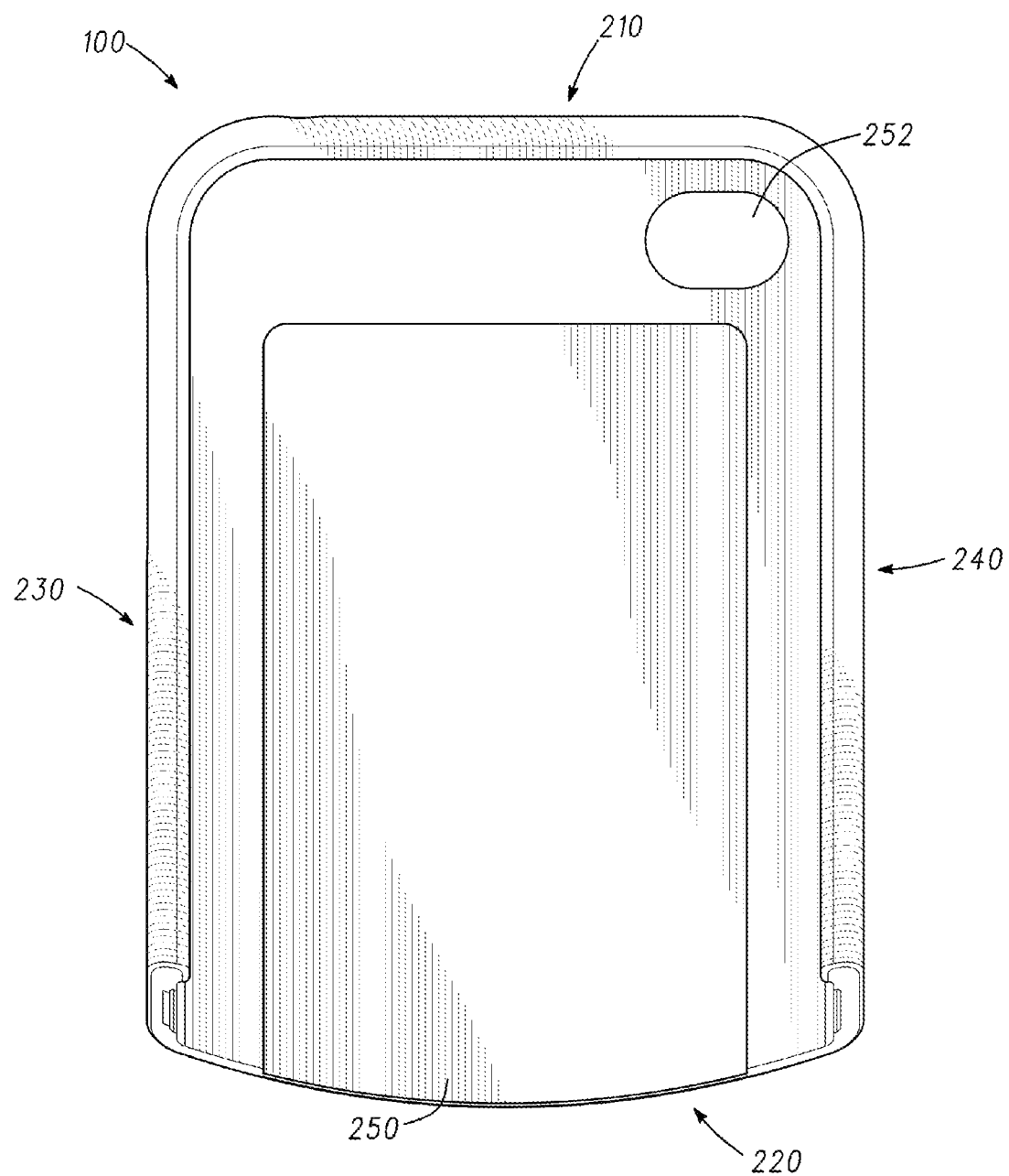
FIG. 3 depicts a front view of the example portable electronic device holder of FIG. 1.
Figure 4:
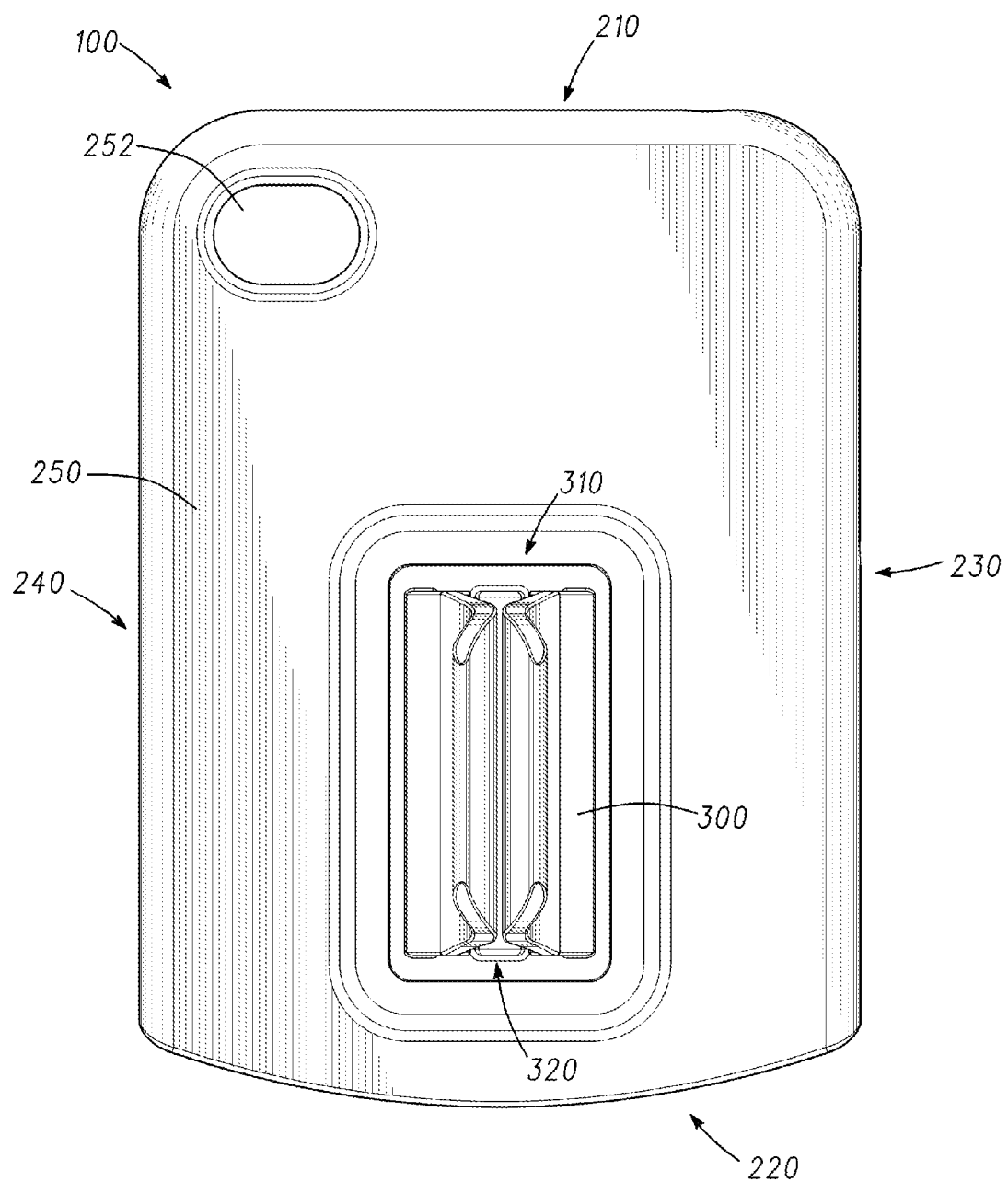
FIG. 4 depicts a back view of the example portable electronic device holder of FIG. 1.
Figure 5:
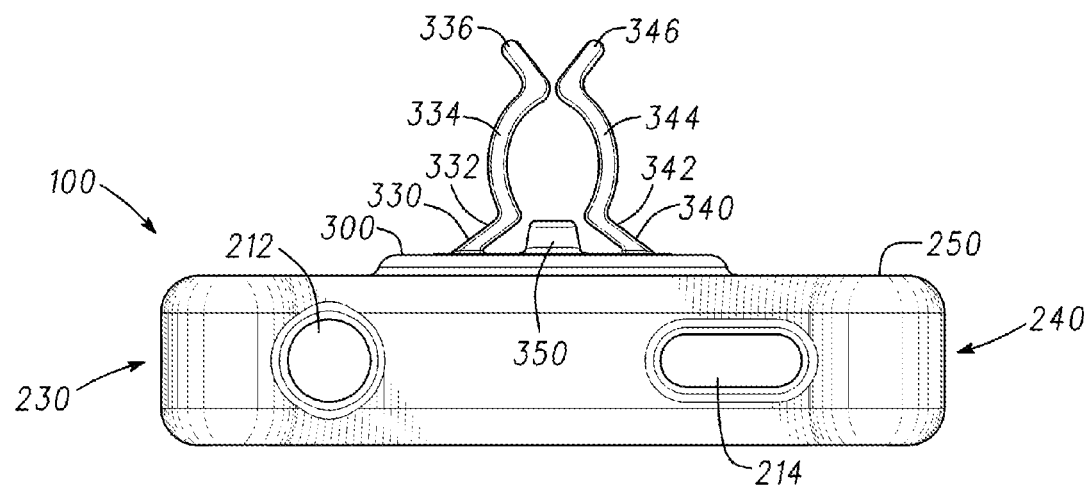
FIG. 5 depicts a first end view of the example portable electronic device holder of FIG. 1.
Figure 6:
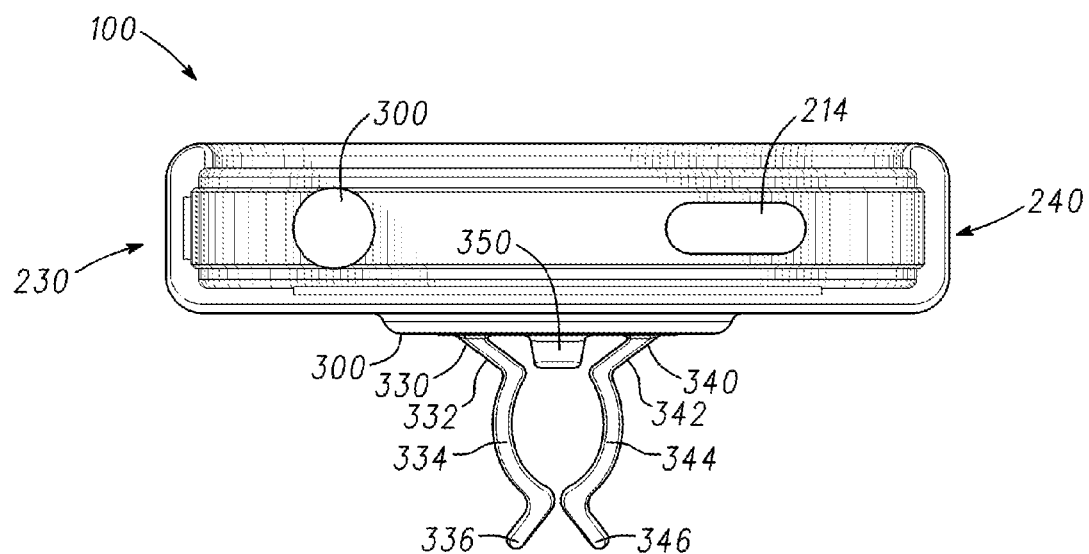
FIG. 6 depicts a second end view of the example portable electronic device holder of FIG. 1.

In the example of FIGS. 1-12, a portable electronic device holder 100 may include a body portion 200 (e.g., generally shown in FIG. 2) and a clamp portion 300 (e.g., generally shown in FIG. 3). As described in detail below, and generally shown in FIGS. 10 and 11, the portable electronic device holder 100 may be configured to removably attach and secure a portable electronic device 1000 such as a wireless communication device and/or a portable media player to a golf club 798. In particular, the portable electronic device holder 100 may be configured to removably attach and secure the portable electronic device 1000 to a golf shaft 800 of the golf club 798. As generally shown in FIG. 12, the portable electronic device holder 100 may also be configured to removably attach and secure the portable electronic device 1000 to a golf flagstick 810. For example, the portable electronic device 1000 may be a media player (e.g., an IPOD® mobile digital device from Apple Inc., Cupertino, Calif.), a wireless telephone (e.g., an IPHONE® mobile digital device from Apple Inc., Cupertino, Calif.), a watch (e.g., an APPLE WATCH® digital watch from Apple Inc., Cupertino, Calif.), a handheld computer, a global positioning system (GPS) device, a game console device, a digital camera and/or a video camera. As described in detail below, the portable electronic device 1000 may be configured to operate as a training device, a gaming device and/or a social networking device (e.g., the portable electronic device 1000 may include a processor to execute a software application). In addition or alternatively, the portable electronic device 1000 may be configured to operate as a telephone or a speaker broadcasting music. The apparatus and articles of manufacture described herein are not limited in this regard.

In particular, the body portion 200 of the portable electronic device holder 100 may include a first body end 210, a second body end 220, a first side portion 230, a second side portion 240, and a back portion 250. One or more portions of the body portion 200 may include one or more openings to accommodate for buttons, switches, ports, etc. of the portable electronic device 1000, generally shown as 212, 214, 222, and 232. In one example, the first body end 210 may include an opening 212 to accommodate a headphone jack and an opening 214 to accommodate a power switch of the portable electronic device 1000. The second body end 220 may include an opening 222 to receive the portable electronic device 1000. The first side portion 230 may include an opening 232 to accommodate one or more buttons to control volume. The back portion 250 may include an opening to accommodate a camera lens. The body portion 200 may be made of semi-rigid molded plastic or other suitable type materials. For example, the body portion 200 may be made of polycarbonate material and/or polypropylene material. The apparatus and articles of manufacture described herein are not limited in these regards.

In general, the portable electronic device 1000 may be able to slide in and out the body portion 200 via the opening 222 of the second body end 220. The first body end 210, the second body end 220, the first side portion 230, the second side portion 240, and the back portion 250 may be configured to secure the portable electronic device 900 so that the portable electronic device 1000 does not slide out from the body portion 200 without being pulled away from the portable electronic device holder 100. For example, the first body end 210, the first side portion 230, and/or the second side portion 240 may be curved or contoured in a manner to accommodate the outer shape of the portable electronic device 1000. The back portion 250 may include a material, which helps to retain the portable electronic device 1000 in the body portion 200 via friction. While the above examples may describe various openings at or proximate to particular portions, the apparatus, the methods, and the articles of manufacture described herein are not limited in this regard.

The clamp portion 300 may include a first clamp end 310, a second clamp end 320, a first arm portion 330, and a second arm portion 340. Each of the first and second arm portions 330 and 340 may have a W-shaped configuration. In particular, the first arm portion 330 may include a first support portion 332, a first arcuate portion 334, and a first guide portion 336. The first support portion 332 of the first arm portion 330 may extend from the back portion 240 of the body portion 200. The first support portion 332 may be coupled to the first arcuate portion 334, which in turn, may be coupled the first guide portion 336.

In a similar manner, the second arm portion 340 may include a second support portion 342, a second arcuate portion 344, and a second guide portion 346. The second support portion 342 of the second arm portion 340 may extend from the back portion 250 of the body portion 200. The second support portion 342 may be coupled to the second arcuate portion 344, which in turn, may be coupled the second guide portion 346.

The clamp portion 300 may be made of a semi-rigid material such as plastic and/or other suitable type of materials. For example, the clamp portion 300 may be made of polycarbonate material and/or polypropylene material. The first and second guide portions 336 and 346 may be configured to assist the golf club shaft 800 to engage the first and second arcuate portions 334 and 344. The first and second support portions 332 and 342 may be configured to provide flexibility so that the clamp portion 300 may engage the golf club shaft 800 or the flagstick 810.

Figure 9:
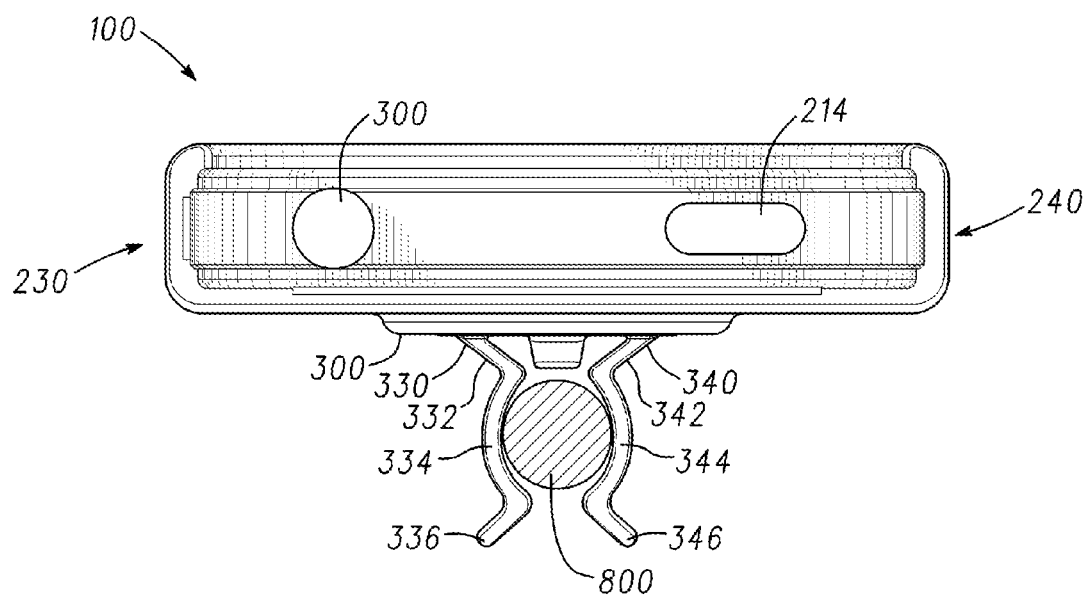
FIG. 9 depicts a bottom view of the example portable electronic device holder of FIG. 1 engaging a golf club shaft.

In one example as shown in FIG. 9, the first and second arcuate portions 334 and 344 may be configured to engage the golf club shaft 800 or the flagstick 810 (i.e., a cross-sectional view of the golf club shaft 800 is shown). The first and second arcuate portions 334 and 344 may be configured to engage golf club shafts or flagsticks with various diameter sizes. For example, the first and second arcuate portions 334 and 344 may be configured to engage golf club shafts having a diameter of at least 0.3 inches. With some golf club shafts taper from one end to another (e.g., 0.335 inches at the tip end and 0.6 inches at the butt end), the first and second arcuate portions 334 and 344 may be configured to engage golf club shafts having a diameter ranging from 0.4 inches to 0.6 inches. The first and second arcuate portions 334 and 344 may be configured to engage flagsticks having a diameter of 0.5-1.0 inch. The apparatus, the methods, and the articles of manufacture described herein are not limited in this regard.

The clamp portion 300 may also include a bumper portion 350. In particular, a portion of the golf club shaft 800 or the flagstick 810 may rest against the bumper portion 350. The bumper portion 350 may prevent or reduce damage to the graphics of the golf club shaft 800, the golf club shaft 800 itself, and/or the flagstick 810.

In the example of FIGS. 8-11, the golf club shaft 800 may include a butt end 810 and a tip end 820. A grip 815 may be located at or proximate to the butt end 810 whereas a golf club head 825 may be located at or proximate to the tip end 820. The portable electronic device holder 100 may engage the golf club shaft 800 of a golf club at or proximate to the butt end 810. To engage the golf club shaft 800, the portable electronic device holder 100 may be rotated 180 degrees from the orientation of the portable electronic device holder 100 shown in FIG. 7. As shown in FIG. 8, for example, the first end portion 210 of the portable electronic device holder 100 may point towards the tip end 820 of the golf club shaft 800 whereas the second end portion 220 of the portable electronic device holder 100 may point towards the butt end 810 of the golf club shaft 800. The apparatus, the methods, and the articles of manufacture described herein are not limited in this regard.

Figure 10:
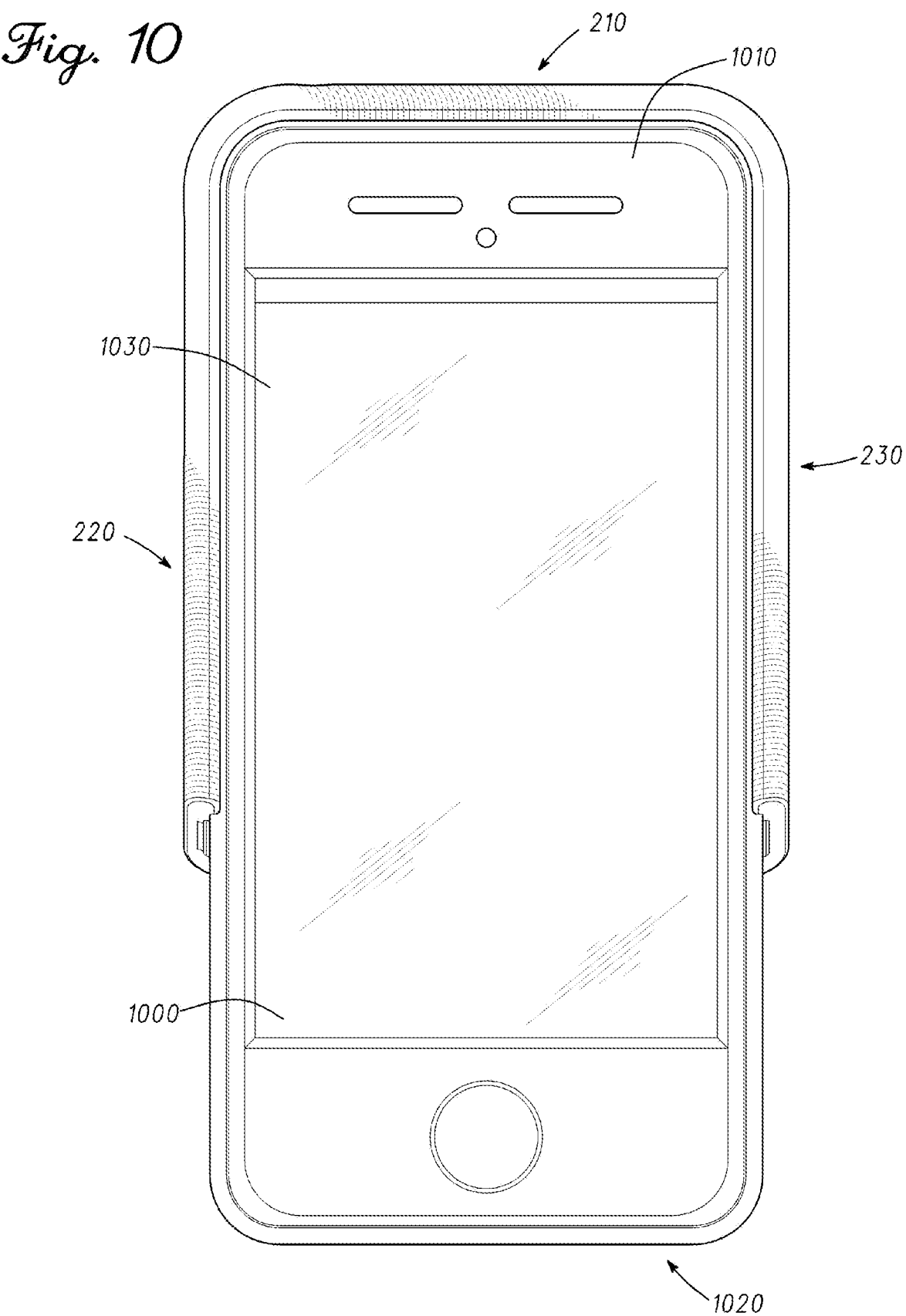
FIG. 10 depicts a front view of the example portable electronic device holder of FIG. 1 engaging a portable electronic device.

In the example of FIG. 10, a portable electronic device 1000 may include a top portion 1010, a bottom portion 1020, and a display portion 1030. The body portion 200 of the portable electronic device holder 100 may receive the portable electronic device 1000. In particular, the top portion 1010 of the portable electronic device 1000 may slide through the opening 222 of the second body end 220. The first body end 210 of the body portion 200 may be configured to abut the top portion 1010 of the portable electronic device 1000. The portable electronic device holder 100 may include an opening so that the display portion 1030 of the portable electronic device 1000 may be visible. In one example, the portable electronic device 1000 may operate as a training device for golf. Accordingly, any visual representation may be generated on the display portion 1030, which can be seen by an individual while the portable electronic device 1000 is secured to the portable electronic device holder 100. The apparatus, and the articles of manufacture described herein are not limited in this regard.

The portable electronic device 1000 may communicate with a server, directly with another portable electronic device, with another portable electronic device through a server, and/or with a network as described in detail below. Referring to FIG. 13, the portable electronic device 1000 may include a processing device 1110, a plurality of sensors 1112, a graphical user interface (GUI) 1114, and a data storage device 1116. The portable electronic device 1000 may also include an input and output port (I/O port, not shown) and/or one or more transceivers (not shown). Furthermore, the portable electronic device 1000 may include one or more Global Positioning Sensors (GPS, not shown) for determining location. The processing device 1110 may execute instructions that are stored in the storage device 1116 to perform any of the processes according to the disclosure. The plurality of sensors 1112 may include accelerometers to measure accelerations and/or gyroscopes to determine an orientation of the portable electronic device 1000, which may be used to determine stroke characteristics of an individual as described in detail below. The GUI 1114 may generate one or more visual displays associated with the processes according to the disclosure. The data storage device 1116, which may be any type of data memory device, may store data associated with any of the processes according to the disclosure. The systems, methods, and articles of manufacture described herein are not limited in this regard.

The portable electronic device 1000 may include one or more user input devices (not shown), such as a touch screen graphical user interface, an alphanumeric keyboard, push-type buttons, rotating dials, a joystick, a trackball, and/or a touchpad. Accordingly, an individual may operate the portable electronic device 1000 and provide input to the portable electronic device 1000 with one or more of the noted input devices if any such input devices are provided on the portable electronic device 1000. According to the disclosed examples, the GUI 1114 of portable electronic device 1000 is a touch-screen display by which an individual can select one or more displayed items, perform certain functions with the portable electronic device, operate the portable electronic device, and/or provide input to the portable electronic device. For example, a virtual keyboard may be provided on the GUI 1114, by which an individual can input alphanumeric characters by touching an area of the GUI 1114 corresponding to the display of each character. In another example, the GUI 1114 may display one or more virtual windows having therein one or more selectable menu items that can be selected by an individual by touching an area of the GUI 1114 corresponding to the display of the menu item. Each menu item when selected may cause the portable electronic device 1000 to perform a certain process or function such as any of the disclosed processes or functions. In yet another example, the GUI 1114 may display a graphical icon, selection of which by an individual may cause the portable electronic device to perform a certain process or function, such as any of the disclosed processes of functions, corresponding to the graphical icon. The displayed icon can be selected by an individual by touching an area of the GUI 1114 where the graphical icon is displayed. The portable electronic device is described herein as having a touch screen GUI 1114. However, any portable electronic device may be used to perform the disclosed processes or function as disclosed. Thus, the systems, methods, and articles of manufacture described herein are not limited in this regard.

Two or more portable electronic devices may directly communicate with each other. Referring to FIG. 14, three exemplary portable electronic devices are shown generally as 1120, 1122, and 1124. The portable electronic devices 1120, 1122, and 1124 may be configured to perform the processes according to the disclosure and/or operate as described herein. The portable electronic devices 1120, 1122, and 1124 may communicate with each other directly via a wireless communication link (e.g., short-range wireless communication link). For example, the portable electronic devices 1120, 1122, and 1124 may operate in accordance with Bluetooth® technology to communicate and/or exchange data with each other. In addition or alternatively, the portable electronic devices 1120, 1122, and 1124 may operate in accordance with the 802.xx family of standards developed by the Institute of Electrical and Electronic Engineers (IEEE) and/or variations and evolutions of these standards (e.g., 802.11x, 802.15, 802.16x, etc.), Ultra Wideband (UWB), Near Field Communication (NFC), and/or radio frequency identification (RFID) to communicate and/or exchange data with each other as described herein. In another example, the portable electronic devices 1120, 1122, and 1124 may be within a particular distance (e.g., up to 100 meters or 328 feet) of each other so that these devices may automatically detect the presence of each other to communicate and/or exchange data. The systems, methods, and articles of manufacture are not limited in this regard.

Figure 15:
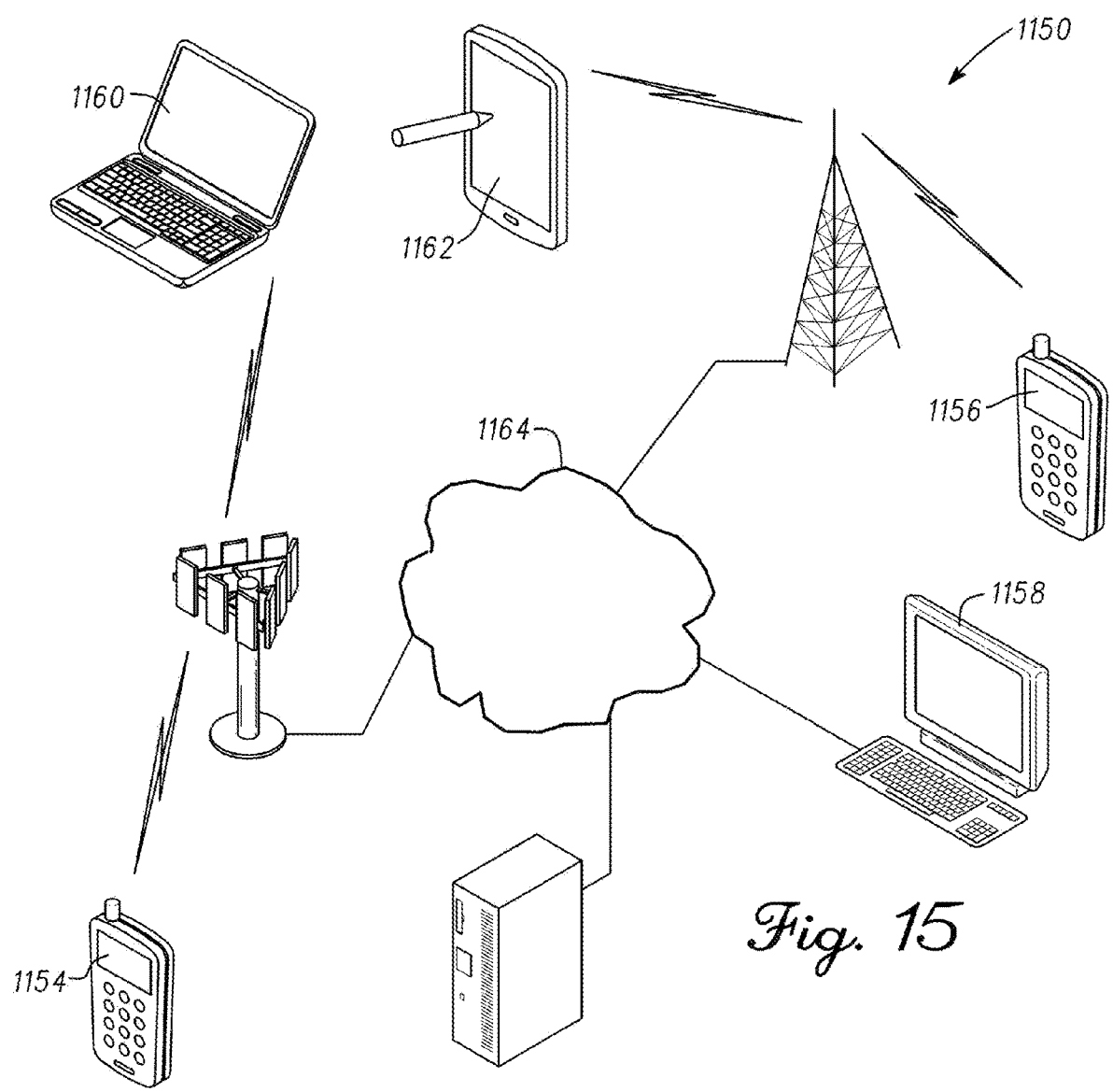
FIG. 15 depicts a schematic diagram of a typical data communication network.
Figure 16:
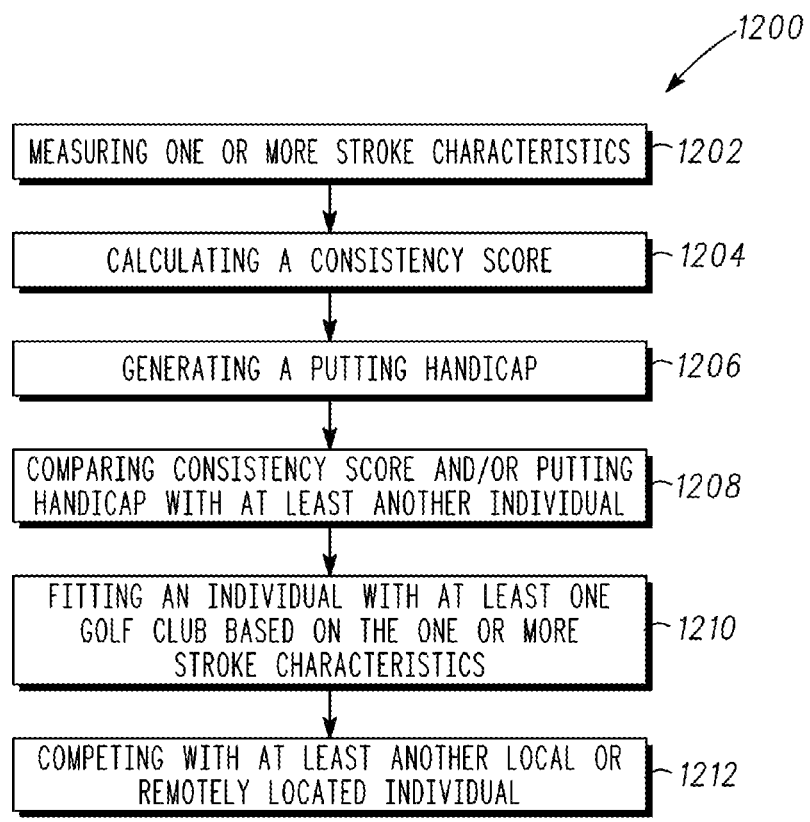
FIG. 16 depicts a block diagram representation of a process associated with the systems, methods, and articles of manufacture according to the disclosure.

Referring to FIG. 15, each portable electronic device may communicate with a network 1150 including a server 1152. The server 1152 may receive data from the portable electronic device and store the data. The portable electronic device 1000 may receive data from the server 1152, receive updated instructions from the server 1152 to perform any of the processes according to the disclosure, and/or to receive new instructions from the server 1152 to perform any of the processes according to the disclosure. Two portable electronic devices are generally shown as 1154 and 1156. In particular, the plurality of portable electronic devices 1154 and 1156 may communicate with the server 1152 directly and/or indirectly via one or more wired and/or wireless communication links, which may be in accordance to a proprietary wireless communication protocol or any of the wireless communication protocols described herein. Data stored on the server 1152 may be shared and accessed by the portable electronic devices 1154 and 1156. Other portable electronic devices such as a desktop computer (e.g., one shown as 1158), a laptop computer (e.g., one shown as 1160), a tablet device (e.g., one shown as 1162), and/or a watch may also send data to and receive data from the server 1152, and access the data stored on the server 1152 via the Internet 1164.

Referring back to FIG. 14, the first portable electronic device 1120 may share data in real time with the second portable electronic device 1122 and/or the third portable electronic device 1124 directly (e.g., via one or more wired and/or wireless communication links). In addition or alternatively, the first portable electronic device 1120 may share data by transmitting to a display or a monitor directly (e.g., via one or more wired and/or wireless communication links).

Referring to FIG. 15, the portable electronic device 1154 may share data with other portable electronic devices via the server 1152 or with systems (i.e., other servers or networks) remotely located from the server (not shown) via the internet 1164. Accordingly, the portable electronic device 1156 and/or other devices (e.g., the desktop computer 1158, the laptop computer 1160, the tablet device 1162, and/or the watch) may access data stored on the server 1152. The systems, methods, and articles of manufacture are not limited in this regard.

While the examples provided herein may describe particular wireless communication protocols, the systems, methods, and articles of manufacture described herein may operate in accordance with other wireless communication protocols such as frequency division multiple access techniques such as frequency division multiple access (FDMA), time division multiple access (TDMA), and/or code division multiple access (CDMA). For example, the wireless communication protocols may include Global System for Mobile communications (GSM), Wideband CDMA (W-CDMA), General Packet radio Services (GPRS), Enhanced Data GSM Environment (EDGE), Universal Mobile Telecommunications System (UMTS), High-Speed Downlink Packet Access (HSDPA), Long Term Evolution (LTR), variations and evolutions of these standards, and/or other suitable wireless communication standards to communicate and/or exchange data. The systems, methods, and articles of manufacture described herein are readily applicable to many specifications and/or standards developed by other special interest groups and/or standard development organizations (e.g., Wireless Fidelity (Wi-Fi) Alliance, Worldwide Interoperability for Microwave Access (WiMAX) Forum, Infrared Data Association (IrDA), Third Generation Partnership Project (3GPP), etc.).

The processes described herein may be implemented as machine-accessible instructions utilizing any of many different programming codes stored on any combination of machine-accessible media embodied in a mobile application (e.g., an app) and/or an online application for various wired and/or wireless communication devices such as handheld computers, smartphones, portable media players, tablet computers, watches, etc. In addition or alternatively, the machine-accessible instructions may be embodied in a volatile or non-volatile memory or other mass storage device (e.g., a floppy disk, a CD, and a DVD). For example, the machine-accessible instructions may be embodied in a machine-accessible medium such as a programmable gate array, an application specific integrated circuit (ASIC), an erasable programmable read only memory (EPROM), a read only memory (ROM), a random access memory (RAM), a flash memory, a magnetic media, an optical media, and/or any other suitable type of medium. The systems, methods, and articles of manufacture described herein are not limited in this regard.

While example systems including, among other components, software or firmware executed on hardware are disclosed herein, it should be noted that such systems are merely illustrative and should not be considered as limiting. In particular, it is contemplated that any or all of the disclosed hardware, software, and/or firmware components could be embodied exclusively in hardware, exclusively in software, exclusively in firmware or in some combination of hardware, software, and/or firmware.

A golf stroke may be defined as the complete movement of a golf club by an individual to strike a golf ball from a setup or address position to the conclusion of a follow through position (i.e. continuous motion of the club after the ball is hit). Examples of golf strokes may be a putting stroke, a chipping stroke or a driving stroke. The disclosed systems, methods, and articles of manufacture are described with respect to putting strokes. However, the disclosed systems, methods, and articles of manufacture are not limited in this regard and are equally applicable to any type of golf stroke such as chipping strokes, driving strokes or any swinging action of a golf club by an individual for actually striking a golf ball or to simulate striking a golf ball.

The disclosed systems, methods, and articles of manufacture are described with respect to a putter type of golf club. However, any type of golf club may be used with the disclosed systems, methods, and articles of manufacture. For example, a golf club for use with the disclosed systems, methods, and articles of manufacture may be a wood-type golf club, such as a driver-type golf club head, a fairway wood-type golf club head (e.g., 2-wood golf club, 3-wood golf club, 4-wood golf club, 5-wood golf club, 6-wood golf club, 7-wood golf club, 8-wood golf club, or a 9-wood golf club), a hybrid-type golf club head or any other suitable type of golf club head with a hollow body or a body with one or more cavities, apertures, recesses or channels. Although the disclosed examples depict putter type golf clubs, the apparatus, articles of manufacture, and methods described herein may be applicable to other types of golf club heads.

FIG. 15 shows a process 1200 (e.g., via the portable electronic device 1000) configured to measure one or more stroke characteristics of an individual associated with one or a plurality of putting strokes (block 1202), generate a consistency score for the individual (block 1204) based on the measure stroke characteristics, and generate a putting handicap for the individual (block 1206) based on one or more consistency scores. The process 1200 may be further configured to compare a consistency score and/or a putting handicap of an individual with other individuals (block 1208), to fit an individual with golf clubs based on the individual's measured stroke characteristics (block 1210), and/or to allow an individual to compete against one or more local or remotely located individuals (block 1212). The process 1200 and operation of the electronic device 1000 when performing the process 1200 is described in detail below.

Stroke characteristics may include closing angle, impact angle, tempo, shaft lie angle and shaft loft angle. Closing angle, for example, may be the amount a striking face of a golf club turns during a downswing of a putting stroke. Impact angle, for example, may be defined by an angle of the striking face at impact. Tempo, for example, may be defined by a ratio of a backswing time to a downswing time. Shaft lie angle, for example, may be defined by the angle between the shaft of a golf club and a vertical line at the moment of impact between the face of the golf club and a ball. Shaft loft angle, for example, may be the defined by the angle between the shaft and a vertical line extending from the club face at the moment of impact between the club face and a ball.

FIGS. 17-19 show an exemplary club head 1212 having a club face 1214 for striking a ball. Based on the closing angle, the process 1200 may identify a stroke type. Any number of stroke types may be identified by the process 1200. Three common stroke types may be a straight-type stroke, a slight arc-type stroke, or a strong arc-type stroke. Referring to FIG. 17, the face 1214 may have relatively less face rotation in a straight-type stroke as illustrated by the generally straight line 1216 whereas the face 1214 may have a greater face rotation in a slight arc-type stroke as illustrated by the arc 1218 of FIG. 18. Referring to FIG. 19, a strong arc-type stroke may be defined by the face 1214 having a larger rotation than in the straight-type stroke and slight-arc-type stroke as illustrated by the arc 1220.

Figure 22:
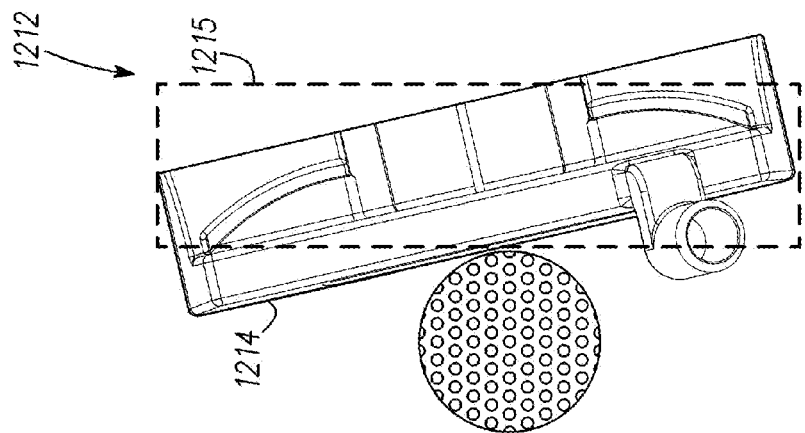
Figure 21:
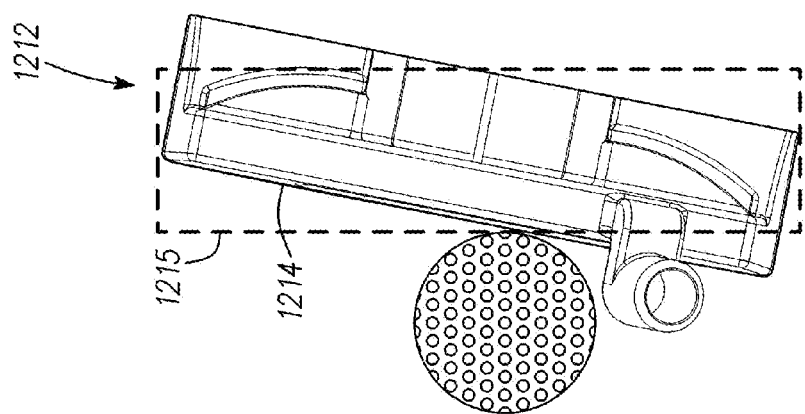
Figure 20:
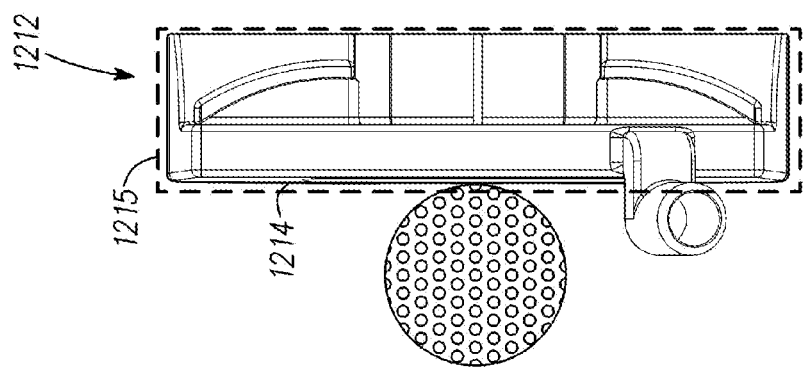

Referring to FIGS. 20-22, the impact angle of a putting stroke may be an angle of the striking face 1214 of the club head 1212 at impact relative to an address position 1215 (shown with dashed lines). FIG. 20 shows the striking face 1214 having an impact angle that is generally similar to the address position 1215. FIGS. 21 and 22 show the impact angle to be open and closed, respectively. An open position for a right handed player, which is generally shown in FIG. 21, may be defined by the striking face 1214 of the club head 1212 oriented toward the right of the address position 1215 whereas a closed position, which is generally shown in FIG. 22, may be defined by the striking face 1214 oriented toward the left of the address position 1215. An open position for a left handed player (not shown), may be defined by the striking face 1214 of the club head 1212 oriented toward the left of the address position 1215 whereas a closed position (not shown) may be defined by the striking face 1214 of the club head 1212 oriented toward the right of the address position.

Figure 23:
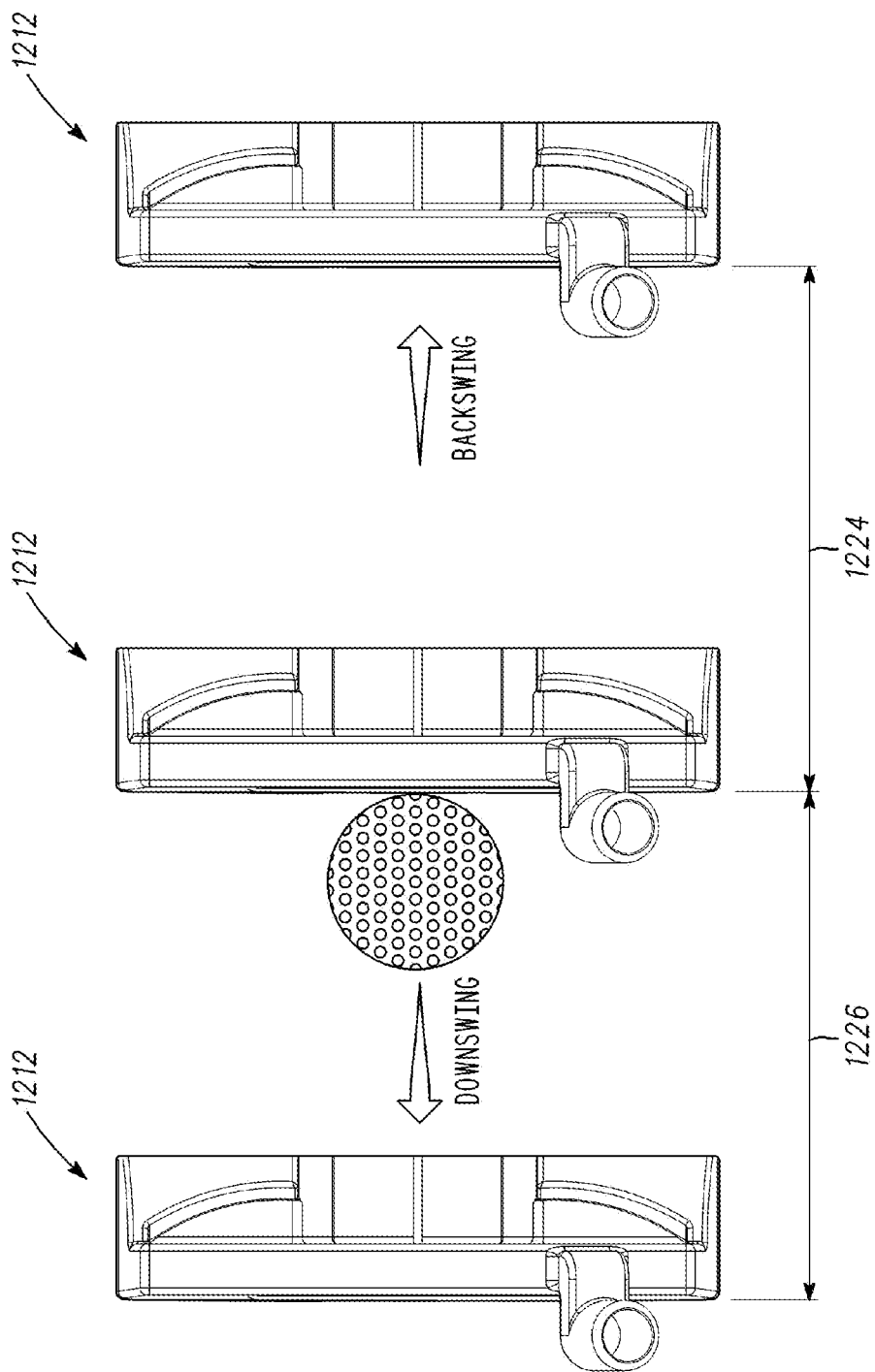

Referring to FIG. 23, the tempo of a putting stroke may be a ratio of backswing time (generally shown as 1224) to downswing time (generally shown as 1226). For example, a back swing time of 700 milliseconds (ms) to a downswing time of 350 ms is a 2-to-1 tempo. A relatively consistent tempo may provide better control of distance.

Figure 24:
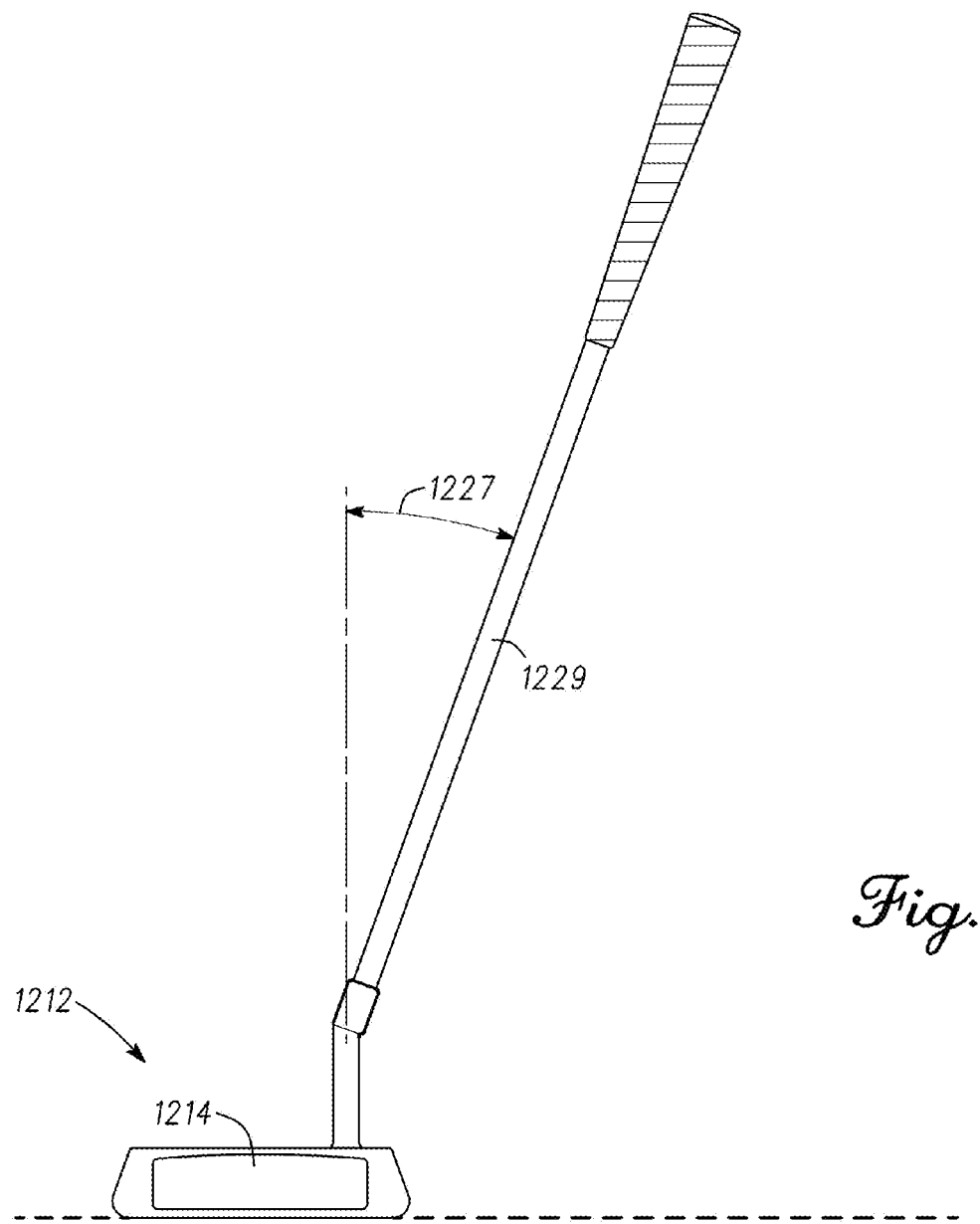
Figure 28:
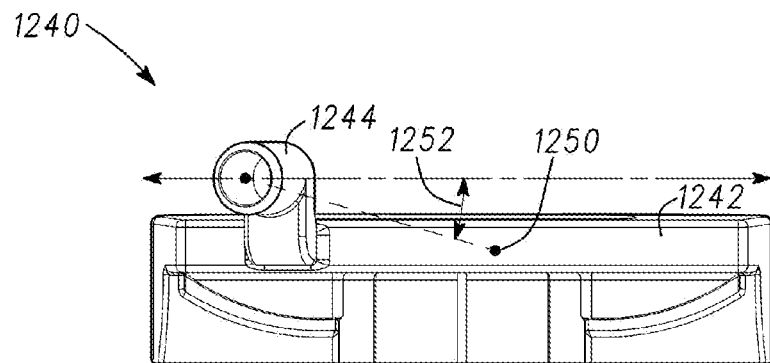
Figure 29:
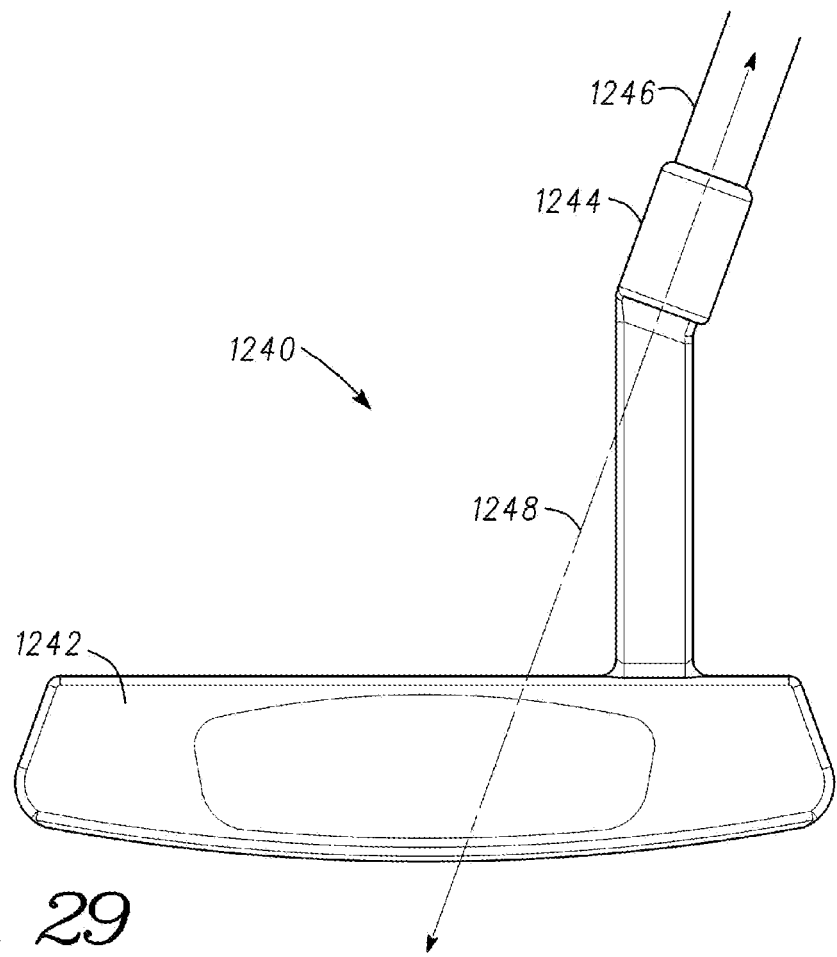

Referring to FIG. 24, a shaft lie angle 1227 of a golf club may be defined by the angle between the shaft 1229 and the vertical at the moment of impact between the club face 1214 and a golf ball.

Referring to FIGS. 25-27, shaft loft angle 1232 may be defined as the angle between the club shaft 1229 and a vertical line 1234 at the moment of impact between the club face 1214 and the golf ball. The club head may have a loft relative to the shaft that is built into the golf club. Accordingly, the club head may have a different loft angle than the shaft loft angle 1232 at the moment of impact. Therefore, a non-zero shaft loft angle 1232 has the effect of adding or subtracting to the built-in loft angle of the club face 1214 at the moment of impact. The vertical line 1234 may represent an address position of the shaft. However, certain individuals may orient the shaft at an angle relative to vertical when in the address position. The shaft loft angle 1232 may also determine an offset distance 1236 by which an individual's hands gripping the shaft 1229 are offset relative to the club face 1214 at the moment of impact between the club face 1214 and the golf ball. As shown in FIG. 25, the shaft loft angle 1232 may position the individual's hands gripping the shaft 1229 to a position behind the club face 1214 at the moment of impact between the club face 1214 and the golf ball, which may be referred to herein as the hands back position. In FIG. 26, the shaft loft angle 1232 is shown to be approximately zero. In FIG. 27, the shaft loft angle 1232 may position the individual's hands gripping the shaft 1229 to a position forward of the club face 1214 at the moment of impact between the club face 1214 and the golf ball, which may be referred to herein as the hands forward position.

Figure 11:
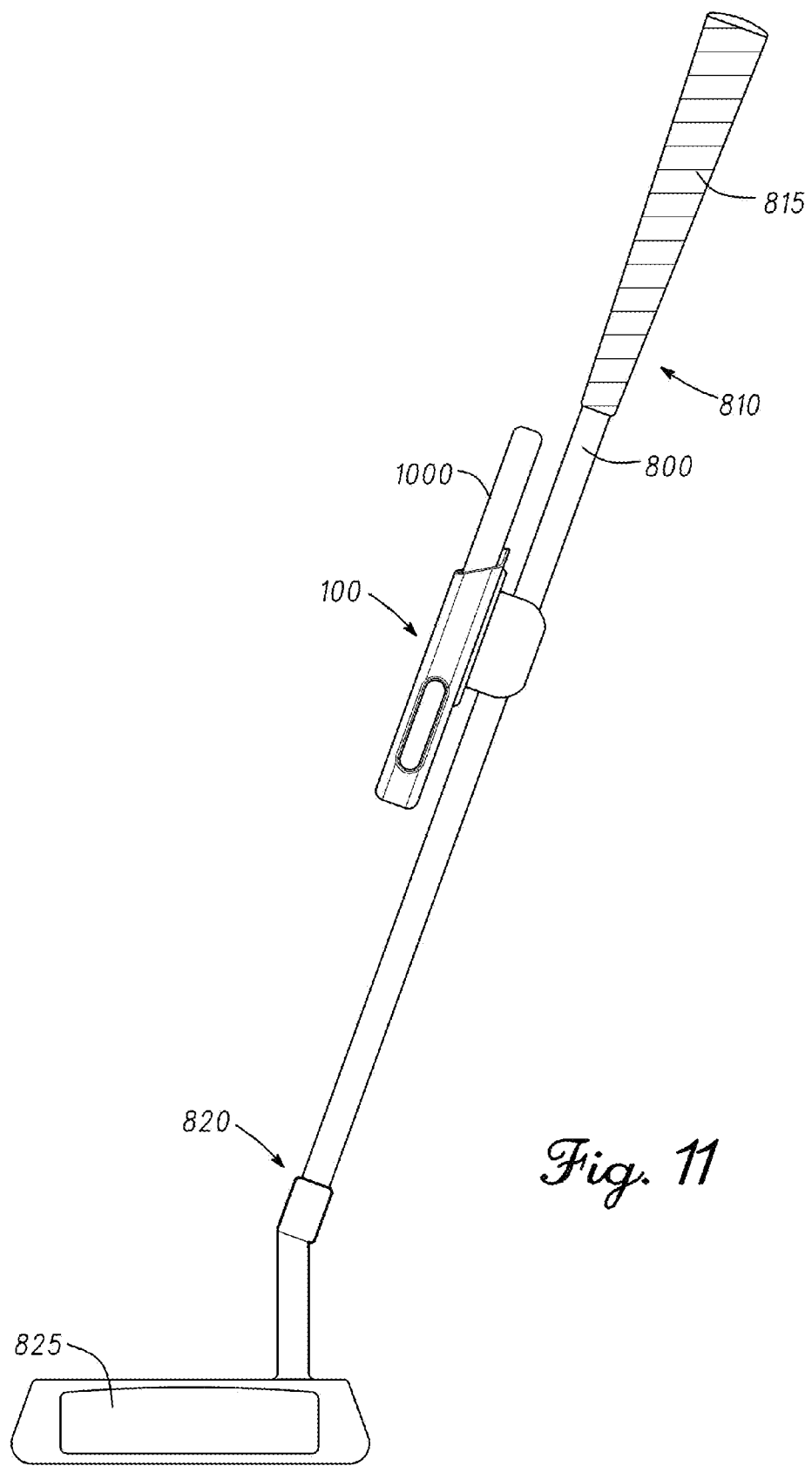
FIG. 11 depicts a visual representation of the example portable electronic device holder of FIG. 1 engaging a golf club.

To perform the process 1200, the portable electronic device 1000 may be attached to a golf club (e.g., a putter-type golf club) via the portable electronic device holder 100 as shown in FIG. 11. In a putting session, for example, the process 1200 may measure one or more stroke characteristics (block 1202) associated with one or several putting strokes. For example, five putting strokes may be used by the process 1200 to measure one or more stroke characteristics.

To measure one or more stroke characteristics as described above, the portable electronic device 1000 may measure linear and/or angular positions and/or linear and/or angular motions (e.g. accelerations) of a section of the club shaft to which the portable electronic device 1000 is attached along one, two or three axes continuously or at certain time intervals prior to and after a face of the club head strike a ball. FIGS. 28-31 show an exemplary golf club 1240 for illustrating measurements that may be made by the portable electronic device 1000 to determine one or more stroke characteristics and/or fitting an individual with golf clubs as described in detail below. The golf club 1240 may include a strike face 1242, a hosel 1244, and a shaft (a portion shown as 1246). The hosel 1244 may receive one end of the shaft 1246 whereas the opposite end of the shaft 1246 may include a grip (not shown). An axis may extend through the shaft 1246 (i.e., a shaft axis 1248). A center of gravity (CG) 1250 of the golf club 1240 may be defined relative to the shaft axis 1248 and/or a CG angle 1252 relative to a horizontal plane 1254 passing through the shaft axis 1248.

In one example, the portable electronic device 1000 may determine face rotation of the golf club 1240 relative to the shaft axis 1248 during the entire backswing and downswing sections of a golf stroke to determine stroke type of an individual. The portable electronic device 1000 may measure linear and/or angular accelerations in one or more axes continuously or at discrete intervals during the entire golf swing starting from the address position. Impact of the club head with the ball may signal the end of the downswing. By measuring linear and/or angular accelerations from the address position to the impact position of the club head at continuous or discrete intervals, an angle of the club head may be calculated at each of the time intervals relative to the angle of the club head or the club face at the address position. Therefore, rotation of the club face during the entire backswing and downswing sections of a golf stroke may be determined.

In another example, the portable electronic device 1000 may measure an angle of rotation of the face of the golf club 1240 relative to an angle of the face at the address position 1215 shown in FIGS. 20-22. The portable electronic device 1000 may measure the angle of rotation of the face of the golf club 1240 continuously or at certain intervals during the entire golf swing relative to the address position 1215 shown in FIGS. 20-22. Therefore, the angle of the face of the golf club 1242 at the address position 1215 may be used as a reference angle relative to which all rotation angles of the club face during the entire golf swing are measured.

The change between the first rotation angle 1258 and the second rotation angle 1262 or between any rotation angle and the angle at the address position 1215 may be used by the portable electronic device 1000 to determine the stroke type for an individual. By measuring stroke characteristics based on multiple putt attempts, consistency in the putting stroke characteristics can be identified in order to provide an accurate measurement of putting stroke characteristics. In one example, a change in face rotation of less than 3.5 degrees may be classified as a straight stroke type. A change in face rotation in a range from 3.5 to 7.5 degrees may be classified as a mid-arc stroke type. A change in face rotation of greater than 7.5 degrees may be classified as a strong-arc stroke type. While the above examples may provide particular ranges of change in face rotation for various stroke types, the systems, methods, and articles of manufacture described herein may use other suitable ranges to classify stroke type.

As described in detail below, the process 1200 may generate a putting handicap (block 1204) based on measuring an individual's stroke characteristics (block 1202). In particular, the process 1200 may calculate a consistency score associated with each putting session to define the repeatability of an individual's putting stroke. In one example, a relative low number may indicate a relatively consistent putting stroke whereas a relatively high number may indicate a relatively inconsistent putting stroke. Each putting session may include at least one putting stroke (e.g., at least five putting strokes by an individual). The process 1200 may generate the putting handicap based on one or a plurality of consistency scores (e.g., consistency scores from last ten putting sessions). The systems, methods, and articles of manufacture described herein are not limited in this regard.

The process 1200 may display the individual's stroke characteristics on the graphical user interface (GUI) 1114. For example, the portable electronic device 1000 may determine the individual's stroke type, impact angle, tempo, shaft lie angle and/or shaft loft angle as discussed in detail below. The portable electronic device 1000 may then display in alphanumeric text, graphics or a combination thereof the individual's stroke type, impact angle, tempo, shaft lie angle and/or shaft loft angle.

Referring back to FIGS. 13 and 15, the process 1200 may be performed with the portable electronic device 1000 by instructions being executed with the processing device 1110. The instructions may include one or a plurality of program codes and related data collectively defining software stored in the data storage device 1116 and retrieved by the processing device 1110. Any instructions being executed with the processing device 1110 to perform any of the disclosed processes including the process 1200 may be generally referred to herein as the software.

An individual may start any of the disclosed processes including the process 1200 by touching a graphic icon on the GUI 1114 corresponding to the process. Alternatively, the individual may start a process by pressing one or more buttons on the portable electronic device 1000 and/or with voice commands. Performing any of the disclosed processes, including the process 1200 may entail the processing device 1110 retrieving at least a part of instructions such as a program code and any data associated with the retrieved part of the program code from the storage device 1116 and executing the program code to operate the portable electronic device 1000 to perform the process.

The GUI 1114 may display an icon representing the software, which as described in detail above, includes instructions that are executable by the processor of the portable electronic device to perform any of the disclosed processes including process 1200. For example, the icon may be an image of a golf club and a golf ball. To start the software (i.e., execute instructions by the processor), an individual can touch the GUI 1114 at or near the location where the icon is displayed. Subsequently, a main display 1300 is shown on the GUI 1114, an example of which is shown in FIG. 32. The main display 1300 may include a main menu 1302 by which the individual can select one or more of several functions of the software to be performed by the portable electronic device 1000.

The main menu 1302 may include a practice icon 1304, a measure icon 1306, a compare icon 1308 and a sub-menu icon 1310 for providing additional options to an individual as described in detail below. Each of the icons 1304, 1306, 1308 and 1310 may include graphics and/or alphanumeric symbols to convey to an individual the process and/or function that is performed upon selection of the icon. For example, as shown in FIG. 32, the practice icon 1304 may display the word "Practice" along with a graphic representation of a putting green with a flagstick (not shown). The measure icon 1306 may display the word "Measure" along with a graphic representation of a measurement device, such as ruler (not shown). The "Compare" icon 1308 may display the word "Compare" along with a graphic symbol that may convey to an individual a compare function (not shown). The sub-menu icon 1310, for example, may display the word "More" indicating more menu options. Each of the main menu icons may be selected by an individual touching the display of the icon on the GUI 1114. However, an individual may select each icon by scrolling through the main menu 1302 with one or buttons, scroll wheels, joysticks and/or like user input devices on the portable electronic device 1000. Touching the display of an icon on the GUI 1114, i.e., selecting the icon, may change the color, contrast and/or brightness of the icon so as to visually show the individual that the icon has been selected. For example, touching an icon having a dark blue background color may change the color of the background to light blue so as to emulate a lighted switch or button that has been turned on.

Figure 33:
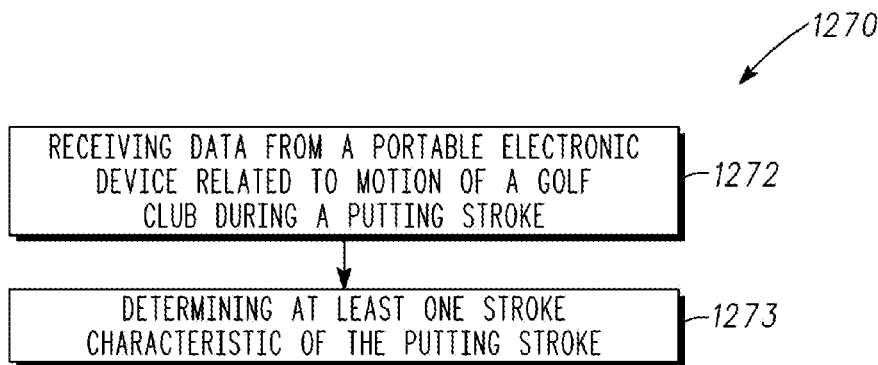
FIGS. 33-34 depict block diagram representations of processes associated with the systems, methods, and articles of manufacture according to the disclosure.
Figure 34:
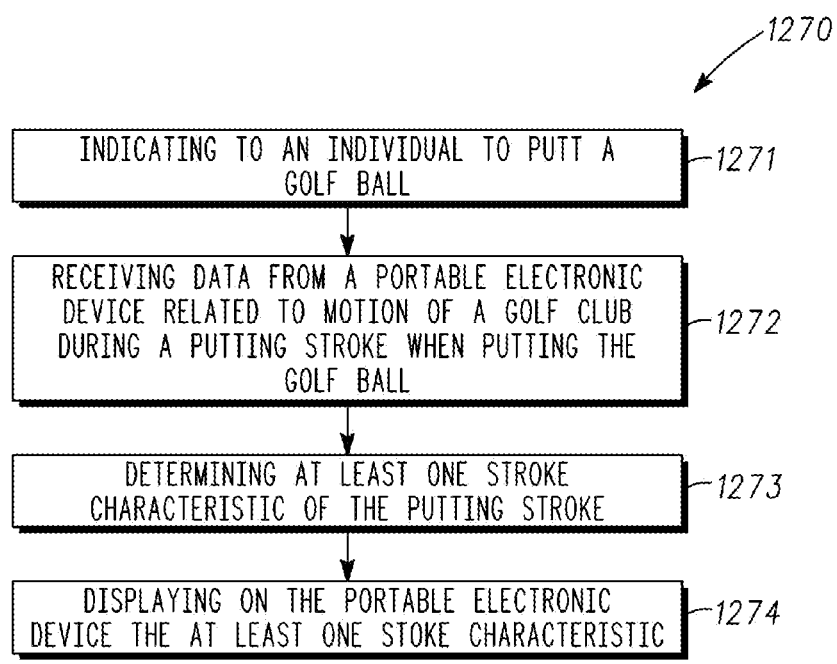

An individual may perform a practice session during which one or more of the individual's stroke characteristics may be determined. The process 1200 may determine one or more stroke characteristics of an individual associated with one putting stroke (FIG. 15, block 1202). Accordingly, an individual may choose to practice putting and receive data regarding his or her stroke characteristics for each putt as shown by the process 1270 of FIG. 33. The process 1270 includes receiving data from the portable electronic device 1000 related to the motion of a golf club during a putting stroke by an individual (block 1272), and determining at least one stroke characteristic of the putting stroke of the individual based on the received data (block 1273). Referring to FIG. 34, the process 1270 may further include indicating to an individual to perform a putting stroke (block 1271) so that sensors 1116 of the portable electronic device 1000 can provide data related to the motion of the individual's golf club during the putting stroke. The process 1270 may further include displaying on the GUI 1114 of the portable electronic device 1000 the at least one stroke characteristic (block 1274). The process 1270 and operation of the electronic device 1000 when performing the process 1270 is described in detail below.

Figure 35:
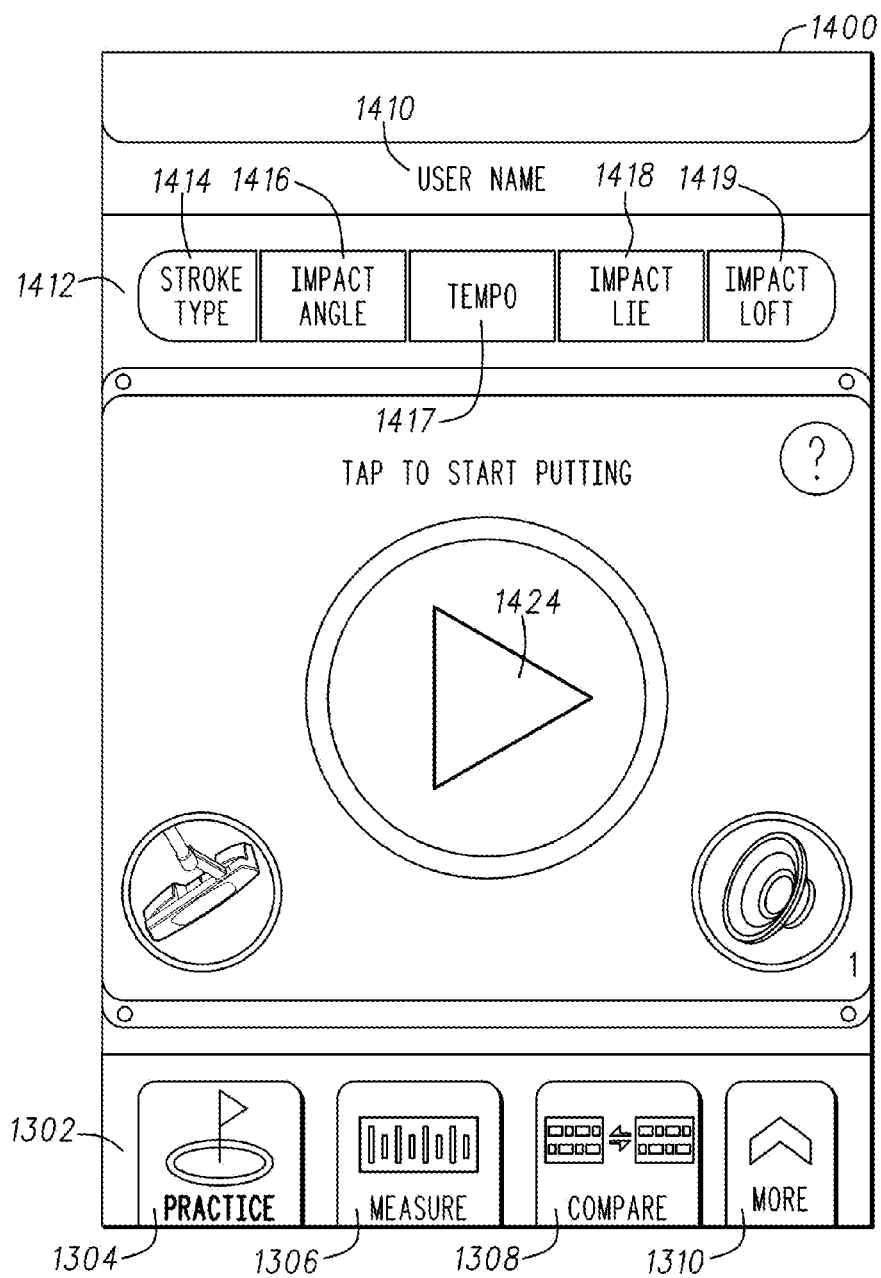
FIGS. 35-41 depict visual diagram representations of example displays according to the disclosure.

To perform the process 1270, an individual may select the practice icon 1304 by touching the practice icon 1304, which causes the GUI 1114 to display a practice display 1400 as shown in FIG. 35. The practice display 1400 includes the main menu 1302 and may further include a stroke characteristics menu 1412, by which an individual may select which of his or her stroke characteristics to be determined in a practice session. The stroke characteristic menu 1412 may be represented by a stroke type icon 1414, an impact angle icon 1416, a tempo icon 1417, an impact lie icon 1418 and/or an impact loft icon 1419. An individual can select one or more of the stroke characteristics icons by touching the icons on the GUI 1114. Touching each icon may change the display of the icon, such as changing the color, contrast and/or brightness of the icon to convey to the individual that the icon has been selected.

Figure 36:
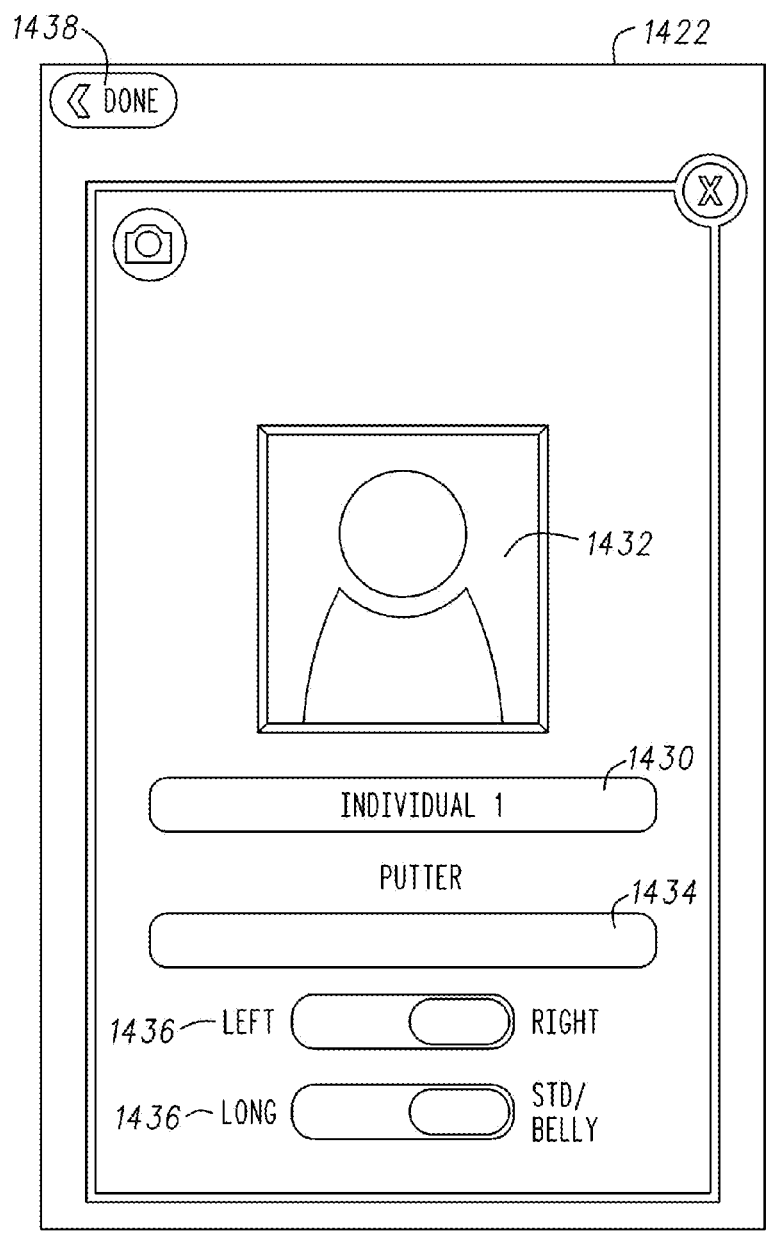

The practice display 1400 may also show an individual identification area 1420 in which the identification of an individual, such as his or her name or any other type of identification associated with an individual (e.g., nickname, user name for accessing a network, email address, etc.) is displayed. In the example of FIG. 35, the identification area 1420 appears above the stroke characteristics menu 1412 and is shown to have the generic identification "User Name." An individual can input his or her identification by touching the identification area 1420. Upon touching the identification area 1420, the individual is presented by the GUI 1114 with an identification input display 1422, an example of which his shown in FIG. 36. The individual may input his or her name in an identification window 1430, provide his or her photograph in a photograph area 1432, designate a putter for the practice session in a putter designation window 1434, and/or specify the type of putter being used by the putter selection sub-menus 1436. Upon providing information according to the identification input menu 1422, the individual can return to the practice display 1400 by pressing a return icon 1438, which may display an arrow indicating a reverse direction, i.e., going back, and/or text indicating that an individual is finished inputting information such as the word "Done" as shown in FIG. 36. An individual's identification information may be stored on the portable electronic device 1000 as the information is entered by the individual or when the return icon 1438 is selected by the individual.

Referring back to FIG. 35, upon providing information in the identification input menu 1422, the individual's identification appears in the identification area 1420 instead of the generic identification "User Name." An individual may select the stroke type icon 1414, the impact angle icon 1416, the tempo icon 1417, the impact lie icon 1418 and/or the impact loft icon 1419 to activate any one or all of these functions so as to receive information about his or her stroke type, impact angle, tempo, impact lie angle and/or impact loft angle, respectively. The practice display 1400 may include a play icon 1424, which an individual can touch to start a practice session.

Figure 37:
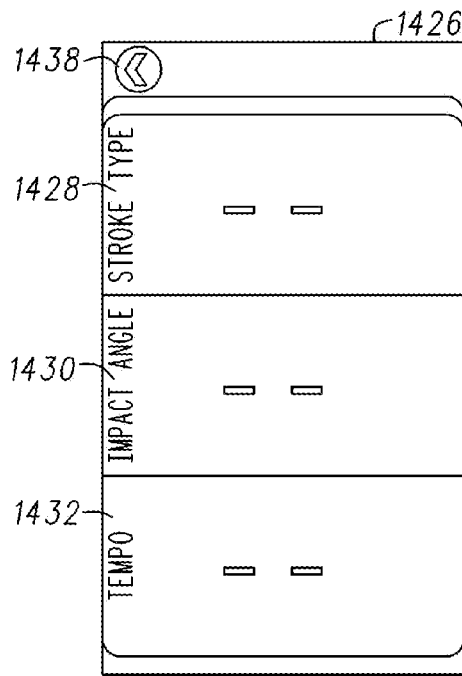
Figure 38:
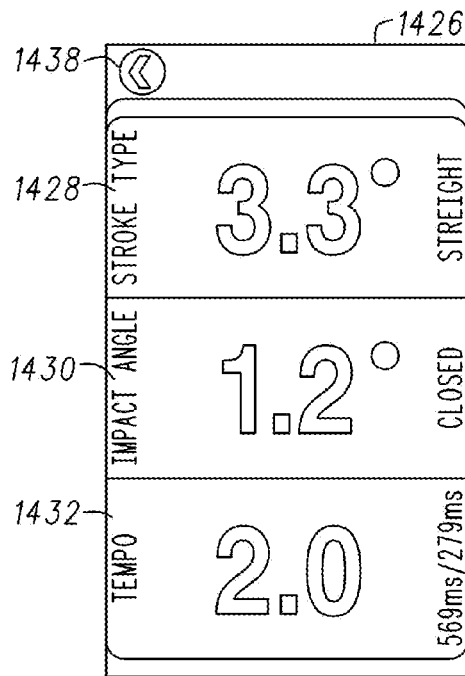
Figure 39:
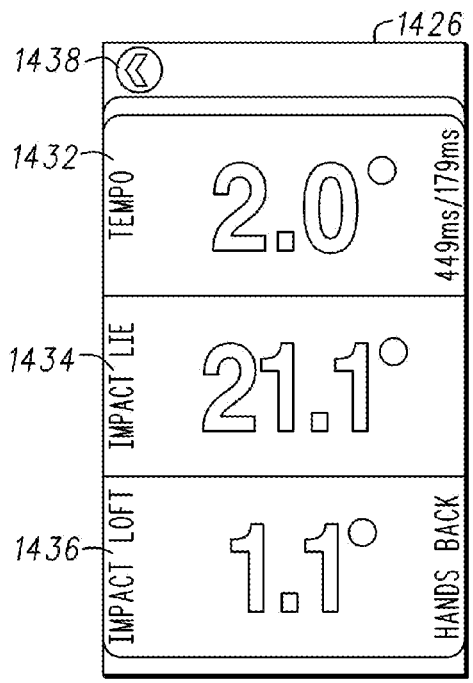

Before starting the practice session as described above, the individual can attach the portable electronic device 1000 to the shaft of the putter with the device holder 100. Upon starting a practice session, i.e., touching the play icon 1424, a practice result display 1426 may be displayed on the GUI 1114 as shown in FIG. 37. FIGS. 38 and 39 show results displayed on the practice results display 1426 after a putting stroke. FIG. 39 shows a continuation of the practice result display 1426, which may be viewed by scrolling down the practice result display 1426 of FIG. 38. The results display 1426 includes a stroke type window 1428, and impact angle window 1430, a tempo window 1432, an impact lie window 1434 and an impact loft window 1436.

The stroke type is shown in the stroke type window 1428 to be a straight stroke type with an angle of 3.3° (i.e., the angle of rotation of the head from the beginning of the downswing to impact, which is also referred to herein as the closing angle), the impact angle is shown in the impact angle window 1430 to be a closed impact angle of −1.2°, the tempo is shown in the tempo window 1432 to be 569 ms/279 ms or approximately 2.0, the impact lie is shown to be 21.1°, and the impact loft is shown to be 1.1°, representing a hands back position (see FIG. 25).

Figure 40:
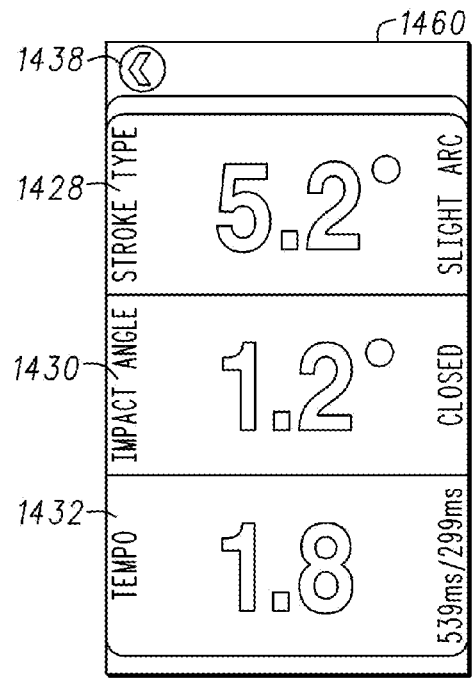
Figure 41:
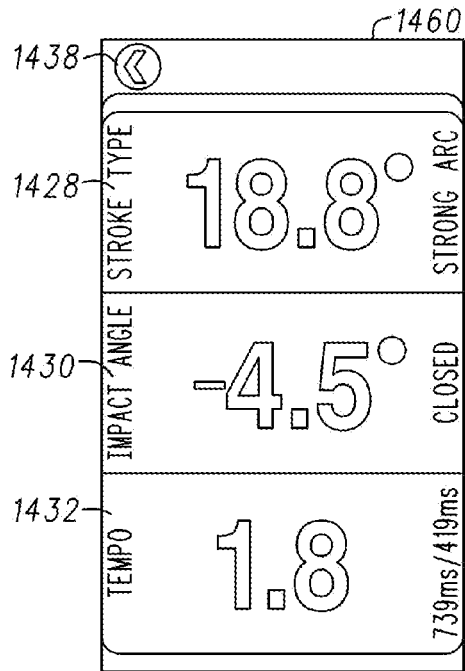

Referring to FIGS. 40 and 41, with each subsequent putting stroke, the practice results display 1426 is refreshed to show the results of the latest putting stroke (only stroke type, impact angle and tempo are shown in FIGS. 40 and 41). FIG. 40 shows the result of another putting stroke, where the stroke type is shown to be a slight arc stroke type with an angle of 5.2°, the impact angle is shown to be an open impact angle of 1.2°, and the tempo is shown to be 539 ms/299 ms or approximately 1.8. FIG. 41 shows the result of yet another putting stroke, where the stroke type is shown to be a strong arc with an angle of 18.8°, the impact angle is shown to be a closed impact angle of −4.5°, and the tempo is shown to be 739 ms/419 ms or approximately 1.8. An individual can continue putting and view the corresponding results on the practice results display 1426. The individual can end the putting practice session and return to the practice display by touching a return icon 1438.

Referring back to FIG. 14, some or all of the data and/or results from an individual's practice session may be transmitted to other portable electronic devices. Referring back to FIG. 15, some or all of an individual's putting practice data may be uploaded by the portable electronic device 1000 to a server 1152 and stored on the server 1152. Accordingly, an individual may be able to remotely access the data stored on the server 1152 at any time for further viewing and/or analysis with the portable electronic device 1000 or any other remote access device, such as a laptop 1160, a tablet computer 1162, a desktop computer 1158, a watch, and/or other computer devices that are capable of directly or indirectly communicating with the server 1152. Additionally, an individual may authorize the sharing of all or certain portions of his or her practice session data with other individuals for comparison purposes as described in detail below.

Figure 42:
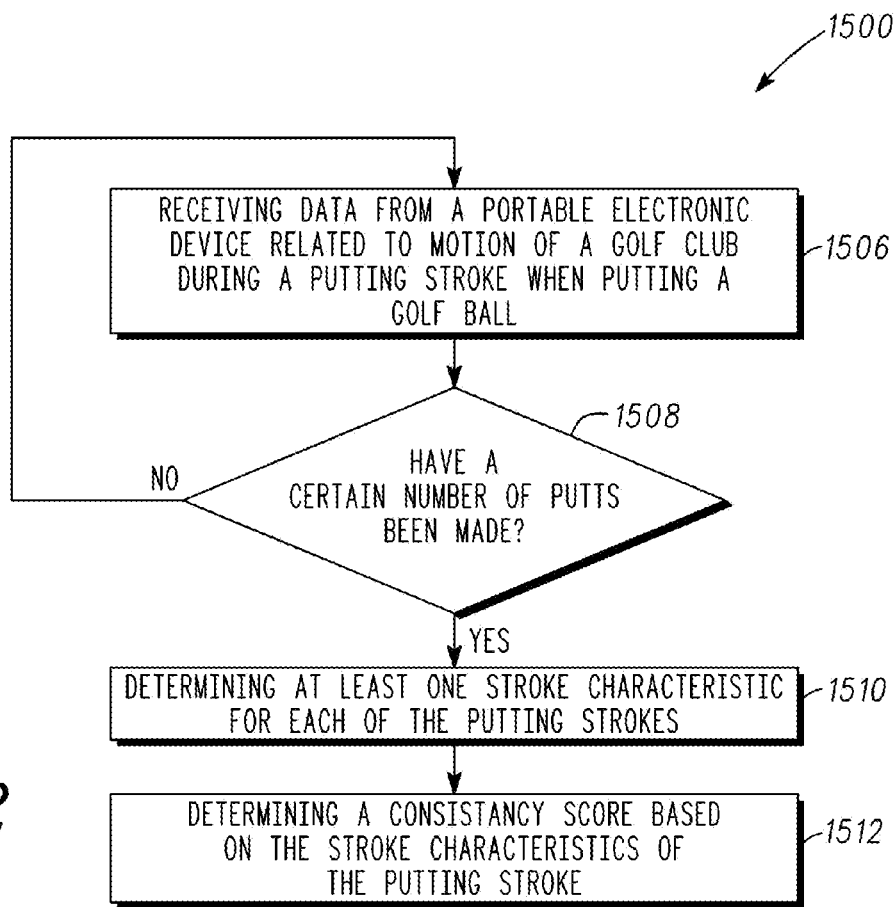
FIGS. 42-43 depict block diagram representations of processes associated with the systems, methods, and articles of manufacture according to the disclosure.
Figure 43:
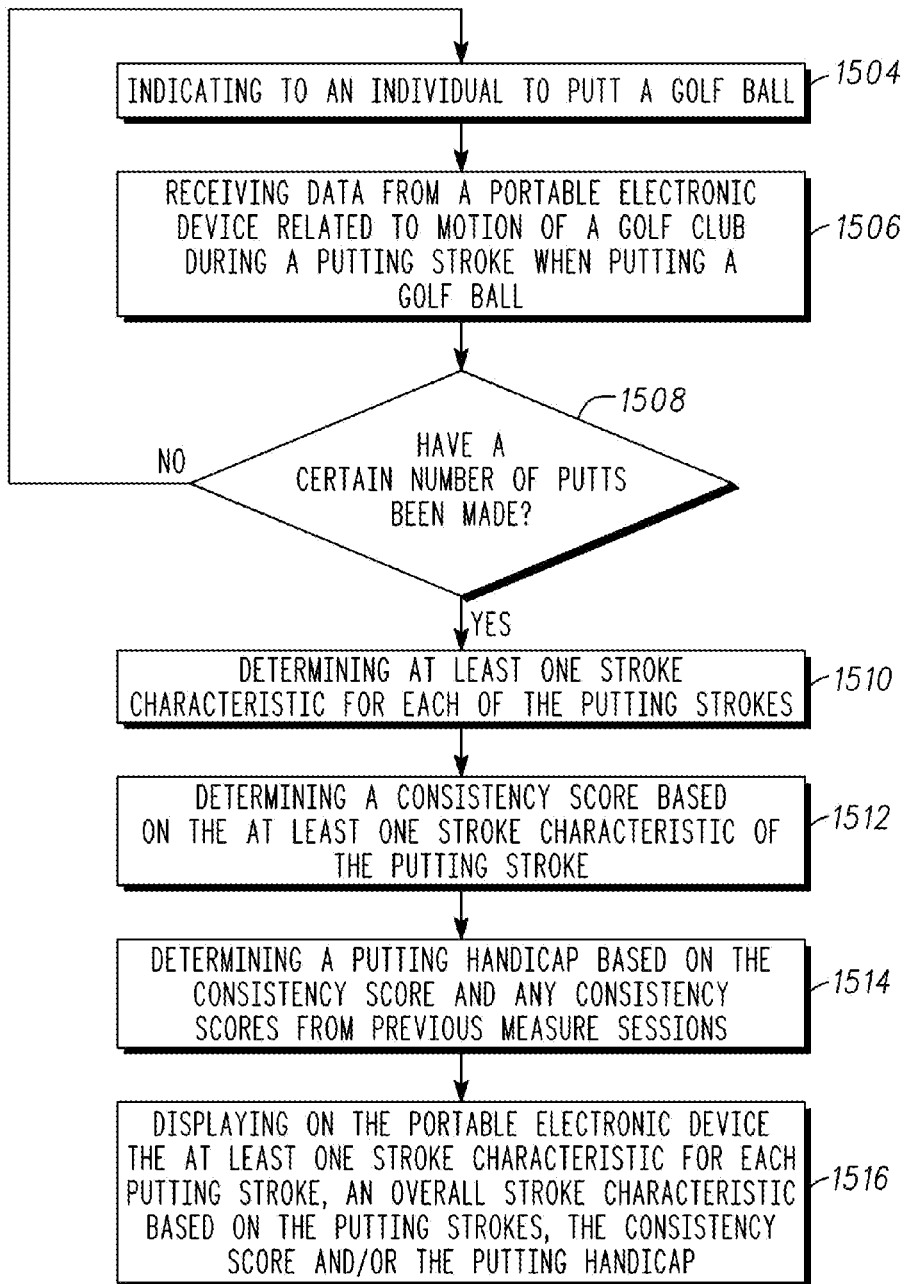

An individual may perform a measure session, during which a consistency score may be calculated for the individual and a putting handicap (PHcp) may be determined from at least one consistency score. A Consistency score for an individual may be calculated by measuring a consistency in the individual's stroke characteristics for a plurality of putting strokes. FIG. 42 shows a process 1500 for determining a consistency score for an individual. The process 1500 includes receiving data from the portable electronic device 1000 related to the motion of a golf club during a putting stroke by an individual (block 1506). At least two putting strokes are required to determine consistency in an individual's stroke characteristics by comparing the stroke characteristics of the two putting strokes. However, a larger number of putts may provide a more accurate consistency score for an individual. Accordingly, a consistency score may be determined from a certain number of putts, such as 3, 5, 7 or 10 putts. The process 1500 determines if a certain number of putting strokes have been made (block 1508). The certain number of putting strokes may be predetermined and/or specified by the individual. If the certain number of putting strokes has not been made, the individual can attempt another putting stroke. The portable electronic device 1000 can then receive data related to the motion of the golf club during the additional putting stroke (block 1506). If, however, the certain number of putting strokes has been made, the process 1500 determines at least one stroke characteristic of each of the putting strokes of the individual based on the received data for each putting stroke (block 1510). The process 1500 then determines a consistency score based on the putting stroke characteristics of the individual (block 1512). The consistency score may then be used to determine a putting handicap (PHcp) for the individual Referring to FIG. 43, the process 1500 may further include an individual starting a putting stroke measure session, after which the portable electronic device 1000 may indicate to the individual to perform a putting stroke (block 1504). When performing each putting stroke, the plurality of sensors 1112 of the portable electronic device 1000 may record and provide data related to the motion of the individual's golf club during his or her putting stroke (block (1506). As described above, if a certain number of putting strokes has not been made (block 1508), the portable electronic device may indicate to the individual to perform another putting stroke (block 1504). If, however, the certain number of putting strokes has been made (block 1508), the process 1500 determines at least one stroke characteristic for each of the putting strokes (block 1510). A consistency score may then be determined based on the at least one stroke characteristic of the putting strokes (block 1512). The consistency score may be used to determine a putting handicap (block 1514). The putting handicap for the individual may also include any putting handicap scores from previous measurement sessions (block 1514). The portable electronic device may then display the at least one stroke characteristic for each putting stroke, an overall stroke characteristic based on the putting strokes, the consistency score and/or the putting handicap on the GUI 1114 (block 1516). The process 1500 and operation of the electronic device 1000 when performing the process 1500 is described in detail below.

Figure 44:
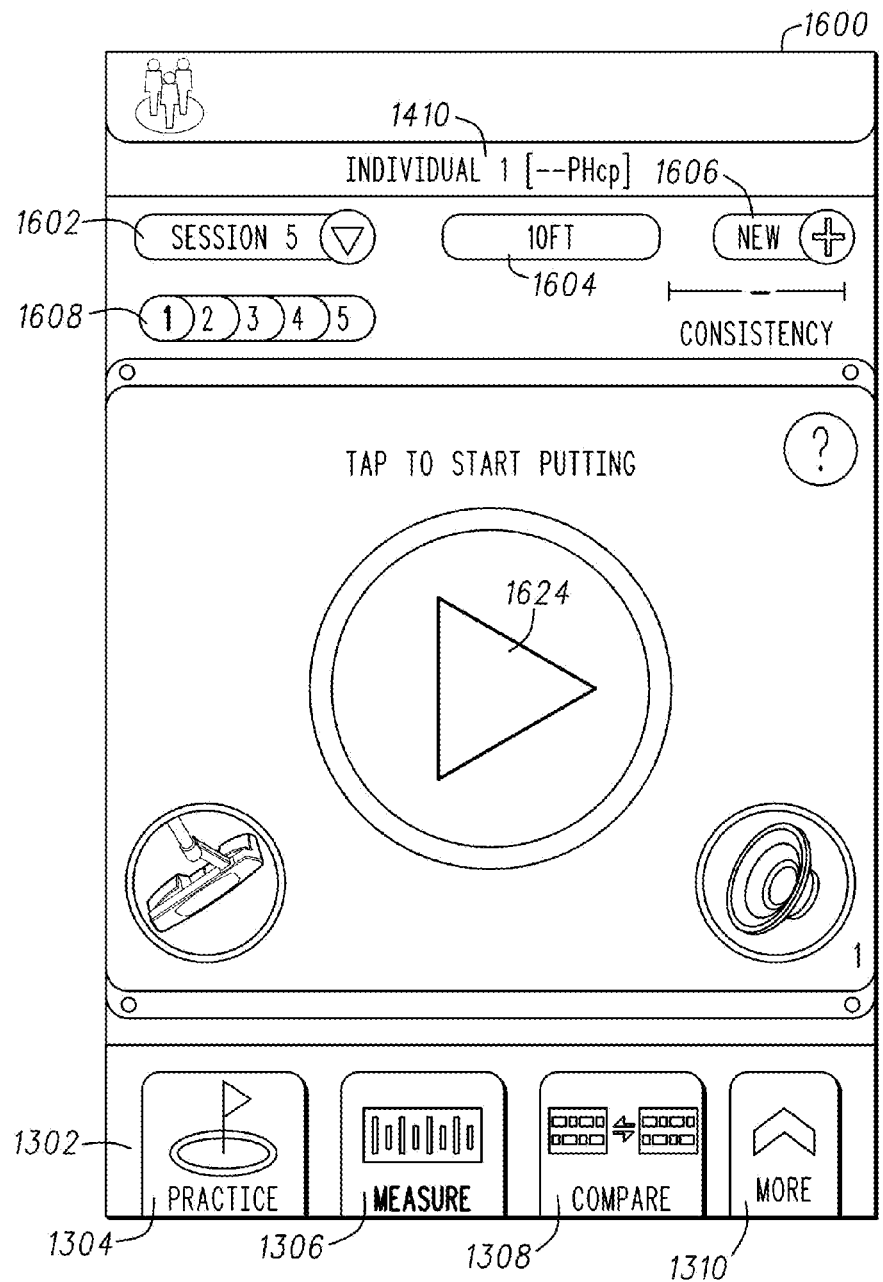
FIGS. 44-50 depict visual diagram representations of example displays according to the disclosure.

To determine consistency of an individual's stroke characteristics, i.e., calculate a consistency score, by which a putting handicap for the individual may be determined, the individual can touch or press the measure icon 1306 of the main menu 1302 to start a measure session. Referring to FIG. 44, when the measure icon 1306 is touched or pressed, a measure display 1600 is displayed on the GUI 1114. The measure display 1600 may include the main menu 1302, a session number indicator 1602, a putting distance indicator 1604, a session selection icon 1606, and/or a graphical representation of the number of putting strokes 1608 for consistency score calculation. The measure display 1600 may also include the user identification area 1420, in which a user's identification is displayed as described in detail above with respect to FIG. 36.

Figure 45:
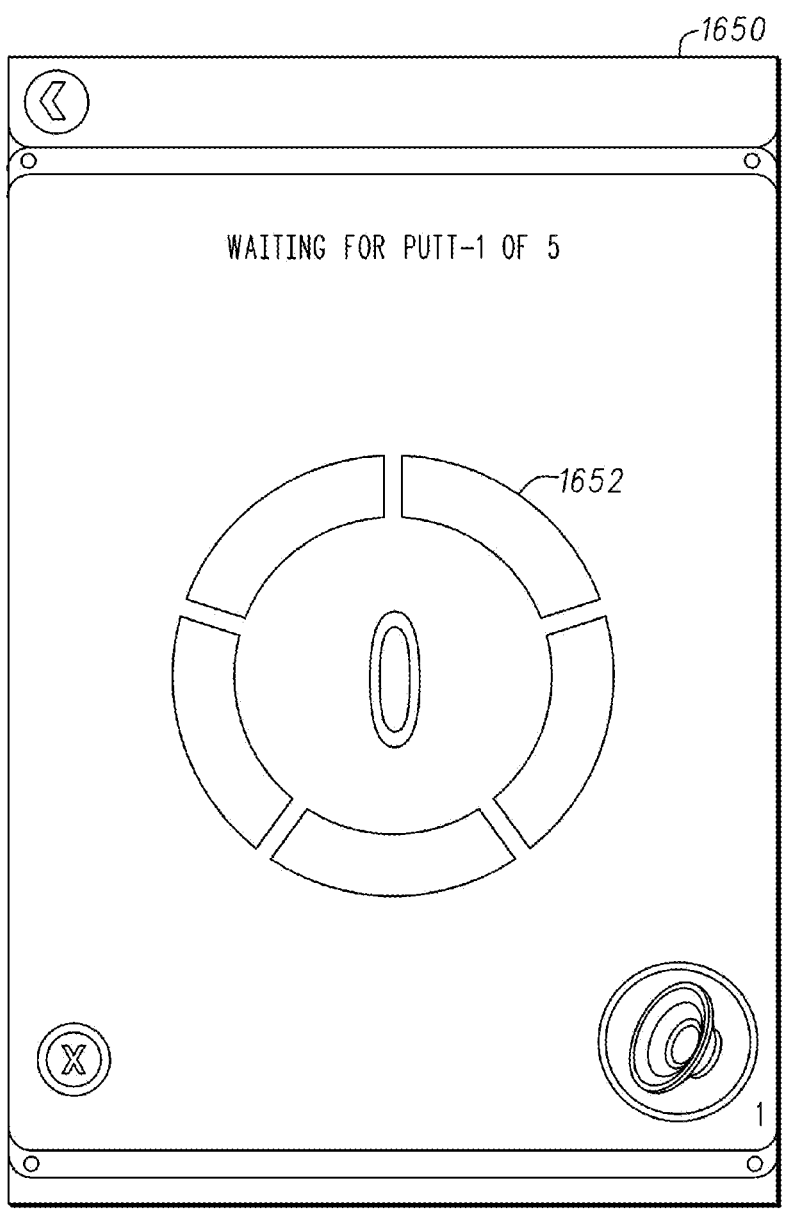
Figure 46:
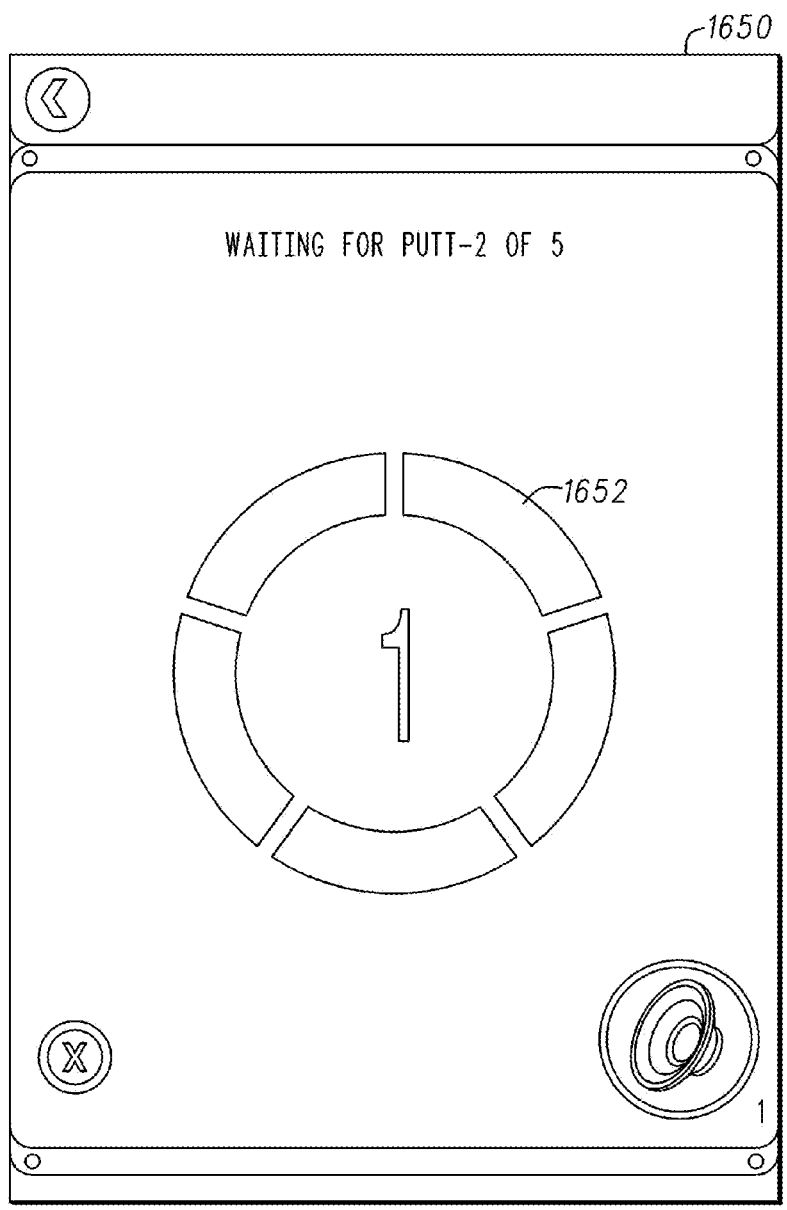

To start a measure session, an individual can attach the portable electronic device 1000 to his or her putter with the device holder 100. The individual may then touch a play icon 1624 on the GUI 1114 to activate or start the measure session. After the play icon 1624 is selected, the GUI 1114 displays the counter display 1650 as shown in the example of FIGS. 45 and 46. The counter display 1650 may show the number of putts completed and the number of putts remaining in numeric and/or graphical manner. In the example of FIGS. 45 and 46, a segmented annulus 1652 is shown. Each segment of the annulus 1652 may represent a putt. After each putt, a corresponding segment is highlighted (i.e., shown with different color, contrast, brightness, etc.) to show that the putt is completed. Furthermore, the number of the putts may be numerically shown inside the annulus 1652. The counter display 1650 may also display other information regarding the putting session. After the number of putts shown on the counter display 1650 have been completed, either the individual can touch the GUI 1114 to view a measure results display 1660 shown in FIG. 47 or the measure results display 1660 may be automatically shown.

Figure 47:
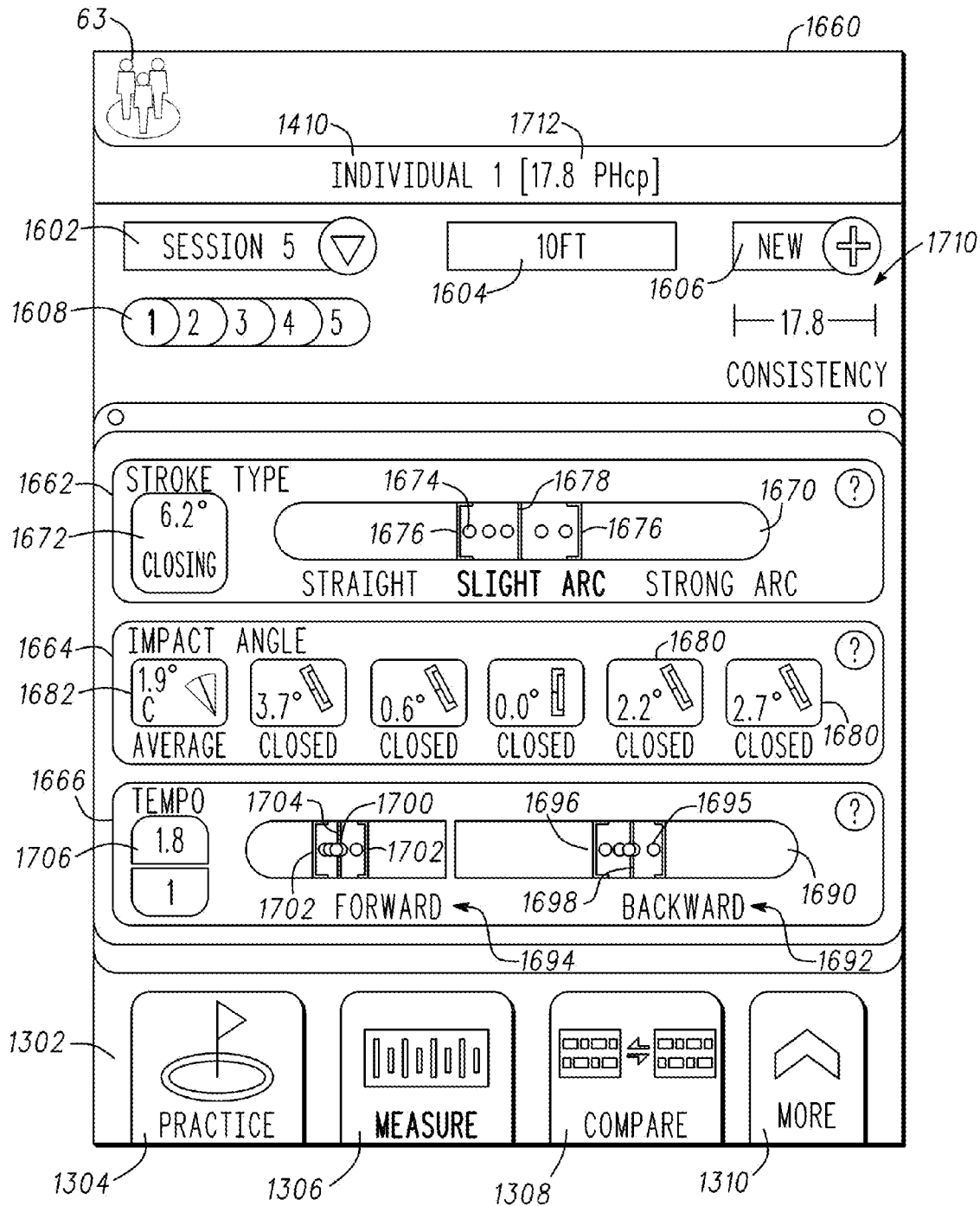
Figure 48:
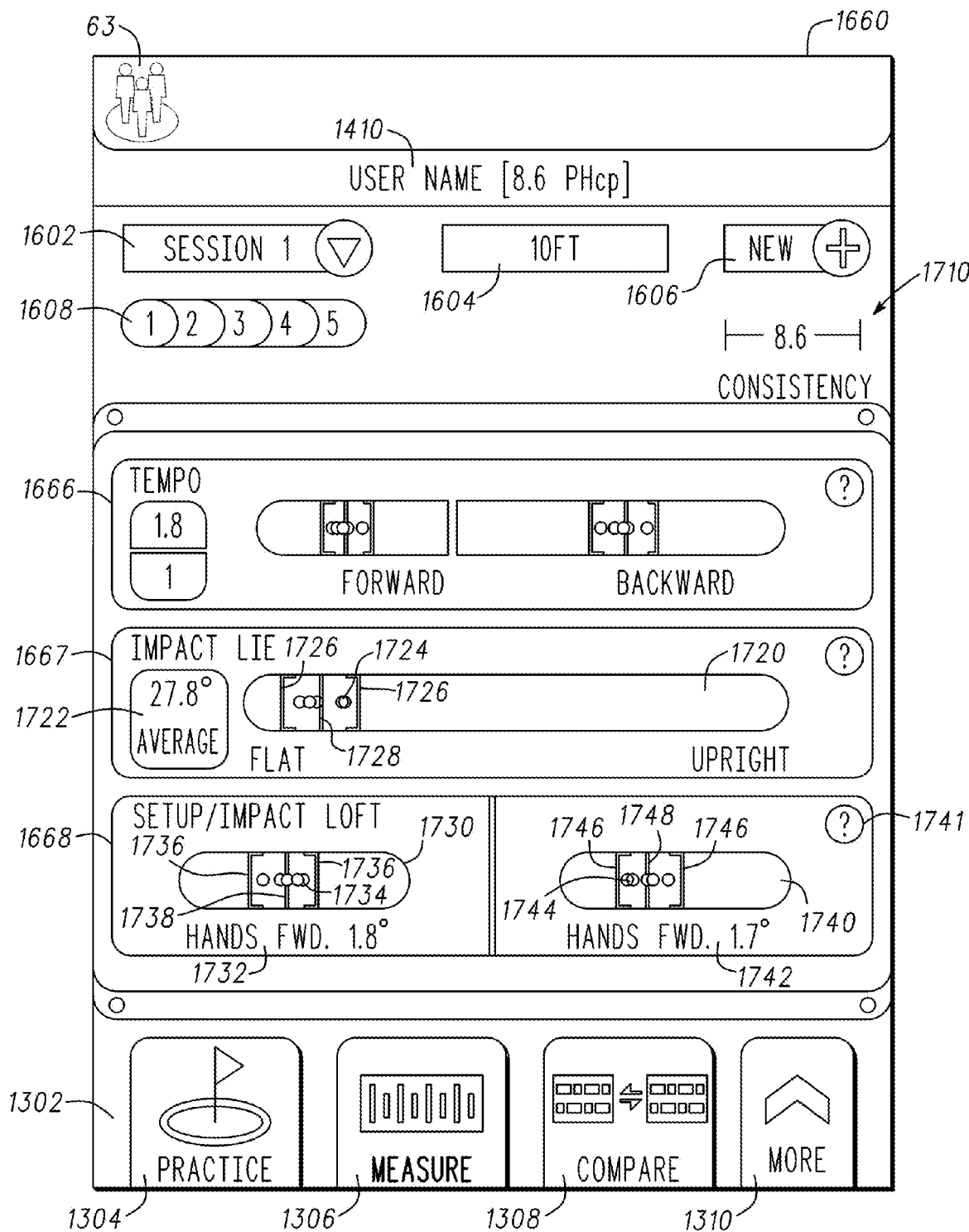

Referring to FIGS. 47 and 48, the measure results display 1660 may include the main menu 1302, a stroke type display 1662, an impact angle display 1664, a tempo display 1666, an impact lie display 1667 and a loft display 1668. FIG. 48 shows a continuation of the measure results display 1660, which may be viewed by scrolling down the measure results display 1660 of FIG. 47.

The stroke type display 1662 includes a stroke type scale 1670 that defines a straight stroke type at one end and a strong arc stroke type at the opposite end. The stroke type display 1662 may also include a closing angle display 1672, which shows an average of the closing angles for the number of putts attempted in each measure session, which in the example of FIG. 47 is five putts. Each of the putts in the measure session is visually represented on the stroke type scale 1670 with a symbol 1674, such as a circle 1674 as shown in FIG. 47. Because five putts are attempted in each measure session in the example of FIG. 47, the stroke type scale 1670 shows five circles 1674 representing the five putts. The position of each symbol 1674 on the stroke type scale 1670 represents the value of the closing angle of the corresponding putt. The stroke type scale 1670 may also include opposing range brackets 1676, which show the range of closing angles or stroke types for an individual based on the five putts. The stroke type scale 1670 may also include an average stroke type line 1678 that represents an average of the closing angles for the five putts. The numerical value of the location of the stroke type line 1678 on the stroke type scale 1670 may be the same as the closing angle shown in the closing display 1672.

The impact angle display 1664 includes a number of club face angle displays 1680 corresponding to the number of putts in the measure session. Each face angle display 1680 may display a numerical value of the face angle upon impact between the club face and a ball. Each face angle display 1680 may also include a graphic depiction of the face angle of a golf club. Each face angle display 1680 may also include a description identifying the impact angle (e.g., "closed" as shown in FIG. 47). An average angle based on the putt attempts may be computed and displayed in an average impact angle display 1682, which may show the numerical value of the average impact angle and a graphical representation of the average impact angle. In the example of FIG. 47, the average impact angle is show to be 1.9°, which is the average of the impact angles shown in the face angle displays 1680.

The tempo display 1666 may include a tempo scale 1690 having a backward swing section 1692 representing a backswing segment of a putting stroke and a downswing section 1694 representing the downswing segment of a putting stroke. The tempo scale 1690 may be a time scale. In the backward swing section 1692, the tempo display 1666 displays a symbol 1695, such as circle 1695 as shown in FIG. 47, to represent the backswing time for each putt. The tempo scale 1690 may also display backswing brackets 1696, which define a range of backswing times for the five putts. An average backswing time may be represented by an average backswing timeline 1698 located between the backswing brackets 1696. In the downswing section 1694, the tempo display 1666 displays a symbol 1700, such as circle 1700 as shown in FIG. 47, to represent the downswing time for each putt. The tempo scale 1690 may also display downswing brackets 1702, which define a range of downswing times for the five putts. An average downswing time may be represented by an average downswing timeline 1704 located between the downswing brackets 1702. The tempo display 1666 may further include a tempo value display 1706, which displays a numerical value generally defining a ratio of the average backswing time to the average downswing time. In the example of FIG. 47, the tempo is shown to be 1.8.

Referring to FIG. 48, the impact lie display 1667 includes an impact lie scale 1720 that defines a flat impact lie angle at one end and an upright impact lie angle at the opposite end. A flat impact lie angle and an upright impact lie angle may be relative terms that define the degree of flatness or uprightness of a club head relative to a reference angle. For example, the reference angle may be 20° so that impact lie angles decreasing from 20° may be considered flatter impact lie angles and impact lie angles increasing from 20° may be considered more upright loft angles. The impact lie display 1667 may also include an impact lie angle display 1722, which shows an average of the impact lie angles for the number of putts attempted in each measure session, which in the example of FIG. 48 is five putts. Each of the putts in the measure session is visually represented on the impact lie scale 1720 with a symbol 1724, such as a circle 1724 as shown in FIG. 48. Because five putts are attempted in each measure session in the example of FIG. 48, the impact lie display shows five circles 1724 representing the five putts. The position of each symbol 1724 on the impact lie scale 1720 represents the value of the closing angle of the corresponding putt. The impact lie scale 1720 may also include opposing range brackets 1726, which show the range of impact lie angles for an individual based on the five putts. The impact lie scale 1720 may also include an average impact lie line 1728 that represents an average of the impact lie angles for the five putts. The numerical value of the location of the impact lie line 1728 along the impact lie scale 1720 may be the same as the average impact lie angle shown in the impact lie angle display 1722.

The loft display 1668 may include a setup loft angle scale 1730 and an impact loft angle scale 1740. The setup loft angle scale 1730 represents a range of loft angles of a club shaft at an address or a setup position. The impact loft angle scale 1740 represents a range of loft angles of the club shaft at the impact position, i.e., when the club face impacts a golf ball.

The setup loft angle scale 1730 includes a relative setup loft angle line 1731, which defines if a setup loft angle represents a hands forward position or a hands back position. The setup loft angle scale 1730 may also include a setup loft angle display 1732, which shows an average of the setup loft angles for the number of putts attempted in each measure session, which in the example of FIG. 48 is five putts. Each of the putts in the measure session is visually represented on the setup loft angle scale 1730 with a symbol 1734, such as a circle 1734 as shown in FIG. 48. Because five putts are attempted in each measure session in the example of FIG. 48, the setup loft angle scale 1730 shows five circles 1734 representing the five putts. The position of each symbol 1734 on the setup loft angle scale 1730 represents the value of the setup loft angle of the corresponding putt. The setup loft angle scale 1730 may also include opposing range brackets 1736, which show the range of setup loft angles for an individual based on the five putts. The setup loft angle scale 1730 may also include an average setup loft angle line 1738 that represents an average of the setup loft angles for the five putts. The numerical value of the location of the setup loft angle line 1738 along the setup loft angle scale 1730 may be the same as the average setup loft angle shown in FIG. 48 below the setup loft angle scale 1730.

The impact loft angle scale 1740 includes a relative impact loft angle line 1741, which defines if an impact loft angle represents a hands forward position or a hands back position. The impact loft angle scale 1740 may also include an impact loft angle display 1742, which shows an average of the impact loft angles for the number of putts attempted in each measure session, which in the example of FIG. 48 is five putts. Each of the putts in the measure session is visually represented on the impact loft angle scale 1740 with a symbol 1744, such as a circle 1744 as shown in FIG. 48. Because five putts are attempted in each measure session in the example of FIG. 48, the impact loft angle scale 1740 shows five circles 1744 representing the five putts. The position of each symbol 1744 on the impact loft angle scale 1740 represents the value of the impact loft angle of the corresponding putt. The impact loft angle scale 1740 may also include opposing range brackets 1746, which show the range of impact loft angles for an individual based on the five putts. The impact loft angle scale 1740 may also include an average impact loft angle line 1748 that represents an average of the impact loft angles for the five putts. The numerical value of the location of the impact loft angle line 1748 along the impact loft angle scale 1740 may be the same as the average impact loft angle shown in FIG. 48 below the impact loft angle scale 1740.

The measure results display 1660 may display a numerical consistency score in a consistency score display area 1710. The consistency score may represent an individual's consistency based on the number of putts performed in a measure session. A consistency score for each stroke characteristic may be computed after an individual performs a plurality of putting strokes. For each one of closing angle, impact angle, tempo, impact lie angle and loft angle, a consistency score S may be computed by the following equation:

$$S = f(x) \quad (1)$$

Where x may be the value of a corresponding stroke characteristic (e.g., a closing angle of 3.3°), and f(x) may be a function that defines variation in the corresponding stroke characteristic for a plurality of swings or putts. For example, f(x) may be based on the standard deviation of the measured values of a stroke characteristic after a plurality of swings or putt attempts. An overall consistency score for a plurality of swings or putts may be an average of the closing angle, impact angle, tempo, impact lie angle and loft angle consistency scores. An overall consistency score may be displayed in the consistency score display area 1710 after an individual performs a measure session. In the example of FIG. 41, the consistency score is shown to be 17.8.

A handicap score (PHcp) may be computed by computing an average of a plurality of overall consistency scores. However, the computation of PHcp may depend on the number of past consistency scores for an individual. In one example, if only three or fewer consistency scores are available for an individual, PHcp is computed by taking an average of the available consistency scores. In another example, if four or greater and ten or less consistency scores are available for an individual, the highest consistency score and the lowest consistency score may be discarded. PHcp is then computed by taking an average of the remaining eight consistency scores. In yet another example, if greater than ten consistency scores are available, the most recent ten consistency scores may be considered. Then, the highest and lowest consistency scores may be discarded. PHcp is then computed by taking an average of the remaining eight consistency scores. Achieving better consistency scores in multiple measure sessions (i.e., multiple sessions with each session having several putts) reduces an individual's PHcp while poor consistency scores in multiple measure sessions increase an individual's PHcp. The measure results display 1660 may also include a handicap display area 1712 for displaying the PHcp for an individual. In the example of FIG. 41, PHcp for Individual 1 is shown to be 9.6.

The above consistency score and PHcp calculations represent an example of determining consistency score and PHcp calculations. Therefore, the systems, methods, and articles of manufacture described herein are not limited in this regard. Accordingly, any type of computation by which an individual's stroke characteristics for one putting stroke are compared to the same stroke characteristics for another putting stroke to determine a consistency in the individual stroke characteristics may be used for determining a consistency score and a PHcp.

In addition to the graphical and alphanumeric information provided on the measure results display 1660 as discussed above, one or more color, contrast and/or brightness schemes, which may be referred to herein as display schemes, may be used to graphically convey to an individual information about his or her performance. At least one of the stroke type display 1662, the impact angle display 1664, the tempo display 1666, the impact lie display 1667 and the loft display 1668 may reflect the consistency performance of the individual. For example, when an individual's stroke type measurements are highly inconsistent, the color red may at least partly be used as a color scheme of the stroke type display 1662. In another example, when an individual's stroke type measurements are highly consistent, the color green may at least partly be used as a color scheme of the stroke type display 1662. In yet another example, when an individual's stroke type measurements are neither highly inconsistent nor highly inconsistent, the color yellow may at least partly be used in the color scheme of the stroke type display 1362. The display schemes of the impact angle display 1364 and the tempo display 1366 may be similarly affected based on an individual's consistency in impact angle and tempo during the putting measure session, respectively. A display scheme as disclosed may refer to a background color, a foreground color, an outline color of an icon or a displayed object, a text color, a line colors, a symbol color, and/or a color of any displayed object. For example, if an individual's stroke type measurements are highly inconsistent, the circles 1674 displayed in the stroke type scale 1670 may be displayed with the color red. In another example, if an individual's stroke type measurements are highly inconsistent, the outlines or borders of all objects displayed in the stroke type display 1662, such as the outline or border of the stroke type scale 1670 may be displayed with the color red.

The processes described above (e.g. 1200, 1270, and 1500) may be performed similarly in embodiments where the portable electronic device 1000 is a watch or fitness tracker. In embodiments where the portable electronic device 1000 is a watch or fitness tracker, the portable electronic device 1000 may be configured to attach to the forearm or wrist of a golfer instead of the golf club shaft 800. In these embodiments, the portable electronic device 1000 may be configured to attach to the leading arm or trailing arm of a golfer during a swing based on a default setting of the portable electronic device 1000, or based on a selection or input by the golfer. In these configurations, the portable electronic device 1000 may be used to determine at least one stroke characteristic, a consistency score, and/or a handicap score of a golfer. For example, the sensors (e.g. accelerometers, gyros, magnetometer) in commercially available watches or fitness trackers may be used to measure backswing time, downswing time, tempo (the ratio of backswing time to downswing time), and other characteristics of a golf swing. FIG. 124 illustrates an exemplary display of the swing characteristics determined by the portable electronic device 1000 in these embodiments. In the example of FIG. 124, the portable electronic device displays graphics representing the backswing time, downswing time, and tempo of the swing.

Referring back to FIG. 14, some or all of the data collected for an individual during a measure session by the portable electronic device 1000 may be transmitted to other portable electronic devices. Referring back to FIG. 15, some or all of the data for an individual may be uploaded by the portable electronic device 1000 to a server 1152 and stored on the server 1152. Accordingly, an individual can remotely access the data stored on the server 1152 at any time for further viewing and/or analysis with the portable electronic device 1000 or any other remote access device, such as a laptop 1160, a tablet computer 1162, a desktop computer 1158, a watch, and/or other devices that are capable of directly or indirectly communicating with the server 1152. Additionally, an individual may be able to authorize the sharing of all or certain portions of his or her data with other individuals for comparison and/or competition purposes as described in detail below.

The stroke characteristics of an individual may be displayed on the GUI 1114 of the portable electronic device as disclosed. However, a portable electronic device 1000 may display all data regarding an individual's golf swing in a tabular format either in partially processed or raw form. For example, the GUI 1114 may display in a list or a table the following: backswing time, downswing time, backswing angle, putter speed at impact, clubface angle at impact, lie angle, swing plane information, and/or any other information that may be explicitly or impliedly provided from the data.

Based on the data collected by the portable electronic device 1000 during an individual's golf swing, the software may include instructions executed by the processor of the portable electronic device to visually show an individual a simulation of his or her golf swing based on the collected data. Accordingly, an individual can view the simulation of his or her golf swing and use the simulation to improve his or her golf swing.

Figure 49:
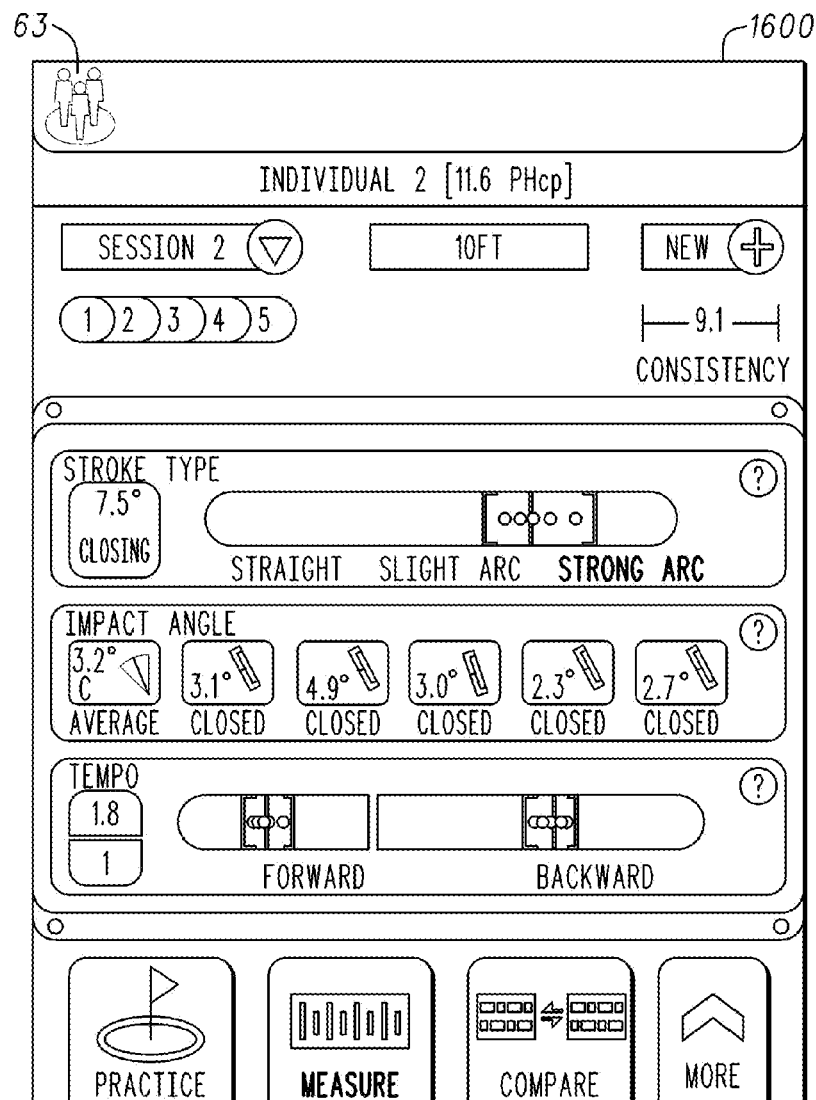
Figure 50:
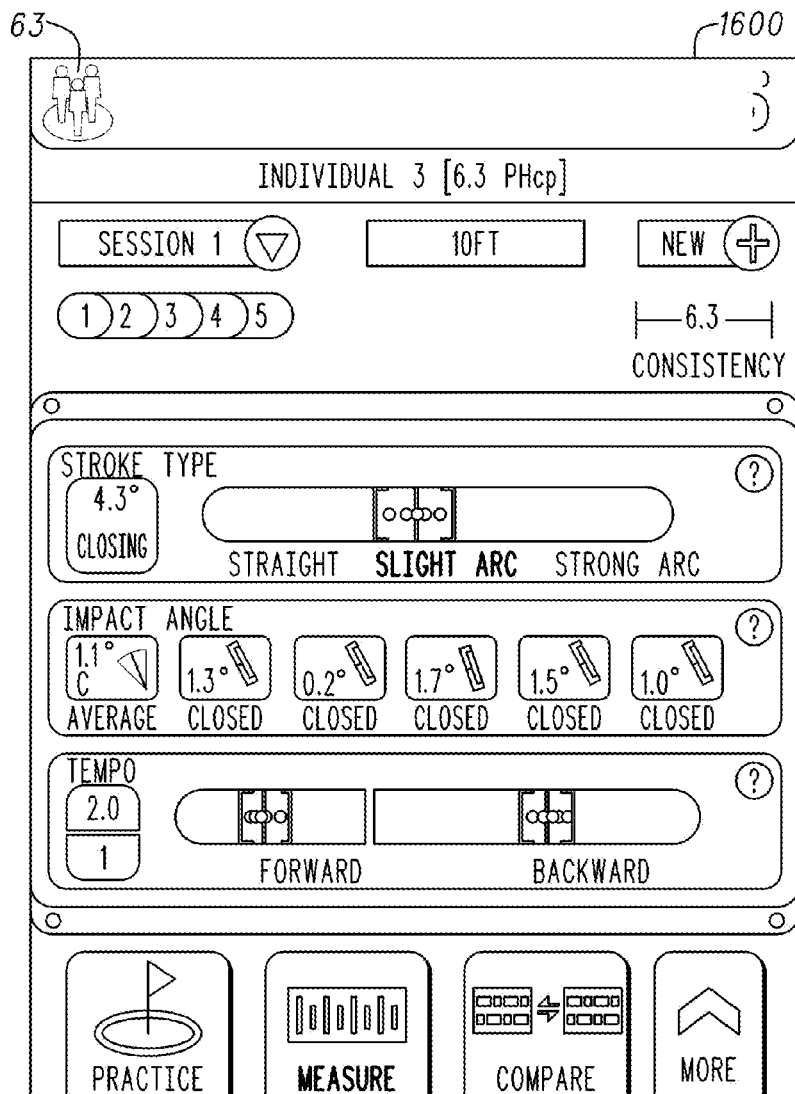
Figure 51:
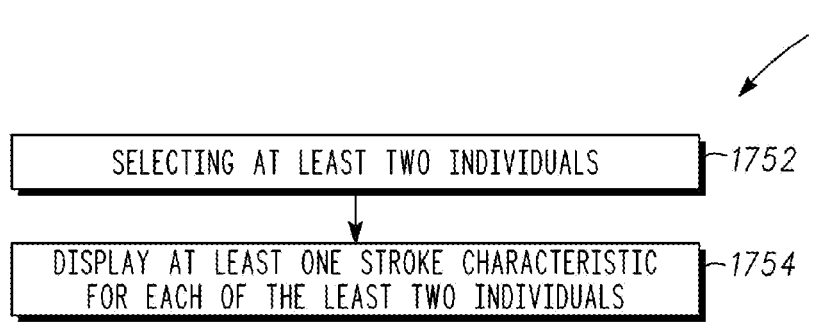
FIG. 51 depicts a block diagram representation of a process associated with the systems, methods, and articles of manufacture according to the disclosure.

FIGS. 47 and 48 show measure session results for a certain individual, which is identified as Individual 1. FIGS. 49 and 50 show measure session results for two other individuals, which are identified as Individual 2 and Individual 3, respectively. As described above, measure session data for each individual may be transmitted to and stored on a server 1152. FIG. 51 shows a process 1750 for comparing stroke characteristics of two or more individuals. At least two individuals may be selected so that their stroke characteristics results can be compared (block 1752). Subsequently, the selected individuals' stroke characteristics results may be displayed on the portable electronic device 1000 (block 1754).

Figure 52:
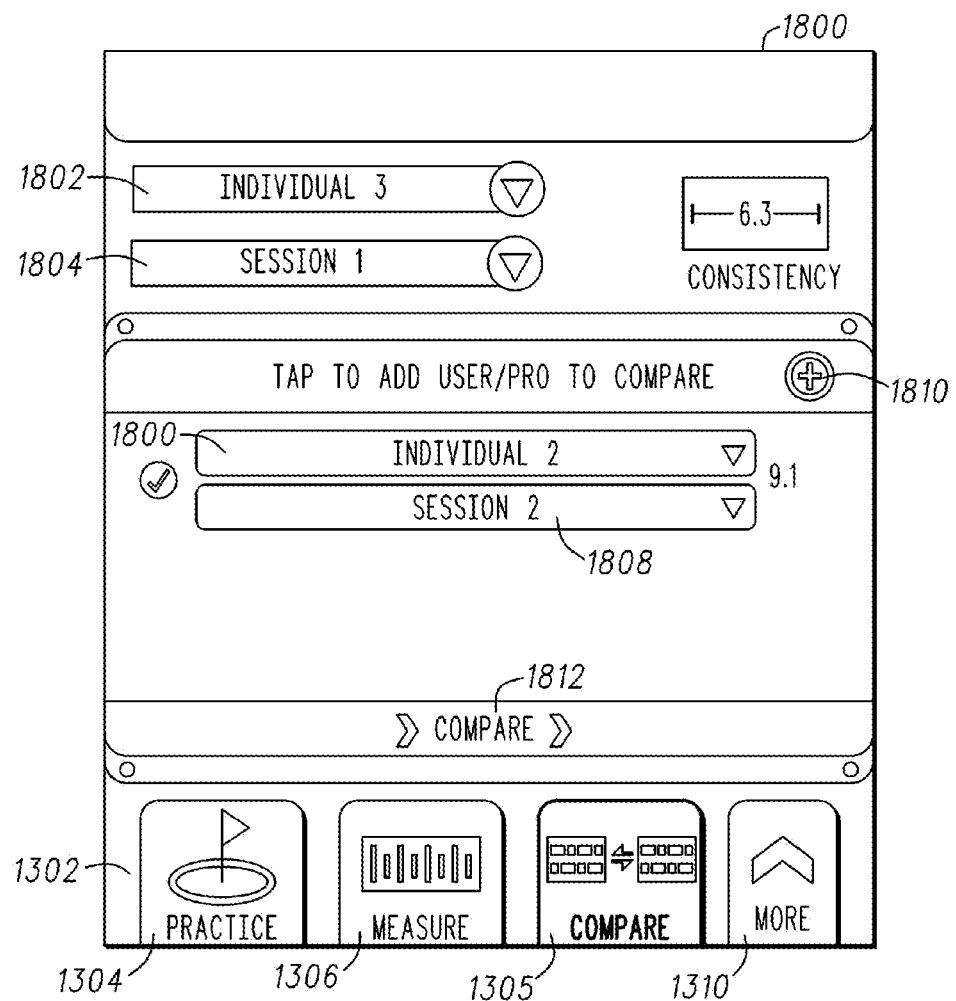
FIGS. 52-58 depict visual diagram representations of example displays according to the disclosure.

FIG. 52 shows an exemplary compare display 1800, which is displayed on the GUI 1114 when an individual touches or presses the compare icon 1308 of the main menu 1302. The compare display 1800 includes a primary individual selection menu 1802 and a measure session selection menu 1804 associated with the individual selected from the primary individual selection menu 1802. An individual can select his or her identity from the primary individual selection menu 1802 and also select one of his or her measure sessions from the measure session selection menu 1804 to compare to another individual. When an individual selects one of his or her measure sessions from the measure session selection menu 1804, his or her consistency score and/or PHcp from the selected measure session may be displayed on the compare display 1800. For example, FIG. 52 shows a consistency score of 6.3 for Session 1 of Individual 3.

The compare display 1800 may also include one or more secondary individual selection menu 1806 and corresponding measure session selection menu 1808. In FIG. 52, only one secondary individual selection menu 1806 and the corresponding measure session selection menu 1808 are shown. The compare display 1800 may include an individual addition icon 1810, by which more individuals can be added. From the secondary individual selection menu 1806, an individual can select another individual for a measure session comparison. The individual to be selected for comparison may be another individual with whom the selecting individual is familiar (e.g., friend or family), a celebrity, a professional athlete, or a professional golfer, or any other individual who may have his or her results stored on a network server to which the individual has access. Upon selecting an individual, the selected individual's consistency score and/or PHcp may be displayed on the compare display 1800. For example, FIG. 52 shows a consistency score of 9.1 for Session 2 of Individual 2. To compare measure session results, an individual can select, e.g., touch or press the compare area 1812 on the GUI 1114 to compare his or her putting session results with the one or more other selected individuals.

Referring to FIGS. 53-56, the selected individuals' stroke characteristics may be compared. In the examples of FIGS. 53-56, only closing angle/stroke type, impact angle and tempo comparisons between the selected individuals are shown. However, the portable electronic device 1000 may also display the impact lie angle and loft angle comparisons between the selected individuals according to the impact lie angle display 1667 and loft angle display 1668 as described above. The systems, methods, and articles of manufacture described herein are not limited in this regard.

Figure 53:
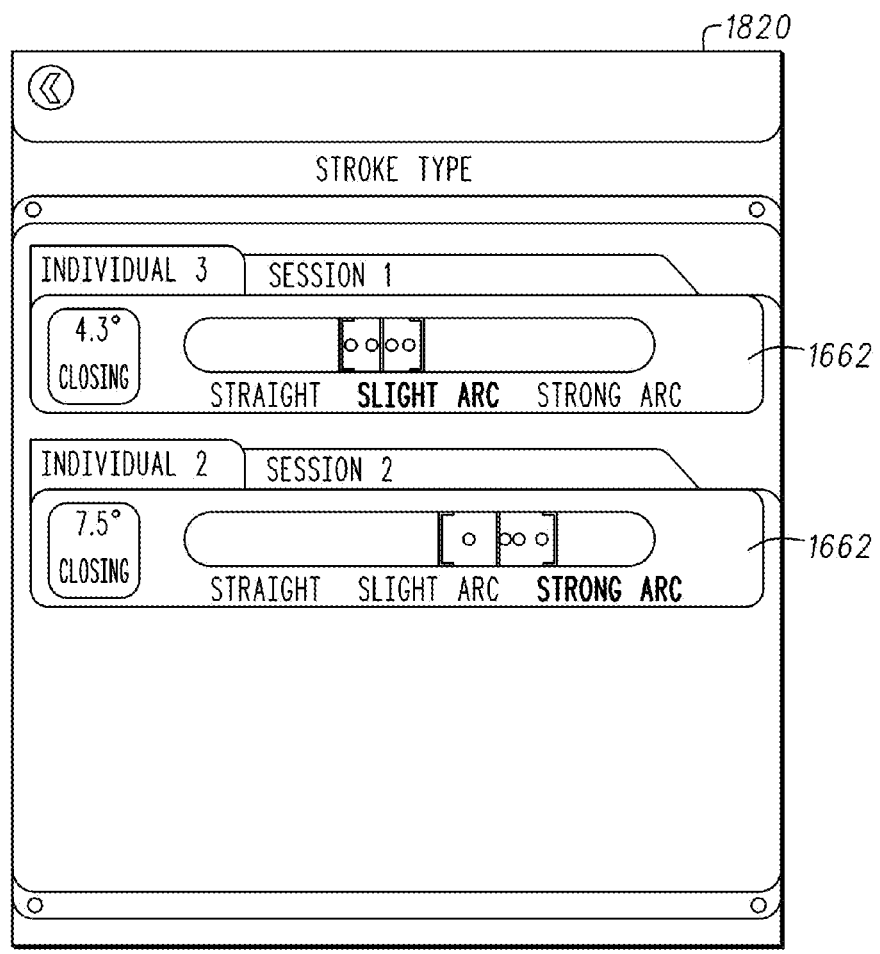

Referring to FIG. 53, after the individual selects the compare area 1812, the GUI 1114 may display a comparison between the stroke type of the primary individual and the secondary individual in a stroke type compare display 1820. Comparing the stroke types of the primary individual and the secondary individual may entail displaying the stroke type result from a selected session for the primary individual adjacent to the stroke type result from a selected session for the secondary individual. As shown in the example of FIG. 53, a stroke type display 1662 as described in detail above and with respect to FIG. 47 may be displayed for each individual.

Figure 54:
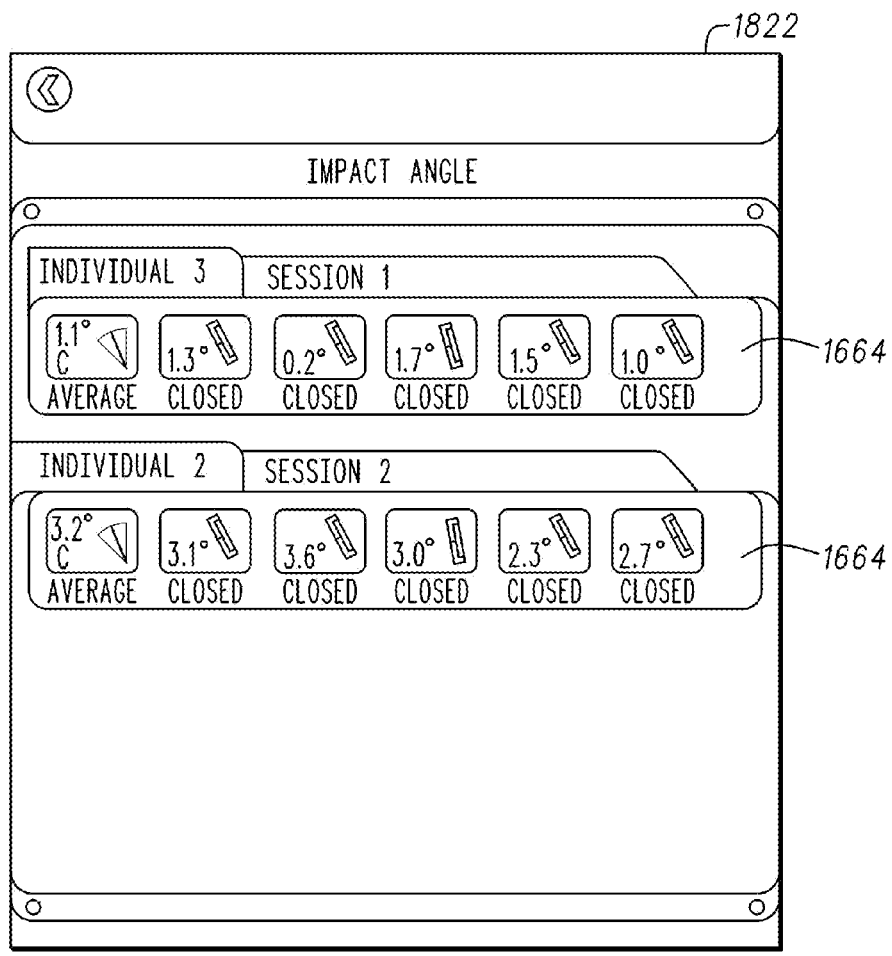

Referring to FIG. 54, the GUI 1114 may also display a comparison between the stroke impact angles of the primary individual and the secondary individual in an impact angle compare display 1822. Comparing the stroke impact angles of the primary individual and the secondary individual may entail displaying the impact angle results from the selected session for the primary individual adjacent to the stroke type result from the selected session for the secondary individual. As shown in the example of FIG. 46, an impact angle display 1664 as described in detail above and with respect to FIG. 47 may be displayed for each individual. An individual can scroll between the displays of FIGS. 53 and 54 by swiping the surface of the GUI 1114, touching one or more areas on the GUI 1114, and/or pressing one or more buttons on the portable electronic device 1000.

Figure 55:
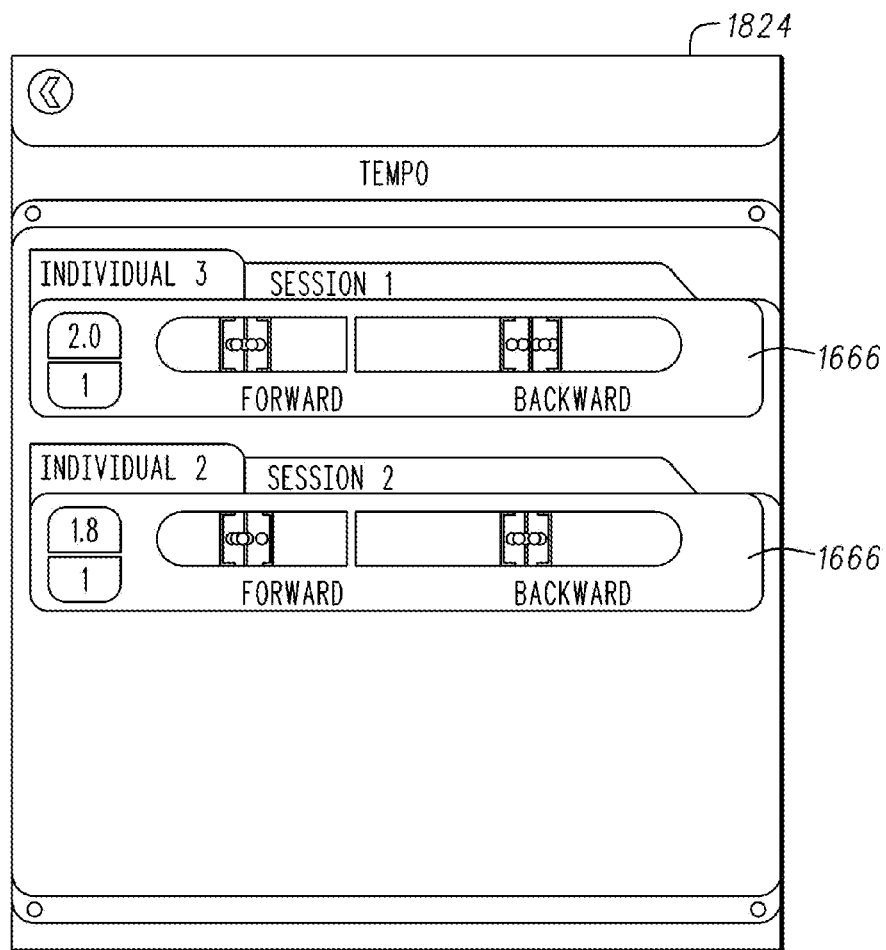

Referring to FIG. 55, the GUI 1114 may also display a comparison between the tempo of the primary individual and the secondary individual in a tempo compare display 1824. Comparing the tempo of the primary individual and the secondary individual may entail displaying the tempo from the selected session for the primary individual adjacent to the tempo result from the selected session for the secondary individual. As shown in the example of FIG. 55, a tempo display 1666 as described in detail above and with respect to FIG. 41 may be displayed for each individual. An individual can scroll between the displays of FIGS. 53-55 by swiping the surface of the GUI 1114, touching one or more areas on the GUI 1114, and/or pressing one or more buttons on the portable electronic device 1000.

Figure 56:
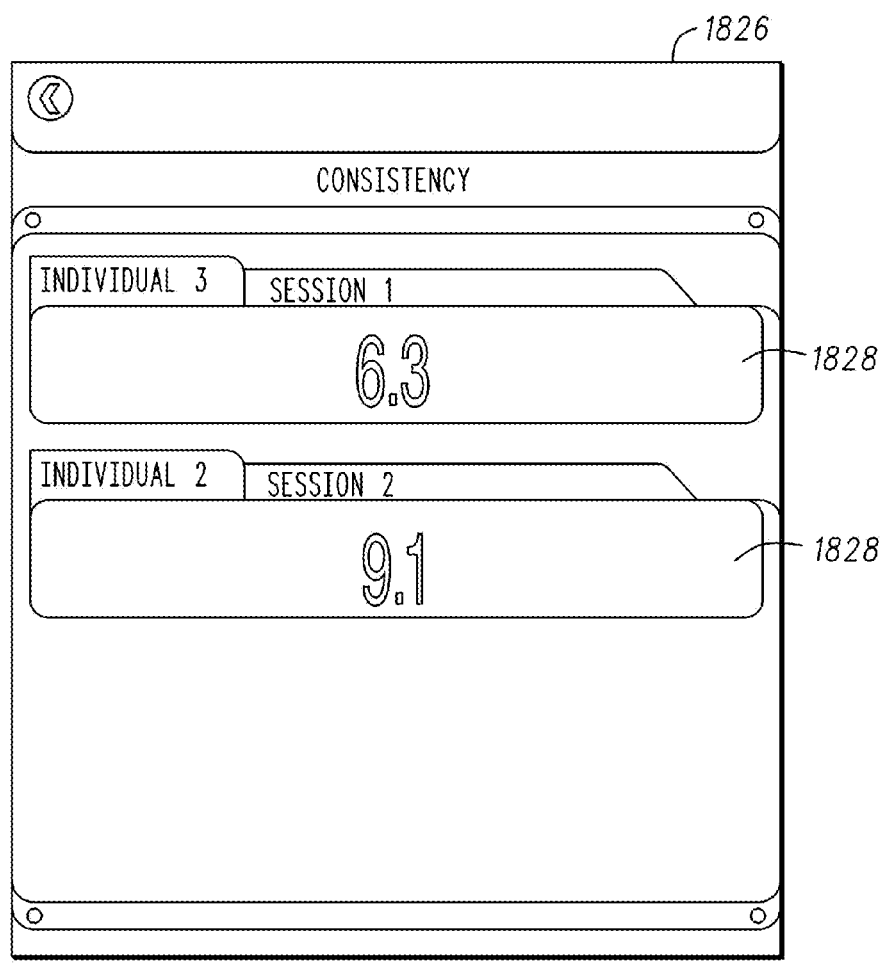

Referring to FIG. 56, the GUI 1114 may also display a comparison between the consistency of the primary individual and the secondary individual in consistency display 1826. Comparing the consistency of the primary individual and the secondary individual may entail displaying consistency score from the selected session for the primary individual in a session consistency display 1828 for the primary individual adjacent to the consistency score from the selected session for the secondary individual in a session consistency display 1828 for the secondary individual. An individual can scroll between the displays of FIGS. 53-56 by swiping the surface of the GUI 1114, touching one or more areas on the GUI 1114, and/or pressing one or more buttons on the portable electronic device 1000.

Although not shown, the GUI may also display and compare the putting handicap PHcp of the primary individual with the putting handicap of the secondary individual (e.g., friends, professional golfers, etc.). For example, the software may include a putting handicap compare display that may show the putting handicaps of two or more individuals in a side-by-side manner. The systems, methods, and articles of manufacture described herein are not limited in this regard.

Figure 57:
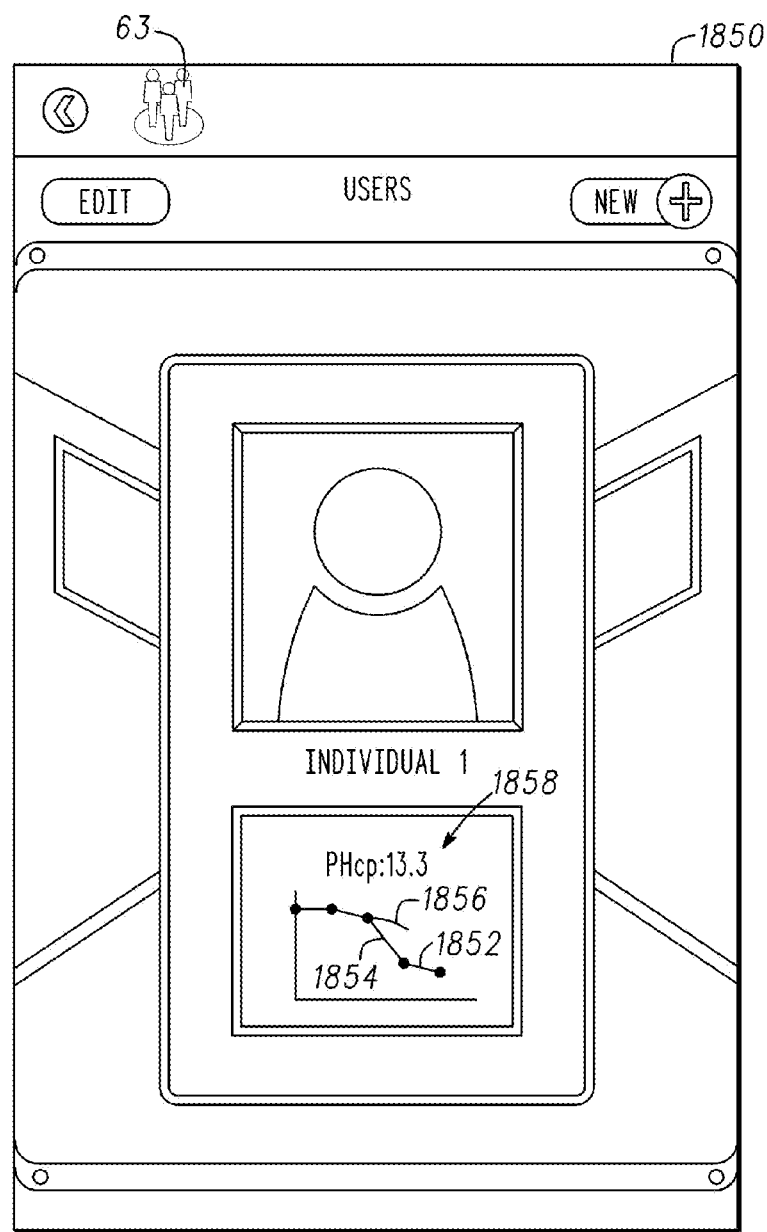

An individual may be able to view his or her profile, photo, stroke characteristics, PHcp and/or consistency scores by touching or pressing the identification area 1420, which may be displayed in the practice display 1400, measure display 1600, measure results display 1660 and the compare display 1800. Subsequently, a user profile display 1850 is displayed on the GUI 1114 as shown in FIG. 57. The user profile display 1850 may include consistency scores 1852 of the individual plotted against corresponding measure sessions that are completed by the individual. The plotted consistency scores 1852 may be connected with a consistency trend line 1854. As shown in FIG. 57, the consistency trend line 1854 visually conveys to the individual his or her consistency trend, i.e., improvement and/or setback.

As described in detail above, a PHcp may be calculated for an individual based on his or her consistency score for each measure session. Accordingly, the PHcp value may be affected, i.e., increases or decreases, based on each consistency score. As shown in FIG. 57, the user profile display 1850 may also include the PHcp of an individual plotted as a PHcp trend line 1856 against corresponding measure sessions that are completed by the individual. The PHcp trend line 1856 visually conveys to the individual his or her PHcp trend. The user profile display 1850 may also include a current PHcp 1858 for the individual. In the example of FIG. 57, the current PHcp 1858 for Individual 1 is shown to be 13.3. Thus, an individual may get a snapshot view of his or her current and historical putting performance with the user profile display 1850.

Figure 58:
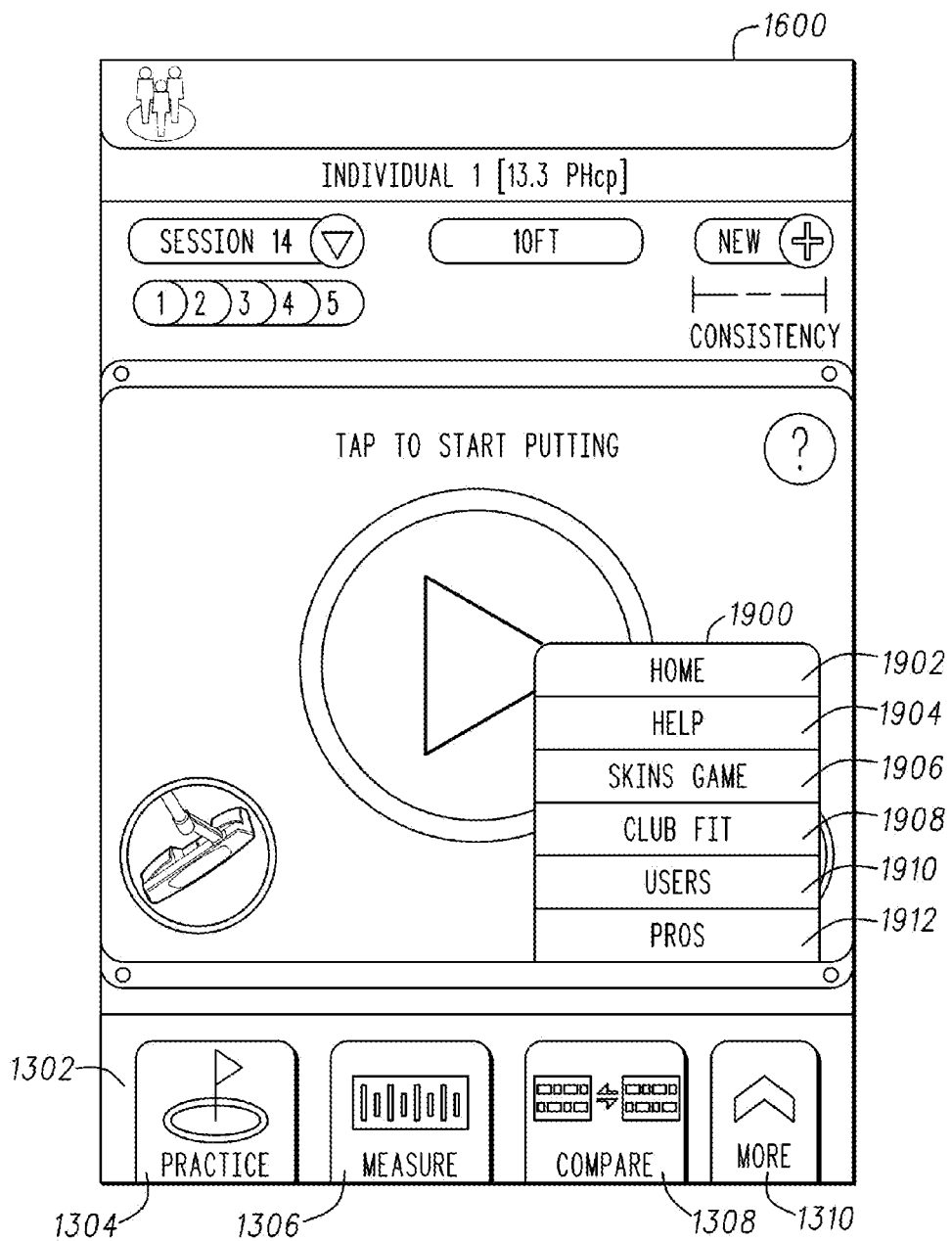

FIG. 58 shows the measure display 1600 and the sub-menu icon 1310 having been activated by an individual to display a sub-menu 1900. The sub-menu 1900 may include selectable options such as a Home option 1902, a Help option 1904, a Skins Game option 1906, a Club Fit option 1908, a Users option 1910 and/or a Pros option 1912. Selecting the home options 1902 may return the display on the GUI 1114 to the main display 1300. Selecting the Help option 1904 may provide an individual with help information regarding using the different menus, options, and/or procedures discussed herein. The Skins Game option 1906 may operate the portable electronic device 1000 according to the process described in detail below by which an individual can compete with one or more locally or remotely located individuals. The Club Fit option 1908, which is described in detail below, provides an individual with guidance regarding selecting a proper golf club for the individual base upon his or her stroke characteristics. The Users option 1910 returns the display on the GUI 1114 to the user profile display 1850, which is described in detail above. The Pros option 1912 displays profiles of golf professionals and their corresponding consistency scores and/or PHcp that may have been stored on the server 1512 by the golf professionals and made available to users of the software for comparison purposes.

According to the foregoing, stroke characteristics of an individual may be measured and displayed to the individual by using a portable electronic device 1000 attached to a golf club with a device holder 100. As described in detail below, the disclosure may also provide an individual result-oriented information, which may refer to speed and/or trajectory of a golf ball from the moment of being struck by a golf club until the ball comes to a stop at a final location, and whether or not a putt was successfully made (i.e., ball falling in a golf cup).

Figure 59:
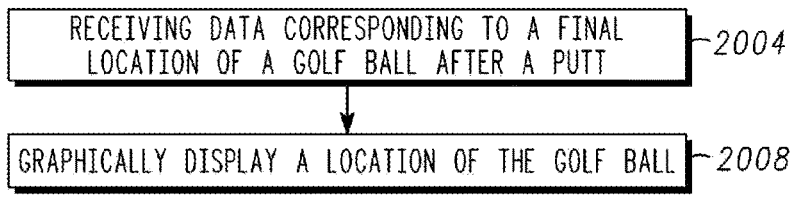
FIGS. 59-60 depict block diagram representations of processes associated with the systems, methods, and articles of manufacture according to the disclosure.
Figure 60:
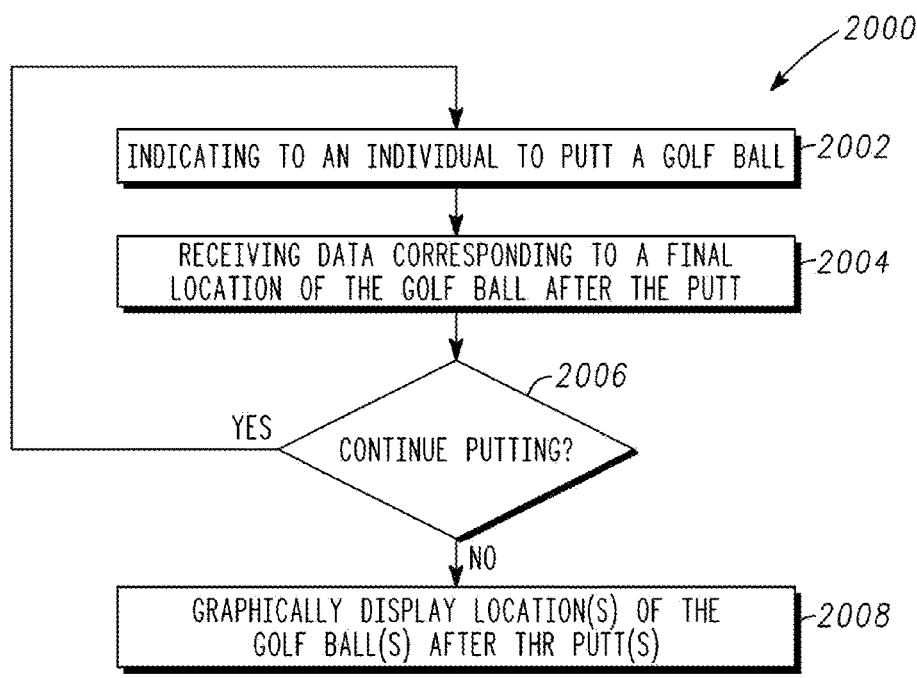

FIGS. 59 and 60 show an exemplary process 2000, by which an individual may determine the results of multiple putts to ascertain various result-oriented information, such as the individual's miss tendencies. An individual may start the process 2000 by touching an icon (not shown) on the GUI 1114 corresponding to the process 2000. Alternatively, the individual may start the process 2000 by pressing one or more buttons (not shown) on the portable electronic device and/or with voice commands. The icon for starting the process 2000 may be provided in the main menu 1302. Alternatively, the process 2000 may be started by using a corresponding option in the sub-menu 1900. Starting the process 2000 may entail the processing device 1110 retrieving at least a part of a program code and any data associated with the retrieved part of the program code from the storage device 1116 and executing the program code to operate the portable electronic device 1000 to perform the process 2000 as described in detail below.

Referring to FIG. 60, the process 2000 includes receiving data corresponding to a final location of a golf ball after a putt (block 2004), and graphically displaying the location of the golf club (block 2008). Referring to FIG. 60, the process 2000 may further include indicating to an individual to putt a golf ball (block 2002). The portable electronic device then receives data corresponding to a final location of the golf ball after the putt (block 2004). The individual may wish to continue putting (block 2006). Accordingly, the individual is again signaled or indicated to putt another golf ball or the same golf ball (block 2002). However, the individual may wish to stop putting and view the results of his or her putts (block 2006), i.e., final locations of the balls. The locations of the golf balls after the putts are then graphically displayed (block 2008). The operation of the electronic device 1000 when performing the process 2000 is described below.

As described above, an individual may select an icon (not shown) on the GUI 1114 to start the process 2000. For example, the main menu 1302 or the sub-menu 1900 may include an icon or option, respectively (not shown), by which an individual can start the process 2000. The icon or sub-menu option may include text or graphics. Alternatively, the process 2000 may be performed contemporaneously with the processes 1270 of FIGS. 33 and 34 and/or the process 1500 of FIGS. 42 and 43. Accordingly, the process 2000 may be performed during a practice session and/or a measure session. Thus, selecting the practice icon 1304 or the measure icon 1306 may also start the process 2000.

Figure 61:
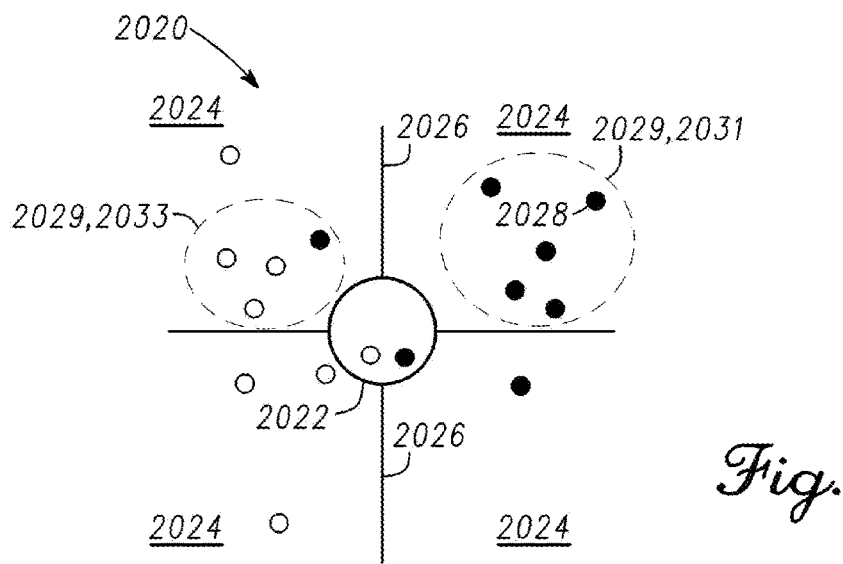
FIG. 61 depicts a visual diagram representation of an example display according to the disclosure.

The individual may attach the portable electronic device 1000 to his or her putter with the device holder 100. The individual can then putt one or more golf balls in a putting area at a certain distance from a golf cup. The distance may be generally a consistent distance so as to allow an individual to determine his or her miss tendencies from a particular distance. For example, the individual may choose to practice putting from 10 feet from the hole. However, the putting distance may be varied. Referring to FIG. 61, the GUI 1114 may present the individual with a schematic display of the putting area 2020 including the target golf cup 2022. The schematic display of the putting area 2020 may be shown to be divided into sections 2024 to allow an individual to more accurately specify a location of a ball as described herein. In the example of FIG. 61, the sections 2024 are quadrants defined by perpendicular lines 2026.

An individual may manually record the result of a putt on the schematic display of the putting area 2020 by touching an area on the GUI 1114 that generally corresponds with the actual position of the ball in the putting area relative to the golf cup. The portable electronic device 1000 may include a zoom function on the GUI 1114 that allows the individual to zoom in on a certain part of the schematic display of the putting area 2020 for a more accurate placement of a representation of the ball. Upon specifying the location of a ball, the ball may be displayed on the GUI 1114 with a symbol 2028. In FIG. 61, the direction of putting is shown with the arrow 2027.

The shape, size and/or color of a symbol 2028 may convey certain information about the position of the ball in the putting area such as the golf club used by an individual to putt the ball, the distance from the golf cup from which the putt is attempted, an individual's stroke characteristics, an individual's setup position for attempting the putt, and/or any other information by which one putt may be distinguished from another putt. For example, the color of the symbol 2028 may indicate whether or not the ball corresponding to the symbol overshot the golf cup 2022. A ball that overshot the golf cup 2022 may be shown with a red symbol, while a ball that did not reach the cup 2022 may be shown with a green symbol 2022. In another example, the shape, size and/or color of the symbol representing the ball may depend on the quadrant 2024 in which the ball comes to rest after a putt. In another example, the shape, size and/or color of the symbol representing the ball may depend on the stroke type, impact angle and the tempo of the individual when putting the ball. In yet another example, the shape, size and/or color of the symbol representing the ball may depend on the type of golf club used by an individual. In the example of FIG. 61, the balls that fell short of the golf cup 2022 are shown with hollow circles, the balls that overshot the golf cup 2022 are shown with filled circles, and the successfully putted balls are shown to be half-filled circles.

The individual may then attempt additional putts and similarly record the result of each putt. At any time or when the individual no longer wishes to continue, the individual may view the schematic display of the putting area 2020 to determine his or her putting tendencies. The schematic display of the putting area 2020 may resemble a scatter plot, which may show patterns or tendencies when a sufficient number of data points are present. For example, after a few putts, such as four or six putts, the number of symbols 2028 on the schematic display of the putting area 2020 may not be sufficient to convey to an individual any pattern or tendency. However, as shown in FIG. 53, after a sufficient number of putts, a pattern may emerge where certain symbols may appear in clusters or groups, thereby representing a certain pattern or tendency. As shown in FIG. 61, clusters or groups of symbols may be shown on the schematic display of the putting area 2020 to be within a tendency cluster area 2029 defining the cluster or group. For example, certain clusters or groups of symbols are shown in FIG. 61 to be enclosed by dashed circles. In another example, symbols in each cluster may be shown to be the same shape, size, color and/or have similar visual characteristics.

Referring back to FIGS. 59 and 60, the process 2000 may be performed without having the portable electronic device 1000 in the device holder 100 and attached to a golf club. Accordingly, after each putt attempt, an individual may retrieve the portable electronic device 1000 from his or her pocket, belt clip, or other storage devices that may be on the individual or in his or her golf bag and record the approximate position of the ball relative to the golf cup 2022 as described above. However, when the portable electronic device 1000 is placed in the device holder 100 and attached to a putter shaft, in addition to an individual graphically recording the approximate position of a ball to generate the above-described scatter plot, the portable electronic device 1000 may also determine an individual's stroke characteristics as discussed in detail above. The miss tendencies of the individual according to the scatter plot and the individual's stroke characteristics may suggest to the individual the corrections in his or her putting stroke that may yield better putting performance. For example, the shapes, sizes and/or colors of the symbols 2028 of the scatter plot may correspond to stroke type, impact angle and/or tempo of the individual for each putt. In another example, any pattern or cluster of symbols 2028 that may visually appear to an individual may be correlated with the individual's consistency scores or PHcp and/or any improvements in consistency scores or PHcp. Thus, the stroke characteristics of the individual as determined by the processes 1270 and 1500, and results of the process 2000 may be correlated to assist the individual in improving his or her putting stroke and performance.

Based on one or more clusters or groups of symbols and/or the tendency cluster areas 2029 visually highlighting patterns or tendencies, an individual may determine his or her putting tendencies and possibly take action to improve his or her putting performance. For example, the tendency cluster area 2031 may represent putts made by an individual with a first putter and the tendency cluster area 2033 may represent putts made by the individual with a second putter that is different in one or more respects from the first putter. The putts made by the first putter are shown to be short of the golf cup 2022 and on the right side of the golf cup 2022, while the putts made with the second putter are shown to have overshot the golf cup 2022 and also on the right side of the golf cup 2022. Based on the patterns shown by the tendency cluster areas 2031 and 2033 and the corresponding putters used, the individual may select a different style putter so as to have better results. In another example, the area 2031 may represent putts made from a certain putting distance and the area 2033 may represent putts made from another putting distance. Accordingly, an individual may determine his or her putting tendencies based on the putting distance.

The schematic display of the putter area 2020 allows an individual to determine his or her putting tendencies based on one or more putting related parameters such as putting stance, stroke characteristics, golf club characteristics and/or fitting for the individual and/or putting style. Accordingly, an individual can use a scatter plot as described in detail above to improve his or her performance for each of the noted putting related parameters or other putting related parameters.

In another example, instead of or in conjunction with the touching of the schematic display of the putting area 2020, the portable electronic device 1000 may graphically query the individual for information about the putt attempt. For example, instead of touching the screen to place a symbol 2028 on the schematic display of the putting area 2020 corresponding to an actual position of the ball, the individual may enter an approximate distance of the ball from the cup, the lateral position of the ball from the cup (i.e., left or right), and/or whether or not the ball overshot the cup.

According to the process 2000, an individual manually provides data regarding location of a golf ball after a putt to the portable electronic device 1000. As discussed below, however, the process of determining speed, trajectory and/or location of the golf ball continuously or at discrete time intervals may be at least partly or fully automated so that an individual's input may not be required.

Referring to FIGS. 62-65, an exemplary golf cup 2100 is generally shown. The golf cup 2100 may generally include a cylindrical wall 2102, a bottom 2104, which may have a center bore 2106 for receiving a flagstick (not shown). When a golf ball enters the golf cup 2100, it falls to the bottom 2104 and remains there until retrieved by an individual.

Figure 63:
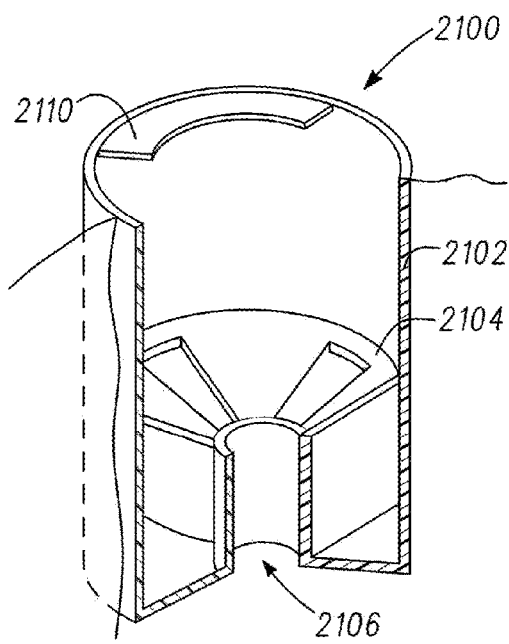
Figure 64:
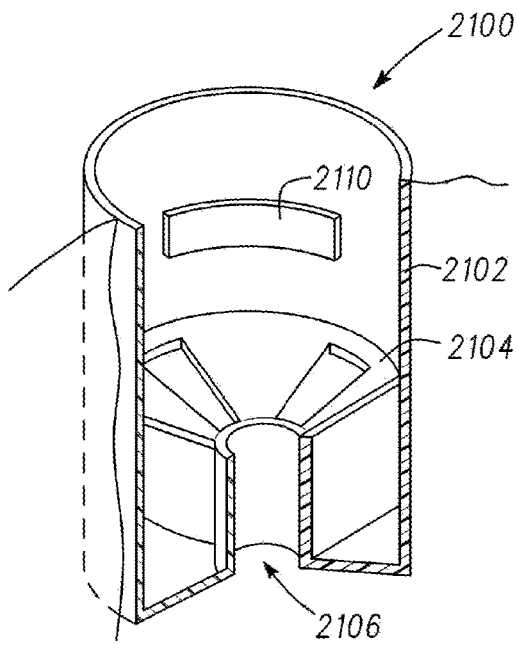
Figure 65:
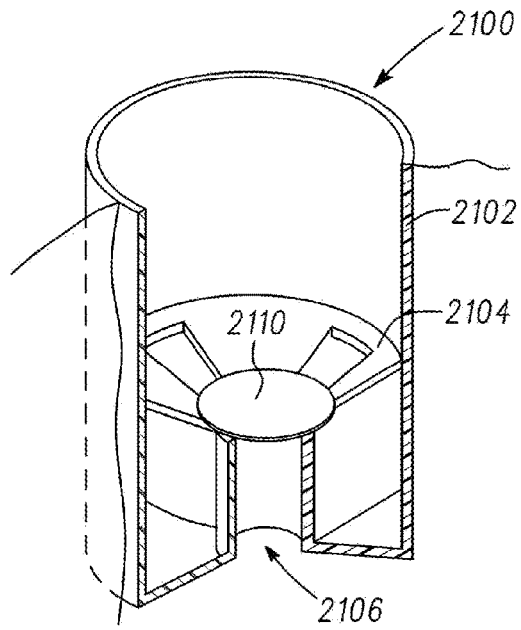

According to one example, a golf cup 2100 may include at least one sensor assembly 2110 for detecting and indicating the presence of a golf ball in the golf cup and/or entry of a golf ball into the golf cup. The sensor assembly 2110 may be located anywhere outside and near the golf cup 2100 as show in FIG. 62, at the lip of the golf cup 2100 as shown in FIG. 63, on the cylindrical walls 2102 as shown in FIG. 64, and/or at the bottom 2104 as shown in FIG. 65. The sensor assembly 2110 of FIGS. 62-64 may partially surround the hole as shown or completely surround the hole (not shown).

Figure 66:
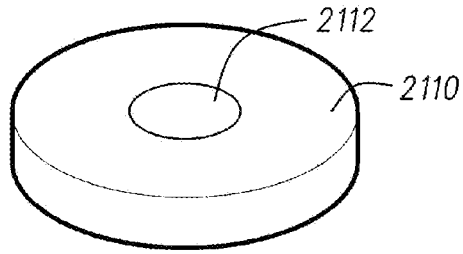
FIGS. 66-67 depict schematic diagrams of an example sensor assembly according to the disclosure.

Referring to FIG. 66, the sensor assembly 2110 may include at least one sensor 2112, which may be any type of sensor that can detect movement, weight, impact, light, and/or any other physical parameter or characteristic by which the presence of the golf ball near the golf cup 2100 and/or inside the golf cup 2100 can be detected. The sensor assembly 2110 of FIG. 66 is shown to be configured for placement on the bottom 2104 of the golf cup 2100 as shown in FIG. 65. Additionally, the sensor 2110 may be a type of sensor that can communicate with a radio frequency identification (RFID) sensor on or inside a golf ball and/or a transceiver on or inside a golf ball. For example, a sensor that detects weight may be placed at the bottom of the golf cup 2100 so as to detect the weight of a golf ball. In another example, a sensor that detects impact may be a piezoelectric sensor or an accelerometer located at the bottom of the golf cup 2100 to detect impact of the ball with the bottom of the golf cup 2100. In yet another example, a light sensor located at the bottom of the golf cup 2100 may detect the presence of a golf ball at the bottom of the golf cup 2100 as a result of the ball at least partially blocking light from reaching the sensor.

Figure 67:
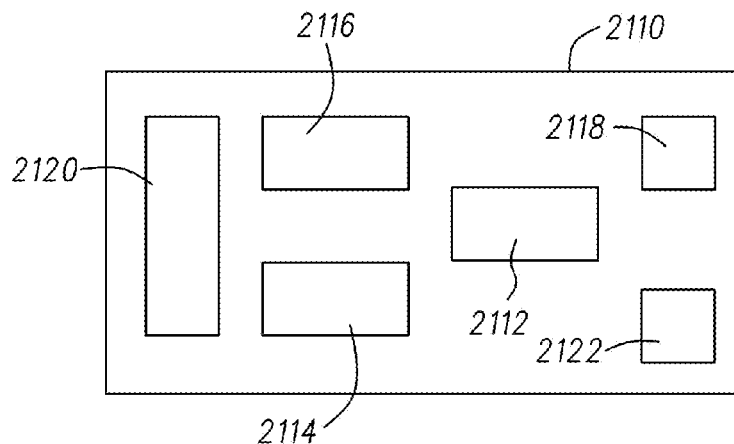

Referring to FIG. 67, an exemplary sensor assembly 2110 may include one or more sensors 2112, a processor 2114, a memory 2116, and at least a transmitter 2118. The sensor assembly 2110 may also include a power source 2120. However, the sensor assembly 2110 may operate without a power source, where a piezoelectric module that generates a short burst of current upon being impacted with a golf ball. Such a current burst may be sufficient for the sensor assembly 2110 to operate as intended, i.e., transmit a signal indicating presence of a ball in the golf cup 2100. A powered sensor assembly 2110 may include a continuous power source 2120 such as a battery and/or one or more photovoltaic cells to power the circuitry of the sensor assembly 2110.

The sensor assembly 2110 may transmit or broadcast a signal with the transmitter 2118 upon detecting a ball entering the golf cup 2100. Accordingly, the sensor assembly 2110 may only be capable of one-way communication, i.e., only transmitting information. However, the sensor assembly 2110 may also include a receiver 2122 to enable two-way communication. Accordingly, the sensor assembly 2110 may establish and maintain communication with an external device. The transmitter 2118 and/or the receiver 2122 may operate in accordance with a proprietary communication protocol, any of the wireless communication protocols described herein, Bluetooth® technology, the 802.xx family of standards developed by the Institute of Electrical and Electronic Engineers (IEEE) and/or variations and evolutions of these standards (e.g., 802.11x, 802.15, 802.16x, etc.), Ultra Wideband (UWB), Near Field Communication (NFC), and/or radio frequency identification (RFID) to communicate and/or exchange data with another device.

The sensor assembly 2110 may be a movable and portable unit that can be used by an individual in combination with the portable electronic device 1000. The sensor assembly 2110 may have a compact form. The sensor assembly 2110 may be in the shape of a relatively thin pad that can be placed by an individual inside the golf cup 2100 at the bottom 2104 of the golf cup 2100 (shown for example generally in FIGS. 64 and 65). Thus, an individual may place the sensor assembly 2110 in any golf cup 2100 to practice putting and have the ability to move the sensor assembly 2110 to another golf cup. The portable electronic device 1000 may communicate with the sensor assembly 2110 to receive data from the sensor assembly 2110 regarding presence and/or entry of a golf ball into the golf cup 2100.

Figure 68:
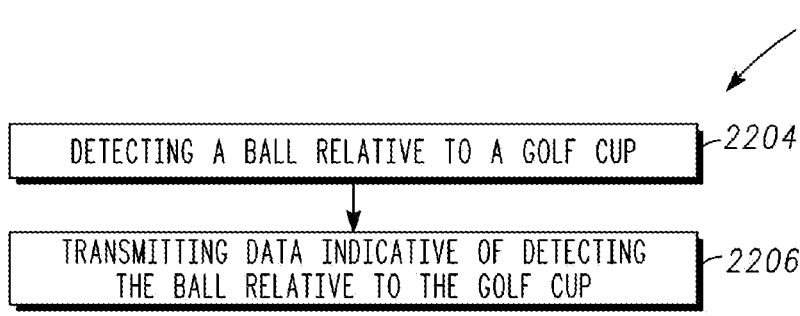
FIGS. 68-70 depict block diagram representations of processes associated with the systems, methods, and articles of manufacture according to the disclosure.

Referring to FIG. 68, a process 2200 for generally determining detecting a ball relative to a cup by using the sensor assembly 2110 is shown. The process 2200 includes detecting a ball relative to golf cup (block 2204) and transmitting data indicative of detecting the ball relative to the golf cup (block 2206). The process of FIG. 68 can be performed with a sensor assembly 2110 that is capable of two-way communication, i.e., transmission and reception, and a sensor assembly 2110 that is only capable of data transmission. If the sensor assembly 2110 is a portable sensor assembly as described above, an individual can place the sensor assembly 2110 at the bottom of a golf cup 2100. The sensor assembly 2110 may be placed in the golf cup 2100 prior to any putting session.

Figure 69:
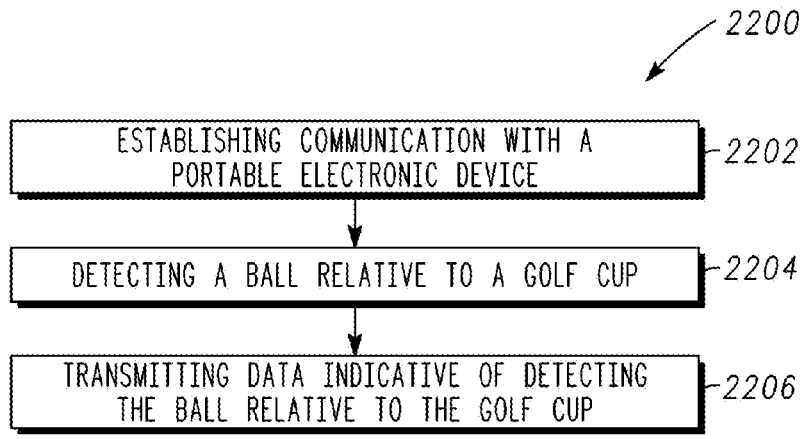

Referring to FIG. 69, the process 2200 may further include establishing communication between the sensor assembly 2110 and a portable electronic device such as the disclosed portable electronic device 1000 (block 2202). The establishment of communication between the sensor assembly 2110 and the portable electronic device 1000 may be performed automatically or by an individual actively performing certain connection procedures to establish communication. For example, when the sensor assembly 2110 and the portable electronic device 1000 are sufficiently close and/or within a certain range of communication, the portable electronic device 1000 may automatically identify the sensor assembly 2110 and establish communication with the sensor assembly 2110. Alternatively, for example, the portable electronic device 1000 may automatically identify the sensor assembly 2110, but communication between the portable electronic device 1000 and the sensor assembly 2110 may only be established if an individual requests such communication. Establishment of communication between the sensor assembly 2110 and the portable electronic device 1000 may have to be performed only once if the identification of the sensor assembly 2110 is stored in the portable electronic device 1000 for future communication. With the latter alternative, an individual has the option of establishing communication between the portable electronic device 1000 and one or more particular sensor assemblies 2110, rather than with all of the sensor assemblies 2110 within a certain range of communication.

The sensor assembly 2110 may detect a ball relative to a golf cup. For example, the sensor assembly 2110 may include one or more proximity sensors that detect nearby objects. The sensor assembly 2110 may be configured to detect nearby objects that resemble in configuration to a golf ball. The sensor assembly 2110 may also detect a ball inside a golf cup. The sensor assembly 2110 is described in detail below as detecting a golf ball in a golf cup. However, the disclosed sensor assembly 2110 may be configured to detect a golf ball relative to a golf cup, i.e., near and/or inside a golf cup.

When an individual strikes a golf ball in a putt attempt and the golf ball enters a golf cup 2100, the sensor assembly 2110 detects the entry of the ball into the golf cup 2100 (block 2004). The sensor assembly 2110 may then transmit data regarding entry of the ball into the golf cup 2100 to the portable electronic device 1000 (block 2006). If the sensor assembly 2110 does not include a receiver, the transmission of data regarding the entry of the ball into the golf cup 2100 may be a continuous broadcast transmission or transmissions at discreet time intervals for a certain period of time. For example, the sensor assembly 2110 may continuously broadcast a signal for a period of 5-10 seconds so that any portable electronic device that is sufficiently close to the sensor assembly 2110 may receive the signal. Alternatively, the sensor assembly 2110 may transmit a signal every 0.5 seconds for a period of 5-10 seconds so that any portable electronic device that is sufficiently close to the sensor assembly 2110 may receive the signal. Accordingly, a portable electronic device, such as the disclosed portable electronic device 1000, can receive one of the transmitted messages successfully and ignore any repeated transmissions. If the sensor assembly 2110 includes both a transmitter and a receiver, the sensor assembly 2110 may inform the portable electronic device through two-way communication that the ball has entered the golf cup 2100. For example, the sensor assembly 2110 may transmit a signal to the portable electronic device 1000 regarding the status of the golf ball and the portable electronic device 1000 may acknowledge receipt by transmitting an acknowledgement to the sensor assembly 2110.

Figure 70:
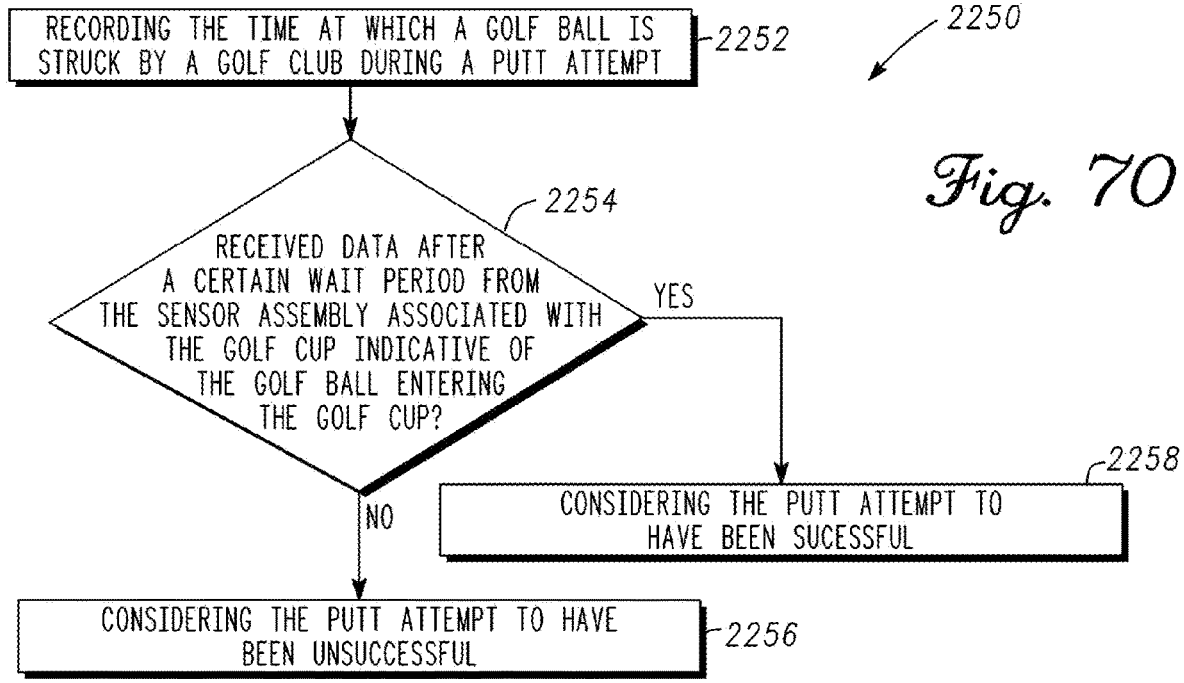

As discussed above, the sensor assembly 2110 may transmit data regarding a successful putt. However, when a golf ball does not enter a golf cup 2100 after a putt attempt, a lack of any signal being transmitted from the sensor assembly 2110 after a certain period of time may be interpreted by the portable electronic device 1000 as an unsuccessful putt. Referring to FIG. 70, a process 2250 for detecting a golf ball in a golf cup is shown from the view point of a portable electronic device, such as the disclosed portable electronic device 1000. The process 2250 includes establishing communication (not shown) with a sensor assembly, such as the sensor assembly 2110, which may be located inside or near a golf cup. When an individual strikes a golf ball toward the golf cup with his or her putter, the portable electronic device may record the time at which the golf ball is struck by the putter (block 2252). If the portable electronic device 1000 does not receive any data from the sensor assembly 2110 indicative of the ball entering the golf cup after a certain wait period (block 2254), the portable electronic device 1000 considers the putt to be a miss (block 2256). However, if the portable electronic device receives data from the sensor assembly 2110 indicative of the ball entering the golf cup after the certain wait period (block 2254), the portable electronic device 1000 considers the putt to be successful (block 2258). The wait period can be set to a greater value than the amount of time generally required in making a putt from the consistent distance (e.g., 10 ft.). Alternatively, the wait period can be set to a certain wait period that is long enough to encompass the time generally required to make a very long putt. In another alternative, when the golf ball is struck by a golf club during a putt attempt, the portable electronic device 1000 may transmit the time of the ball strike to the sensor assembly 2110. If the sensor assembly 2110 does not detect entry of the golf ball in the golf cup 2110 for a wait period after the time the ball was struck by the golf club, the sensor assembly 2110 may transmit a signal to the portable electronic device 1000 indicating a miss.

As described in detail above, the portable electronic device 1000 may also analyze each putt and determine stroke characteristics, the putting consistency and putting handicap for an individual. Accordingly, an individual's stroke characteristics and the individual's putting results for each putt attempt can be correlated to determine certain of the individuals putting tendencies that either resulted in successful putts or unsuccessful putts. Correlating stroke characteristics analysis with the result oriented information as described in detail above may enable an individual to improve his or her putting performance by modifying his or her stroke to make more successful putts. Further, an individual may not be required to record successful putt attempts on the scatter plot of FIG. 61 because the portable electronic device 1000 may receive data from the sensor assembly 1708 indicating each successful putt attempt. Accordingly, the portable electronic device 1000 may record the final position of a golf ball on the scatter plot after receiving information regarding the relative position of the golf ball to the golf cup.

Figure 71:
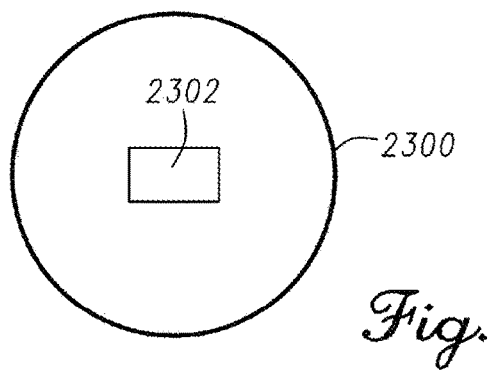
FIG. 71 depicts a schematic diagram of a golf ball having a sensor according to the disclosure.

Referring to FIG. 71, a golf ball 2300 may include at least one sensor 2302, which may be any type of sensor by which the golf ball 2300 can be at least identified by using a portable electronic device, such as the disclosed portable electronic device 1000 and/or a sensor assembly, such as the disclosed sensor assembly 2110. For example, the sensor 2302 may be an RFID sensor that is embedded inside the ball 2300. Accordingly, the sensor assembly 2110 and/or the portable electronic device 1000 may include an RFID reader to identify the ball 2300. Alternatively, the sensor 2302 may be a type of sensor that can provide at least an identification of the ball 2300 to an external device such as the portable electronic device 1000 and/or the sensor assembly 2110

The portable electronic device 1000 may also receive sufficient information from the sensor 2302 to determine the speed, spin characteristics, and/or a location of the ball 2300 at certain time intervals. From the speed and location information obtained from the sensor 2302 and based on general frictional characteristics between the ball 2300 and the ground (e.g., green speed), the portable electronic device 1000 may determine an estimated trajectory for the ball 2300 and/or an approximate location where the ball 2300 may come to rest after a putt. For example, the portable electronic device 1000 may include a GPS sensor such that the location of the ball 2300 at the moment of striking the ball 2300 is known. As the distance between the ball 2300 and the portable electronic device 1000 increases, the portable electronic device 1000 may track the movement of the ball 2300 by communicating with the ball at certain time intervals. The signals received from the ball 2300 at the certain time intervals may be used to determine the speed and rotational characteristics of the ball 2300 by methods such as Doppler shift. The portable electronic device 1000 may then determine the distance of the ball from the portable electronic device 1000 based on the speed information. The systems, methods, and articles of manufacture described herein are not limited in this regard. Accordingly, any type of sensor may be used in a ball 2300 to provide communication with any type of electronic system and/or device in order to provide information regarding the motion and location characteristics of the ball 2300 to the electronic system and/or device.

Figure 72:
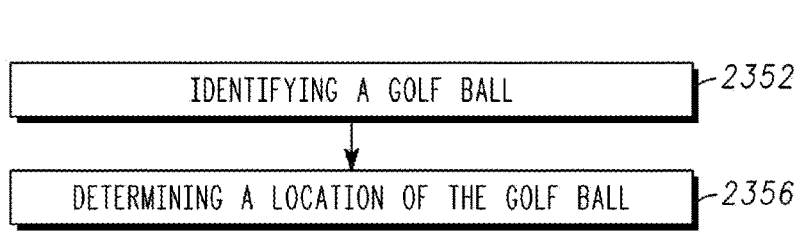
FIG. 72 depicts a block diagram representation of a process associated with the systems, methods and articles of manufacture according to the disclosure.

Referring to FIG. 72, a process 2350 of using the ball 2300 is shown. The portable electronic device 1000 may automatically identify one or more balls 2300 that are to be used by an individual (block 2352). Alternatively or in conjunction with the portable electronic device 1000, the sensor assembly 2110 may also automatically identify the one or more balls 2300 (block 2352). The individual may have several balls 2300 in his or her proximity, such as in the putting area and/or in his or her golf bag. The sensor 2302 of each ball 2300 may have a unique identifier that may be received by the portable electronic device 1000 and/or the sensor assembly 2110. Accordingly, the portable electronic device 1000 and/or the sensor assembly 2110 may recognize and track all of the balls 2300 that are in the proximity of the portable electronic device 1000 and/or the sensor assembly 2110.

An individual may make at least one putt with a ball 2300. As described above, the portable electronic device 1000 and/or the sensor assembly 2110 may detect, track and/or determine a location of the ball 2300 after a putt (block 2356). Additionally, the portable electronic device 1000 and/or the sensor assembly 2110 may detect motion characteristics of the ball 2300 while moving from the golf club toward the golf cup to determine speed, trajectory and/or location of the golf ball continuously or at certain time intervals. The sensor assembly 2110 and the portable electronic device 1000 may communicate with each other data regarding the position of the ball 2300 so that the portable electronic device can determine more accurate motion characteristics and location information for the ball 2300.

As described in detail above, the portable electronic device 1000 may also analyze each putt and determine stroke characteristics, the putting consistency and putting handicap for an individual. Accordingly, an individual's stroke characteristics and information about location, speed, and/or trajectory of a ball for each putt attempt can be correlated to determine certain of the individuals putting tendencies that either resulted in successful putts or unsuccessful putts. Correlating stroke characteristics analysis with the result oriented information as described in detail above may enable an individual to improve his or her putting performance by modifying his or her stroke to make more successful putts.

Referring to FIG. 61, the final location of each ball 2300 after a putt may be known relative to the golf cup 2022 and/or relative to the portable electronic device 1000. Accordingly, based on the location of each ball 2300 as determined by the portable electronic device 1000 as described above, the scatter plot of FIG. 61 may be automatically generated without any input or less input from an individual. Thus, by having one or more sensors 2302 in the ball 2300, an individual may not have to manually input a position of the ball on the electronic device 1000.

Figure 73:
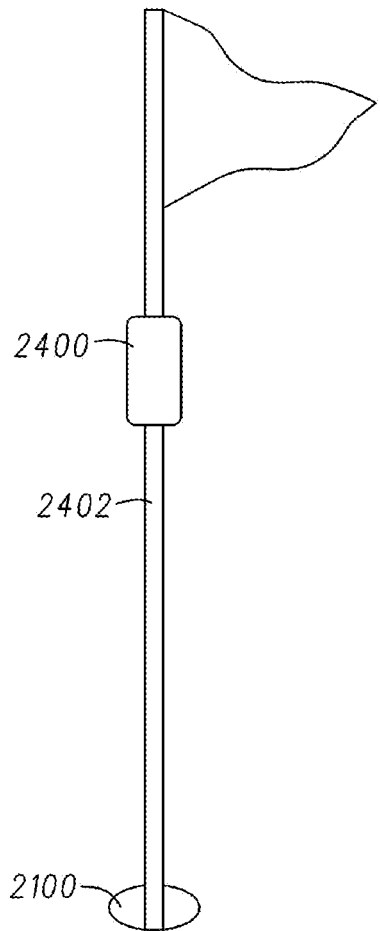
FIG. 73 depicts a schematic diagram of a camera mounted on a flagstick according to the disclosure.
Figure 74:
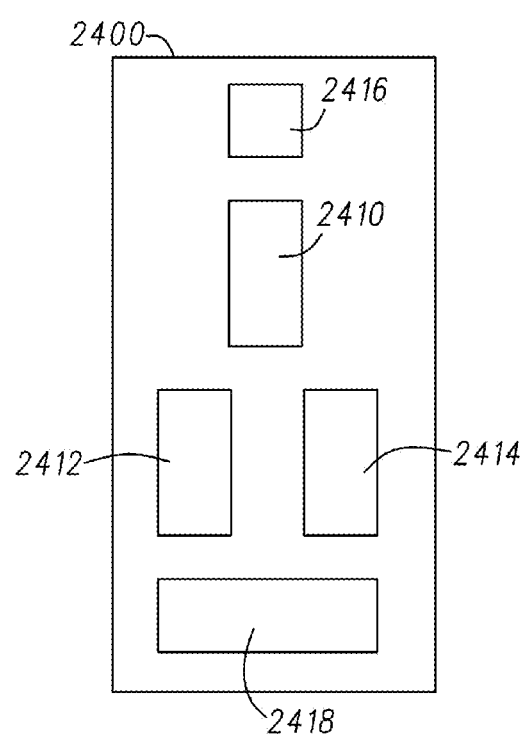
FIG. 74 depicts a schematic diagram of a typical camera.

Referring to FIG. 73, one or more cameras 2400 may be located at or near a golf cup, such as the golf cup 2100, to capture images of a ball, such as a ball 2300, for tracking locations of the ball near the camera or after a putt. For example, the camera 2400 may be mounted on a flagstick 2402 as shown in FIG. 73. The camera 2400 may be a digital camera having one or more charge-coupled devices (CCDs) and/or active pixel sensors (CMOS) to digitally capture images. Referring to FIG. 74, the camera 2400 may include an image capturing device 2410 (CCD or CMOS), a processor 2412, memory 2414, and a transceiver 2416. A portable electronic device, such as the disclosed portable electronic device 1000, may establish communication with the transceiver 2416 to receive captured images and associated data from the camera 2400. The transceiver 2416 and the portable electronic device 1000 may communicate by using any wireless communication method, such as a proprietary communication method or the standard wireless communication standards described herein. The camera 2400 may also include a power supply 2418, which may be a battery or a solar energy device, e.g., photovoltaic cells.

The camera 2400 may capture one or more images of one or more golf balls around the hole and may determine the locations and/or movement patterns of each golf ball. The camera may capture still images or capture video (i.e., a sequence of images captured at a certain frame rate such as a frame rate of between 20 and 60 frames/second). Because golf balls have generally consistent dimensions, a golf ball may be distinguished in an image captured by the camera. For example, a white circle appearing on an image with a shade of green as the background may be identified as a golf ball located on a putting green. The camera 2400 may capture one or more images with the image capture device 2410, store the one or more images in the memory 2414, and/or process the images with the processor 2412 to determine motion characteristics of the golf ball and/or the position of the golf ball relative to the camera 2400 and/or or the golf cup 2100. To determine the speed of the golf ball and/or the trajectory of the golf ball, more than one image may be required. However, one image may be sufficient to determine a location of the golf ball. Thus, the camera 2400 may capture multiple images and determine the speed and/or trajectory of a golf ball with the processor 2412. Alternatively or in conjunction with self processing of captured images, the camera 2400 may transmit image data to the portable electronic device 1000 for processing. Accordingly, the portable electronic device 1000 may process the captured images and determine motion characteristics of the golf ball and/or the distance of the golf ball from the portable electronic device 1000 and/or the golf cup 2100. Although one camera 2400 is described, a plurality of cameras may be provided at or near the golf cup 2100 to perform the disclosed methods. By providing more than one camera at or near the golf cup 2100, the speed, trajectory, and/or location of the ball may be more accurately determined. Additionally, a triangulation method may be applied to captured images from multiple cameras to more accurately determine the motion characteristics and/or the location of a golf ball.

The portable electronic device 1000 may include a digital camera that is capable of performing the disclosed image capture functions. Accordingly, an individual may attach a first portable electronic device 1001 to a putter shaft 800 with a first device holder 101 as shown in FIG. 76, which is similar to FIG. 11 and a second portable electronic device 1002 to the flag stick 2402 with a second device holder 102 as shown in FIG. 75. The second portable electronic device 1002 may function as a digital camera as described above, while the first portable electronic device 1001 may function to determine stroke characteristics and operate the software as also described above. The two portable electronic devices 1001 and 1002 may communicate with each other as described below.

Figure 77:
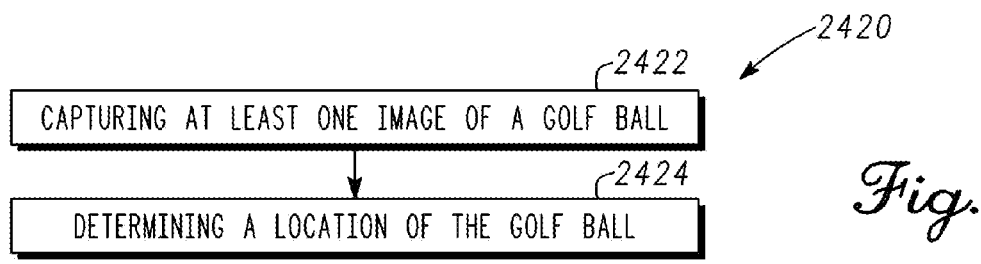
FIGS. 77-78 depict block diagram representations of processes associated with the systems, methods, and articles of manufacture according to the disclosure.

Referring to FIG. 77, a process 2420 for using the camera 2400, which may be a part of the second portable electronic device 1002 is shown. The camera 2400 may be attached to the flagstick 2402 as shown in FIG. 76. Alternatively, if a portable electronic device 1002 is used as a camera, the portable electronic device 1002 may be attached to the flagstick 2402 with the second device holder 102. The camera 2400 may capture at least one image of the ball when an individual putts the ball (block 2422). The image may be captured at approximately the moment when the ball comes to rest or after a certain sufficient wait period so that a ball comes to rest. The at least one captured image is then processed to determine the final location of the golf ball (block 2424). If more than one image is captured while the ball is moving, motion characteristics of the ball may also be determined (not shown). Accordingly, speed, trajectory and/or locations of the ball may be determined continuously or at certain time intervals (not shown).

Figure 78:
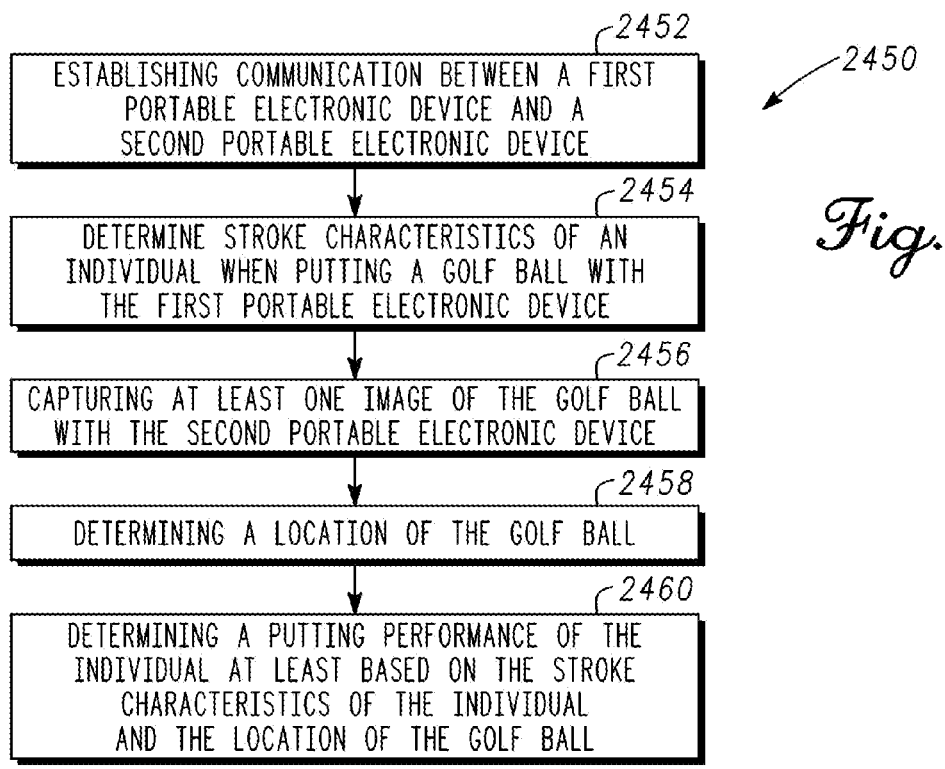

Referring to FIG. 78, a process 2450 for using two portable electronic devices 1001 and 1002 is shown. The second portable electronic device 1002 may be attached to a flagstick 2402 with the second device holder 102. Additionally the camera lens of the second portable device 1002 may be generally pointed in the direction from which an individual may be putting one or more golf balls. The first portable electronic device 1001 may be attached to the individual's putter as described in detail above with the first device holder 101.

The process 2450 includes establishing communication between the first portable electronic device 1001 and the second portable electronic device 1002 (block 2452). After communication is established, an individual may putt a golf ball toward the golf club, i.e., toward the flag 2402. Accordingly, as described in detail above, the first portable electronic device 1001 may determine the stroke characteristics of the individual (block 2454). The second portable electronic device 1002 may capture one or multiple images or a video of the putting area (block 2456). Either the first portable electronic device 1001 or the second portable electronic device 1002 may process the captured images to determine motion characteristics and/or locations of the golf ball (block 2458). If the first portable electronic device 1001 is to process the captured images, the second portable electronic device 1002 may transmit the captured images to the first portable electronic device 1002. The process 2450 can then determine the individual's putting performance based on the stroke characteristics of the individual and the motion characteristics and/or locations of the golf ball (block 2460).

The first and second device holders 101 and 102 may be identical or similar in many respects. For example, if the first and second device holders 101 and 102 are identical, the clamp portions (such as the clamp portion 300 of the device holder 100) of both devices may be configured to provide attachment to a putter shaft and a flagstick. Accordingly, because a flagstick may have a larger diameter than a diameter of a typical putter shaft, the clamp portion may be configured to receive poles, rods or shafts of large varying diameters. In another example, the first and second device holders 101 and 102 may be similar in many respects except for their respective clamp portions. The clamp portion of the first device holder 101 may be configured for attachment to a putter shaft, while the clamp portion of the second device holder 101 may be configured for attachment to a flagstick.

According to the process 2420 and 2450, the individual may make several putts from a consistent distance. For each putt, the camera 2400 or the camera of the second portable electronic device 1002 may capture images of the ball. The camera may capture images continuously in a video capture mode or in discrete intervals. In one example, to reduce the space required in memory of the first portable electronic device 1001 and/or the second portable electronic device 1002 for storing images, the camera may be activated when the individual swings his golf club and/or strikes the ball. Accordingly, the first portable electronic device 1001 may transmit a signal to the second portable electronic device 1002 when the individual swings the golf club and/or the golf club strikes the ball so that the second portable electronic device 1002 can capture images of the ball from the moment a putt is initiated or just prior to the golf club striking the ball. The camera of the second portable electronic device 1002 may stop capturing images upon detecting that the ball is no longer in motion. Alternatively, the camera of the second portable electronic device 1002 may stop capturing images after a certain period, such as a time period that is typically required to make a generally long putt.

When the camera 2400 or the camera of the second portable electronic device 1002 captures a plurality of images or video during the same putt attempt, the speed, location and/or trajectory of the ball at every instant in time when the image was captured may be determined. In one example, the second portable electronic device 1002 may determine ball movement characteristics based on the captured images and transmit the ball movement characteristic data to the first portable electronic device 1001. Alternatively, the second portable electronic device 1002 may transmit the captured images to the first portable electronic device 1001 so that the first portable electronic device 1001 can determine the movement characteristics of the ball.

As described in detail above, one of the portable electronic devices 1001 or 1002 that is attached to the putter shaft with the device holder 101 or 102, respectively, may also analyze each putt and determine stroke characteristics, the putting consistency and putting handicap for an individual. Accordingly, an individual's stroke characteristics and information about location, speed and/or trajectory of a ball for each putt attempt as determined by the captured images of the ball him can be correlated to determine certain of the individuals putting tendencies that either resulted in successful putts or unsuccessful putts. Correlating stroke characteristics analysis with the result oriented information as described in detail above may enable an individual to improve his or her putting performance by modifying his or her stroke to make more successful putts.

Referring to FIG. 61, the final location of each ball 2300 after a putt may be known relative to the golf cup 2022 and/or relative to the portable electronic device 1000. Accordingly, based on the location of each ball 2300 as determined by the captured images as described above, the scatter plot of FIG. 61 may be automatically generated without any input or less input from an individual. Thus, by capturing images of a ball during each putt, an individual may not have to manually input a position of the ball on the electronic device 1000.

Referring to FIG. 82, a process 2500 is shown for classifying golf clubs in one or more golf club categories based on at least one golf club characteristic associated with the golf club. The process 2500 includes classifying a golf club in at least one golf club category based on at least one club characteristic (block 2502), associating at least one stroke type with the at least one golf club category (block 2504), and indicating a stroke type on a golf club based on the at least one golf club category of the golf club (block 2506). Accordingly, an individual may select an appropriate type of golf club for optimum or near optimum performance considering the individual's stroke characteristics and skill level.

Referring back to FIGS. 28-31, golf clubs may be classified in categories based on the center of gravity (CG) position 1250 and/or the CG angle 1252. The process 2000 may classify a golf club 1240 in at least one of the club categories. In one example, the golf club 1240 may be a putter-type golf club. Accordingly, the process 2000 may classify the golf club 1240 in a face-balance putter category, a mid-hang putter category, or a toe-down putter category.

Figure 79:
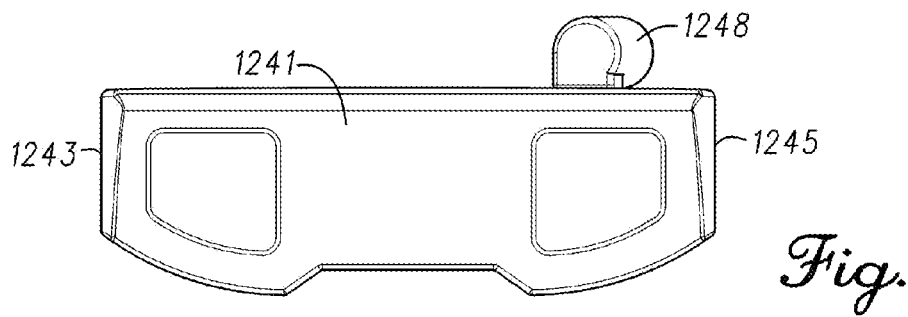
FIGS. 79-81 depict three example putters according to the disclosure.

In one example, a putter-type golf club classified in the face-balance putter category may have a relatively-lower CG angle (e.g., less than six degrees) with varying CG position from the shaft axis 1248 (e.g., from zero to two inches). FIG. 79 shows an example of a face-balanced putter. When the shaft of a face-balanced putter is held in a horizontal position and allowed to freely rotate about the shaft axis (extending through the page in FIG. 79), the head 1241 remains in a horizontal position as shown in FIG. 79. Thus, the position and angle of the CG is such that the portion of the head 1241 from the shaft 1248 to the toe 1243 and the portion of the head 1241 from the shaft 1248 to the heel 1245 balance each other about the shaft axis 1248.

Figure 80:
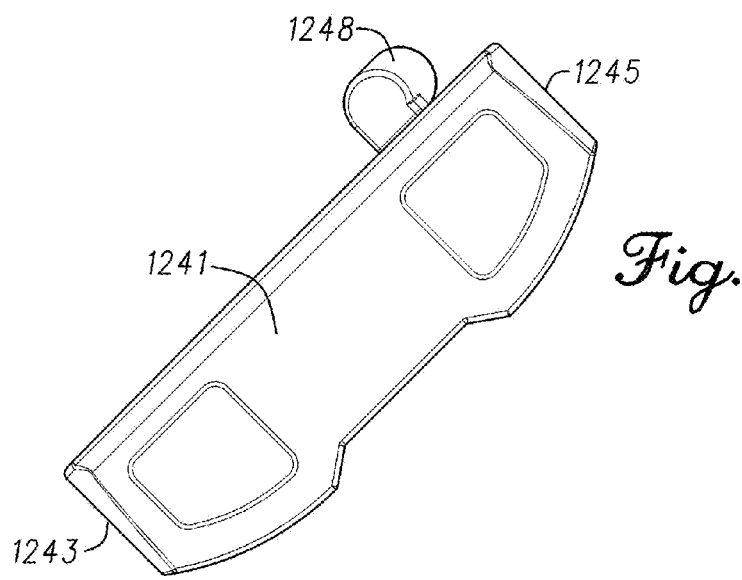

A putter-type golf club classified in the mid-hang putter category may have a relatively-moderate CG angle (e.g., less than 45 degrees) and a relatively-moderate CG position from the shaft axis 1248 (e.g., less than one inch). Further, a putter-type golf club classified in the mid-hang putter category may have a relatively lower CG angle (e.g., less than 20 degrees) but a relatively-farther CG position (e.g., more than one inch) from the shaft axis 1248. FIG. 80 shows an example of a mid-hang putter. When the shaft of a mid-hang putter is held in a horizontal position and allowed to freely rotate about the shaft axis 1248 (extending through the page in FIG. 80), the head 1241 rotates about the shaft axis 1248 until it finds a balanced position generally midway between a horizontal position and a vertical position. Thus, the position and angle of the CG is such that the portion of the head 1241 from the shaft 1248 to the toe 1243 is slightly off balance relative to the portion of the head 1241 from the shaft 1248 to the heel 1245.

Figure 81:
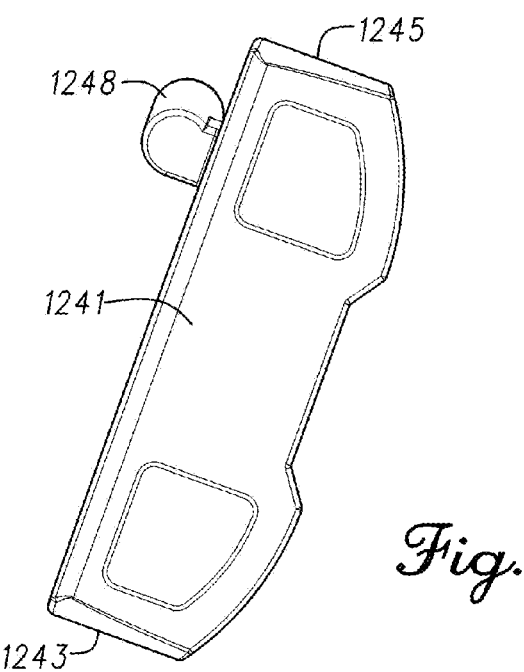

A putter-type golf club classified in the toe-down putter category may have a relatively-higher CG angle (e.g., greater than 45 degrees) and a relatively-shorter CG position from the shaft axis 1248 (e.g., less than one inch) may be classified in the toe-down putter category. In addition, a putter-type golf club classified in the toe-down putter category may have a relatively-lower CG angle (e.g., less than 30 degrees) but a relatively-farther CG position (e.g., more than one inch) from the shaft axis 1248. FIG. 81 shows an example of a toe-down putter. When the shaft of a tow-down putter is held in a horizontal position and allowed to freely rotate about the shaft axis 1248 (extending through the page in FIG. 81), the head 1241 rotates about the shaft axis 1248 until it finds a balanced position generally near a vertical position. Thus, the position and angle of the CG is such that the portion of the head 1241 from the shaft 1248 to the toe 1243 is highly off balance relative to the portion of the head 1241 from the shaft 1248 to the heel 1245.

While the above examples may define the plurality of putter categories in a particular manner, the systems, methods, and articles of manufacture described herein are not limited in this regard. That is, various combinations of CG angles and CG position from the shaft axis 1248 may define the plurality of putter categories.

According to the above, a golf club may be classified in a club category based on at least one club characteristic associated with the golf club, such as CG location and CG angle. A golf club classified in a certain category may then be associated with a stroke type for which that golf club is suitable. In one example, a face-balanced putter may be more suitable for a straight-type stroke, a mid-hang putter may be more suitable for a slight arc-type stroke, and a toe-down putter may be more suitable for a strong arc-type stroke.

Referring to FIGS. 83-85, a putter-type golf club classified in a face-balance putter category may include a stroke type indicator 2510 associated with a straight stroke type. The stroke type indicator 2510 may include a description, a letter, a number, a logo, a symbol, a color, a combination thereof, etc. In on example, a text field 2512, in which a stroke type is described. For example, the text field 2512 may include the description "Straight," "Slight Arc" or "Strong Arc." The stroke type indicator 2510 may also include a graphical stroke type field 2514, in which a stroke type is graphically conveyed to an individual. In the example of FIGS. 83-85, each of the straight, slight arc and strong arc stroke types is graphically represented by a partial circle 2516 and a line 2518, where the curvature of the line 2518 may define the stroke type. The partial circle 2516 may represent a golf cup or hole. A tab 2520 framing any graphical representation of the stroke type in the graphical stroke type field 2514 may identify the stroke type on the stroke type indicator 2510. The partial circle 2516 of the indicated stroke type may also include a small filled circle 2522 representing a golf ball inside a golf cup or a hole.

Although not shown, certain colors used on the stroke type indicator 2510 may indicate a stroke type. For example, the graphical stroke type field 2514 may have a blue, green or red background color associated with straight, slight arc or strong arc stroke types, respectively.

FIG. 83 is an example of a stroke type indicator 2510 associated with a straight type stroke that may be provided on a face-balanced putter. The stroke type indicator 2510 includes the word "Straight" in the text field 2512 to indicate that a golf club having such a visual stroke indicator may be better suited for an individual having a straight type of stroke. The tab 2520 of the graphical stroke type field 2514 is shown to frame the partial circle 2516 and line 2518 that visually convey a straight type stroke to an individual. The line 2518 is shown to be a straight line and the framed partial circle 2516 is shown to have a small filled circle 2522 representing a golf ball in the golf cup. The graphical stroke type field 2514 and/or the word "Straight" in the text field 2512 may also have a certain color associated with a straight type stroke, such as the color blue.

FIG. 84 is an example of a stroke type indicator 2510 associated with a slight arc type stroke that may be provided on a mid-hang putter. The stroke type indicator 2510 includes the word "Slight Arc" in the text field 2512 to indicate that a golf club with such a stroke type indicator may be better suited for an individual having a slight arc type of stroke. The tab 2520 of the graphical stroke type field 2514 is shown to frame the partial circle 2516 and line 2518 that visually convey a straight type stroke to an individual. The line 2518 is shown to be slightly arced and the framed partial circle 2516 is shown to have a small filled circle 2522 representing a golf ball in the golf cup. The graphical stroke type field 2514 and/or the words "Slight Arc" may also have a certain color associated with a straight type stroke, such as the color green.

FIG. 85 is an example of a stroke type indicator 2510 associated with a slight arc type stroke that may be provided on a toe-down putter. The stroke type indicator 2510 includes the word "Strong Arc" in the text field 2512 to indicate that a golf club with such a stroke type indicator may be better suited for an individual having a strong arc type of stroke. The tab 2520 of the graphical stroke type field 2514 is shown to frame the partial circle 2516 and line 2518 that visually convey a straight type stroke to an individual. The line 2518 is shown to have the greatest arc as compared to the lines 2518 of the straight and slight arc stroke type indicators 2510. The framed partial circle 2516 is shown to have a small filled circle 2522 representing a golf ball in the golf cup. The graphical stroke type field 2514 and/or the words "Strong Arc" may also have a certain color associated with a straight type stroke, such as the color red.

Figure 86:
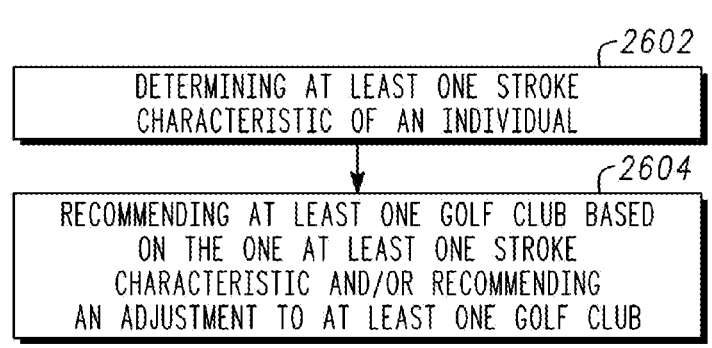
FIG. 86 depicts a block diagram representation of a process associated with the systems, methods, and articles of manufacture according to the disclosure.

Characterizing an individual's golf swing or putting stroke and/or an analysis of the individual's performance may be considered to identify an appropriate type of golf club for the individual to play his or her best. Referring to FIG. 86, a process 2600 may recommend a golf club for an individual based on an individual's stroke characteristics and/or an analysis of the individual's putting performance. The process 2600 may generally include determining at least one stroke characteristic of an individual (block 2602), and recommending at least one golf club based on the at least one stroke characteristic of the individual and/or recommending an adjustment to at least one golf club based on the at least one stroke characteristic of the individual (block 2604).

Figure 87:
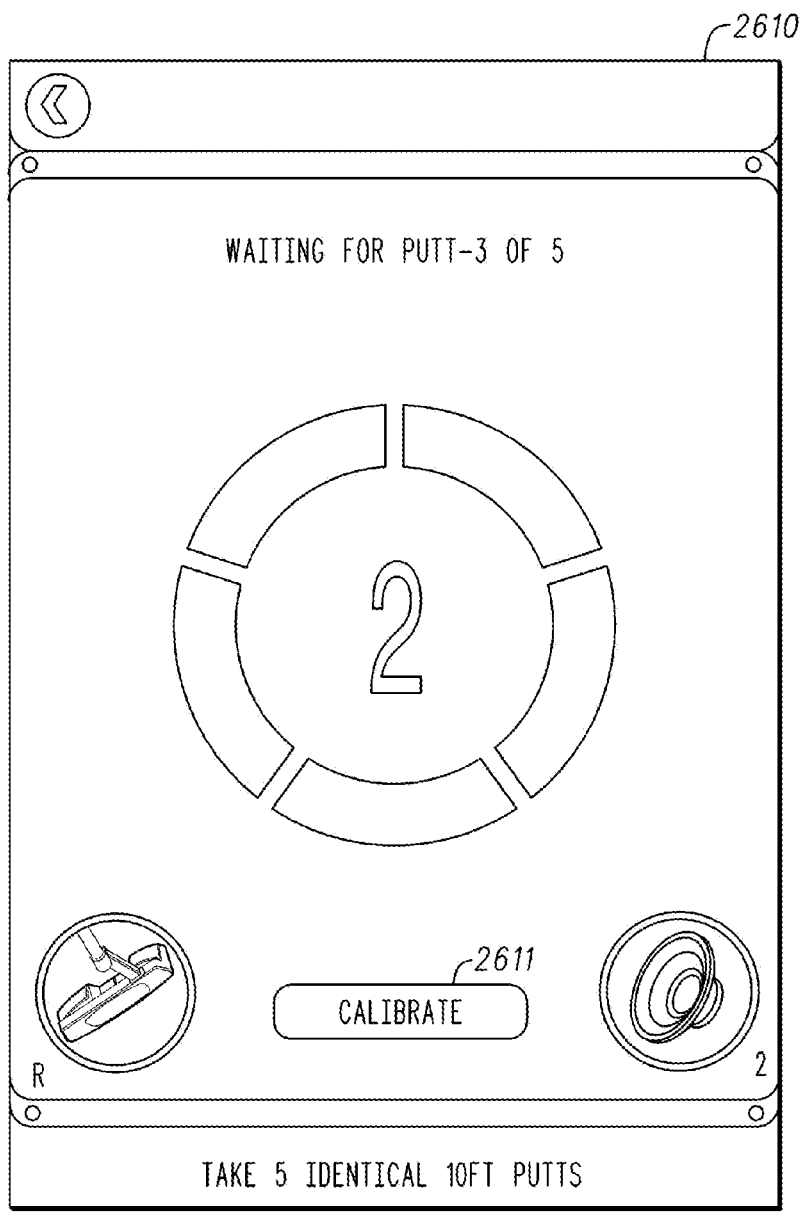
FIGS. 87-95 depict visual diagram representations of example displays according to the disclosure.

An individual may perform the process 2600 by selecting (e.g., touching the GUI 1114) club fitting option 1908 of the sub-menu 1310. Upon selecting the club fitting option 1908, the GUI 1114 of the portable electronic device 1000 displays a counter display 2610 as shown in FIG. 87. The counter display 2610 is similar in many respects to the counter display 1650. Accordingly, a description of similar features and functions of the counter displays 2610 is not repeated herein for brevity. The counter display 2610 may further display instructions for an individual regarding the number of putts to attempt and the distance for the attempted number of putts. For example, the counter display 2610 may instruct the individual to "TAKE 5 IDENTICAL 10 ft PUTTS" as shown in FIG. 87. The individual may take the specified number of putts (e.g. 5 putts) from the specified distance (e.g. 10 feet) until the counter display 2610 shows that all five putt attempts have been completed.

Figure 88:
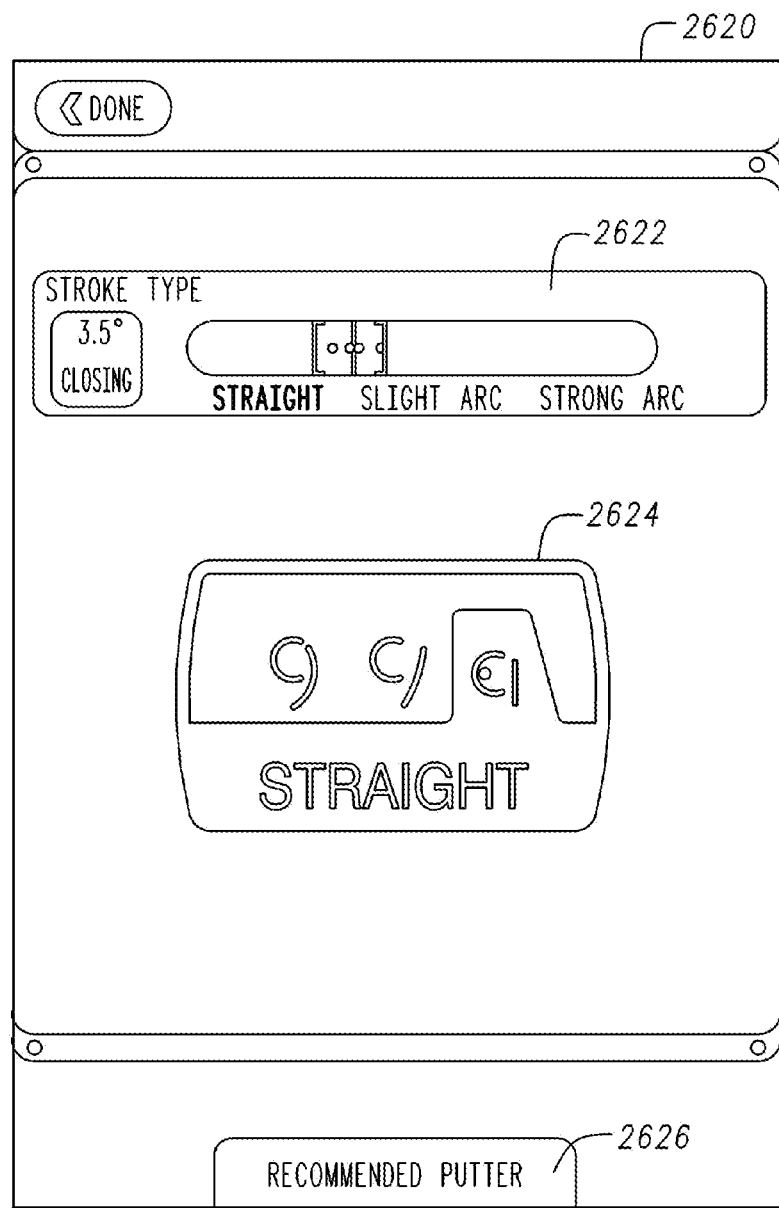

Upon completing the specified number of putts from the specified distance, the stroke type of the individual may be displayed on a stroke identification display 2620 as shown in FIG. 88. The stroke identification display 2620 may include a stroke type display 2622, which is similar to the stroke type display 1662 of FIG. 47. Accordingly, a detailed description of the stroke type display 2622 is not provided herein for brevity. The stroke identification display 2620 may also include a stroke type indicator 2624. According to the process 2500 as described above, a stroke type indicator 2510 may be provided on a golf club to associate the golf club with a certain stroke type. The stroke type indicator 2624 displayed on the stroke identification display 2620 may be similar or identical to the stroke type indicator 2510 associated with the same stroke type. Therefore, a detailed description of the stroke type indicator 2624 is not provided herein for brevity. As described below, an individual may readily match up the displayed stroke type indicator 2624 with a similar stroke type indicator 2510 on a golf club when selecting an appropriate golf club based on the stroke characteristics of the individual.

According to one example, the stroke type indicator 2510 may be a sticker that is affixed to a corresponding golf club. According to another example, the stroke type indicator 2510 may be painted on a corresponding golf club during manufacturing thereof. According yet another example, the stroke type indicator 2510 may be etched, embossed or be made as an integral piece of the golf club. Thus, the stroke type indicator 2510 may be placed at any location on the golf club with any method.

Figure 89:
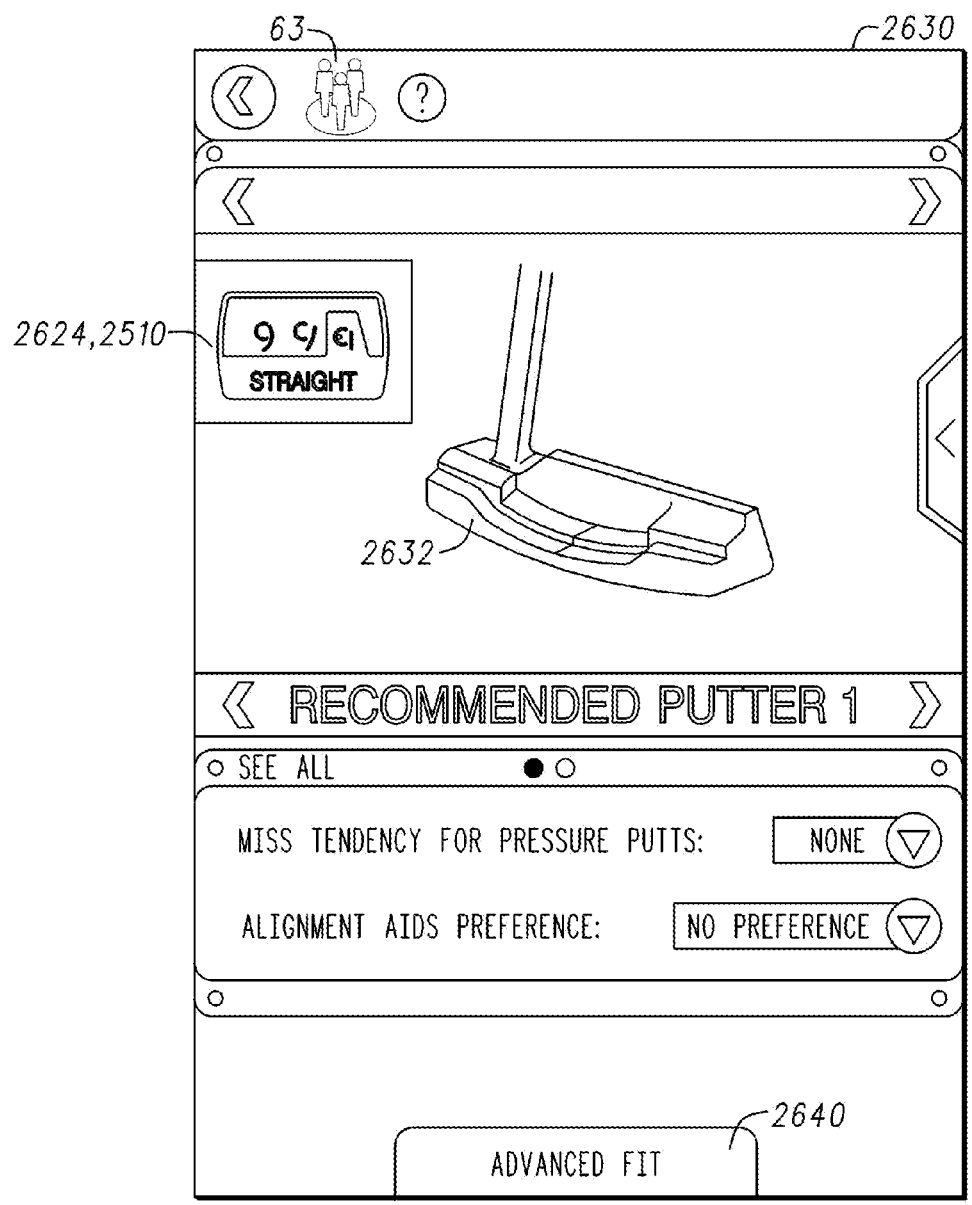
Figure 90:
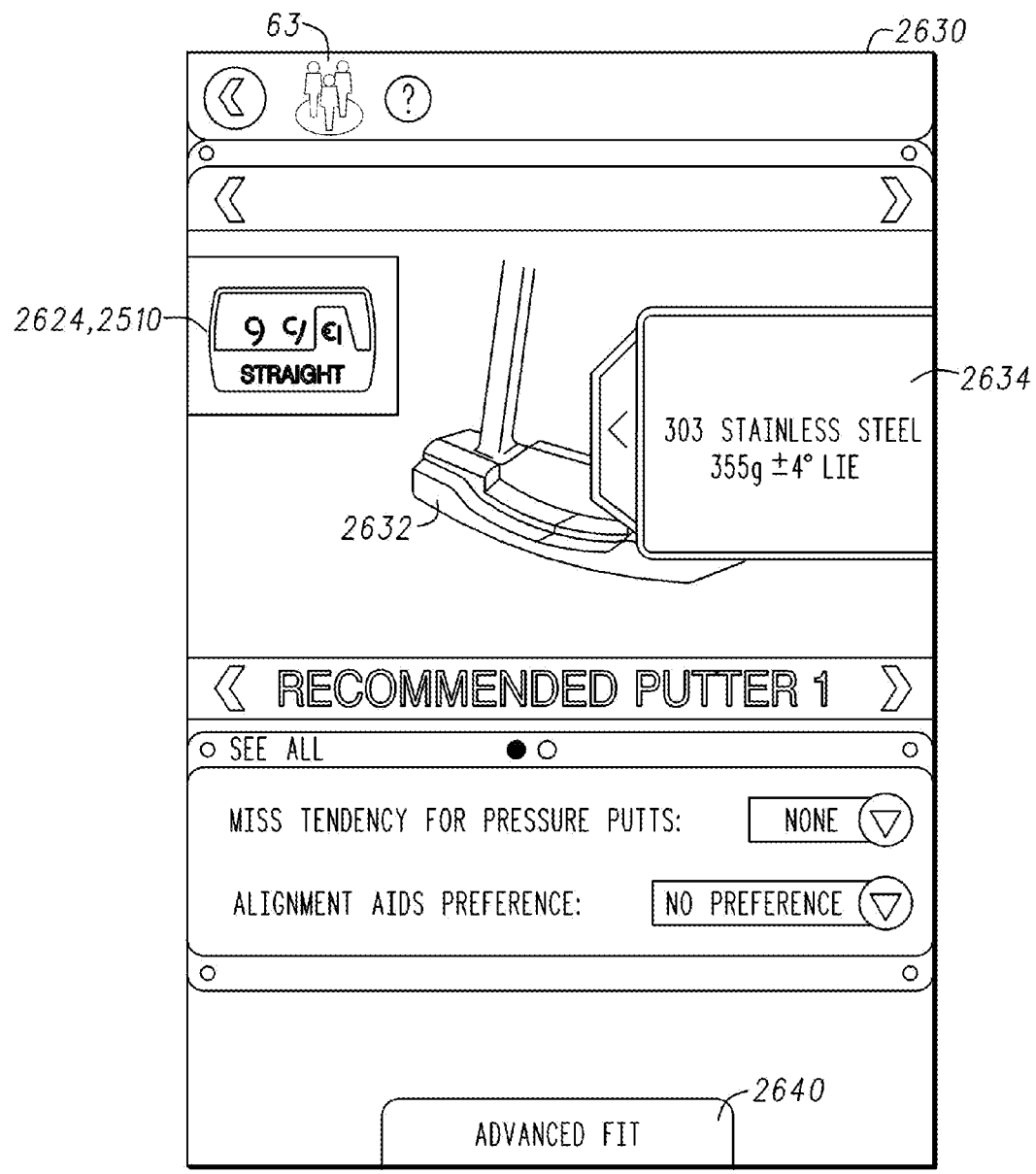

The stroke identification display 2620 may also include a "Recommend Putter" icon 2626 that when selected by an individual identifies a putter that may be best suitable for the individual based on his or her stroke type on a recommended putter display 2630 as shown in FIG. 89. The recommended putter display 2630 may show at least one recommended putter 2632. The recommended putter 2632 may be identified by manufacturer and model. The recommended putter display 2630 may also display the stroke type associated with the recommended putter in the form of the stroke type indicator 2624 and/or 2510. An individual may have the option of viewing other recommended putters on the recommended putter display 2630 by scrolling between several recommended putters. The individual may also have the option of viewing technical specifications of the recommended putter 2632. Referring to FIG. 90, the recommended putter display 2630 may include a smaller sub-display 2634, which may be displayed over the recommended putter display 2630 and include technical specifications of the recommended putter 2632, such as the material from which the recommended putter 2632 is constructed, the weight of the recommended putter 2632 and/or the lie angle of the recommended putter 2632. The sub-display 2634 may be activated by an individual touching a certain icon (e.g., an arrow or the like) on a certain part of the recommended putter display 2630.

Figure 91:
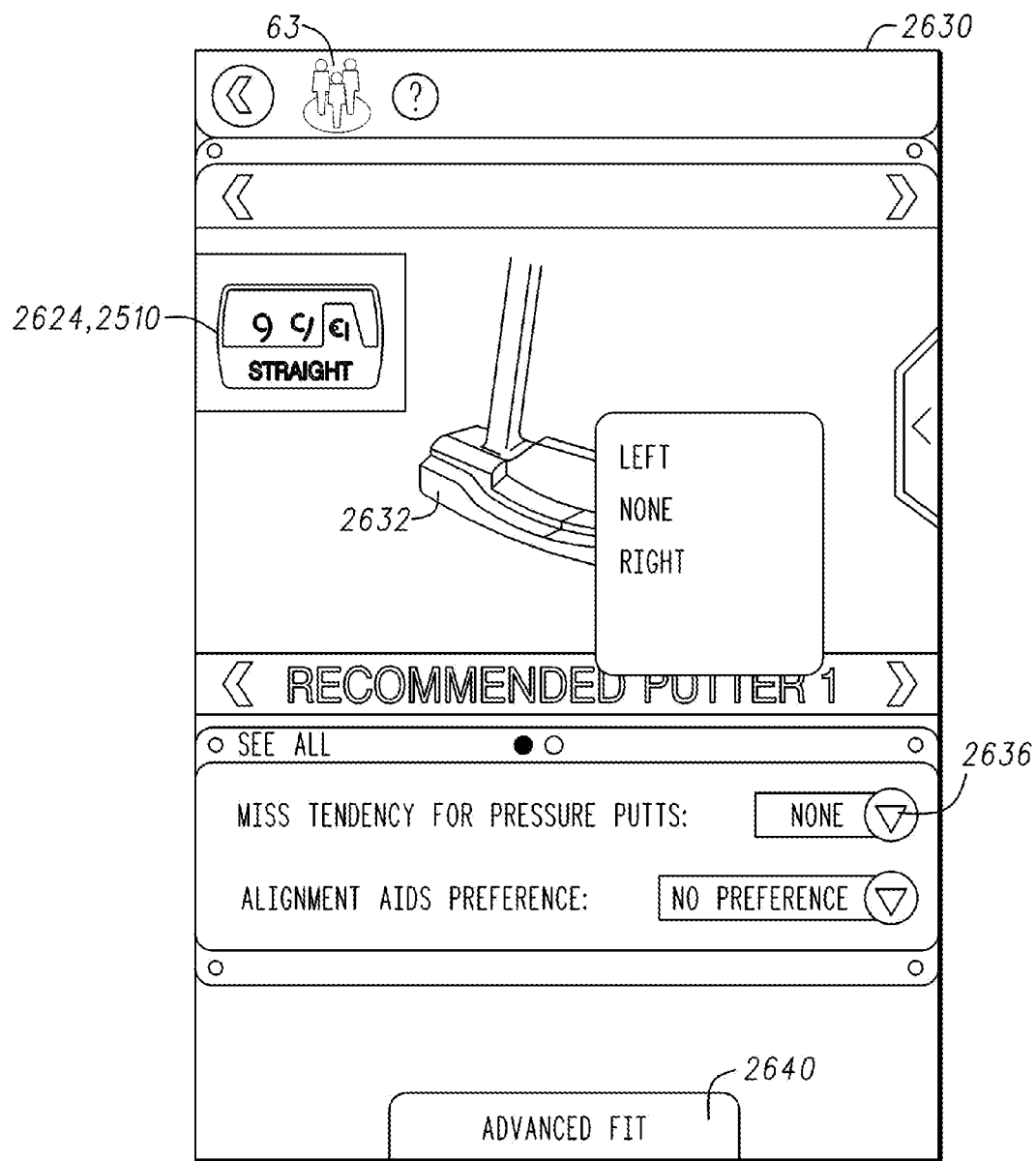
Figure 92:
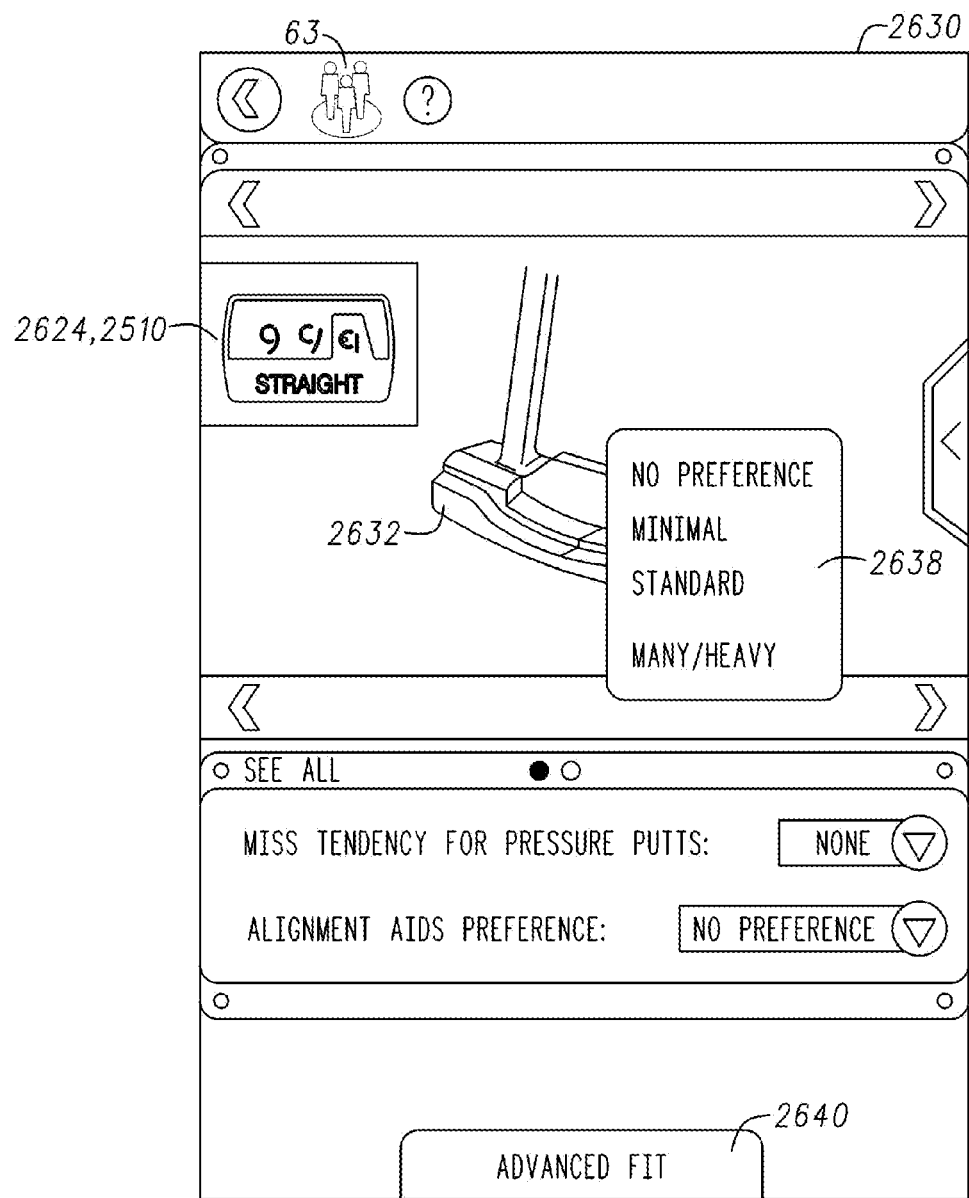

Referring to FIG. 91, the recommended putter display 2630 may include a miss tendency sub-menu 2636, by which an individual can select miss tendency options such as Left, None or Right. For example, a right-handed individual who has the tendency to miss to the left of a golf hole with his or her current golf club may benefit from a golf club that is more toe-down (i.e., more in the toe-down direction) than his or her current golf club. Accordingly, such an individual may selected the Left miss tendency option from the sub-menu 2636. In another example, an individual who has the tendency to miss to the right of a golf hole with his or her currently golf club may benefit from a golf club that is more face-balanced (i.e., more in the face-balance direction) than his or her current golf club. Accordingly, such an individual may select the Right miss tendency option from the sub-menu 2636. Referring to FIG. 92, the recommended putter display 2630 may also include an alignment aid sub-menu 2638, by which an individual can select the style and/or type of alignment aid that he or she prefers on a putter. For example, the options that may be selectable from the alignment aid sub-menu 2638 may be No Preference, Minimal, Standard, or Many/Heavy.

Figure 93:
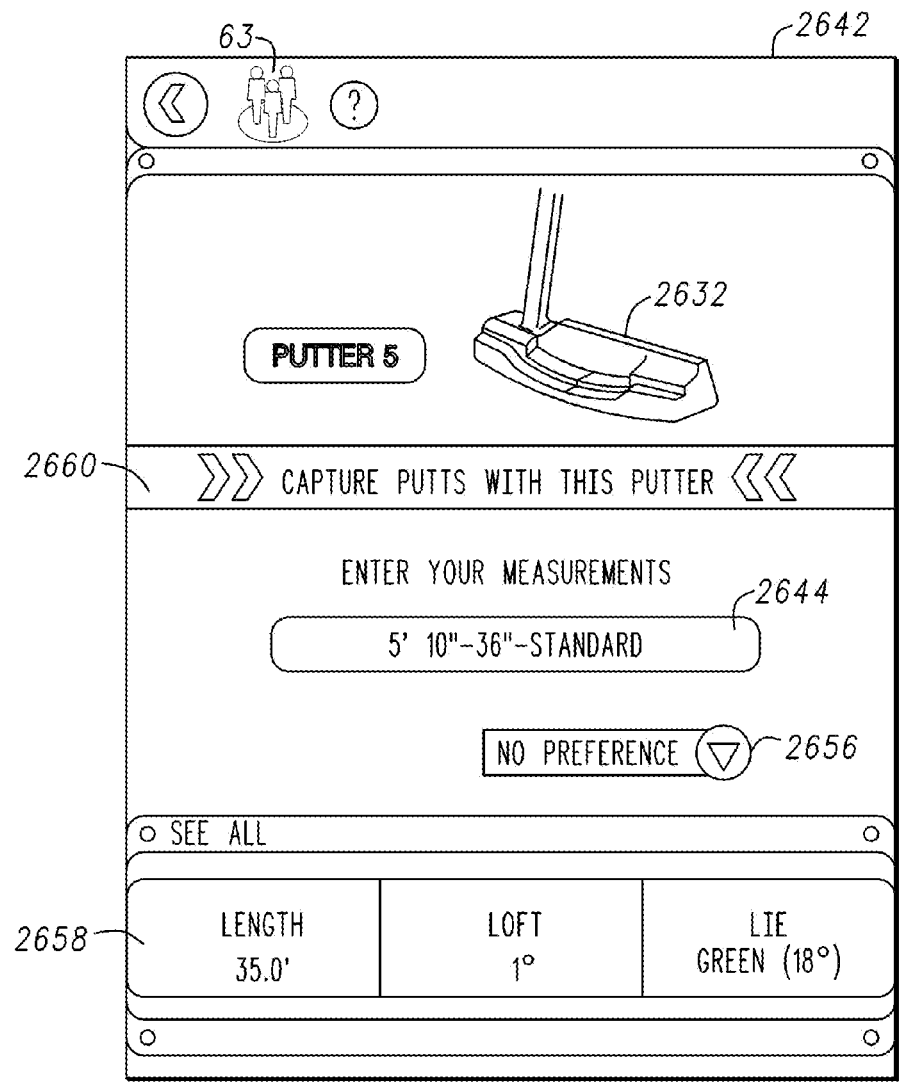
Figure 94:
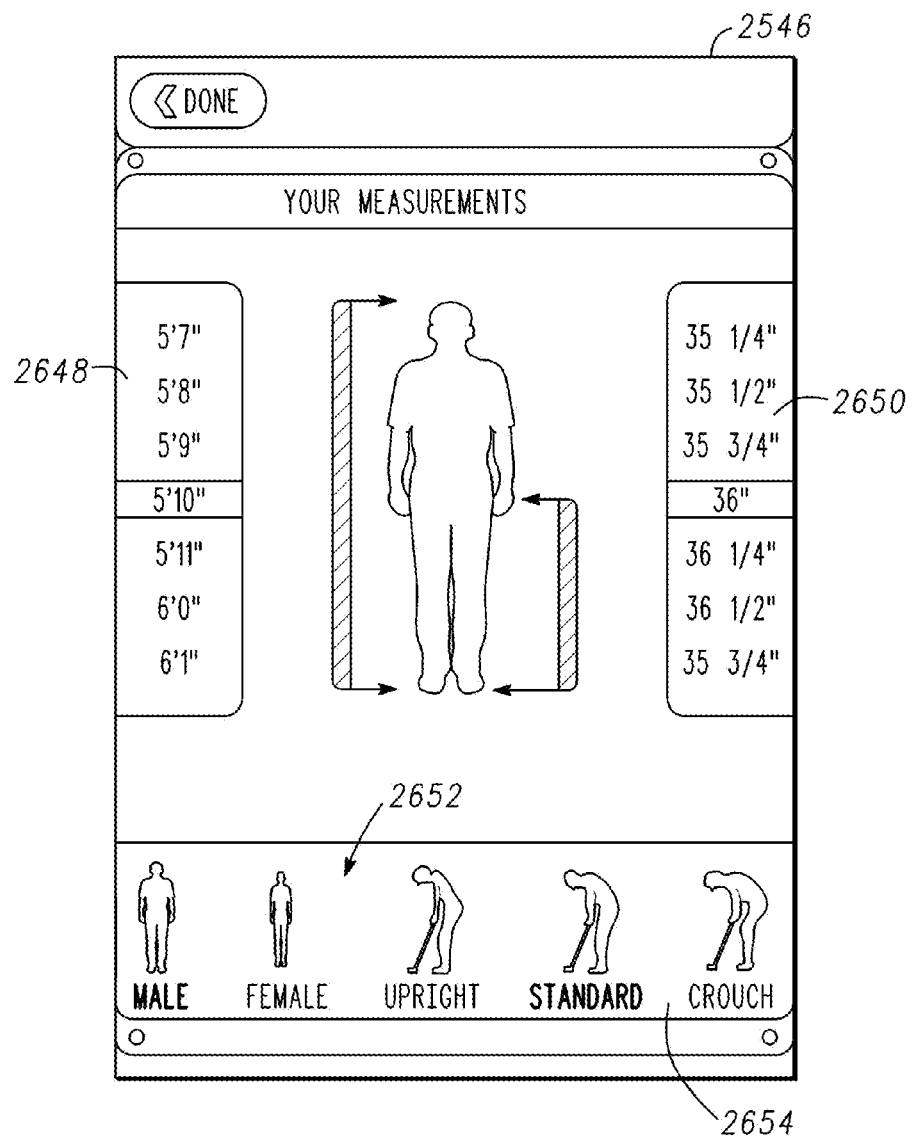
Figure 95:
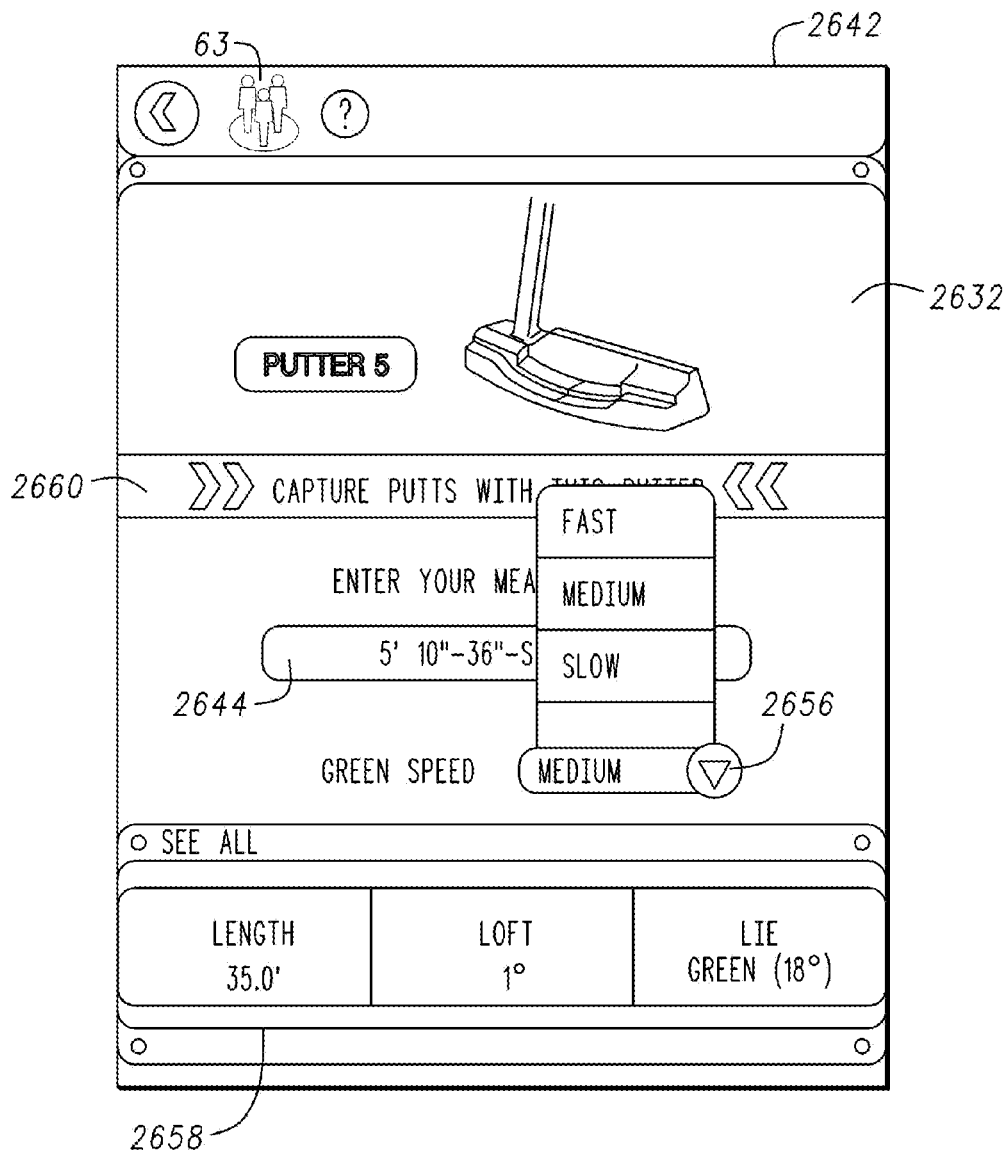

The recommended putter display 2630 recommends a putter for an individual based on his or her stroke type. However, the individual may require advanced fitting so that the recommended putter is sized for the individual. Accordingly, the recommended putter display 2630 may include an advanced fitting option 2640, selection of which by an individual displays an advanced fitting display 2642 shown in FIG. 93. An individual may enter his or her measurements in a measurement input area 2644 by activating a measurement display 2646 as shown in FIG. 94. The measurement display 2646 may include an overall height input area 2648 for an individual to input his or her height, a wrist to floor height input area 2650 for the individual to input the distance from his or wrist to the floor, gender identification input area 2652 for selection of the individual's gender, and stance type input area 2654 for selection of the individual's putting stance, such as upright, standard, or crouch. Upon returning to the advanced fitting display 2642, the individual may have the option of selecting the green speed such as fast, medium or slow from a green speed menu 2656 as shown in FIG. 95. The advanced fitting display 2642 may display a recommended putter configuration sub-display 2658 for the recommended putter 2632. The recommended putter configuration sub-display 2658 may include a recommended length, loft and lie angle as shown in FIGS. 93 and 95. The speed of a putting green of a golf hole may be considered when adjusting the recommended loft angle. For example, the loft angle may decrease by one degree for a fast putting green whereas the loft angle may increase by one degree for a slow putting green. The loft angle may not be adjusted for a medium speed putting green. The advanced fitting display 2642 may also provide the individual to capture or practice putts with the recommend putter 2632 by selecting a putt capture or practice area 2660 on the GUI 1114. The systems, methods, and articles of manufacture described herein are not limited in this regard.

The process 2600 may also recommend one or more adjustments to a golf club based on the at least one stroke characteristic of the individual (block 2604). For example, a golf club that may already be in use by an individual may be modified to adjust the length, loft and/or lie of the golf club to better fit the individual.

Figure 96:
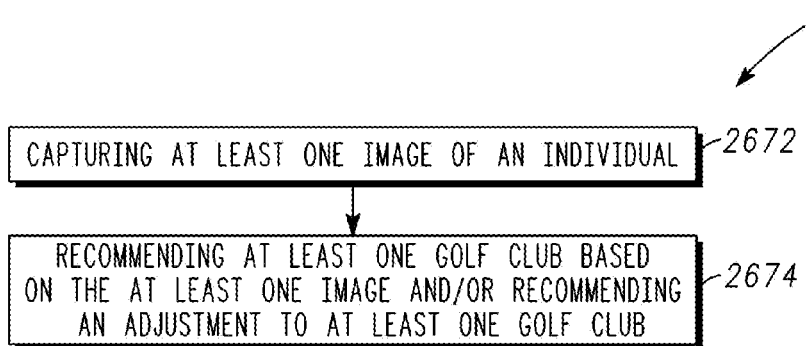
FIGS. 96-101 depict block diagram representations of processes associated with the systems, methods, and articles of manufacture according to the disclosure.

FIG. 96 illustrates a process 2670 for fitting one or more golf clubs for an individual based on one or more photos of the individual. The process 2670 includes capturing at least one image of an individual (block 2672), and recommending at least one golf club based on the at least one captured photo of the individual and/or recommending an adjustment to at least one golf club based on the at captured photo of the individual (block 2674).

According to one example, the process 2670 utilizes a camera of a portable electronic device, such as the portable electronic device 1000, to capture one or more images of an individual. The one or more captured images may be analyzed by the portable electronic device 1000 to determine the individual's stroke characteristics as described in detail herein, physical attributes (height and other bodily measurements) as shown in FIG. 94, and/or putting stance, such as upright, standard, or crouch as shown in FIG. 94. For example, the information shown in FIG. 94 may be determined by the portable electronic device 1000 according to one or more captured images of an individual. In another example, one or more captured images of an individual may be correlated with stroke characteristics and/or putting results of an individual as described in detail herein to recommend an appropriate golf club for the individual considering the individual's skill level. Further details of fitting one or more golf clubs to an individual based on capturing one or more images of the individual are provided in U.S. patent application Ser. No. 13/465,304, filed on May 7, 2012, the entire disclosure of which is incorporated herein by reference.

Figure 97:
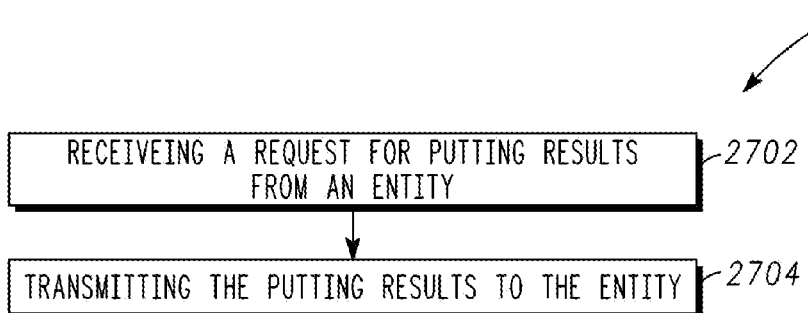

Referring to FIG. 97, a process 2700 for an individual to share his or her putting results, such as stroke characteristics, consistency scores, and/or putting handicap is shown. An individual, which may be referred to herein as a first individual, may receive a request from a second individual to share putting results (block 2702). The first individual may accept the request and transmit his or her putting results to the second individual (block 2704). The putting results may be transmitted directly from the portable electronic device of the first individual to the portable electronic device of the second individual by wired transmission, wireless transmission according to the disclosed wireless transmission standards, and/or any type of removable memory module. For example, two individuals who are playing golf may share their putting results with each other through their portable electronic devices via communication with Bluetooth® technology. Although an individual may request and/or receive putting results from another individual, the request for putting result may be from an entity. For example, an entity may be any individual, a group of individuals, or an organization. The entity may also be an electronic device, which may request putting results without any guidance or intervention from an individual. For example, an electronic device may be configured to request putting results from certain individuals at certain time intervals.

Figure 98:
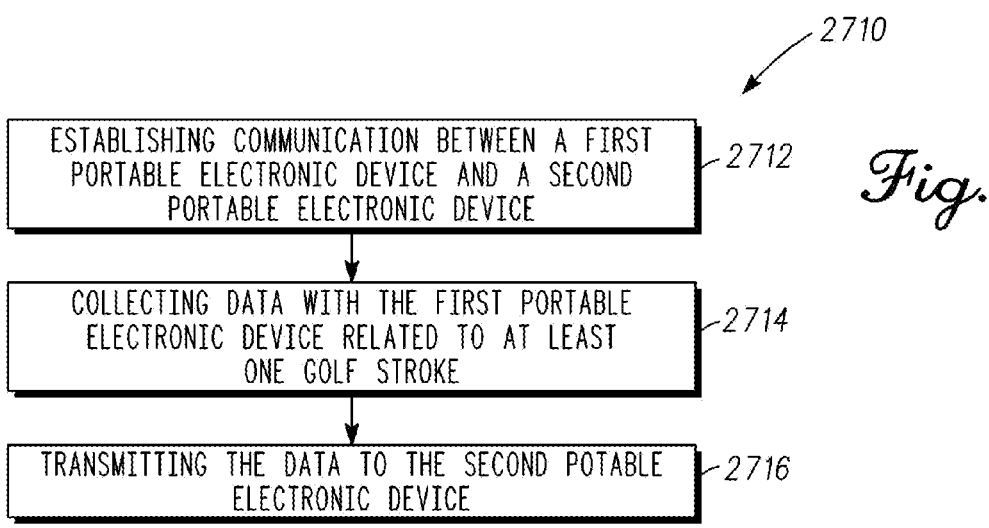

FIG. 98 shows a process 2710, which is a more detailed example of the process 2700. At least two individuals, who may be referred to herein as the first individual and the second individual, may wish to share putting results. The sharing of the putting results may be in real time or based on prior putting results. However, the process 2710 shows an example of real time sharing. The first individual may activate the software on a first portable electronic device. Similarly, the second individual may activate the software on a second portable electronic device. The process 2710 may include establishing communication between the first portable electronic device and the second portable electronic device (block 2712). To establish communication, each individual may select a communication/link feature (not shown) of the software of his or her portable electronic device to seek, select and establish communication with the other individual's portable electronic device. For example, upon selecting a communication/link feature (not shown) of the software, the first portable electronic device may display any Bluetooth® enabled device that is within sufficient proximity of the first portable electronic device for Bluetooth® communication. The first individual may then select the second portable electronic device to establish communication with the second portable electronic device.

Each of the first individual or the second individual may attach his or her portable electronic device to his or her golf club with a device holder. Each of the first individual or the second individual may perform at least one putting stroke. The at least one putting stroke may be performed according to a practice session and/or a measure session as described in detail above. Alternatively, the first individual may perform at least one putting stroke while the second individual only participates as an observer. If the second individual only participates as an observer, he or she may not have to attach his or her portable electronic device to his or her golf club. According to process 2710, the first individual performs at least one putting strokes. The first portable electronic device may then collect data related to the at least one putting stroke (block 2714) and transmit data related to the at least one putting stroke to the second portable electronic device (block 2716). The transmitted data may be raw data collected by the portable electronic device during the performance of the at least one putting strokes. Alternatively, the raw data collected by the first portable electronic device may be analyzed and the resulting stroke characteristics of the putting stroke may be transmitted to the second portable electronic device. The second portable electronic device may store the received data and/or display the received data on the GUI of the second portable electronic device. The received data may also be used by the second electronic device for comparison purposes as disclosed.

Figure 99:
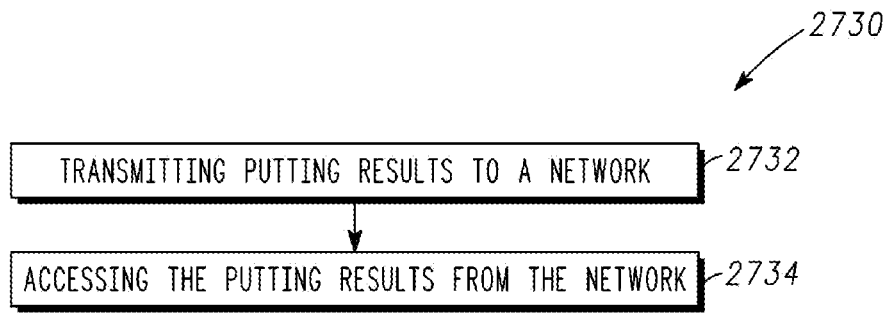

FIG. 99 shows a process 2730 for an individual to share his or her putting results with others via electronic mail, a posting on a social media network such as FACEBOOK® social networking service of Facebook, Inc., Palo Alto, Calif. or TWITTER® social networking service of Twitter, Inc., San Francisco, Calif., and/or any communication network to which one or more other individuals may have access. According to the process 2730, an individual may transmit his or her putting results to a network (block 2732). Referring back to FIG. 15, an example of a network 1150 is shown that may provide communication and data sharing between different network devices via the Internet 1164. After the individual transmits his or her putting results to the network 1150 via the Internet 1164, the putting results 1150 may be stored on the server 1152. The transmission of the putting results by the individual may be performed by the individual emailing the results to another individual or entity (e.g., a group of individuals, social group, organization or the like). The email message including the results may be received and stored on the server 1152 (e.g., an email server) and then transmitted from the server 1152 to one or more other entities. The transmission of the putting results by the individual may be performed by the individual uploading the results and/or any associated messages, comments, descriptions or the like to the server 1152, which may be a social media server, a game server, or the like to which other individuals or entities have access for sharing data. The transmission of putting results from any individual via his or her portable electronic device may be performed without the individual's control either in real time or at certain time intervals.

According to the process 2730, another individual, a plurality of individuals and/or one or more entities may access the individual's putting results from the network 1150 by communicating with the server 1152 via the Internet 1164 (block 2734). Accessing the results may be defined as viewing and/or downloading the results. Further, the individual who transmitted his or her results to the server 1152 may also access the results from the network 1150 if the individual no longer has the putting results stored on his or her portable electronic device.

Referring back to FIG. 52, comparing results of a measurement session of a first individual, which shown in FIG. 52 as Individual 1, with the results of a measurement session of another individual, which is shown in FIG. 52 as Individual 2, may require that Individual 1 have access to measurement session results for one or more certain putting sessions of Individual 2. According to processes 2700 and 2710, measurement session results for one or more putting sessions of individual 2 may be transmitted from the portable electronic device of Individual 2 to the portable electronic device of individual 1 upon Individual 1 requesting such results. According to process 2730, one or more measurement session results of Individual 2 may be downloaded by the portable electronic device of Individual 1 from a server, such as the server 1152, which may be an email server, a social networking server, a game server or any type of server that provides data to various electronic devices. Upon receiving certain measurement session results of Individual 2, the received measurement session results may be stored in the memory of the portable electronic device of Individual 1 for future use. The systems, methods, and articles of manufacture described herein are not limited in this regard.

Two or more individuals may share their putting and/or golf game results with each other in real time according to any of the processes 2700, 2710 and 2730. The sharing of results in real time may enable social gaming as described in detail below. Referring to FIG. 14, two or more individuals may share information in real time by the individuals' portable electronic devices directly communicating with each other. As shown in FIG. 98, the portable electronic device of two or more individuals may establish communication with each other as described in detail above (block 2712). The portable electronic devices of the two or more individuals can then transmit to each other in real time (block 2716) the information collected by the portable electronic device related to each individual's putting stroke and game play (block 2714).

Figure 100:
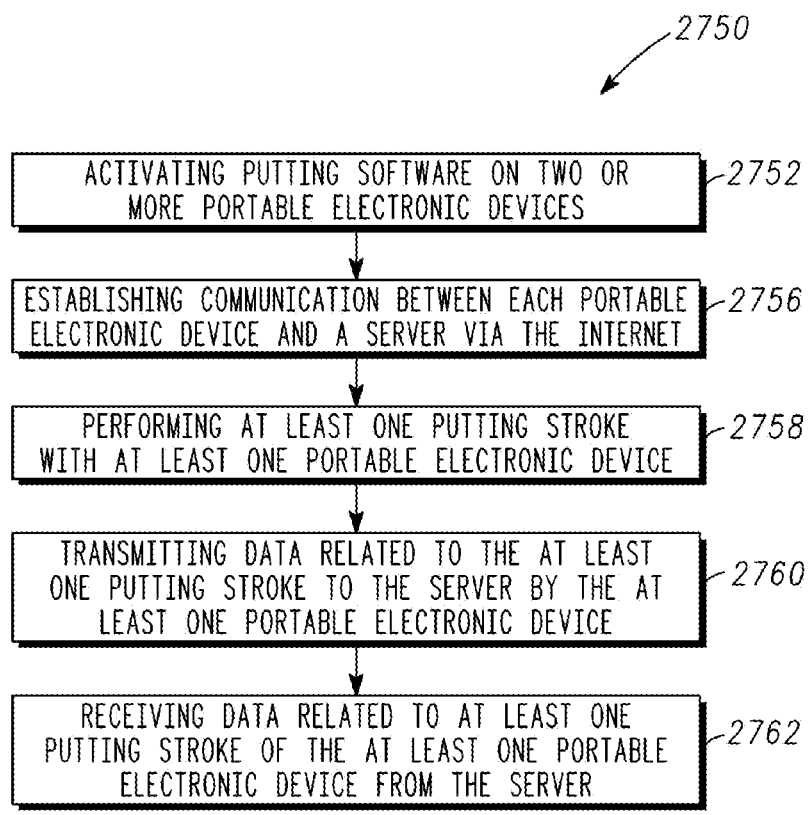

Two or more individuals may share information with each other in real time via the Internet by using a network server 1152, which may be a social media server, a game server, an email server, or any type of data server to which other individuals or entities may have access for sharing data. FIG. 100 shows in detail a process 2750 of sharing information in real time via the Internet. The process 2750 shows sharing of information between two portable electronic devices, namely a first portable electronic device and a second portable electronic device. However, the process 2750 is applicable to a large number of portable electronic devices (e.g., cell phones, smart phones, laptop computers, tablet computers, digital music players, watches etc.).

Each of the first portable electronic device and the second portable electronic device may execute the software (block 2752). If the first and second portable electronic devices are not connected to the Internet, then the first and second portable electronic devices may be connected to the Internet. For example, the first electronic device or the second electronic device may have a continuous connection to the Internet for email, messaging, voice, or other IP (Internet Protocol) applications. Each of the first and second portable electronic devices may establish connection with a server, through which data is shared (block 2756). Establishing a connection with a server may entail logging into an account provided on the server for a certain individual, organization, social group, gaming group, professional group or the like to provide an individual access to all or certain data stored on the server and associated with the account. Each of the first portable electronic device and/or the second portable electronic device may be attached to a putter with the device holder as disclosed. At least one of the portable electronic devices may then be used to perform one or more putting strokes (block 2758), which may be in a practice session or a measure session as described in detail above. Data related to the one or more putting strokes may be transmitted to the server and stored on the server in a data storage space associated with the individual operating the first portable electronic device. The data may be transmitted after each putting stroke or after a putting session (i.e., a plurality of putting strokes). For example, after each putting stroke, the data may be automatically transmitted to the server via the Internet. The data may be raw measurement data or data including results of one or more putting strokes as determined by the portable electronic devices, such as stroke characteristics, consistency scores, and/or putting handicap. The server may then transmit the data to the second portable electronic device (block 2760). The second portable electronic device may then receive (block 2762), store, analyze, compare and/or display the received data as disclosed herein.

Any information provided to an individual on the GUI 1114 of the portable electronic device 1000 may be shared by the individual with the general public or select individuals. For example, stroke characteristics of an individual and/or the club fitting results for an individual may be shared. An individual may directly share with another electronic device or upload information about his or her practice session, measure session, compare session, result based practice session (i.e., by which miss tendencies may be determined), club fitting session, and/or competition with others session to a server, which may be a social media server, a game server, an email server, or any type of data server to which other individuals or entities may have access for sharing data. The sharing of information, which may be direct sharing with another electronic device or sharing with others via a server, may be performed by an individual selecting a share icon 63 during a practice session, a measure session, a compare session, a result based practice session, a club fitting session, and/or a competition with others session. The share icon 63 may be shown on the GUI 1114 so as to be selectable by an individual. For example, the share icon 63 is shown is FIGS. 44 and 47. By activating the share icon 63, the results of the corresponding session may be shared with others either directly or via a server as described in detail herein.

Two or more local and/or remotely located users may engage in competition by sharing stroke characteristics, consistency scores, putting handicap, and/or result oriented performance data as described in detail above. According to one example, a competition between two or more individuals may be in the form of a skins game, which is a type of scoring for golf, where players compete for prize money on each individual hole. Each hole is assigned certain point value or prize money. To get the points or prize money for a hole, the player with the best score wins the hole. If two or more players tie (e.g., halving) on a hole, the points may be carried over to the next hole. The player who accumulates the most points or prize money is the winner of the skins game.

Figure 101:
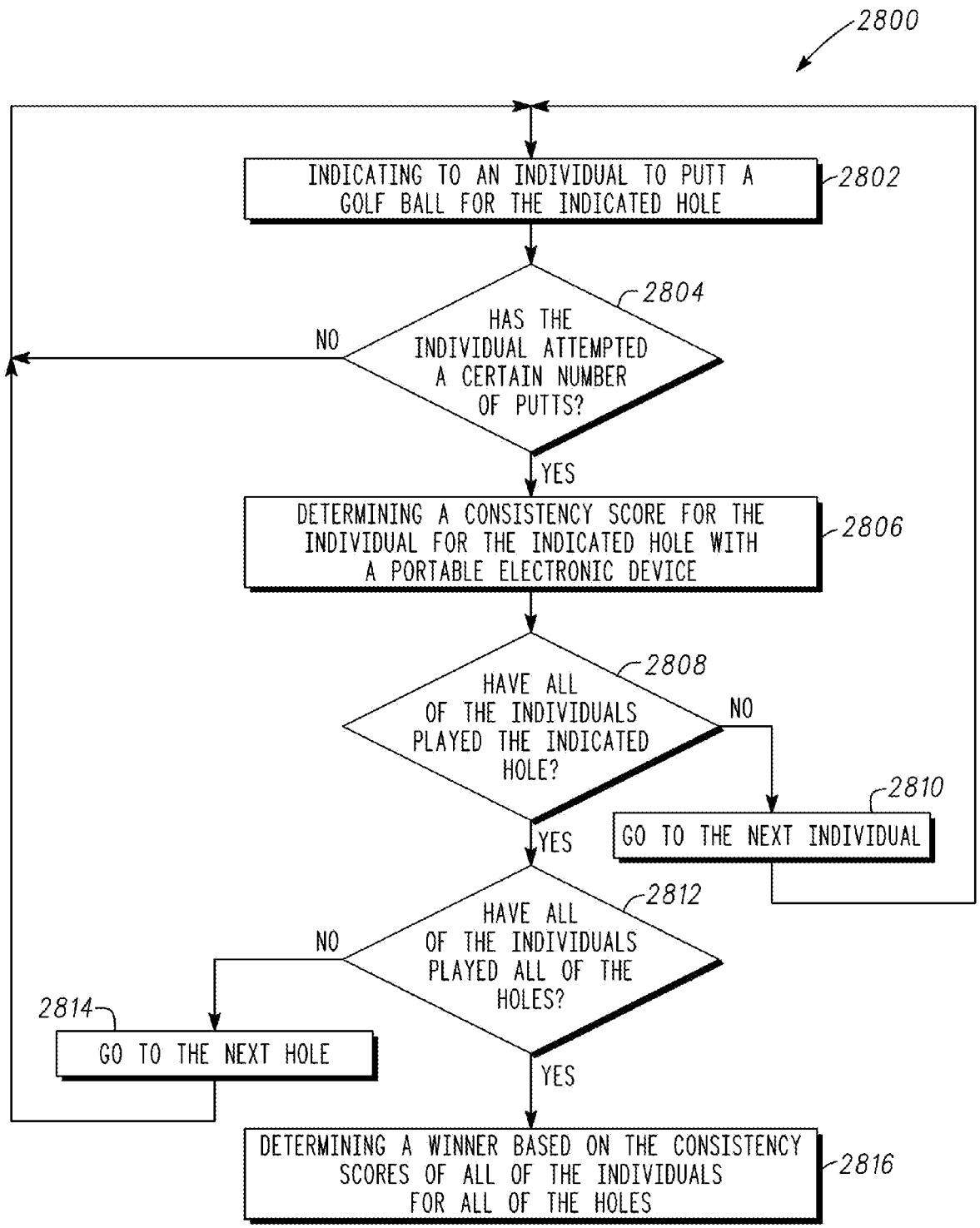

Referring to FIG. 101, a process 2800 for local and/or remotely located individuals to engage in a skins game is shown. The process 2800 may determine a winner based on the consistency scores of the individuals participating in the game for each hole. The skins game may be played for one or more holes. The process 2800 includes indicating to one individual among several participating individuals to attempt a certain number of putts for an indicated hole (blocks 2802 and 2804). The individual's consistency score is then determined by a portable electronic device as described in detail above (block 2806). If all of the individuals who are participating in the skins game haven not played the indicated hole (block 2808), then the process of playing the first hole is repeated for all participating individuals. Accordingly, the next participating individual plays the first hole (block 2810 and block 2802). The process 2800 then checks whether or not all of the participating individuals have played all of the holes (block 2812). For example, if the first hole has been played by all of the participating individuals, then the participating individuals should play the next hole or the second hole. Accordingly, the next hole is played by all of the participating individuals. Thus, if all of the participating individuals have not played all of the holes, the process of playing each hole is repeated as described above (block 2814 and block 2802). However, if all of the participating individuals have played all of the holes, a winner of the skins game is determined based on the consistency scores of all of the participating individuals for all of the holes (block 2816). Further detail of the process 2800 and the operation of a portable electronic device 1000 when performing the process 2800 is described below.

Figure 103:
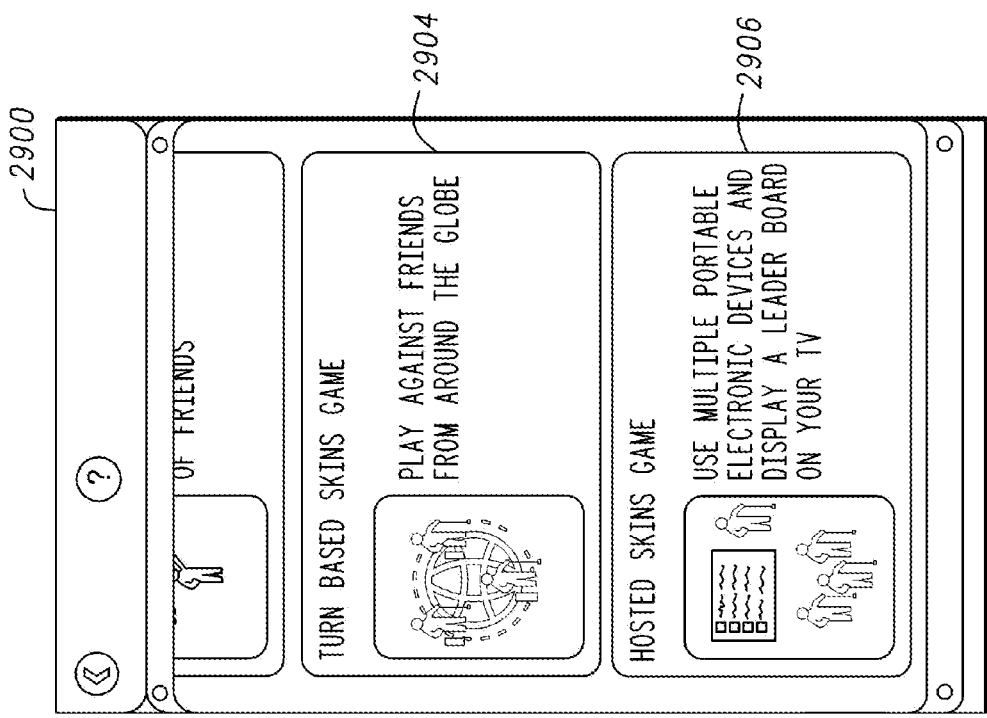
FIGS. 102-103 depict visual diagram representations of example displays according to the disclosure.
Figure 102:
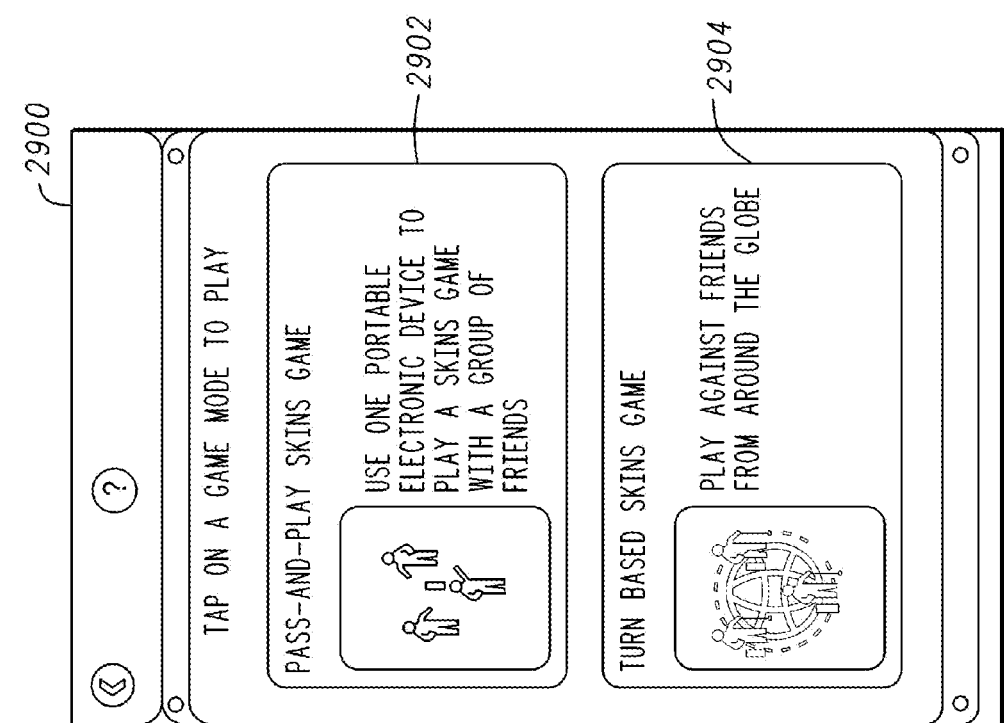

Referring back to FIG. 58, an individual may select the Skins Game option 1906 to start a skins game. Upon selecting the Skins Game option 1906, the GUI 1114 of the portable electronic device 1000 displays the game selection menu 2900 shown in FIGS. 102 and 103. The game selection menu 2900 shown in FIG. 103 is a continuation of the game selection menu 2900 of FIG. 102 and can be viewed by scrolling down the game selection menu 2900 of FIG. 102. The game selection menu 2900 includes a Pass-And-Play option 2902, a Turn Based option 2904 and a Hosted option 2906, all of which relate to different procedures by which local or remotely located individuals may participate in a skins game. The Pass-And-Play option 2902 allows several local individuals to play a skins game with a single portable electronic device. Accordingly, a single portable electronic device is passed from one individual to another during game play based on each individual's turn at playing the game. The Turn-Based option 2904 allows several local or remotely located individuals to play one or more skins games by communicating through a network. The Hosted option 2906 allows several local or remotely located individuals to play one or more skins game and display the results in a leader board on a large display device such as a television or a large display monitor. The process 2800 and the operation of a portable electronic device 1000 when each of options in the game selection menu 2900 is selected are described in detail below.

Figure 104:
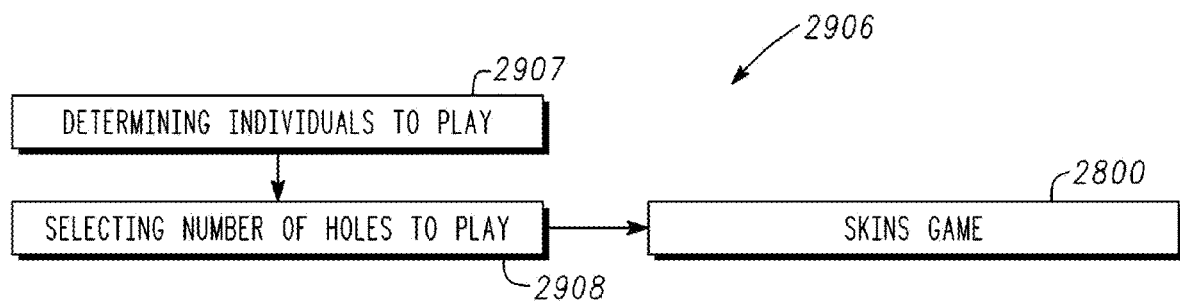
FIG. 104 depicts a block diagram representation of a process associated with the systems, methods, and articles of manufacture described herein.

An individual can select the Pass-And-Play option 2902. According to process 2906 shown in FIG. 104, after the individuals who may be participating in the skins game are determined (block 2907), the number of holes to play may be determined (block 2908). The participating individuals may then play a skins game according to the process 2800 and as described in detail below.

Figure 105:
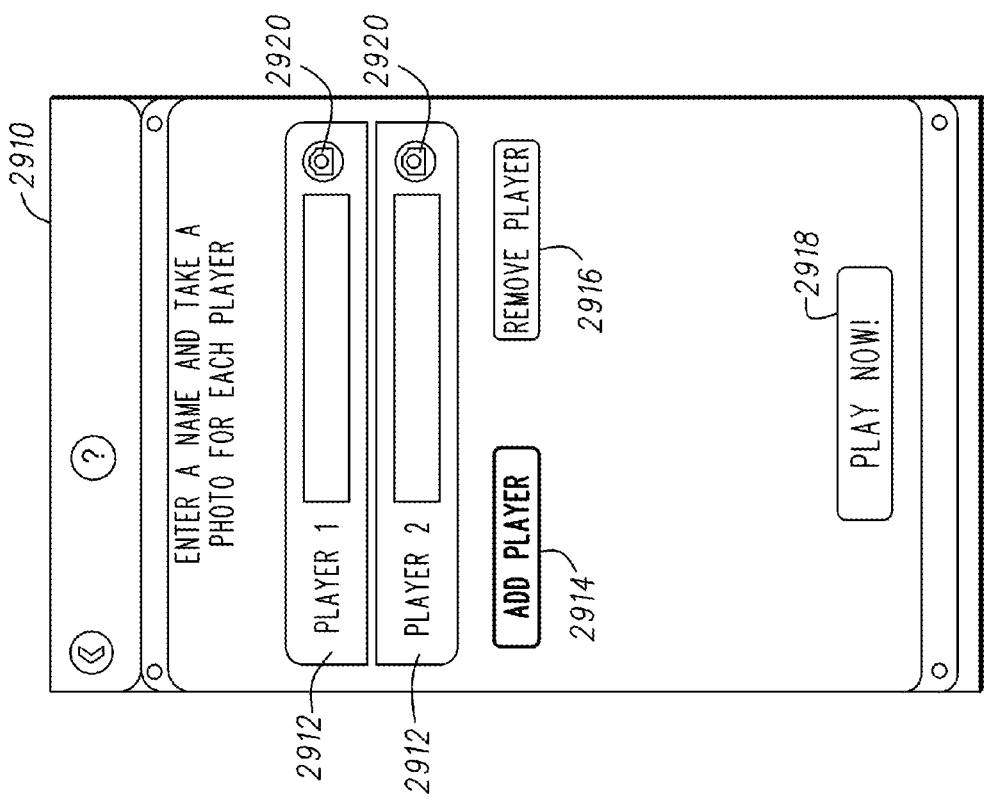

Referring to FIG. 105, after selecting the Pass-And-Play option 2902, the portable electronic device 1000 displays the player menu 2910 from which the individuals who may be participating in the skins game may be determined (block 2906). The player menu 2910 includes player entry windows 2912, an add player icon 2914, a remove player icon 2916, and a play icon 2918. A first individual, who may be referred to herein as Individual 1, can enter his or her name in the "Player 1" player entry window 2912. The first individual may also have the option of providing his photograph by using the photo entry icon 2920. A second individual, who may be referred to herein as Individual 2, can enter his or her name in the "Player 2" player entry window 2912. The second individual may also have the option of providing his photograph by using the photo entry icon 2920. To add more players, the add player icon 2914 can be selected, by which additional player entry windows 2912 may be provided on the player menu 2910 so that additional individuals can enter their names and/or photographs. To remove a player, the remove player icon 2916 may be used. After entry of players' names is finished, one of the individuals can select the play icon 2918, which in FIG. 93 is shown to display "Play Now!"

Figure 106:
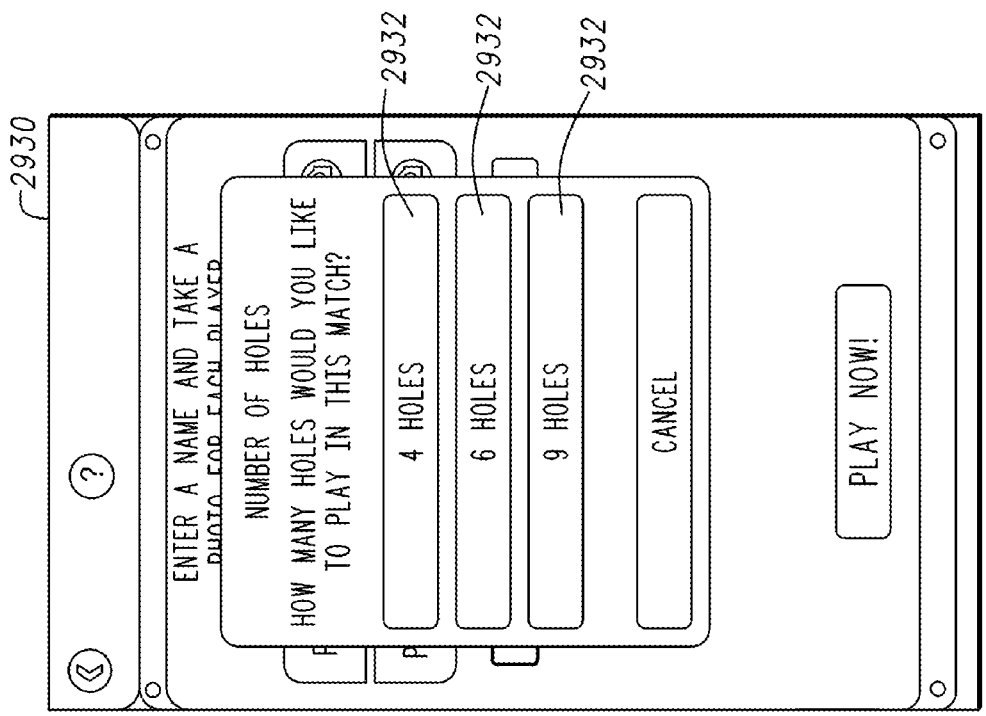
FIGS. 105-112 depict visual diagram representations of example displays according to the disclosure.

The number of holes to play may be selectable by one or more individuals playing a skins game. Referring to FIG. 106, the portable electronic device 1000 may display an option for selecting the number of holes to play after an individual selects the play icon 2918 (block 2908). According to the exemplary hole selection display 2930, the GUI 1114 of the portable electronic device may provide several hole selection icons 2932, where each icon corresponds to a certain number of holes. In the example of FIG. 106, the hole selection display 2930 shows three hole selection icons 2932 corresponding to 4 holes, 6 holes and 9 holes. Alternatively, the portable electronic device 1000 may provide an entry window so that an individual can manually enter the number of holes to play.

Figure 107:
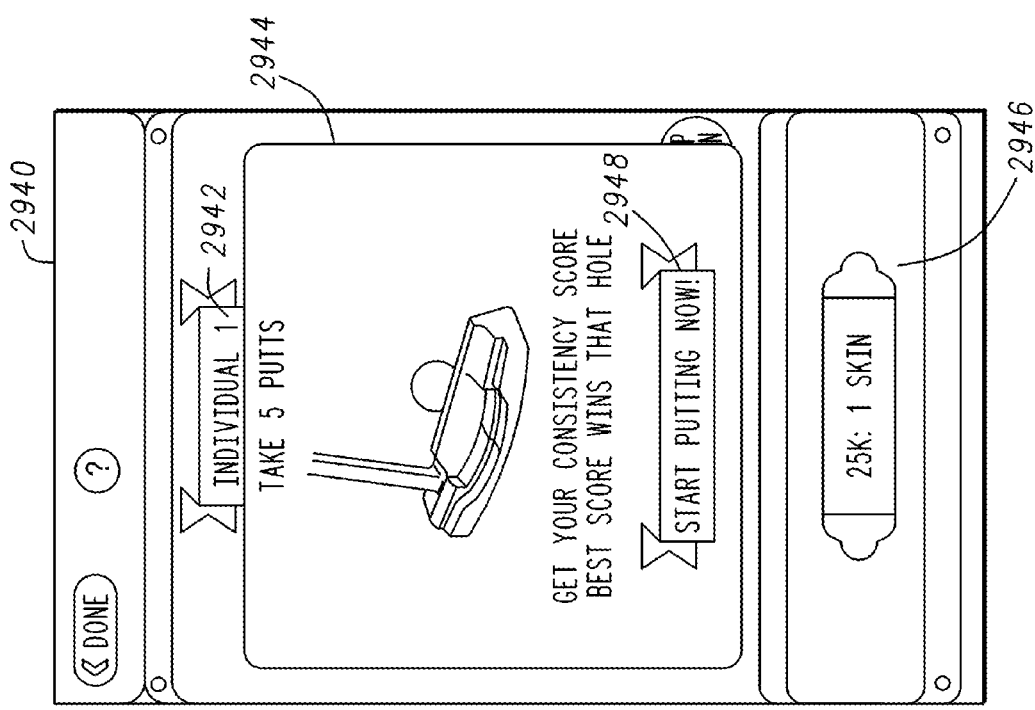

After selecting the number of holes to play, the portable electronic device 1000 may display a game start display 2940 as shown in FIG. 107. The game start display 2940 may represent the start of the process 2800 (block 2802). The game start display 2940 may include an individual identification display 2942, an instruction window 2944 and a skins point value window 2946 by which information about the skins game is provided. As shown in FIG. 107, the individual identification display 2942 may identify the individual who should play next or whose turn as arrived. The individual identification display 2942 may display the name of the first individual to play, which is shown for example to be Individual 1. The instruction window 2944 may provide general instructions to an individual about the game. In the example of FIG. 107, an individual is instructed to take 5 putts so that the individual's consistency score can be determined as discussed in detail above. Accordingly, each individual may be instructed to perform a measure session as described in detail herein. The instruction window 2944 may also display a start icon 2948, selection of which starts the skins game. The skins value window 2946 may specify information about the values of the holes in the skins game. For example, FIG. 107 shows the skin value of the first hole to be 25000 or 1 skin.

Figure 108:
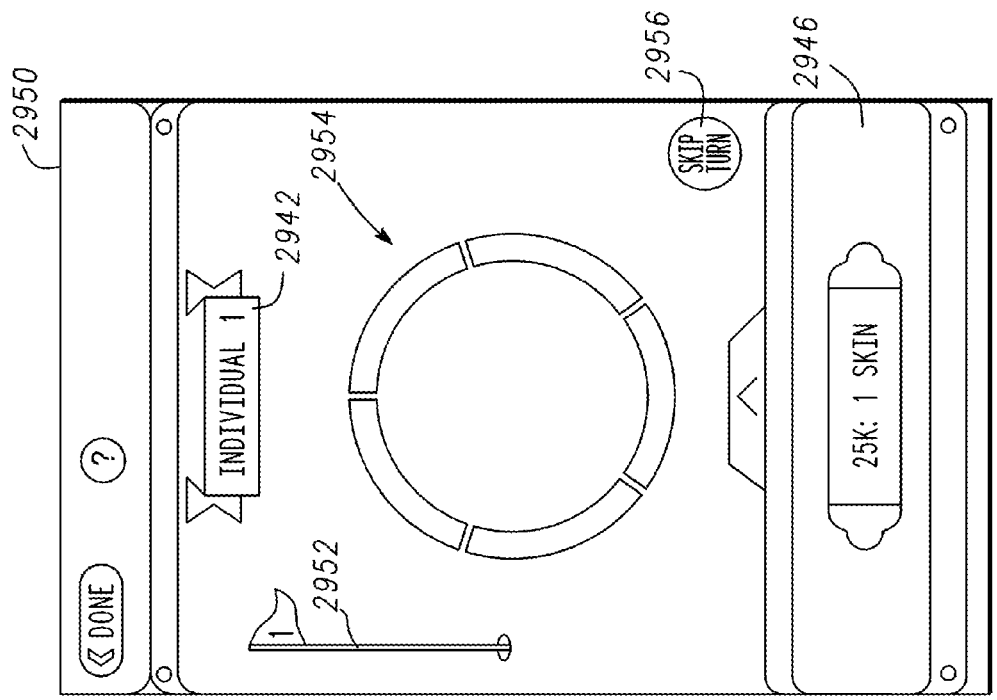

FIG. 108 shows a play display 2950 that is displayed after the start icon 2948 is selected. The play display 2950 may include a hole indicator 2952 and a counter display 2954. The hole indicator 2952 indicates the hole that is being currently played. The hole indicator 2952 may visually resemble a hole with a flagstick inserted therein as shown in the example of FIG. 108. The counter display 2954 is similar to the count display 1650 of FIGS. 45 and 46, hence a detailed description thereof is not provided herein. The counter display 2954 may show the number of putts completed and the number of putts remaining in numeric and/or graphical manner. The play display 2950 may also include the individual identification display 2942 and the skins value window 2946. An individual may be allowed to skip his or her turn in the skins game. Accordingly, the play display 2950 may also include a skip turn icon 2956, by which an individual can skip his or her turn in the game.

Figure 110:
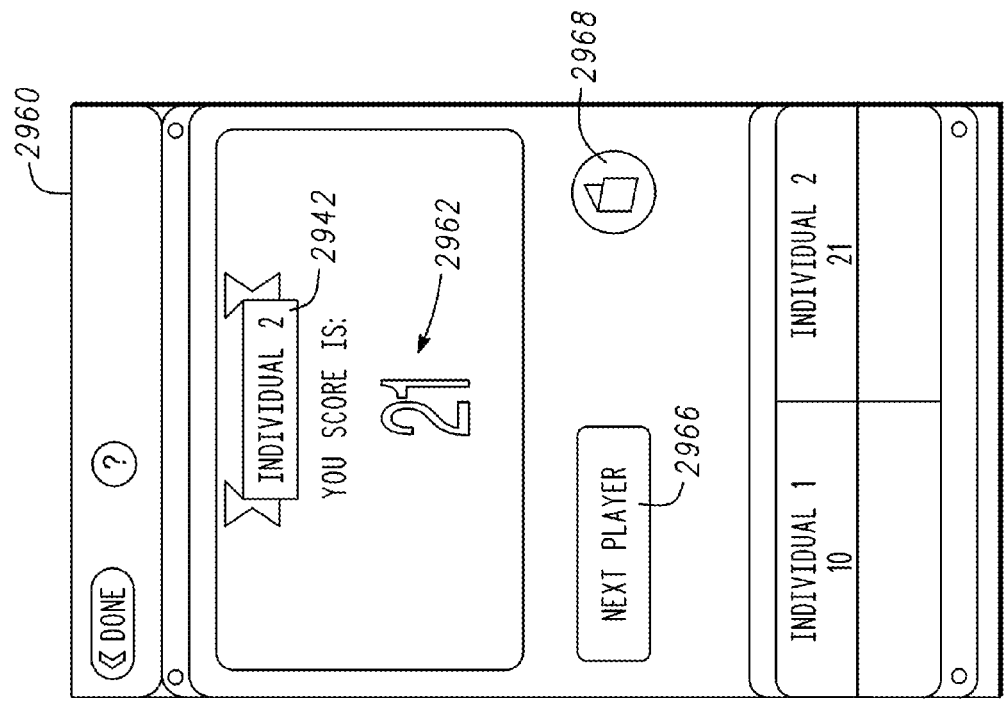
Figure 109:
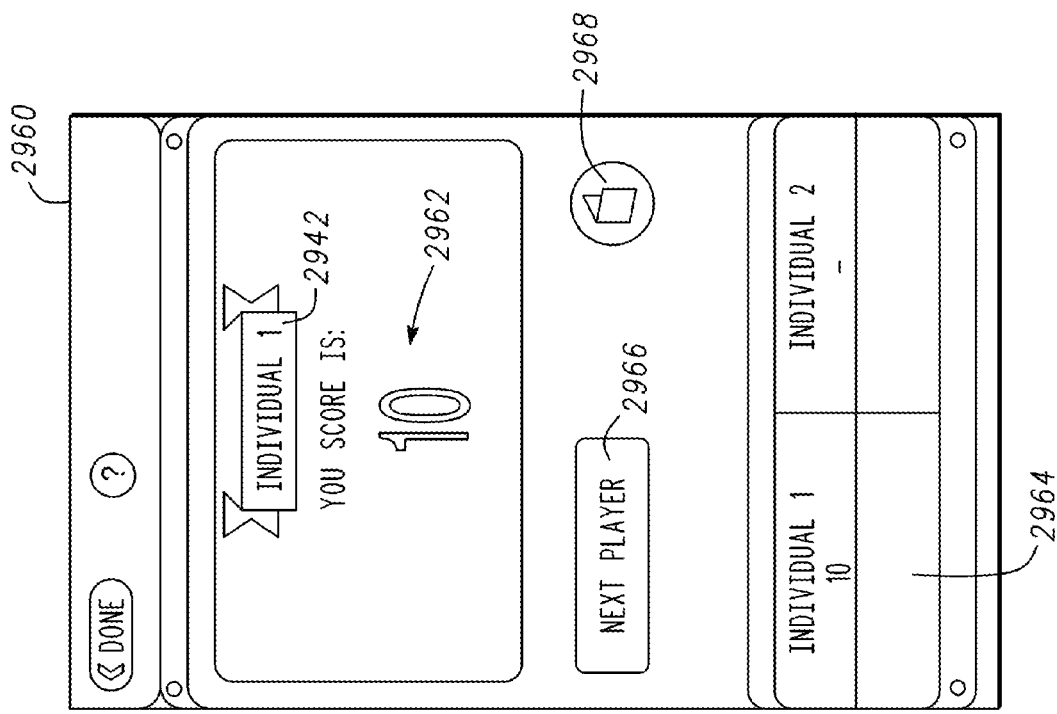

Referring to FIGS. 109 and 110, an individual results display 2960 is displayed on the GUI 1114 of the portable electronic device 1000 after an individual performs a measure session, e.g., attempting 5 putts. FIG. 109 shows an example of the individual results display 2960 for Individual 1. After the first individual, e.g., individual 1, performs a measure session, he or she passes the portable electronic device 1000 to the second individual, e.g., individual 2, to perform a measure session as described in detail above. Individual 1 and individual 2 may choose to play with the same golf club. Accordingly, individual 1 can pass his golf club including the portable electronic device 1000 attached thereto to individual 2 to perform his or her measure session. FIG. 110 shows an example of the individual results display 2960 for Individual 2. The individual results display 2960 may include an individual identification display 2942, a score display 2962 and a results table display 2964. The score display 2962 displays the consistency score of an individual after a measure session. The results table display 2964 shows the current results for all individuals in tabular format. The individual results display 2960 further includes a next player icon 2966. After an individual views his or her results on the individual results display 2960, the next individual can select the next player icon 2966 to play his or her turn. The individual results display 2960 may also include an overall results icon 2968, selection of which displays the current overall results of the skins game in tabular form (see for example FIG. 100).

Figure 111:
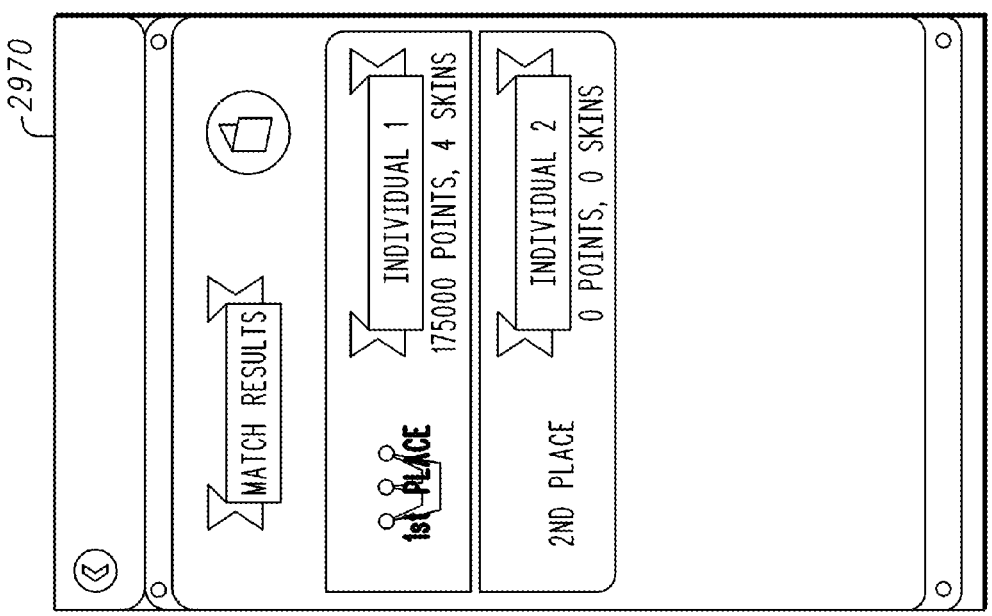

Referring to FIG. 111, a match results display 2970 may be displayed after all of the players have performed measure sessions for all of the holes. The match results display 2970 may show the points and skins achieved by each participating individual and the placement of each participating individual (i.e., 1st place, 2nd place, etc.). The match results display 2970 may also include the overall results icon 2968, selection of which displays the overall results of the match in tabular form as shown by the score card display 2980 of FIG. 112. The scorecard display 2980 includes a results table 2982 having each row represent one of the holes played in the skins game and each column corresponding to one of the players who participated in the skins game. The last row in the results table 2982 may display the overall points and skins achieved by each participating player.

Figure 113:
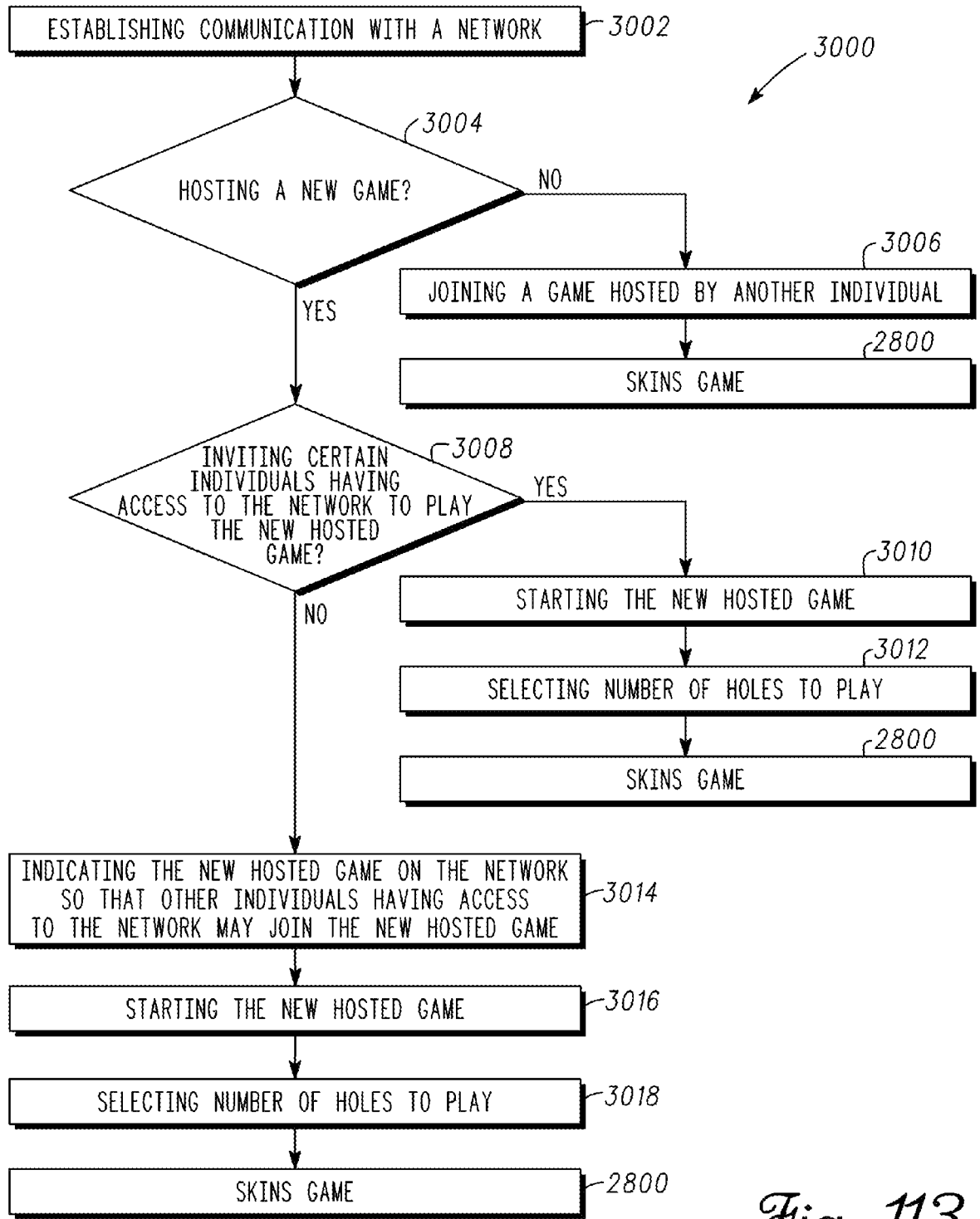
FIG. 113 depicts a block diagram representation of a process associated with the systems, methods, and articles of manufacture according to the disclosure.

Selecting the Turn Based option 2904 allows several local or remotely located individuals to play one or more skins games through a network. FIG. 113 shows an exemplary process 3000 by which several individuals can play a skins game through a network. The process 3000 includes an individual establishing communication with a network (block 3002). To establish communication with a network, an individual may for example be required to login to a network server via the Internet. The network server may be a social media server, a game server, or the like to which other individuals or entities have access for sharing data. For example, the network server may be Apple's Game Center network from Apple Inc., Cupertino, Calif. After establishing communication with the network, the individual may choose to join a skins game that is hosted (i.e., has already been started) by another individual who has access to the network (blocks 3004 and 3006). Accordingly, the individual can play the skins game that is hosted by another individual (block 2800).

The individual may choose, however, to host a new skins game (block 3004). The individual may invite certain other individuals to join in the new hosted skins game (block 3008). The certain other individuals may be friends, family members, or others with whom the individual is familiar. As discussed in detail below, the individual can send invitations to others through the network to play the new hosted game (block 3008). The individual can then start the new hosted game (block 3010). Because the individual is the host of the game, he or she may be required to select the number of holes to play (block 3012) or specify other parameters of the game. The individual can then play the new hosted skins game as described in detail above with respect to process 2800 (block 2800).

Instead of inviting certain other individuals to play a new hosted skins game, the individual may choose to have other individuals who have access to the network and wish to play a skins game to join in the game. In other words, the individual hosting the new game may be automatically matched up with other individuals who wish to play the new hosted game. As discussed in detail below, an indication may be provided on the network that a new hosted game is available so that other individuals may be notified of the indication and choose to join the new hosted game (block 3014). The individual can then start the new hosted game (block 3016). Because the individual is the host of the game, he or she may be required to select the number of holes to play (block 3018) or specify other parameters of the game. The individual can then play the new hosted skins game as described in detail above with respect to process 2800 (block 2800).

Figure 114:
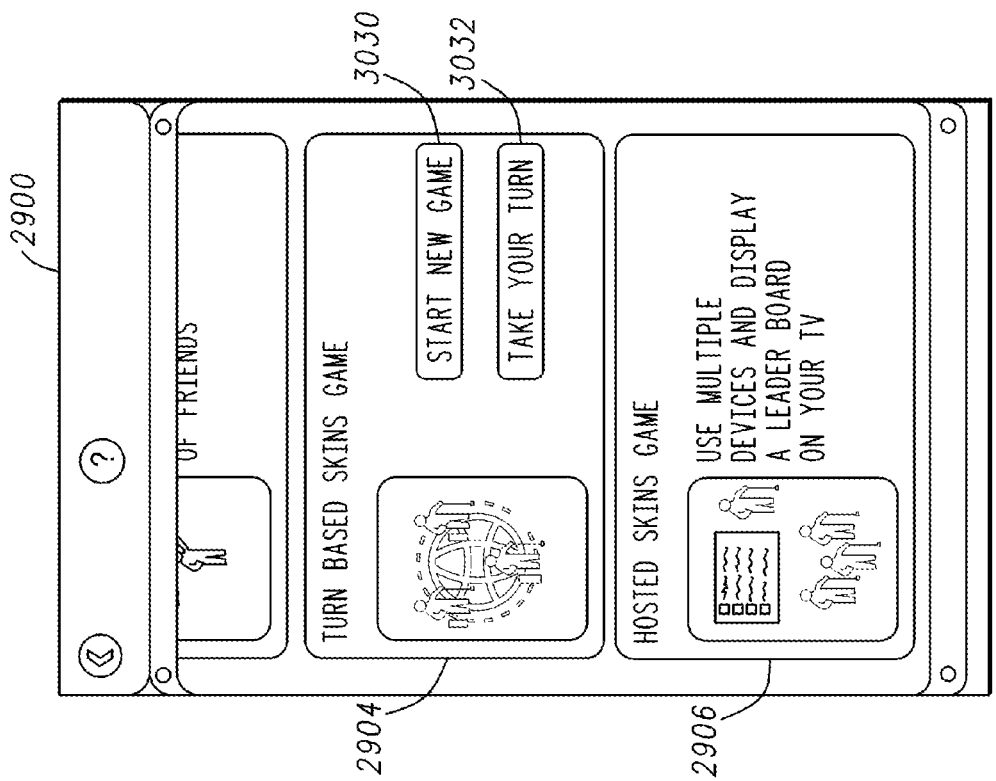

The processes 3000 (including the process 2800) and the operation of a portable electronic device 1000 when the Turn-Based option 2904 is selected are described in detail below. Referring to FIG. 114, when the Turn-Based option 2904 is selected, a new game icon 3030 is displayed, by which the individual may host a new game. Additionally, an existing game icon 3032 is displayed, by which the individual may join a new game that is hosted by another individual. The existing game icon 3032 is shown in FIG. 114 to display "Take Your Turn", which is indicating to an individual to take his or her turn in a new game that is hosted by another individual.

Figure 115:
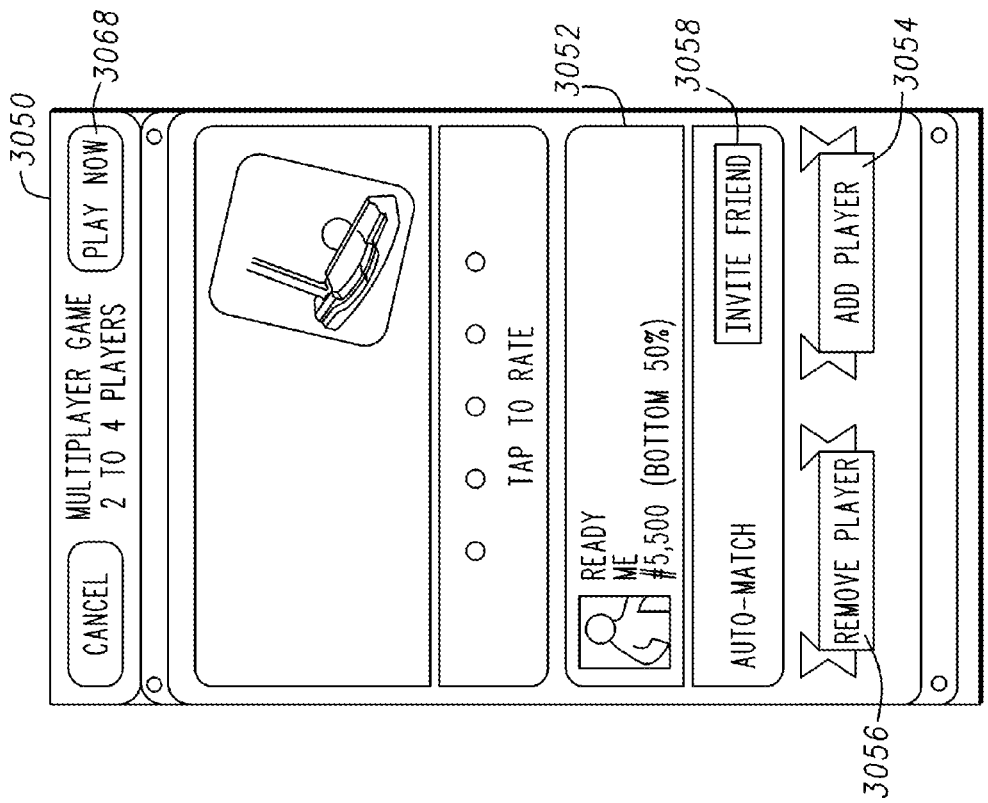

When an individual selects the new game icon 3030, a new game display 3050 is displayed on the portable electronic device 1000 as shown in FIG. 115. The new game display 3050 includes a player identification window 3052, which shows the identification of the individual using the portable electronic device 1000 and who is hosting the new game. The identification may refer to the individual by name, email address, nickname, network username or user identification, or any text, numbers and/or symbols. In the example of FIG. 115, the individual is identified as "Me". Additionally the player identification window 3052 may show each player's ranking among all other local and/or remotely located participants based on previously played matches. In the example of FIG. 115, the player identified as "Me" is shown to have a ranking of "#5,560 (Bottom 50%)." The individual may wish to add one or more players with an add player icon 3054 or remove one or more players with a remove player icon 3056.

Figure 117:
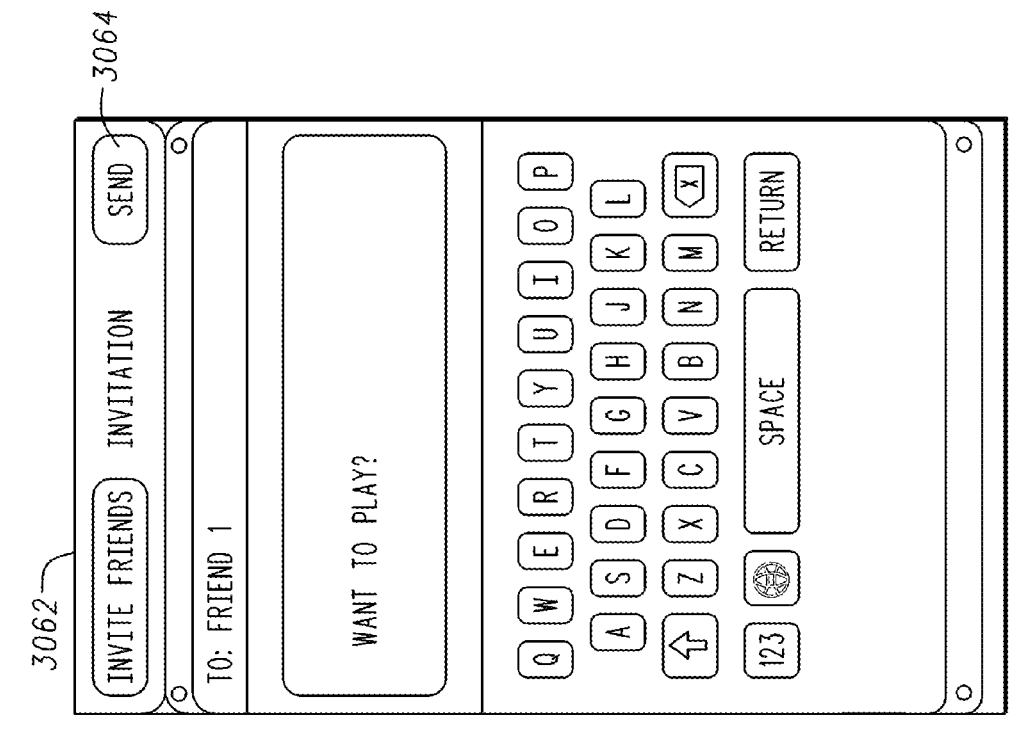
Figure 116:
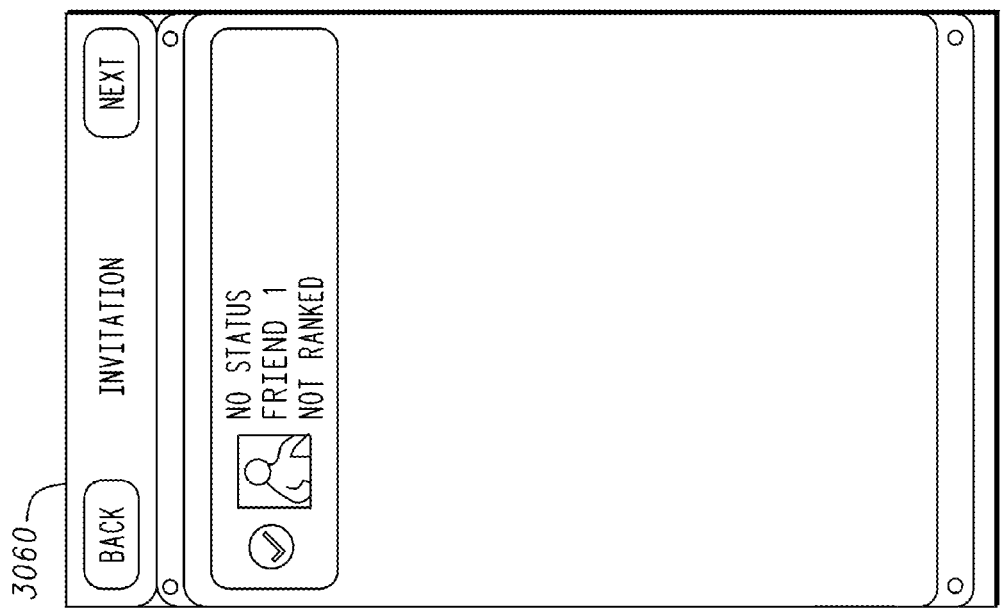
Figure 118:
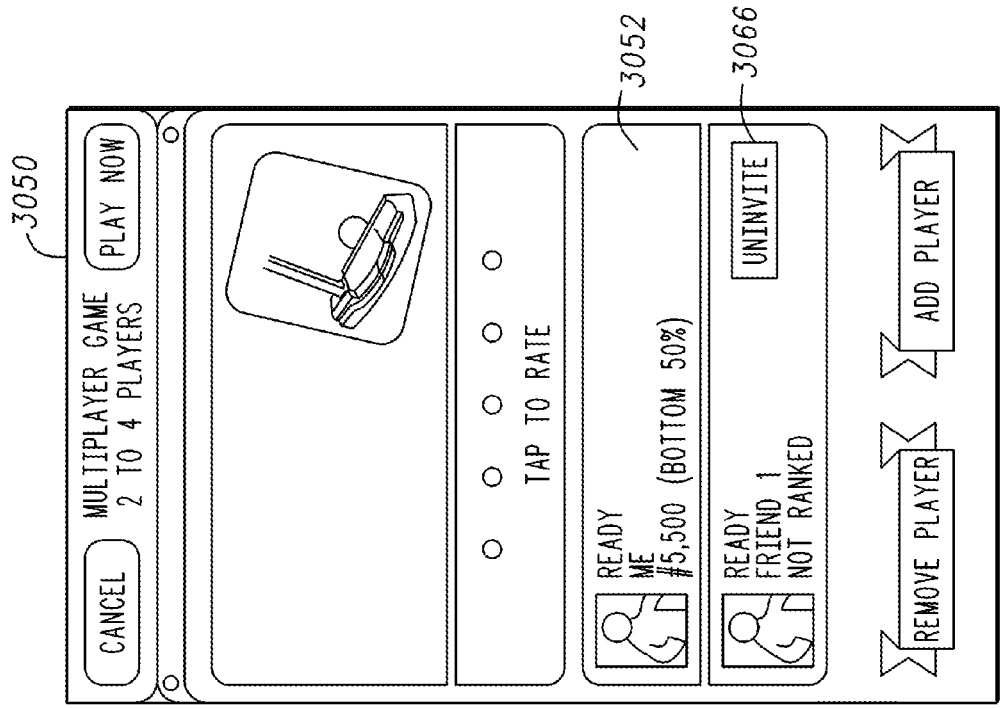

As shown in the player identification window 3052, the individual who hosts a new game may either choose to be automatically matched up with other local or remotely located players through the network or invite friends to play by selecting the Invite Friend icon 3058. Referring to FIG. 116, after the individual selects the Invite Friend icon 3058, a list of the individual's friends who have access to the network may be displayed in one or more friend windows 3060. The individual can select one or more friends from the list to invite to play the skins game by selecting the corresponding friend windows 3060. As shown in the example of FIG. 116, selecting each friend may be accomplished by touching the display of the corresponding friend window 3060, which may cause a check mark confirming the selection to appear in each friend window 3060. Alternatively, the friend window may be highlighted, changed to show different colors, displayed with different text, or changed as compared to unselected friend windows 3060 to visually convey to the individual which friends have been selected. Upon selecting one or more friends, the individual may send an invitation to each selected friend to join the new hosted game as shown by the message window 3062 shown by example in FIG. 117. Upon sending a message such as "want to play a skins game?" by selecting a send icon 3064, the individual is returned to the new game display 3050 as shown in FIG. 118. However, the new game display 3050 of FIG. 118 may now display the name of the one or more friends who have been invited to play the new hosted game. The individual may have the option of uninviting one or more of his or her invited friends by selecting the un-invite icon 3066. The individual may also wish to add players by using the add player icon 3054 or remove players by using the remove player icon 3056. For example, the individual can select the add player icon 3054 so as to invite another friend to play the game.

Figure 112:
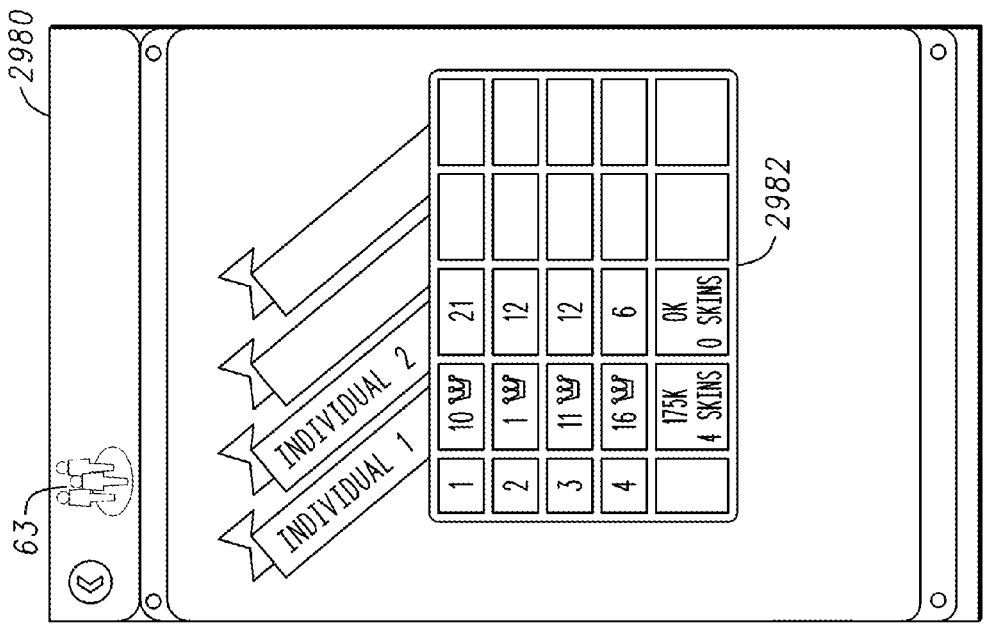
Figure 119:
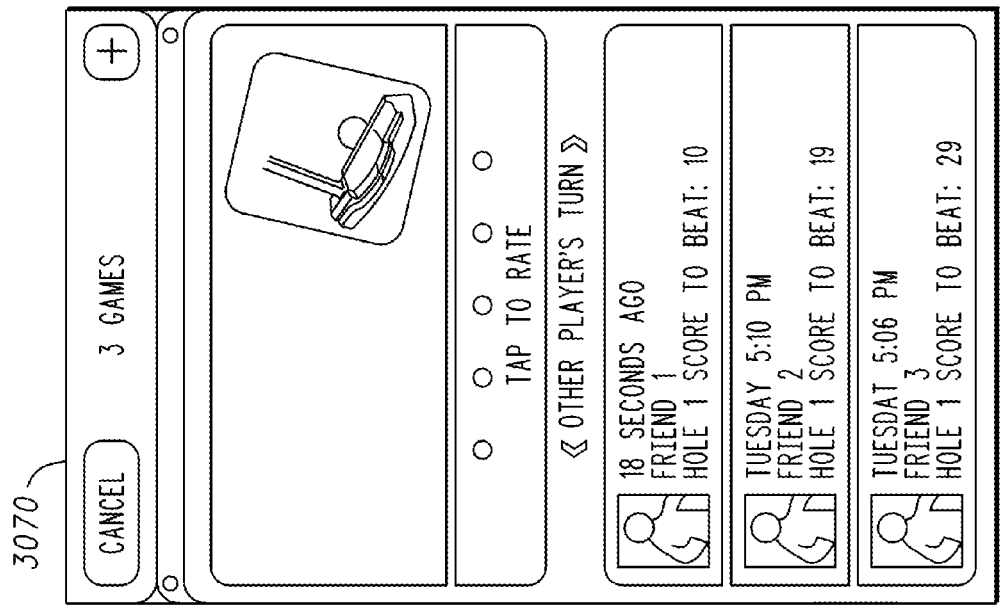

After inviting one or more friends to play the new hosted game, the individual can start the game by selecting the play now icon 3068. The individual may be presented with a hole selection display 2930 as shown in FIG. 106. After selecting the number of holes to play, the individual may attempt a certain number of putts for the first hole as disclosed according to the process 2800 and with respect to FIGS. 107-109. After the individual plays the first hole, his or her results, e.g., a consistency score, may be displayed on the portable electronic device 1000 as shown in FIG. 109 and also transmitted to the network by the portable electronic device 1000. The individual may then have to wait for the one or more invited friends to play their turn. Accordingly, as shown in FIG. 119, the portable electronic device 1000 of the first individual displays a game display 3070, which may show that one of the invited friends should take his or her turn. The portable electronic device 1000 may send a notification through the network to one or more individuals whose turns have arrived to take their turns in playing the game. The notification may be in the form of visual and/or audible messages. For example, when an individual's turn has arrived, the individual may be notified by email, text, SMS (short message service), and/or any type of audio and/or visual notification. Each individual playing the game may then take his or her turn according to the process 2800 until all of the holes have been played by all of the individuals so that a winner of the game may be determined. After a winner is determined according to the process 2800, a match results display 2970 as shown in FIG. 111 may be displayed. The match results display 2970 may show the points and skin values achieved by each participating individual and the placement of each participating individual (i.e., 1st place, 2nd place, etc.). Furthermore, a scorecard display 2980 as shown in FIG. 112 and disclosed herein may be displayed to all of the participating individuals.

Instead of inviting one or more friends to play, the individual can allow other individuals on the network to join the new hosted game. Referring back to FIG. 115, to play with other individuals who have access to the network, the individual (i.e., Me) can select the play now icon 3068 to start a new game without selecting any friends to play. Accordingly, the individual is Auto-Matched with remotely located individuals. The individual may be matched with any other individual regardless of the players' skill level. Alternatively, the individual may be matched with another individual based on his or her skills, such as consistency scores and/or PHcp. The individual may be presented with a hole selection display 2930 as shown in FIG. 94. After selecting the number of holes to play, the individual may perform a measure session as disclosed according to the process 2800 and FIGS. 107-109. After the individual plays the first hole, his or her results, e.g., a consistency score, may be displayed on the portable electronic device 1000 as shown in FIG. 109 and also transmitted to the network by the portable electronic device 1000. The individual may then have to wait for one or more individuals who have access to the network to join the game. Another individual may join the game and compete with the first individual as described in detail below.

As described above, an individual can host a new game, i.e., start a new game and play with friends or others who may join the game through the network. However, an individual may choose to join a game that is hosted by another individual. Referring back to FIG. 114, an individual may choose the take your turn icon 3032 to join a game that is hosted by another individual. After selecting the take your turn icon 3032, a game display 3072 may be displayed on the portable electronic device 1000 as shown in FIG. 120. The games display 3072 may show games that have been started by another individual, who has performed a measure session for the first hole, is waiting for others to join so as to also perform a measure session for the first hole, and to play the game according to the process 2800 and FIGS. 107-109. As shown in the example of FIG. 120, the game display 3072 may show several game windows 3074 that represent several hosted games that may be available for an individual to join. In the example of FIG. 120, the games that may be joined are identified by the identifications of the individuals who have hosted the games. For example, FIG. 120 shows the individuals hosting new games to be Player 1, Player 2 and Player 3. Each corresponding game window 3074 may include the time when the individual who started the game played the first hole and the consistency score of the individual for the first hole. An individual may join a game by selecting one of the game windows 3074 and then selecting play now icon 3068, after which he or she may perform a measure session for the current hole as disclosed. The game may continue according to the process 2800 and FIGS. 107-109 until all of the players have performed measure sessions for all of the holes. A winner is then determined according to process 2800. After a winner is determined, a match results display 2970 as shown in FIG. 111 may be displayed. The match results display 2970 may show the points and skins achieved by each participating individual and the placement of each participating individual (i.e., 1st place, 2nd place, etc.). Furthermore, a scorecard display 2980 as shown in FIG. 112 and disclosed herein may be displayed to all of the participating individuals.

Figure 121:
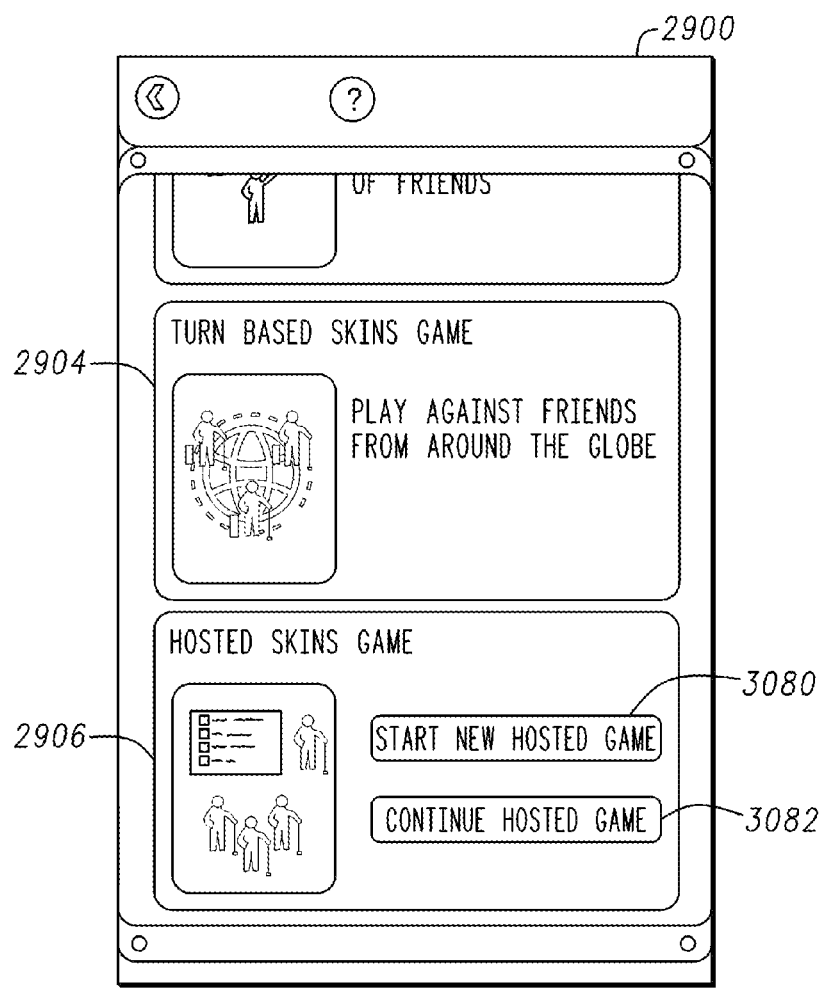

Referring back to FIG. 103, the Hosted option 2906 as shown on the game selection display 2900 allows several local or remotely located individuals to play one or more skins game and display the results in a leader board on a large display device such as a television or a large display monitor. When an individual selects the Hosted option 2906, a new game icon 3080 is displayed, by which the individual may start or host a new game as shown in FIG. 121. Additionally, an existing game icon 3082 is displayed, by which the individual may join a new game that is hosted or started by another individual. Starting a new game or joining a new game that is hosted by another individual under the Hosted option 2906 are similar to starting a new game and take your turn options of the Turn-Based option 2904. Accordingly, two or more local or remotely located individuals may play a skins game under the Hosted option 2906 according to the processes 3008 and FIGS. 107-109.

Figure 122:
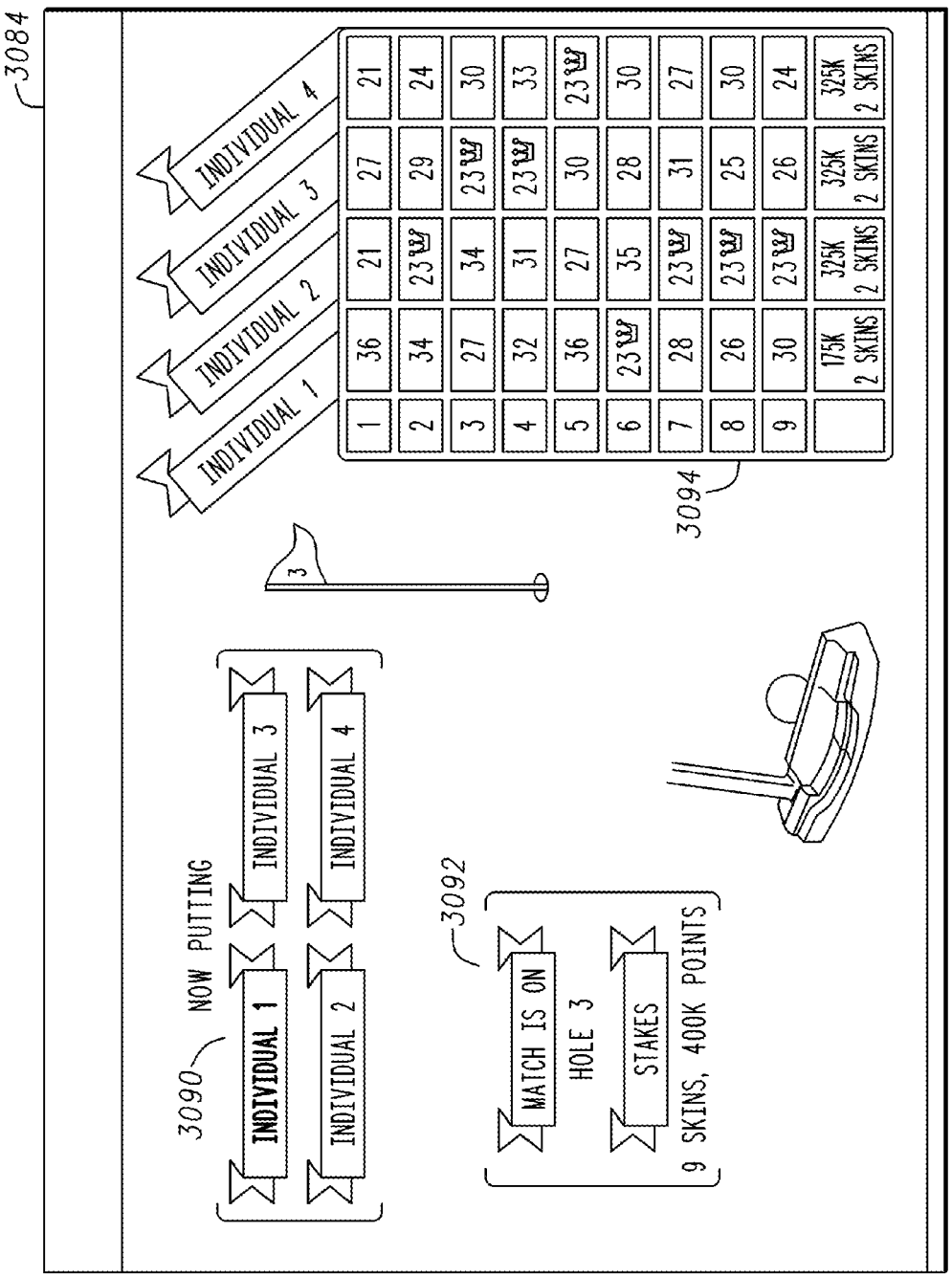

Referring to FIG. 122, real time results of the game may be displayed on a large display device such as a television screen, a computer monitor, a projection screen or the like for viewing for one or more observers. The real time results may be transmitted to an external monitor or television directly and/or via a digital media receiver (e.g., an APPLE TV® digital media extender via the AIRPLAY® software feature from Apple Inc., Cupertino, Calif.).

The real time results may be displayed as a leader board display 3084, which may show the identifications of all participating players in a players area 3090 including an indication of which player is currently playing, an indication of the hole being currently played and the skins value/points for the hole in a current hole display area 3092, and a current score card 3094. The players area 3090 may show the identification of each play in a listing or bracket format. An indication of the player who is currently playing may be provided by visually distinguishing that player's identification. For example, a player's identification may be highlighted, shown with different colors, shown with different style of text, shown with a flashing display, or displayed in any manner so that an observer can instantly determine that the particular player identified on the players area 3090 is taking his or her turn. The existing game icon 3032 is shown in FIG. 122 to display "Take Your Turn", which is indicating to an individual to take his or her turn in a new game started by another individual. Thus, one, a few or a large number of observers and view real time information about a skins game with the leader board display 3084.

Displaying a leader board display 3084 is not limited to the Hosted option 2906 and may be provided with the Pass-And-Play option 2902 and the Turn Based option 2904. For example, with the Pass-And-Play option 2902, the portable electronic device 1000 that is used by all of the players may transmit display data corresponding to the leader board display 3084 to a remote display such as a television screen by any of the disclosed wireless transmission processes described herein. With the Turn Based option 2904, for example, all of the players may choose to transmit display data corresponding to the leader board display 3084 to at least one remote display device, such as a television or a monitor. Thus, the leader board display 3084 may be provided as a display option for the Pass-And-Play option 2902, the Turn Based option 2904 and the Hosted option 2906.

Referring back to FIG. 13, the sensors of the portable electronic device 1000 may require a calibration so that correct linear and/or angular orientation, acceleration, positions and other motion related parameters are measured by the portable electronic device 1000 during operation and/or performance of any of the disclosed processes. According to one example, any of the disclosed operational displays may include a calibration icon 2611, selection of which causes the portable electronic device 1000 to perform a calibration process. Referring for example to FIG. 87, the calibration icon 2611 is shown. Upon selecting of the calibration icon 2611, a calibration screen 3500 is displayed as shown in FIG. 123. The calibration screen 3500 may instruct an individual to move the portable electronic device to a certain position for calibration. In the example of FIG. 123, the calibration screen 3500 is shown to instruct an individual to move the portable electronic device to a vertical position, which may be accurately performed by placing the portable electronic device against two perpendicular walls as shown. Upon correct placement as shown, the individual can press the "calibrate now" icon 3502 so that the portable electronic device records the position as a generally accurate vertical position. All measurements of the sensors 1112 may then be referenced according to the calibrated position. The individual may decide to skip the calibration step by selecting the skip icon 3504. The individual may also decide to reset the calibration by selecting the reset icon 3506.

Referring back to FIG. 61, an individual may attach the portable electronic device 1000 to his or her putter with the portable electronic device holder 100 or use the portable electronic device 1000 without the portable electronic device holder 100 to manually record the result of each putt to generate the scatter plot of FIG. 61. As described herein, the result of each put may entail an individual manually indicating on the display of the portable electronic device the position of each ball on a green and/or relative to a golf hole.

FIG. 123 shows a method 4000 for determining a motion characteristic of a golf ball before, during and/or after a golf stroke with the portable electronic device 1000. The method 4000 includes determining positions of a golf ball with a portable electronic device at least one of before, during and after at least one golf stroke performed with a golf club (block 4002), and determining a motion characteristic of the golf ball with the portable electronic device based on data associated with the positions of the golf ball (block 4004). Additionally, the method 4000 may determine at least one stroke characteristic based on the data associated with the positions of the golf ball. According to the example of FIG. 61, an individual can manually indicate on the display of the portable electronic device an observed position of a golf ball on a green after performing a putting stroke. According to the method 4000, the portable electronic device may determine the position of the ball on the green and/or relative to a golf hole. As described in detail herein, the portable electronic device may also have data associated with the start position of the ball (i.e., ball at address position). The portable electronic device can then determine one or more motion characteristics of the ball. According to another example as described below, determining one or more motion characteristics of the golf ball may be based on capturing one or more images of the golf ball performed before, during and after at least one golf stroke performed with a golf club. Determining the positions of the golf ball may be performed, for example, by an individual selecting a location on a virtual representation of a golf course on a display of the portable electronic device, the location selected by the individual representing a position of the golf ball on the golf course.

FIG. 124 shows a method 4050 for determining a motion characteristic of a golf ball before, during and/or after a golf stroke with the portable electronic device 1000. The method 4050 includes capturing a plurality of images of a golf ball with an image capture device of a portable electronic device at least one of before, during and after at least one golf stroke performed with a golf club (block 4052), and determining motion characteristics of the golf ball with the portable electronic device based on data associated with the captured images of the golf ball (block 4054). Additionally, the method 4000 may determine at least one stroke characteristic based on the data associated with the captured images of the golf ball. Results of determining the motion characteristics of the ball and/or the stroke characteristics based on one or more positions of the ball and/or captured images of the ball may be generally referred to below as the "ball motion results." The methods 4000 and 4050 described herein may be implemented by, for example, using a computer-readable medium having instructions stored therein, which when executed by a computer or the portable electronic device 1000, cause the computer or portable electronic device 1000 to perform method 4000 or method 4050. The instructions stored in the computer-readable medium may cause the computer or portable electronic device 1000 to capture a plurality of images of the golf ball, and display a trajectory of the golf ball on a display of the portable electronic device 1000.

Figure 62:
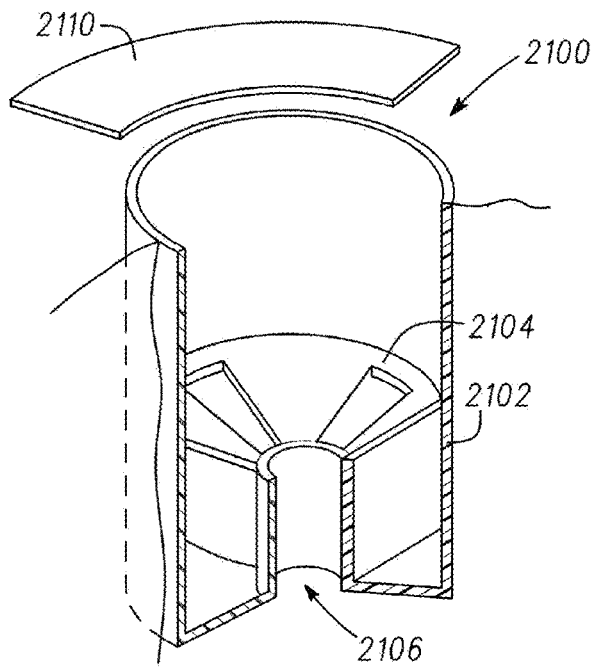
FIGS. 62-65 depict diagrams of a golf cup including a sensor assembly according to the disclosure.

Before capturing images of the golf ball, however, the method 4000 and/or the method 4050 may include attaching a camera to the golf club with a portable electronic device holder (an example shown in FIG. 62). Referring to FIG. 125, a portable electronic device holder 4100 according to one example is shown attached to the shaft 800 of a golf club, which is similar to the golf club shown in FIG. 11. The portable electronic device holder 4100 is similar in some respects to the portable electronic device holder 100. Accordingly, corresponding parts of the electronic device holders 100 and 4100 may be referred to with the same reference numbers. To capture images of a golf ball and determine ball motion results, the portable electronic device holder 4100 can be attached to the shaft 800 with the clamp portion 300 as described in detail herein. The body portion 200 of the portable electronic device holder 4100 is rotatable relative to the clamp portion 300. Accordingly, the rotational position of the body portion 200 can be adjusted relative to the clamp portion 300 at any preferred angle. In the example of FIG. 125, the body portion 200 is rotated relative to the clamp portion 300 such that the portable electronic device 1000 is oriented generally horizontally. To maintain the relative rotational positions between the body portion 200 and the clamp portion 300, an interface between the body portion 200 and the clamp portion 300, i.e., the area of contact between the body portion 200 and the clamp portion 300, may include any type of actively operated or passively operated locking mechanisms. Examples of actively operated locking mechanisms may be one or more latches, one or more locking mechanisms using spring-loaded pins on one of the body portion 200 or the clamp portion 300 that engage a correspondingly sized hole on the other one of the body portion 200 and the clamp portion 300, and/or one or more fasteners that can secure the body portion 200 to the clamp portion 300. Examples of passively operated locking mechanisms may include frictional engagement between the body portion 200 and the clamp portion 300 and/or a ratcheting mechanism between the body portion 200 and the clamp portion 300. The above-described mechanisms are only examples of mechanisms by which the body portion 200 can be maintained at a certain angle relative to the clamp portion 300 while also holding the portable electronic device 1000. The apparatus, methods, and articles of manufacture described herein are not limited in this regard.

The portable electronic device 1000 may be mounted in the portable electronic device holder 4100 before or after the electronic device holder 4100 is attached the shaft 800 as described in detail herein. The portable electronic device 1000 may include at least one camera (not shown) having a camera lens 4110. The portable electronic device 1000 is mounted in the portable electronic device holder 4100 such that the camera lens 4110 faces the direction of the golf stroke as shown in FIG. 125. If the portable electronic device 1000 has multiple camera lenses (e.g., lenses on the back and front), the portable electronic device 1000 can be mounted in the portable electronic device holder 4100 such that the camera to be used faces the direction of the golf stroke. Furthermore, the portable electronic device holder 4100 may include at least one opening 252 for a camera lens of the portable electronic device 1000.

An individual may select an icon (not shown) on the GUI 1114 to start the process 4000 and/or the process 4050. For example, the main menu 1302 or the sub-menu 1900 may include an icon or option, respectively (not shown), by which an individual can start the process 4000 and/or the process 4050. The icon or sub-menu option may include text or graphics. Alternatively, the process 4000 and/or the process 4050 may be performed contemporaneously with the processes 1270 of FIGS. 33 and 34 and/or the process 1500 of FIGS. 42 and 43. Accordingly, the process 4000 and/or the process 4050 may be performed during a practice session and/or a measure session. Thus, selecting the practice icon 1304 or the measure icon 1306 may also start the process 4000 and/or the process 4050.

The individual may attach the portable electronic device 1000 to his or her putter with the portable electronic device holder 4100 as described above. The individual can then putt one or more golf balls in a putting area at a certain distance from a golf cup. The distance may be generally a consistent distance so as to allow an individual to determine his or her miss tendencies from a particular distance. For example, the individual may choose to practice putting at a distance of about 10 feet from the hole. However, the putting distance may be varied.

When the process 4000 and/or the process 4100 is activated or executed as described herein, the camera of the portable electronic device 1000 may capture images in the direction of the golf stroke or golf swing. The camera may be activated by any motion of the golf club. Alternatively, the camera may be activated when the golf club strikes the golf ball. As described in detail herein, the portable electronic device 1000 may include sensors by which impact of the golf club with the golf ball can be sensed. The camera can capture images of the golf ball as the golf ball travels from a position prior to being struck by the head of the golf club towards its target, which may be a golf hole.

Figure 126:
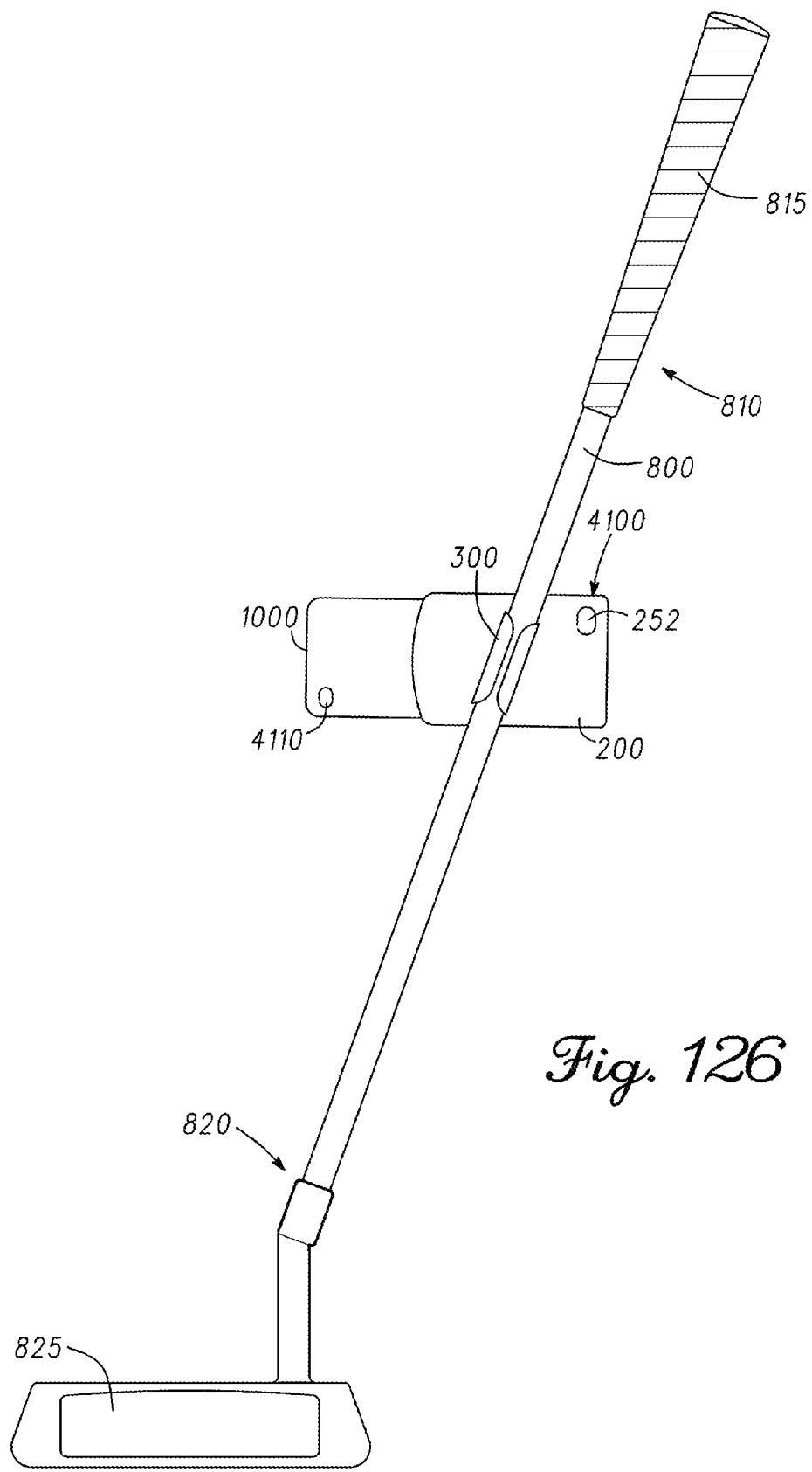
FIG. 126 depicts a golf club having attached thereto a portable electronic device holder having a portable electronic device therein according to one example.

FIG. 126 is a diagram that may be displayed on the display screen or touch screen 4011 of the portable electronic device illustrating a plurality of images of a golf ball 4012 captured by the camera as the golf ball travels toward the golf hole 4014. The camera may capture still images of the ball at certain intervals to determine the position of the ball relative to the golf hole. For example, the camera may capture still images every 0.1, 0.25 or 0.5 seconds. Alternatively, the camera may capture video of the golf ball at certain frame rate, such as 30 frames per second or 60 frames per second. The camera may stop capturing images when the golf ball comes to a stop. A golf ball coming to a stop may be defined by the golf ball missing the golf hole and coming to a stop at a location on the green. The camera may stop capturing images when the golf ball no longer appears in the captured images. A golf ball no longer appearing in the captured images may indicate that the golf ball has fallen into the golf cup. If the golf ball is far from the cup as may be determined by a sequence of captured images and the ball no longer appears in later captured images, the ball may be considered to have been putted outside the measurable putting range. Thus, the portable electronic device can determine based on the motion and/or position of the ball from earlier captured images if a ball has fallen into the golf cup. In the example of FIG. 126, eight images of the golf ball are shown by which a trajectory 4080 of the golf ball may be determined as described below.

The portable electronic device 1000 may determine an approximate distance from where an individual is attempting a putt by capturing an image of the golf hole and/or the flag pole that is inside the golf hole and comparing the size of the golf hole shown in the image to an actual size of the golf hole. The portable electronic device 1000 may also determine an approximate position of the golf ball relative to the address position and/or the golf hole by comparing an image of the golf ball captured with the camera to an actual size of the golf ball. The elapsed time between each captured image of the golf ball can then be used along with the position of the golf ball as determined from each captured image to determine the acceleration of the golf ball, the velocity of the golf ball, the trajectory of the golf ball, the distance of the golf ball from the golf hole, the distance of the golf ball from the address position, the rate and direction of spin of the golf ball and/or an approximate location at which the golf ball comes to a stop. Furthermore, a prediction of whether or not the golf ball will reach and drop in the golf hole may be made based on the above-described parameters.

The above-described motion and position parameters for the golf ball may be used to convey to an individual his or her stroke characteristics. Referring back to FIG. 61, the GUI 1114 may present the individual with a schematic display of the putting area 2020 as described herein including the target golf cup 2022. The portable electronic device 1000 may display the result of a putt on the schematic display of the putting area 2020 based on the above-described motion and position parameters determined from the images captured by the camera. For example, the portable electronic device 1000 may display the trajectory of each ball. As described herein with respect to FIG. 61, the shape, size and/or color of symbols 2028 may convey certain information about the position of the ball in the putting area such as the golf club used by an individual to putt the ball, the distance from the golf cup from which the putt is attempted, an individual's stroke characteristics, an individual's setup position for attempting the putt, and/or any other information by which one putt may be distinguished from another putt. Thus, the display shown in FIG. 61 can be created by using the camera as described about and without the individual manually inputting any data associated with the ball into the portable electronic device.

The portable electronic device 1000 may further use the data associated with motion of the ball and position of the ball relative to the golf hole to determine an individual's stroke characteristics as described in detail above. For example, the rotational direction and speed, trajectory, translational speed, acceleration and/or distance of a golf ball from the golf hole as determined from images captured by the camera can be used to determine an individual's stroke characteristics. Furthermore, the portable electronic device 1000 may determine the miss tendencies of the individual by analyzing the final position of a golf ball relative to a golf hole for a plurality of putting strokes in a similar manner as the analysis of the scatter plot of FIG. 61 as described in detail herein. For example, any pattern or cluster of final positions of a plurality of golf balls as determined by images captured with the camera may be correlated with the individual's consistency scores or PHcp and/or any improvements in consistency scores or PHcp. An individual may then determine his or her putting tendencies and possibly take action to improve his or her putting performance. According to one embodiment, the camera may capture an image of the face of the golf club at the moment of impact with the golf ball. Accordingly, the location on the face of the golf club that impacts the ball may be measured and/or determined. For example, the location may be measured from a center of the face of the golf club (i.e., off-center location). The location information captured from the camera may be used to determine the consistency of the individual in striking the ball with the same location on the face of the golf club, which may be at least partly indicative of the overall stroke consistency of the individual. According to one embodiment, a stationary object in each captured image may be used to determine absolute motion (translation and/or rotation) information for the golf club. Accordingly, the absolute motion information of the golf club either alone or in combination with relative motion information that may be determined by a portable electronic device attached to the golf club may be used to determine an individual's swing and/or stroke characteristics. The stationary object may be an object near the individual such as a tree, flag pole, one or more plants, or the like. The stationary object may be a particular object that may be provided to the individual to place near his or her putting area. The stationary object may be a cone, a pole, or another portable object that may be carried by the individual. The stationary object may also include certain markings that when captured by the camera can assist in determining the absolute motion of the golf club.

The display shown in FIG. 61 shows final positions of one or more balls after an individual attempts a plurality of putts. The portable electronic device 1000 may also provide a diagram to an individual that shows the trajectory of each ball and/or the topographical characteristics of the putting green, which may affect the trajectory of each ball. The diagram may be displayed on the display screen of the portable electronic device 1000 and provide an interactive GUI for the individual. An example of such a diagram is shown in FIG. 126. In another example, an initial diagram may be similar to the diagram shown in FIG. 61. However, an individual can select each ball by touching the ball on the screen of the portable electronic device 1000 to reveal motion characteristics of the ball and/or stroke characteristics associated with the putting stroke for the selected ball as described in detail herein. Selecting a ball on the diagram of FIG. 61 may show the diagram of FIG. 126 for the selected ball. Additionally, the diagram of FIG. 126 may be animated to show the motion of the ball, display a stop-motion image capture animation, or display a captured video of the motion of the ball. According to another example, an individual may touch each of the balls displayed on the display of FIG. 61. The portable electronic device 1000 may display the trajectory of the selected ball to the individual. The portable electronic device 1000 may also display various motion characteristics of the selected ball. Thus, the images of a ball captured by a camera as described above can be used to provide an individual with information regarding his or her stroke characteristics, the resulting motion of a golf ball and the individual's putting performance.

The ball motion results as described above may be used to determine the stroke type of an individual, provide recommendation for golf clubs, share ball motion results of the individual with others, and/or use the ball motion results to compete with other individuals as described in detail herein. Thus, the ball motion results can be used in any of the systems, methods, and articles of manufacture described herein and are not limited in this regard.

FIGS. 128-139 illustrate other embodiments of the present disclosure comprising a wearable device 5000, similar to the portable electronic device 1000 discussed herein, being used in combination with a golf club such as the golf club 798 to measure swing characteristics during motion of the golf club 798 (e.g., during a golf swing). The wearable device 5000 combined with the golf club 798 forms, defines, or otherwise provides a swing aid apparatus 5001. Utilizing the wearable technology of the wearable device 5000 with the golf club 798 as disclosed enables a golfer to improve upon the separate existing technology of the golf club 798 such that the golf club 798 may not only be used for standard gameplay, but in addition, may also be used as a practice aid (swing aid apparatus 5001) by incorporating the wearable device 5000. Swing data generated by the wearable device 5000 (as the golf club 798 moves during a swing), including accelerometer data and gyroscope data, may be used to measure swing characteristics of a golfer such as tempo, hand speeds (max, impact, etc.), swing path visualizations, power/efficiency scores, and the like. As discussed herein, the wearable device 5000 may be coupled to a body part of a golfer during a golf swing, and/or coupled directly to the golf club shaft 800 to generate the swing data.

The wearable device 5000 may comprise a watch (e.g., an APPLE WATCH® or APPLE WATCH SERIES 2® digital watch from Apple Inc., Cupertino, Calif.), an electronic wristband or fitness device, an electronic ring, an electronic glove, or other such wearable electronic device capable of generating movement measurements using one or more sensors as described herein. In one embodiment, the wearable device 5000 comprises at least one of a processor (e.g., a dual-core processor), gyroscope for measuring a rate and extent of rotation, and an accelerometer for measuring acceleration.

In one embodiment, the gyroscope and accelerometer of the wearable device 5000 may be implemented using a chipset from e.g., STMicroelectronics, specifically, a STMicroelectronics 3 mm×3 mm land grid array (LGA) package with a 3D digital gyroscope and a 3D accelerometer such that the gyroscope and accelerometer are integrated together within a single component and the accelerometer is not external. The aforementioned chipset may be configured as a 6 axis sensor for acceleration and roll, and pitch and yaw. The present disclosure is not limited in this regard.

In one embodiment, the accelerometer and the gyroscope of the wearable device 5000 may be embodied within one or more sensors, or one or more of a micro electro-mechanical system MEMS. In one embodiment, the wearable device 5000 may be outfitted with a gyroscope that comprises a three (or more) axes MEMS-based gyroscope. Utilizing one or more of the accelerometers, the wearable device 5000 may consequently provide at least six component motion sensing in the form of acceleration X, Y, and Z movement, and one or more of the gyroscopes for measuring the extent and rate of rotation in space (roll, pitch, and yaw). The wearable device 5000 may optionally include a magnetometer to provide absolute angular measurements relative to the Earth's magnetic field. The wearable device 5000 may further include additional MEMS-based inertial measurement units to provide nine (or more) axes of motion sensing in a single integrated circuit package within the wearable device 5000. The apparatus and articles of manufacture described herein are not limited in this regard.

The wearable device 5000 may further comprise a built-in GPS, and may operate in accordance with Bluetooth® technology to communicate and/or exchange data with other devices. In addition or alternatively, the wearable device 5000 may operate in accordance with the 802.xx family of standards developed by the Institute of Electrical and Electronic Engineers (IEEE) and/or variations and evolutions of these standards (e.g., 802.11x, 802.15, 802.16x, etc.), Ultra Wideband (UWB), Near Field Communication (NFC), and/or radio frequency identification (RFID) to communicate and/or exchange data with other devices as described herein. The systems, methods, and articles of manufacture are not limited in this regard.

In one embodiment, a processor within or otherwise coupled to the wearable device 5000 may execute one or more operating systems such as the Apple OS 2 or 3 and may also execute one or more motion measurement applications such as Apple CoreMotion. The operating system and/or applications of the wearable device 5000 may communicate with the gyroscope and the accelerometer to generate or otherwise access the swing data (and optionally make such information available to other devices). In some embodiments, a different computing device, such as a desktop computer, tablet, smartphone, laptop, or server, (e.g. laptop 1160) including one or more processors and one or more memory units, may access the swing data from the wearable device 5000 by, e.g., utilizing one or more application programming interfaces (APIs) integrated with an application executed by the processor of the wearable device 5000. As one specific example, the laptop 1160 may execute an API call to an application of the wearable device 5000 to access the swing data, optionally in real time. As such, the laptop 1160 may utilize the swing data accessed from the wearable device 5000 to generate one or more swing characteristics such as swing tempo (while the club and wearable device 5000 is in motion). The laptop 1160 may also utilize at least one processor to execute one or more applications and perform functions described herein for identifying data signatures from the swing data associated with different points of a swing, determining time intervals based on the data signatures, and using the time intervals to generate a swing tempo. The laptop 1160 may access the swing data of the wearable device 5000 in real time, i.e., during the swing of the club 798. The swing data may be accessed and/or generated by the laptop 1160 at a rate of approximately 0-100 hz per second, 100-150 hz per second, or 150 hz to 500 hz per second, although the present disclosure is not limited in this regard.

Figure 128A:
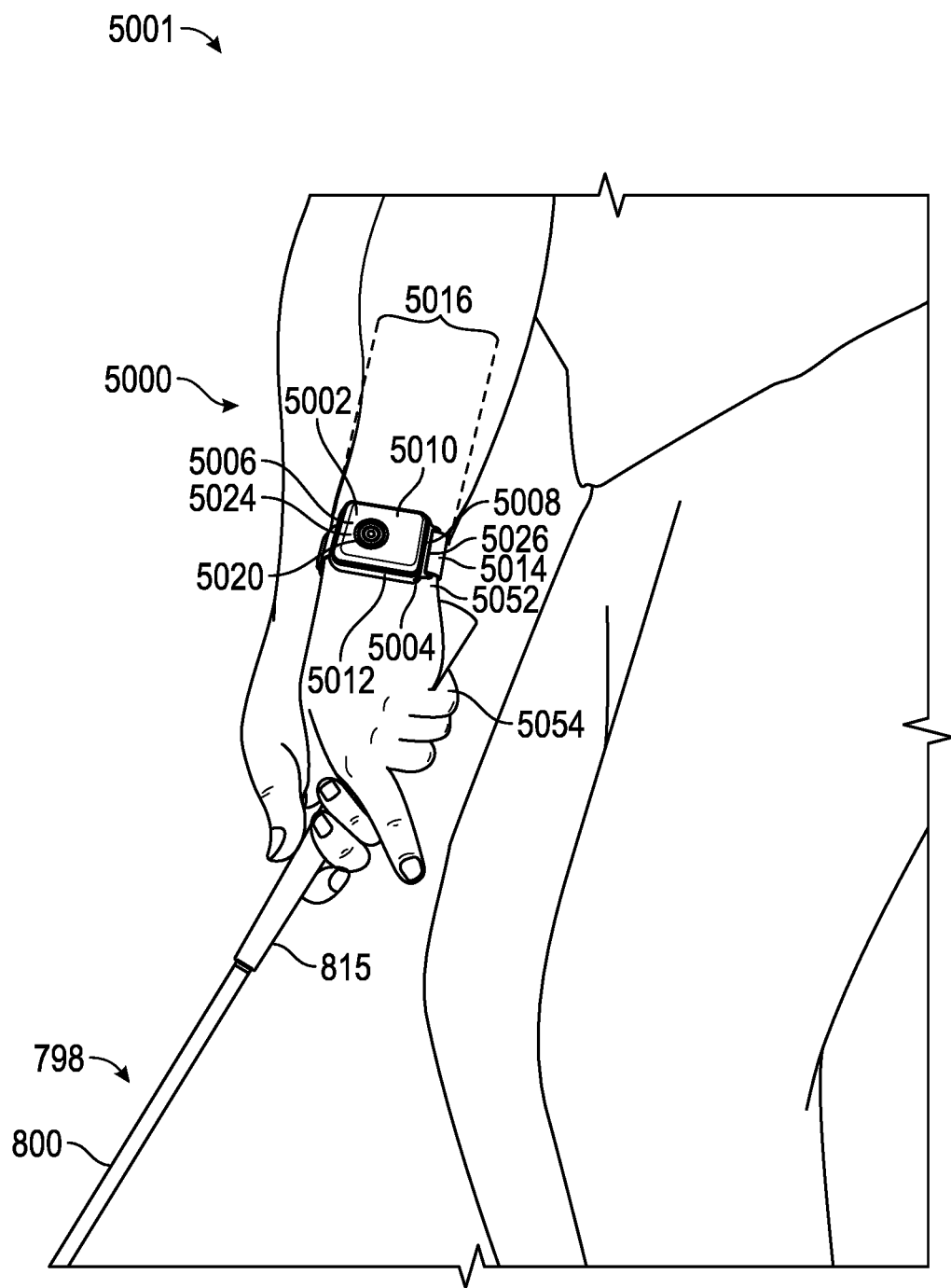
FIGS. 128A-128D depict a swing aid apparatus comprising a wearable device according to one embodiment.
Figure 128B:
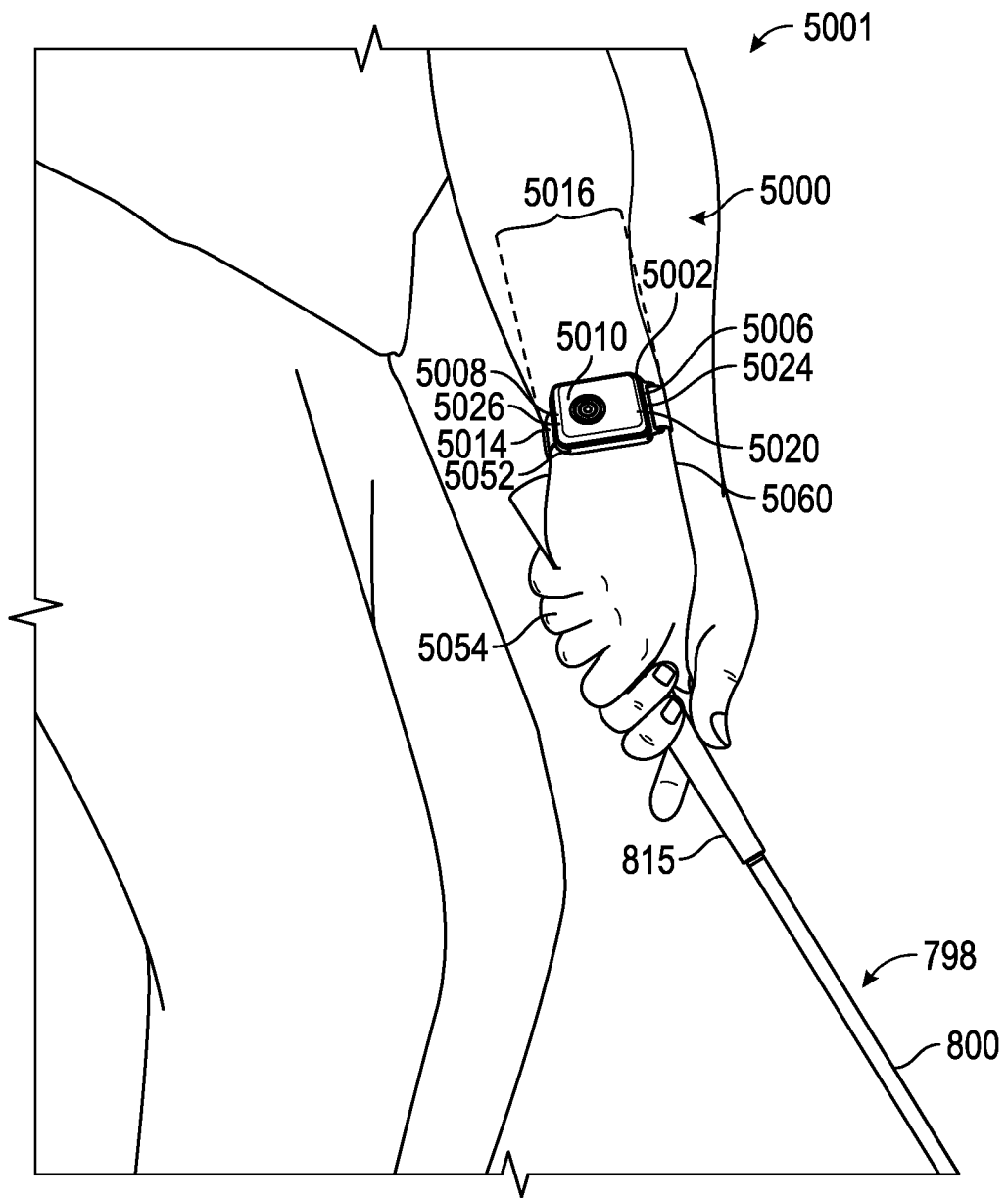

As shown in FIGS. 128A and 128B, one embodiment of the wearable device 5000 comprises a top side 5002 including a face portion 5020, a bottom side portion 5004, a side portion 5006, and an opposing side portion 5008. The face portion 5020 of the wearable device 5000 may include a display 5010 and an input component 5012 (e.g., touch screen, one or more buttons, dials, or the like). The wearable device 5000 may further include a band 5014 defining an opening 5016, with a first end 5024 of the band 5014 extending from the side portion 5006, and a second end 5026 of the band 5014 extending from the opposing side portion 5008. A size, or diameter of the opening 5016 may be modified by manipulating the band 5014 depending upon the type of band utilized with the wearable device 5000. As some examples, the band 5014 of the wearable device 5000 may include any variety or combination of adjustment or closure means to modify the opening 5016, such adjustment/ closure means including a buckle, a butterfly closure, a clasp, an elastic band, a hook and loop closure, and the like. As such, for example, the band 5014 may be manipulated to modify the opening 5016 where the band 5014 is overlapped upon itself (as in the case where the band utilizes a buckle enclosure); or where a length of the band 5014 is extended (or reduced) to fit around an object such as a wrist (using e.g. an elastic band), and the like. The apparatus and articles of manufacture described herein are not limited in this regard.

Figure 128C:
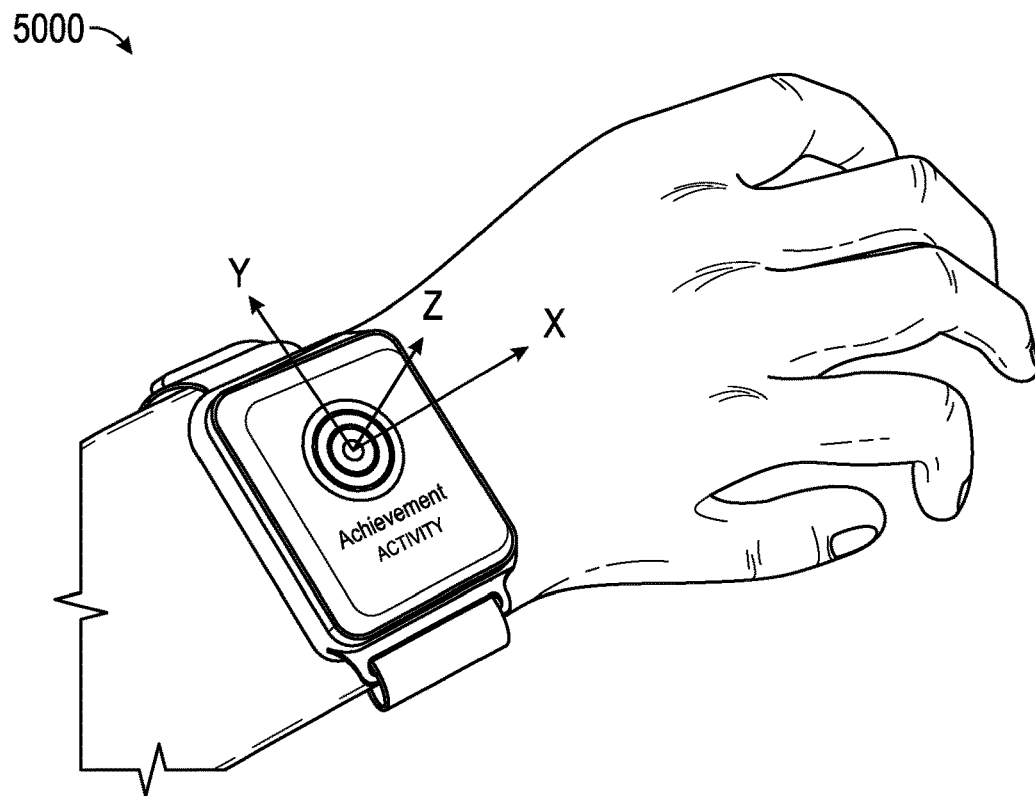
Figure 128D:
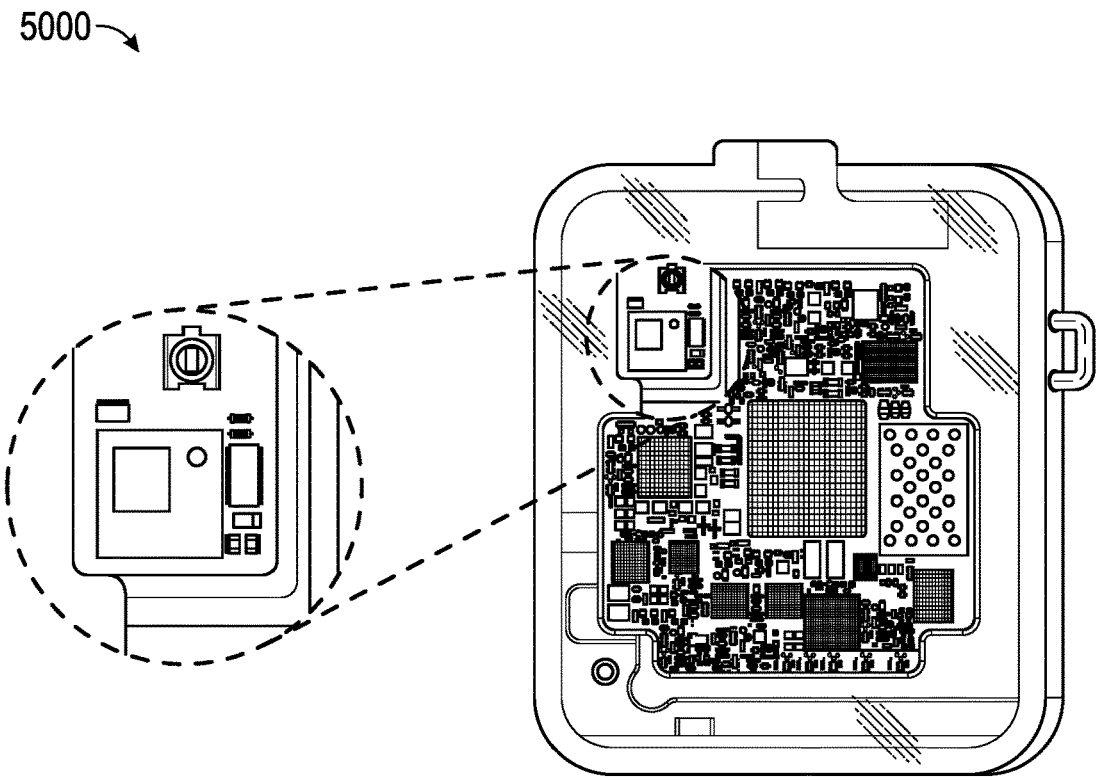

In FIG. 128A, the band 5014 of the wearable device 5000 is wrapped around a left wrist of an individual, such as a golfer. As shown, the face portion 5020 of the wearable device is oriented over a top wrist portion 5052 of the wrist of the individual substantially adjacent a base of the golfer's hand 5054. As further shown, the golfer's hand 5054 is grasping a grip 815 of a golf club 798. Similar to the embodiments described above, the golf club 798 may include a putter, iron, driver, hybrid, or the like. In some embodiments, the wearable device 5000 is wrapped around the left wrist of the golfer such that the face portion 5020 of the wearable device 5000 is oriented over a predetermined portion of the left wrist, and the band 5014 is tightened against skin of the left wrist to reduce movement of the wearable device 5000 and face portion 5020 away from the predetermined portion of the left wrist. FIG. 128B provides a similar depiction of the wearable device 5000 disposed on a golfer with the difference being that the wearable device 5000 is disposed on a right wrist as opposed to the left wrist in FIG. 128A. FIG. 128C provides a closer view of the wearable device 5000 demonstrating the ability of the portable electronic device 5000 to generate accelerometer and gyroscope data along a plurality of different axes. FIG. 128D provides a cut-away and magnified view of one embodiment of the wearable device 5000 with the magnified view focusing on an exemplary chipset for the wearable device 5000, the chipset including a 3D digital gyroscope and a 3D digital accelerometer as a single hardware component (as described herein).

Figure 129:
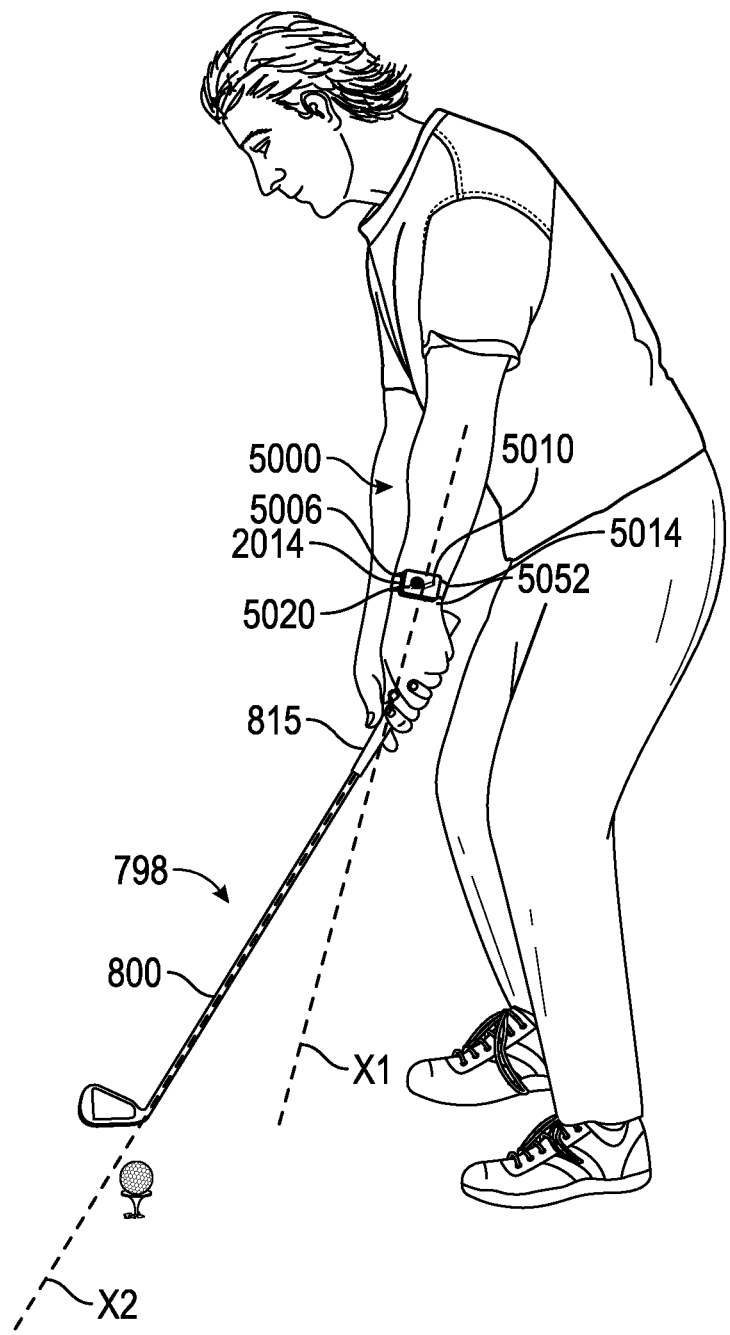
FIG. 129 depicts a side view of the swing aid apparatus according to one embodiment.
Figure 130A:
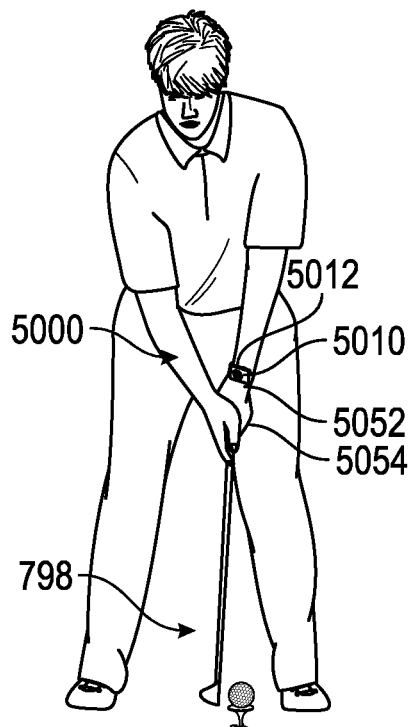
FIGS. 130A-130I illustrate different positions of a golf swing analyzed using the swing aid apparatus according to one embodiment.
Figure 130B:
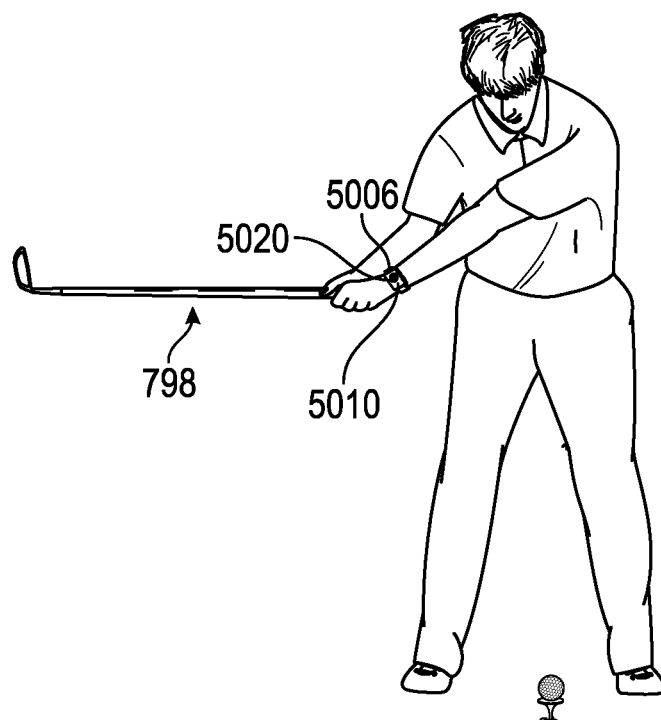
Figure 130C:
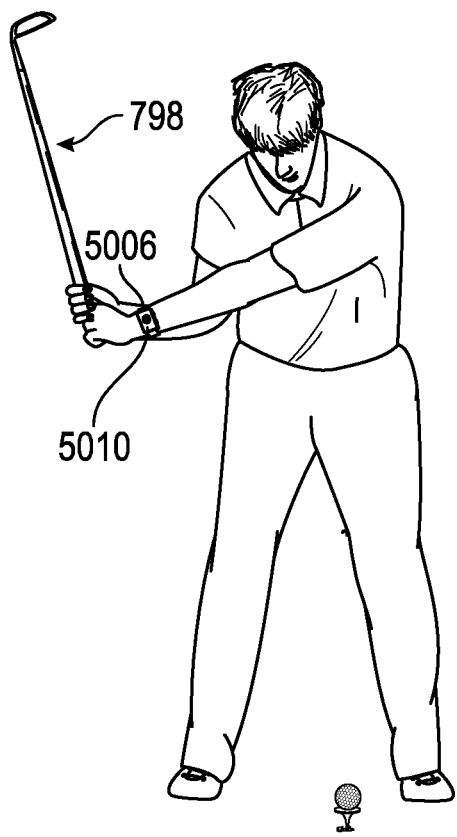
Figure 130D:
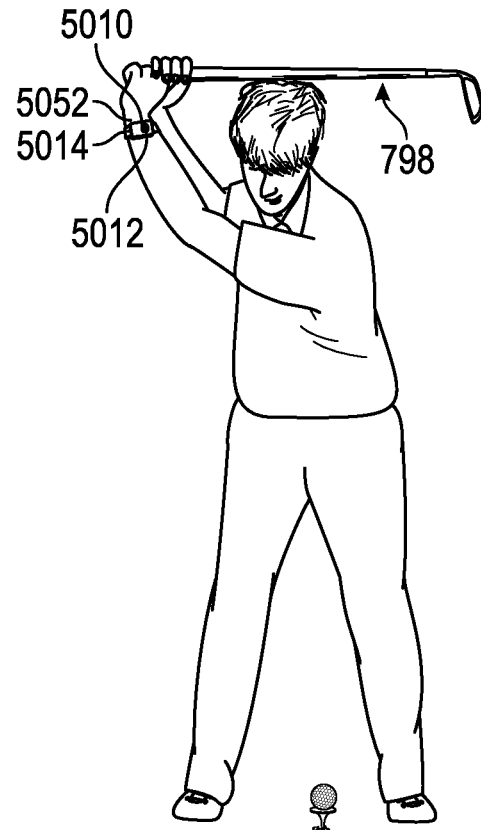
Figure 130E:
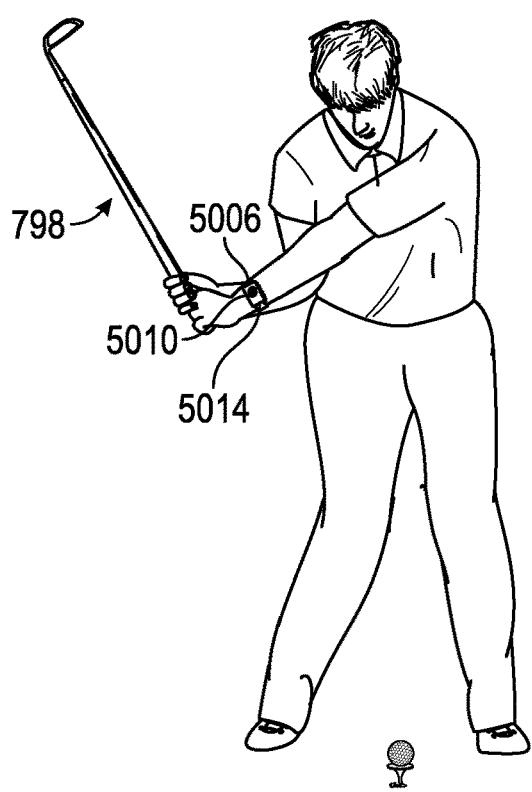
Figure 130F:
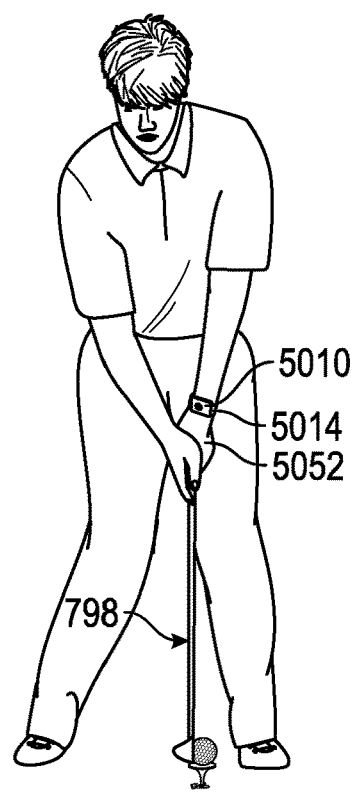
Figure 130G:
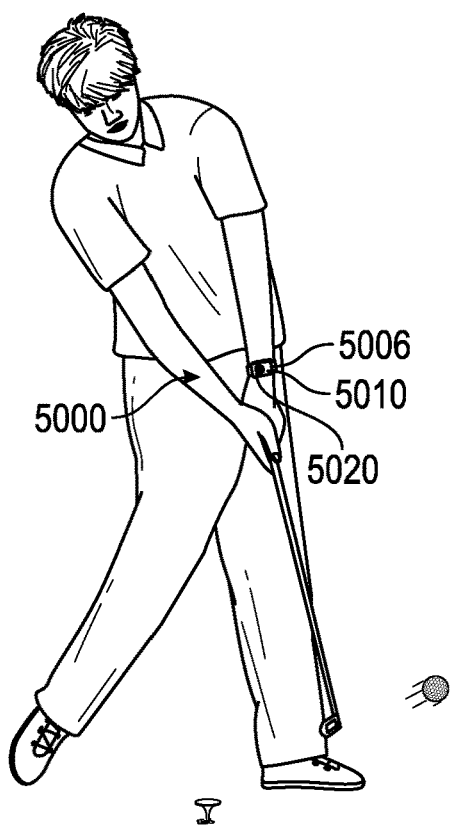
Figure 130H:
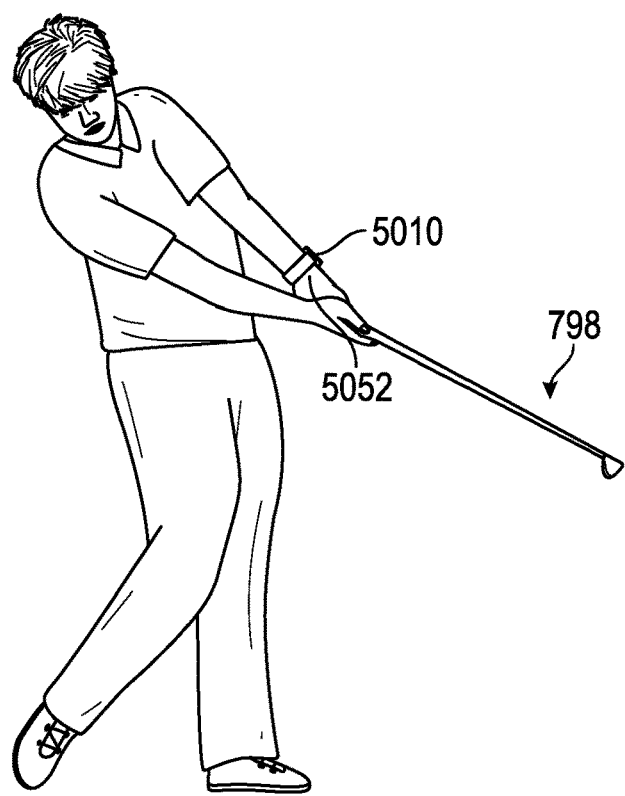
Figure 130I:
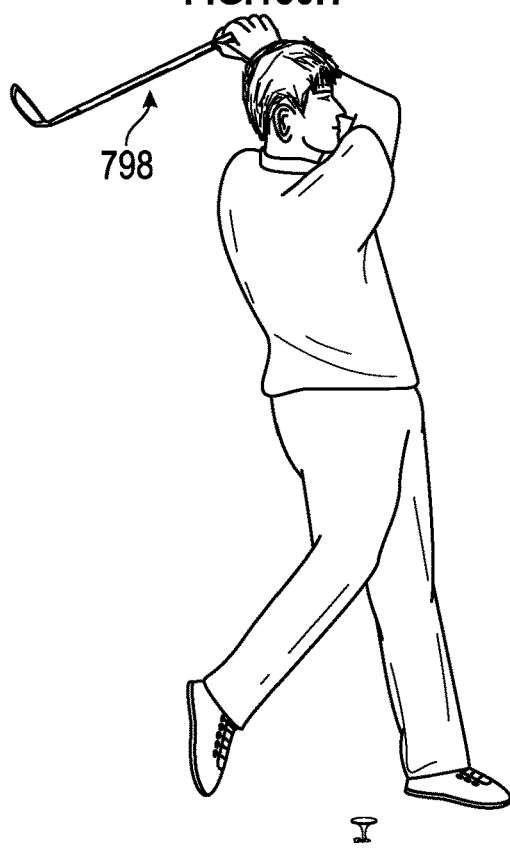

FIG. 129 illustrates a side view of the golfer illustrated in FIGS. 128A-B. As described herein, the wearable device 5000 may be specially located on a wrist of a golfer, such as a left wrist to measure swing tempo, swing path/s, and the like. As shown, the face portion 5020 of the wearable device 5000 may extend along an axis X1 and the golf shaft 800 may extend along an axis X2. FIGS. 130A-130I illustrate a front view of the golfer discussed herein swinging the golf club 798, with each of FIGS. 130A-130I showing different positions of the golf club 798 corresponding to specific time intervals during the golf swing.

As shown, using the wearable device 5000, the golfer is not encumbered with larger technology or other materials to analyze his/her own swing. Rather, because the wearable device 5000 for the swing aid apparatus 5001 may be embodied in a shape and form (such as a watch) which may be wearable and is already familiar to the golfer, (i.e., the golfer may already wear and be accustomed to wearing a watch while swinging a golf club), the swing aid apparatus 5001 immediately assists the golfer with analysis and adjustment to his/her own swing tempo without having to adjust to different materials, weights, or the like.

Figure 131:
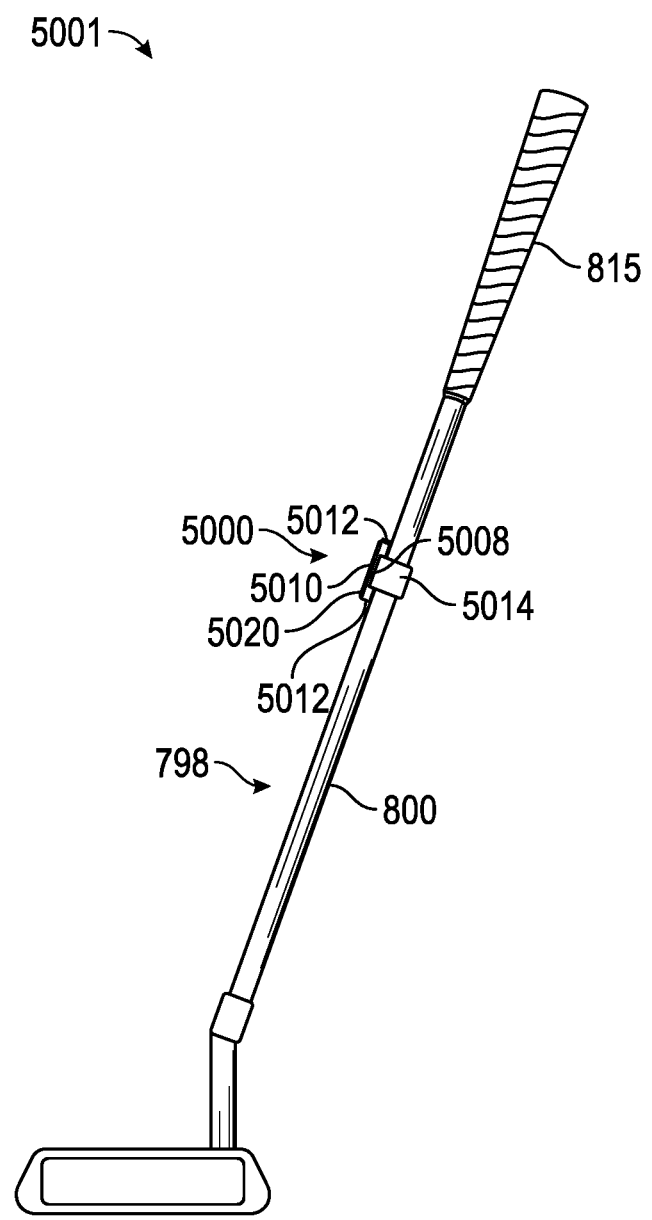
FIG. 131 is another embodiment of the swing aid apparatus with a wearable device disposed on a golf club according to one embodiment.

FIG. 131 illustrates another embodiment of a swing aid apparatus 5001 where the wearable device 5000 is disposed on or otherwise engaged to the golf club 798 instead of an individual's wrist or other body part. The band 5014 of the wearable device 5000 may be coupled to the golf club shaft 800 proximate a butt end of the golf club 798. The face portion 5020 or display 5010 of the wearable device 5000 may be oriented over the golf club shaft 800 similar to the above embodiments shown with respect to the portable electronic device 1000.

The swing aid apparatus 5001, including the wearable device 5000, may operate as a training device, a gaming device, and/or a social networking device and may utilize a processor (embodied within the wearable device 5000 and/ or implemented by a separate device) to execute one or more applications and execute functions for analyzing tempo of a golf swing (and generating analysis regarding other swing characteristics) according to the steps described herein. Utilizing the wearable device 5000, including the gyroscope and accelerometer, swing data (accelerometer data and gyroscope data) in the form of data velocities and accelerations (both translational and rotational) may be accessed and/or computed. Such values may be associated with specific time intervals or points in time, and may be assigned to points along an entire swing path of the golf club 798. As one particular example, a point of impact, when the golf club 798 makes contact with a golf ball during a golf swing, may be identified using the accelerometer data. Specifically, raw accelerometer channels or streams extracted from the accelerometer of the wearable device 5000 during a predefined period of time (corresponding to a golf swing), in units of gravity corresponding to each of an X, Y, and Z axis, may be converted or otherwise used to generate the gradient of acceleration corresponding to each data stream. An absolute value or an acceleration gradient threshold (corresponding to e.g., the X-axis gradient or the Z-axis gradient of acceleration) may be identified during the predetermined period of time (during a time when the golf swing occurred). Specifically, this accelerometer gradient threshold or spike in a rate of change in the accelerometer data may identify a time interval or point in time associated with a golf club's point of impact with a golf ball. Specific time intervals associated with the backswing end and the start of the golf swing may be identified using the gyroscope data of the swing data before the club's point of impact with the golf ball. Specifically, in some embodiments, the gyroscope data may define or otherwise be used to generate a set of resultant angular rate values. The angular rate values may define a particular angular rate or change in angular rate where the angular rate value drops below a predetermined minimum threshold; within the predefined period of time, but before the point of impact of the club against the golf ball. An angular rate value at this predetermined minimum threshold corresponds to another unique time interval which may be associated with the end of the backswing. A time interval associated with the start of the swing may further be identified, using the same aforementioned angular rate values of the gyroscope data, by moving back from the end of the backswing to determine a point where the resultant angular rate meets or drops below another predetermined minimum threshold (before the backswing). Time differences between the time intervals associated with the start of the swing, the backswing, and the point of the swing where the golf club 798 impacts a golf ball, may be used to calculate a swing tempo.

As such, the present disclosure contemplates transforming raw gyroscope and accelerometer data streams, generated by accelerometer and gyroscope components during the physical movement of the wearable device 5000 (and golf club 798) in a 3D space in the course of a golf swing, into a plurality of new datasets (e.g., accelerometer gradients and angular rate values over a predetermined period of time associated with a golf swing), working backwards in time to identify specific data signatures from the new data sets (corresponding to particular time intervals during a swing), which encompasses a novel and inventive concept uniquely suitable for analyzing a golfer's swing tempo. As described below, the present inventive concept may further include additional meaningful limitations to carry out the functionality described herein.

The new datasets may generate increased feedback, which may be provided to the golfer about their swing, and can allow the golfer to better understand and track their swing characteristics; all packaged within a compact and portable package of the swing aid apparatus 5001. The swing aid apparatus 5001 further provides enhanced precision and may allow the golfer to adjust his/her swing without the aid of a coach or other human trainer based on quantitative and qualitative data generated by the wearable device 5000 as the golfer swings a golf club.

Figure 132A:
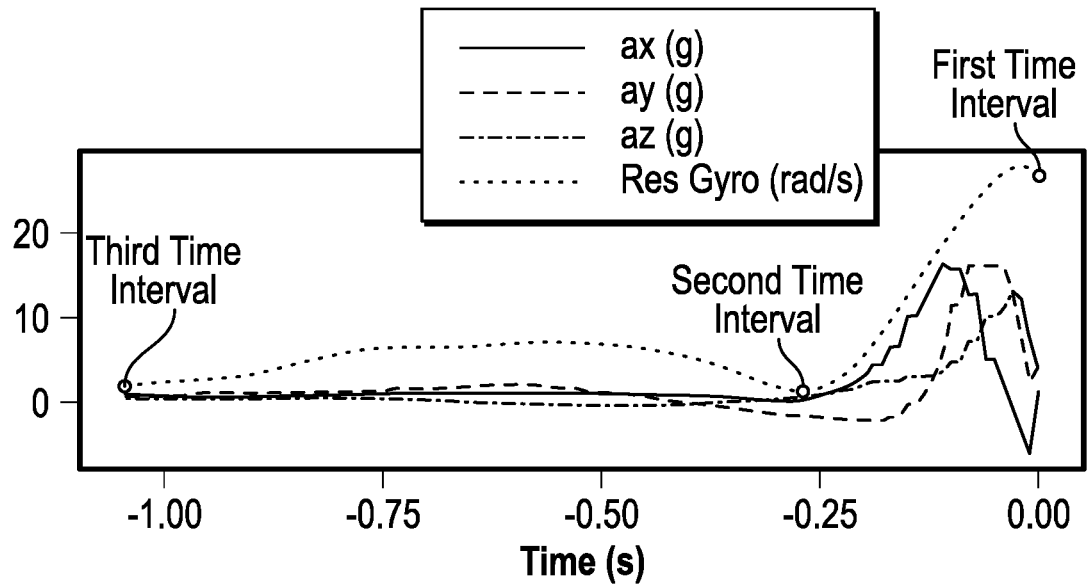
FIGS. 132A-132C are a set of two-dimensional graphs illustrating accelerometer and gyroscope data generated from the swing aid apparatus over a predefined period of time according to one embodiment.
Figure 132B:
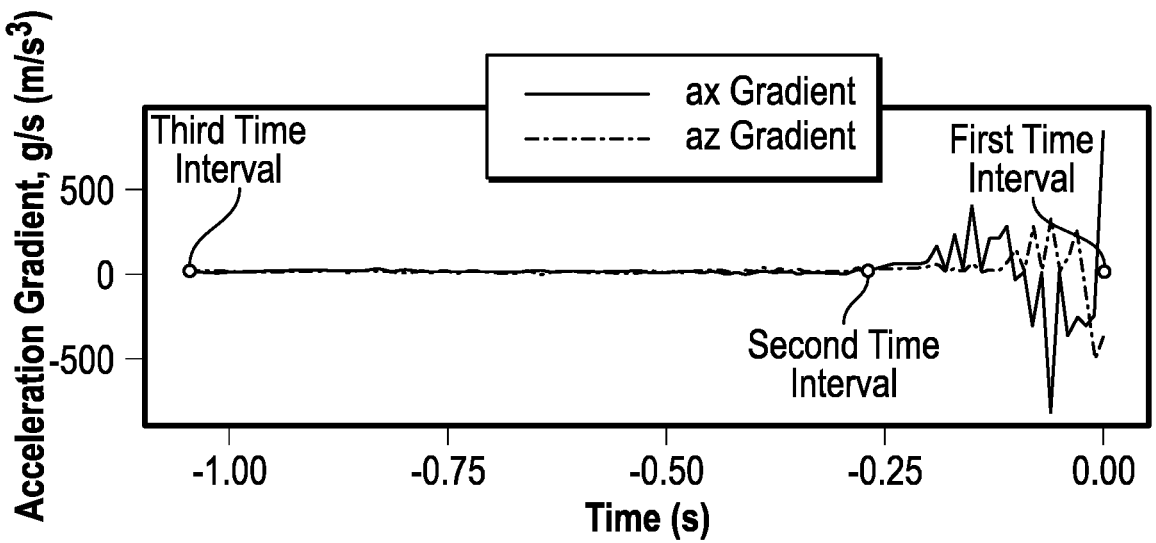
Figure 132C:
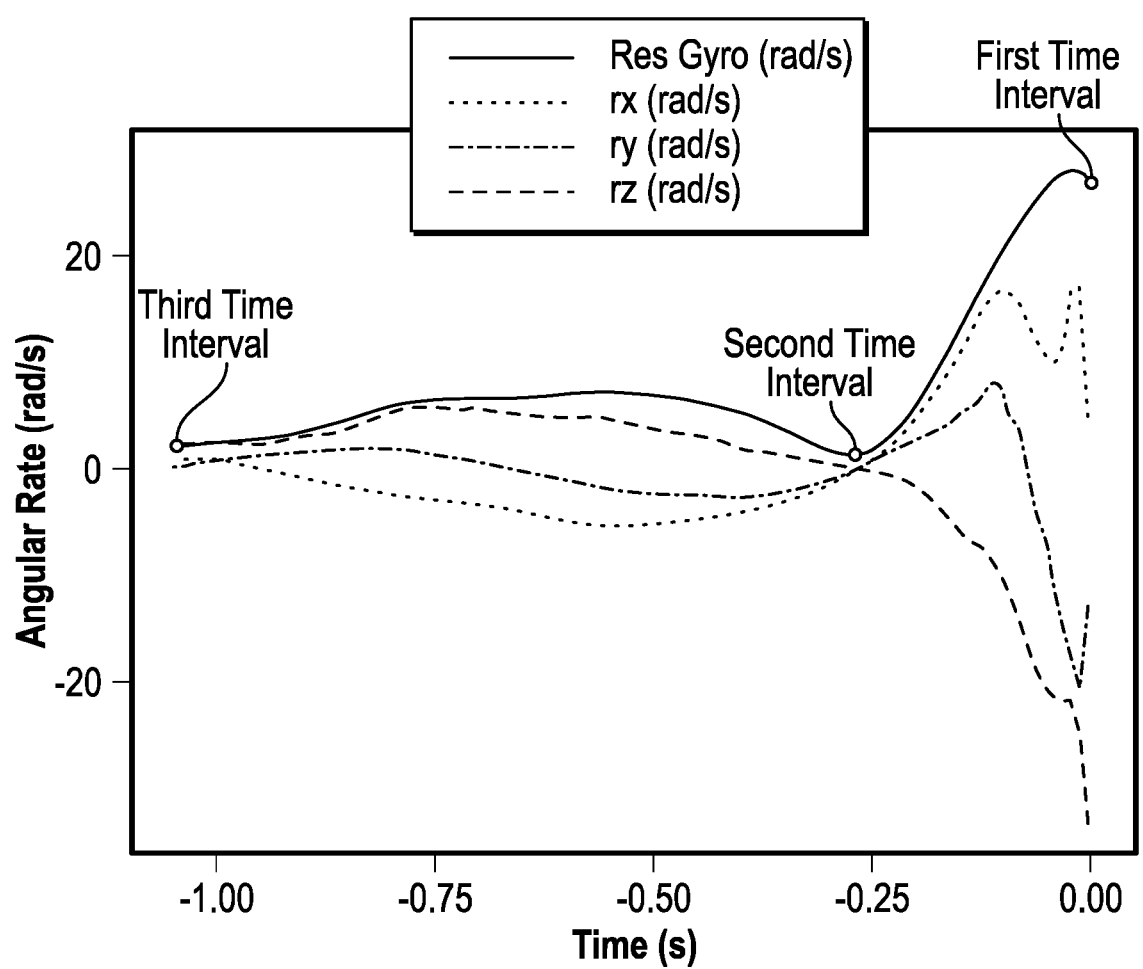
Figure 133A:
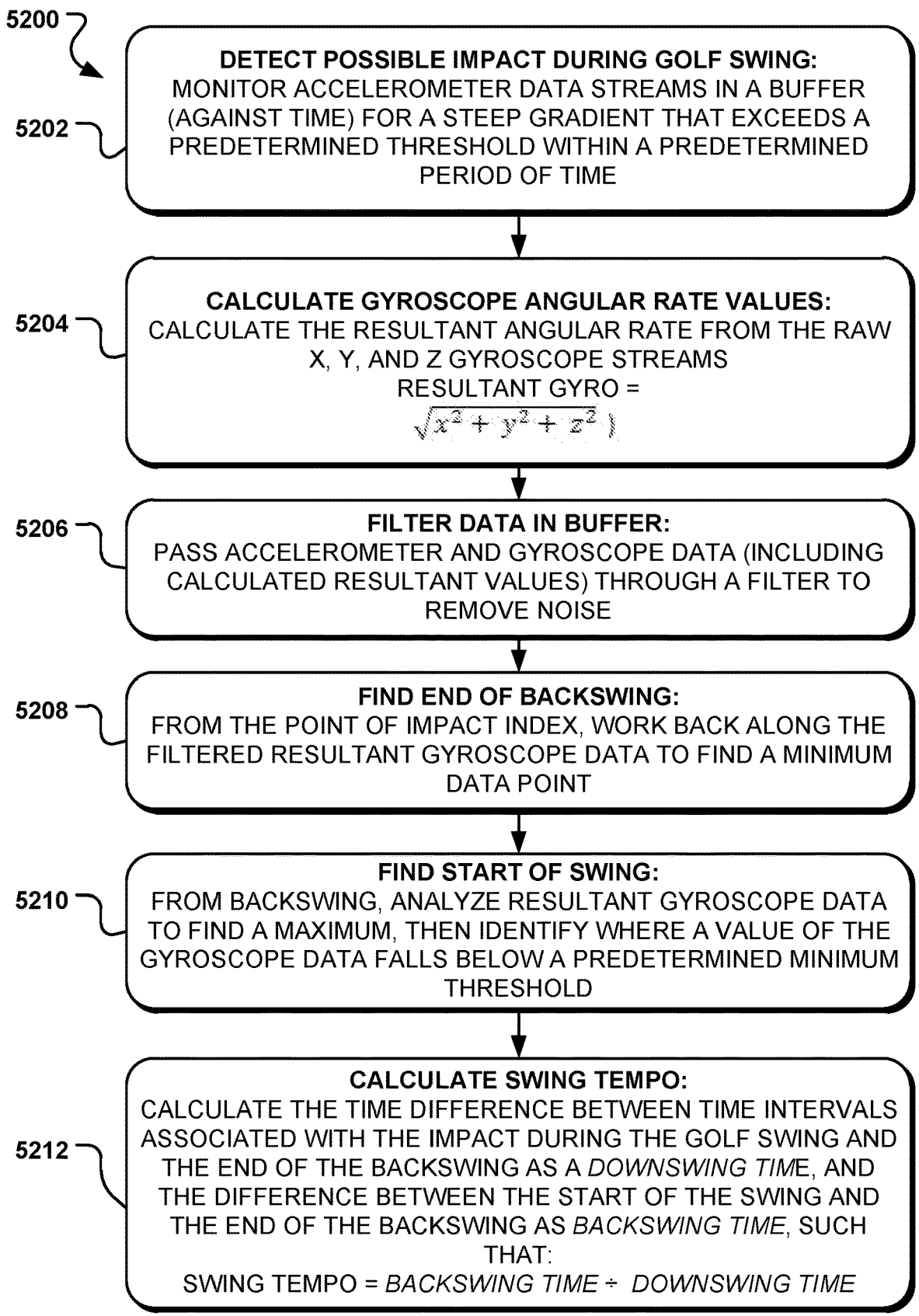
FIGS. 133A-133B are exemplary process flows for implementing the swing aid apparatus to generate a swing tempo according to one embodiment.

A more detailed discussion regarding determining a tempo of a golf swing for an individual utilizing the swing aid apparatus 5001 may be articulated by the exemplary process flow 5200 of FIG. 133A with reference to the graphs of FIGS. 132A-132C and FIGS. 130A-130I. FIG. 132A illustrates a two-dimensional graph with data points of the swing data plotted on the graph. The graph of FIG. 132A includes both the gyroscope data and accelerometer data, as generated over a predefined period of time by the wearable device 5000. Specifically, as shown, the swing data may be analyzed over a predefined period of time approximately equal to a second of time with certain data signatures identified to the millisecond. The time units are displayed for explanatory purposes in negative units to illustrate that in one embodiment the swing data may be analyzed to generate a swing tempo by working backwards in time from a first data point and time interval of the swing data associated with an impact of the golf club with a golf ball (in order to identify additional time intervals associated with the end of the backswing and the start of the swing before the point of impact).

As further shown in the graph of FIG. 132A, the data points of the swing data collectively define data streams which may be plotted on the graph as curves for each of the different types of measurements generated by the accelerometer or the gyroscope. In other words, the X-axis defines a set of time intervals, and the Y-axis defines motion measurements of the swing data (accelerometer and gyroscope data) plotted along the set of time intervals of the X-axis. In the graph of FIG. 132A, a start of the swing is identified from swing data, which may refer to the swing position demonstrated by FIG. 130A. An end of the backswing is identified, which may refer to the swing position demonstrated by FIG. 130D. A point of impact is further shown, which may refer to the swing position of FIGS. 130F (and 130G). Each of the graphs of FIGS. 132A-132C show unique measurements and comparisons of different aspects of the swing data. The graph of FIG. 132A in particular shows angular rate values generated from raw gyroscope data (as described herein) as compared to raw accelerometer data streams over a predefined period of time. The graph of FIG. 132B shows accelerometer gradient measurements (generated from the raw accelerometer data streams of the graph of FIG. 132A) plotted across the same predefined period of time of FIG. 132A. The graph of FIG. 132C shows raw gyroscope data streams (during the same predefined period of time) used to generate resultant angular rate values displayed in FIG. 133A.

The swing data may be generated by the wearable device 5000 as the wearable device 5000 moves during the predefined period of time associated with a swing of the golf club 798. The swing data comprises the accelerometer data generated by an accelerometer or other component which may be used to generate rates of change in acceleration and the swing data further comprises gyroscope data generated from the gyroscope which measures the extent and rate of rotation of the wearable device 5000 during the swing of the golf club 798. The unique data points and more particularly the unique steps of generating the data points and time intervals from raw gyroscope and accelerometer data streams during a golf swing (as illustrated in FIGS. 132A-132C) collectively provides an inventive concept for generating a swing tempo (and which may also be used to adjust a golfer's swing tempo). It should be understood that generation of the graphs of FIGS. 132A-132C is merely made for explanatory purposes and a processor generating the swing tempo according to the steps described herein may utilize aspects of the data illustrated by the FIGS. 132A-132C (without having to generate visual graphs for each analysis).

Returning to the exemplary process flow 5200A, the process flow describes one possible set of steps for determining a swing tempo of a golfer. A processor, implemented within the wearable device 5000 or within a different device, may be utilized to perform one or more functions and generate the data points of FIGS. 132A-132C and the processor may further generate swing tempo data from the swing data depicted in FIGS. 132A-132C. In some embodiments, the processor may be configured using a swing tempo application executed by the processor which is encoded with logic and steps to carry out functionality described herein. Before the steps described in process flow 5200A, the processor may access the swing data of the wearable device 5000. Specifically, the swing tempo application may utilize one or more interfaces or APIs to communicate with the wearable device 5000 and access the swing data. The swing data as discussed herein includes raw accelerometer data streams and raw gyroscope data streams.

In block 5202, accelerometer data may be used to detect a first time interval associated with the possible impact or point when the golf swing results in an impact of the golf club 798 with a golf ball. Specifically, the aforementioned swing tempo application in conjunction with the processor monitors individual (X, Y, and Z) raw accelerometer data streams of the swing data generated by the wearable device 5000 as e.g. the raw accelerometer data streams pass within a buffer of the swing tempo application (as the swing data is accessed by e.g. laptop 1160) for a steep gradient (a noticeable change in the rate of acceleration) during a predetermined period of time. As shown in FIG. 132A, the individual raw accelerometer data streams may comprise "ax (g)", "ay (g)", and "az (g)" corresponding to different axes measurements with "(g)" indicating a particular value of gravity for each axis at a particular point in time. The swing tempo application, in conjunction with the processor, may convert the aforementioned raw accelerometer data streams to a gradient of acceleration corresponding to each data stream. For example, FIG. 132B shows accelerometer gradients (values associated with rate of change of acceleration) for accelerometer data streams corresponding to the X axis ("ax Gradient") and the Z-axis ("az Gradient"). The swing tempo application may utilize a conversion equation such as:

$$\text{Acceleration Gradient} = \frac{(a_i - a_{i-1})}{(t_i - t_{i-1})}$$

where a=acceleration in gravity units, t is the time in seconds, and i is the data sample number. It should be understood that additional or variations to the above equation are contemplated and the present inventive concept is not limited in this regard.

The processor may compute a point in time when an absolute value, of either of the acceleration gradient associated with the X-axis or the Z-axis is met or exceeded; or, a time interval or point in time when the acceleration gradient associated with the X-axis or the Z-axis peaks (positively or negatively) e.g. above 350 g/s. In other words, in some specific embodiments, the predetermined maximum threshold or accelerometer gradient threshold used to identify the first interval may be identified where an accelerometer gradient exceeds a value of 350; although the present disclosure is not limited in this regard. For example, FIG. 132B shows the X-axis acceleration gradient exceeding 350 and actually approaching an acceleration gradient value of approximately 700-750 which is a strong indication that at that point in time the golfer has made impact with a golf ball during a golf swing.

As described herein, the predetermined period of time (which may define the size of the buffer and data captured therein) may be estimated to be a particular period of time in which a golf swing of the golf club 798 is likely to have begun and also terminated. For example, as shown in FIG. 132A or FIG. 132B, the predefined period of time may be 0 seconds to approximately 1.1 seconds. As noted herein, the time along the X-axis of the graphs of FIGS. 132A-132C is presented in the negative, or using negative values to demonstrate that swing tempo calculation in some embodiments involves working backwards from the impact point. It should be understood that in the examples shown in FIGS. 132A-132C, the predefined time period generally falls within a range of about zero to two seconds of time (or more), depending on the swing tendencies and characteristics of the particular golfer being analyzed.

The described steep gradient change may be a rate of change that exceeds a predetermined maximum threshold at a particular point in time (the first time interval). This sudden and pronounced gradient corresponds to an impact point when the golf club 798 strikes a golf ball during the golf swing, and is typically, with most golfers, associated with a point in time when acceleration change is at or near a maximum. In some embodiments, the swing data accessed by the processor may include gyroscope and accelerometer data that includes measurements associated with time intervals or ranges of time where outside of the golf swing. In other words, determining the first time interval associated with the impact point (where a golf swing impacts a golf ball) may actually help to define the predefined time period for subsequent measurements and determination of time intervals associated with the end of the backswing and the start of the swing (by identifying an outermost or latest point in time that may be associated with the golf swing).

In other words, an impact data point from the swing data may (accelerometer gradient data) be determined where an acceleration rate of change exceeds a predetermined maximum threshold within a predetermined period of time. The impact data point may be associated with or otherwise correspond to a first time interval during the duration of the golf swing of the golf club 789 ("FIRST TIME INTERVAL" of FIGS. 132A-132C). The impact data point may be associated with either of or a combination of the swing positions of FIGS. 130F and 130G.

Gyroscope data may be utilized to identify time intervals associated with additional points of the golf swing; such as when an end of the backswing occurs, and when the start of the golf swing occurs. In block 5204, resultant angular values may first be calculated from the raw gyroscope data streams generated by the wearable device 5000. The raw gyroscope data streams are illustrated in FIG. 132C as "rx (rad/s)" for radians per second associated with X-axis gyroscope measurements, "ry (rad/s)" for radians per second associated with Y-axis gyroscope measurements, and "rz (rad/s)" for radians per second associated with Z-axis gyroscope measurements. As shown in FIG. 132A, the resultant angular rate values of the gyroscope data may be plotted alongside the raw accelerometer data streams to observe relationships between the different types of motion measurement data (and identify further key time intervals as discussed herein).

The resultant angular rate, or a set of values for the resultant angular rate from the X, Y, and Z gyroscope data streams for each data sample point in the buffer may be calculated as:

$$\sqrt{x^2+y^2+z^2})$$

i.e., the above equation may be utilized by the swing tempo application and the processor to generate the gyroscope values or resultant angular rate at points in time within the predefined period of time. It should be understood that additional or variations to the above equation are contemplated and the present inventive concept is not limited in this regard.

In block 5206, the swing data, i.e., the accelerometer data and the gyroscope data (including the calculated resultant values) in the buffer may be filtered to remove noise; such as undesirable features, unnecessary features, or erroneous data not necessary or otherwise irrelevant for determining swing tempo as disclosed herein. In some embodiments, a Butterworth filter may be used in this capacity, but the apparatus, methods, and articles of manufacture described herein are not limited in this regard.

In block 5208, a second time interval associated with the end of the backswing for the swing of the golf club 798 may be determined using the resultant angular rate values generated in block 5204. Specifically, from the data point associated with the impact of the golf club 798 against the golf ball, or more particularly, from the first time interval, additional data points of the gyroscope data of the swing data, before the first time interval, may be analyzed by the processor to identify a minimum value, or a value of the resultant angular rate values of the gyroscope data (before the first time interval and within the predetermined time period associated with the golf swing) that falls below a predetermined minimum threshold. In other words, a backswing-end data point of the swing data may be determined by the processor as a minimum value of the resultant angular rate values. That minimum value of the resultant angular rate values may define or be associated with a second time interval before the first time interval. For example, an angular rate before the first time interval in the graph of FIG. 132A is at or close to zero radians per second. The time interval where the angular rate is around zero radians per second in the graph of FIG. 132A may be identified as a second time interval indicative of a backswing end point.

In other words, from a data signature or index point associated with the golf swing impacting a golf ball, the processor as instructed by the swing tempo application may work back along the filtered resultant gyroscope data to find the minimum at the bottom of the first valley seen as shown in FIG. 132A as the "SECOND TIME INTERVAL". In some embodiments, an algorithm of the swing tempo application may take the resultant angular rate values at the first time interval, and work backwards in time from that point for the resultant angular rate values until the resultant angular rate values fall below a pre-determined threshold. The time interval or point in time where the angular rate values meets or falls below this predetermined minimum threshold may be described as the second time interval, which is associated with the end of the backswing. In another embodiment, an algorithm of the swing tempo application may take the resultant angular rate values at the first time interval, and to work backwards until the resultant angular rate is half the rate at the first time interval, and then continue to work backwards until the gradient of the resultant angular rate changes direction (i.e. the gradient changes from a positive to negative value, or vice versa). The time interval or point in time where the gradient of the angular rate changes direction may be described as the second time interval which is associated with the end of the backswing. The end of the backswing may be associated with the swing position demonstrated in FIG. 130D.

In block 5210, a third time interval associated with the start of the golf swing (a point in time when the golfer begins to wind up a swing or commence motion associated with a swing) may be determined using the gyroscope data (e.g. the resultant angular rate values over time as generated in block 5204). Specifically, working backwards in time from the second interval across the gyroscope data, a predetermined maximum value with respect to angular rate (within the predefined period of time and before the second interval) may be identified. This predetermined maximum value of the gyroscope data before the second time interval may be associated with a rate of change during the wind up to the back swing, during a time period or point in time just after the start of the swing. For example, in FIG. 132A, this predetermined maximum value may be approximately 5 or 6 radians per second which in FIG. 132A is an angular rate value just before the second time interval. In a subsequent step, changes to the angular rate (of the gyroscope data) before the predetermined maximum value of the angular rate (and before the second time interval) may be analyzed or monitored for a particular reduction in the angular rate; where the angular rate meets or drops below a minimum predefined threshold. In other words, moving backwards in time from, before the predetermined maximum value of the angular rate (before the second time interval), a measurement of the angular rate may be identified where the angular rate of the gyroscope data meets or drops below the predetermined maximum value to (or below) the minimum predefined threshold, e.g. a value of 2 radians per second (although the present disclosure is not limited in this regard). As a specific example shown in FIG. 132A, it can be seen that working backwards in time from the second time interval across the resultant angular rate values of the gyroscope data, the values peak at around 5 radians per second, and then at an earlier point in time drop to around 2 radians per second such that the point in time (third time interval) where the angular rate drops to 2 radians per second may be associated with the start of the swing.

In other words, this time interval (third time interval) associated with an angular rate that meets (or drops below) the minimum predefined threshold may be identified as a point in time where the swing begins (a start of the swing). The minimum predefined threshold before the second interval may be determined by analyzing a plurality of golf swings, to identify an average data point with respect to the angular rate of the gyroscope data where a swing typically begins. In some cases this minimum predefined threshold may be an angular rate value of around 1-3 radians per second, although the present disclosure is not limited in this regard. An ideal angular rate value for the predetermined maximum value or minimum predefined threshold balances between determining a start of the swing too late and determining a start of the swing too early, although the present disclosure is not limited in this regard.

Stated another way, a swing-start data point of the swing data may be identified, the swing-start data point associated with a third time interval before the second time interval (of the backswing). The swing-start data point may be determined by (i) identifying a data point (or set of data points) defining a predetermined maximum value of the angular rate or rate of change in the gyroscope data, or a value that exceeds a predetermined maximum threshold before the second time interval; and (ii) moving back in time, and selecting the swing-start data point of the gyroscope data where the angular rate of change drops below a predetermined minimum threshold before the second time interval. The start of the swing may be associated with the swing position demonstrated in FIG. 130A.

In some embodiments, after block 5210, redundant data, irrelevant data, or data within the buffer utilized by the swing tempo application that falls outside the predefined time period may be discarded. More specifically, after identifying the point of impact including the first time interval, the backswing including the second time interval, and the start of the swing including the third interval, data that does not fall within a range of time beginning with the first time interval and ending with the third time interval may be discarded. Irrelevant data may also be discarded which may include abnormal spikes or reductions in movement across the predefined time period (with respect to either the accelerometer data or the gyroscope data) that is not indicative of a golf swing, but rather, for example, indicates a fidgeting motion of the golfer.

In block 5212, the swing tempo may be calculated by analyzing the downswing time and the backswing time. Specifically, a downswing time may be determined as a difference in time between the first time interval (impact with the ball) and the second time interval (end of backswing), and a backswing time may be determined as a difference in time between the second time interval (end of backswing) and the third time interval (start of the swing). Thereafter, the swing tempo may be defined as the backswing time divided by the downswing time.

Figure 133B:
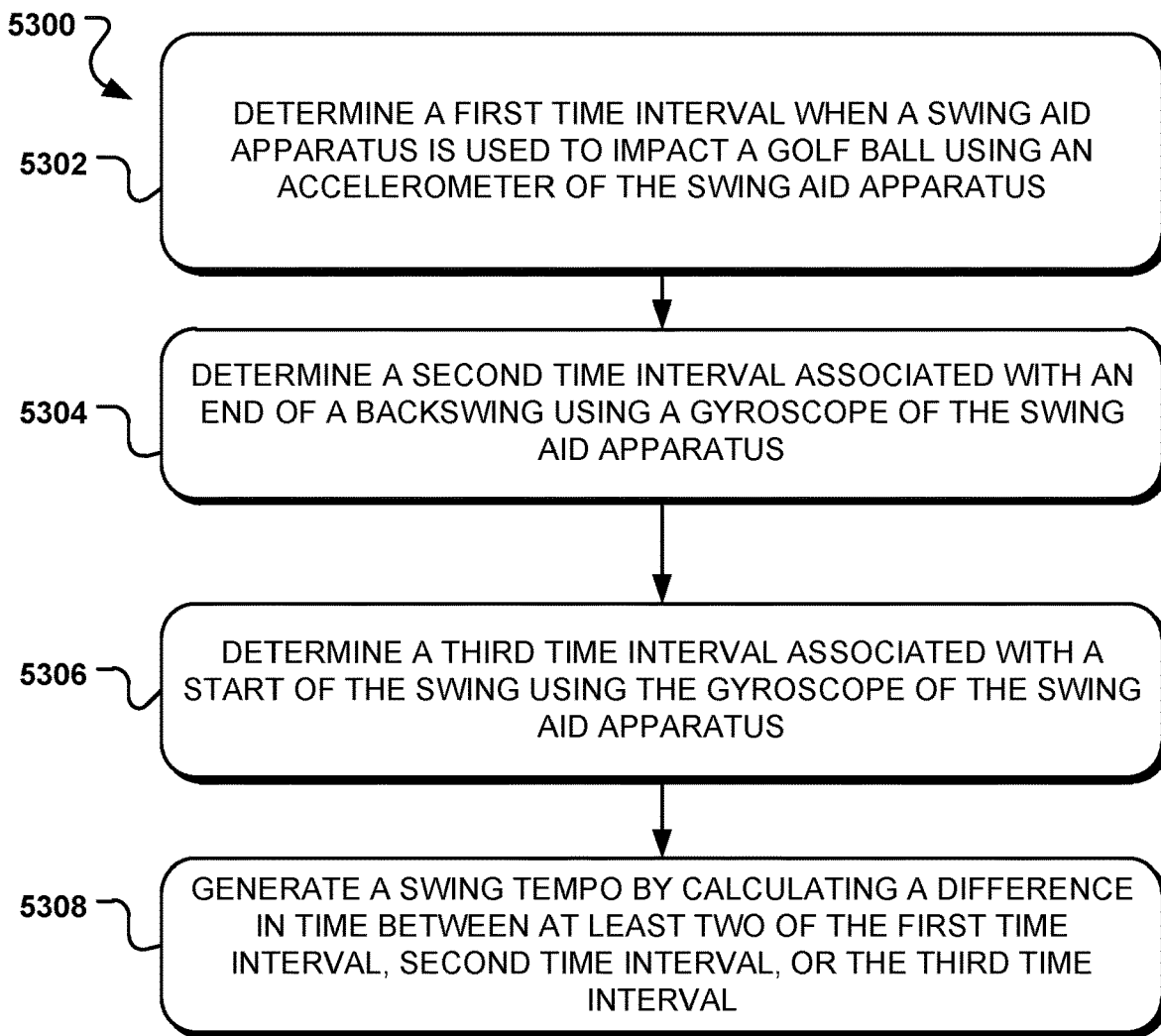

FIG. 133B depicts another process flow 5300 similar to process flow 5200. As shown in block 5302, a first time interval may be determined when the swing aid apparatus 5001 is used to impact a golf ball. The first time interval may specifically be detected using an accelerometer of the swing aid apparatus 5001. In block 5304, a second time interval, before the first time interval and associated with an end of a backswing, may be determined using a gyroscope of the swing aid apparatus 5001. In block 5306, a third time interval before the second time interval may be determined. The third time interval may be associated with a start of the swing and may be determined using the gyroscope of the swing aid apparatus 5001. In block 5308, a swing tempo may be generated by calculating time differences between at least two of the time intervals described herein.

Generating the swing data including the accelerometer and gyroscope data using the wearable device 5000 as described may provide a number of benefits and advantages. In addition to the swing data being used to generate, tempo and timing of swing points (back/down etc.), the swing data may further be used to generate maximum hand speed during a swing, impact hand speed, transition acceleration at the top of the swing, hand deceleration into impact from maximum hand speed (e.g. a form of efficiency/power rating, determining how much the hands are slowing before impact (typically the higher this is the more club speed a player generates relative to their maximum), and the like. With access to gyroscope data alongside accelerometer data, the swing aid apparatus 5001 is operable to calculate position and orientation of the hand path gripping the golf club 798 and the wearable device 5000 throughout the swing by generating data about the orientation of the wearable device 5000 and the acceleration of the device at each point in time (in particular during a predefined time period associated with a golf swing). Using such data, hand path visualizations may be further generated in three-dimensional space. Swing planes may be categorized relative to backswing, e.g. on plane, under plane, over the top. A global coordinate system may be utilized to provide hand path angles. Consistency values of all these measurements can be generated for the golfer and transmitted to other devices. Swing tools such as a metronome with audio or vibration feedback may be implemented by the wearable device 5000 for helping with the swing tempo. Audio, visual, or vibrational feedback may be generated or otherwise made available to the golfer by the wearable device 5000 (or other component of the swing aid apparatus 5001) to indicate a bad swing, e.g. when someone's path is over the top, and/or to indicate to the golfer when an end of a backswing should occur. For increased orientation accuracy, another device such as a phone can be used in conjunction with the wearable device 5000 to establish a target line orientation.

Additional outputs and feedback may be generated from the swing data where multiple golf swings of a golfer are analyzed. For example, swing tempo, wrist motion, hand path, and swing path models may be analyzed (e.g. averaged) over a number of swings to determine consistency across a plurality swings with respect to the particular golfer.

Figure 134:
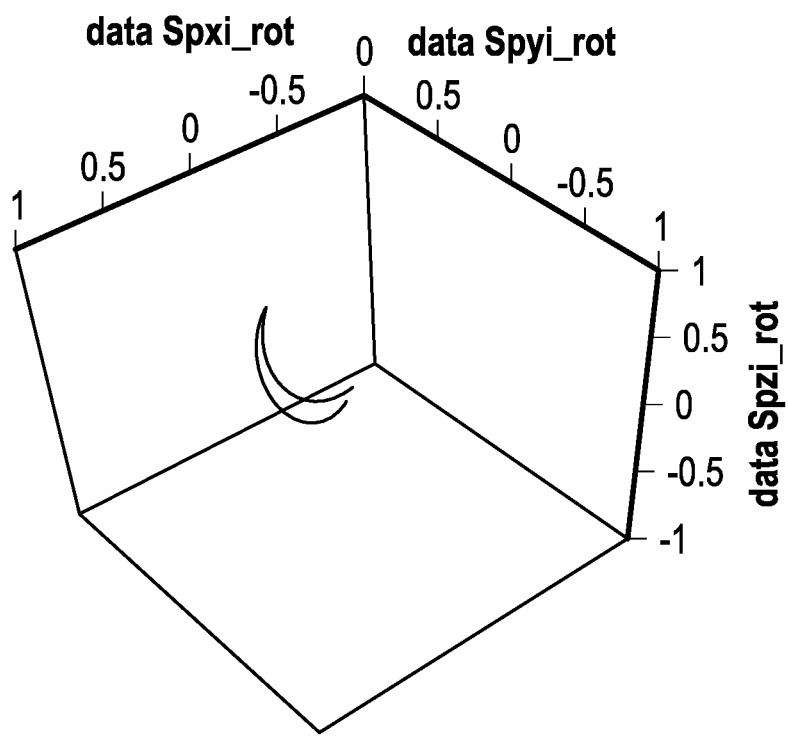
FIG. 134 is a three-dimensional swing path visualization generated using the swing aid apparatus according to one embodiment.
Figure 135:
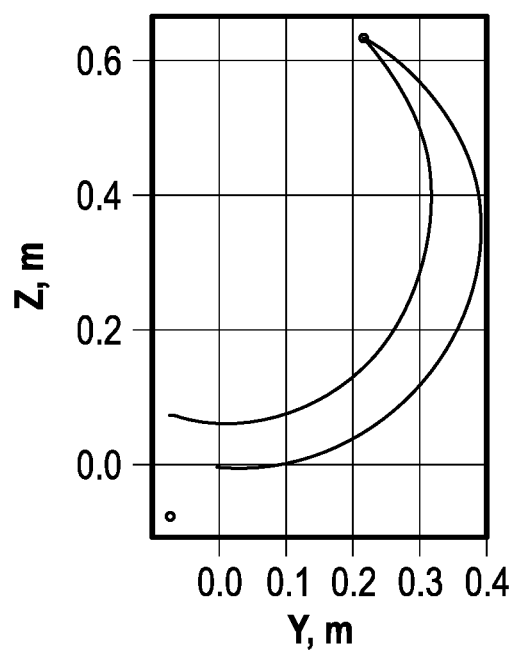
FIG. 135 is a side view of a hand path generated using the swing aid apparatus according to one embodiment.
Figure 136:
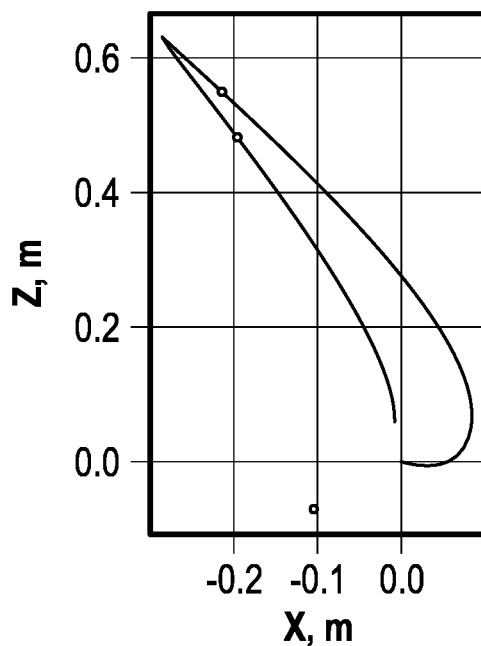
FIG. 136 is a rear view of a hand path generated using the swing aid apparatus according to one embodiment.

As specific examples as to the advantages and potential utilities of the swing data, reference is made to FIG. 134 which shows a three dimensional swing path visualization which may be generated using the wearable device 5000 (including the accelerometer/s and gyroscope/s) in combination with the golf club 798 as a swing aid apparatus 5001. FIG. 135 shows a hand path from a side view generated using the swing aid apparatus 5001. The information provided may assist a golfer to understand that throughout a swing, the golfer's hand is shifting in one direction or another. Using the swing aid apparatus 5001, the golfer may make adjustments to his/her swing, complete additional swings using the swing aid apparatus 5001, and review any additional swing data generated to determine whether the golfer has modified his/her hand path as desired. FIG. 136 shows a hand path similar to FIG. 135 from a rear view. In some embodiments, all or a portion of the swing data demonstrated by FIGS. 132, and 134-136 including other aspects may be displayed via the display 5010 of the wearable device 5000 and/or other devices.

Figure 137:
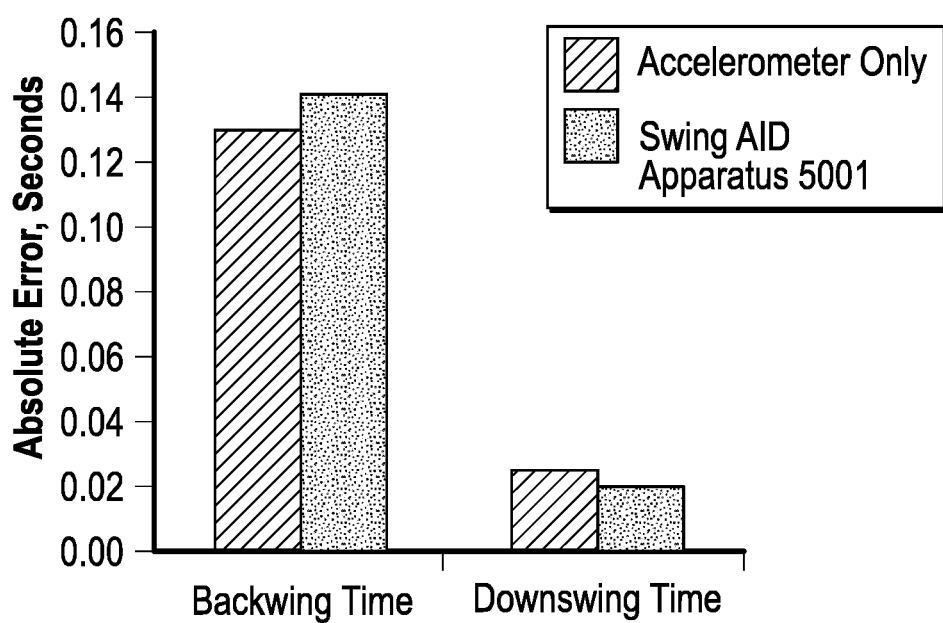
FIG. 137 is a graph showing average absolute timing error using the swing aid apparatus as compared to using a different device with only accelerometer data according to one embodiment.
Figure 138:
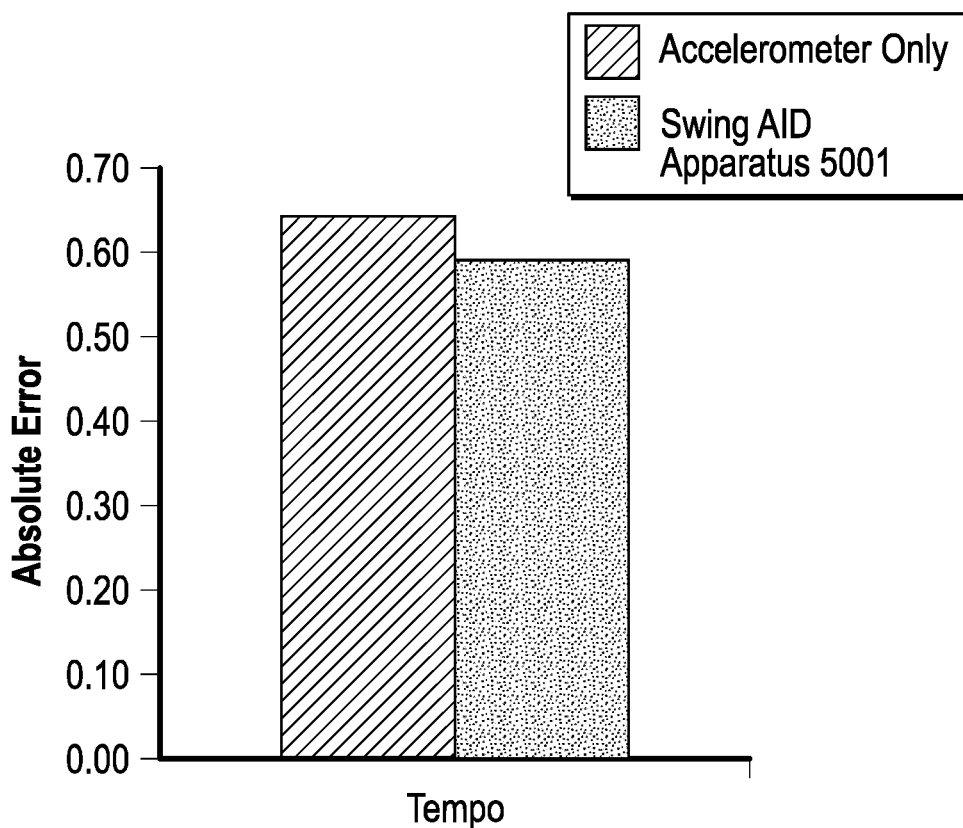
FIG. 138 is another graph showing average absolute timing error using the swing aid apparatus as compared to using a different device with only accelerometer data according to one embodiment.
Figure 139:
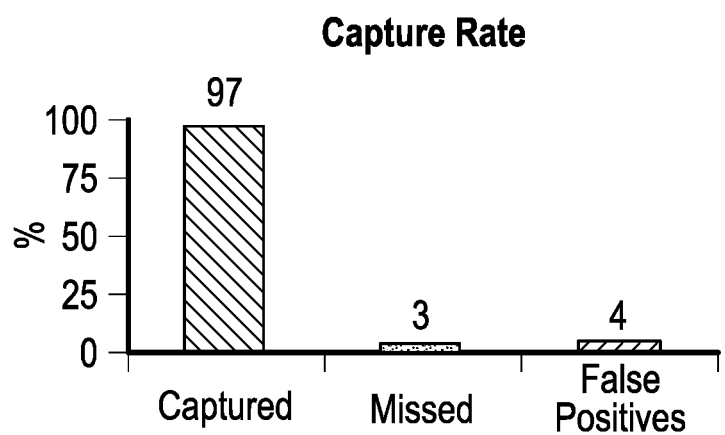
FIG. 139 is a graph showing capture rate using the swing aid apparatus according to one embodiment.

FIGS. 137-139 depict performance data and illustrate evidence regarding the efficacy of the swing aid apparatus 5001. In particular, the FIGS. were generated by analyzing a plurality of golf swings using the swing aid apparatus 5001, and also analyzing a plurality of golf swings using other methods (e.g., using only accelerometer data). As shown, the swing tempos generated by the swing aid apparatus 5001 are generally more accurate at least in part because the gyroscope data (including the resultant angular rate values) described may be utilized to more accurately detect the end of the backswing. As specifically shown in FIG. 139, informal testing using over twenty players and capturing close to 250 golf swings showed a capture rate of around 97% with a false positive capture rate of 4%, which indicates significant improvement in the capture rate using the swing aid apparatus 5001 and the methods described herein. Particularly, using the gyroscope data, the swing aid apparatus 5001 is capable of detecting swings for players with very slow speeds and chip shots which other methods have struggled to capture and/or detect with respect to both the backswing end and the start of the swing. Overall, the unique combination of gyroscope data and accelerometer data generated maintains accuracy while improving capture rate. In particular, the present inventive concept utilizes the resultant angular rate values to generate much cleaner data signatures that are easier to identify for swing points rather than analyzing individual X, Y, and Z motion measurement streams. The resultant gyroscope values may also be used for additional checks on the accuracy of the impact point detected by the accelerometer/s by using them as a reference.

As demonstrated herein, the swing aid apparatus 5001 is an improvement to technology within the area of swing practice aids for analyzing swing tempo (and other features of a golf swing). Conventional swing aids may require larger or multiple devices to be coupled to the golf club or a human coach to analyze a golfer's swing data. In contrast, the wearable device 5000 may be embodied within a watch or other accessory that a golfer may already wear during play which would reduce the probability of the wearable device 5000 interfering with or otherwise distracting the golfer during practice swings or golf swings during actual gameplay. Further, the steps described in process flow 5200 and process flow 5300 and elaborated upon herein do not preempt all use of wearable devices for assisting with golf swing measurements and analyzing swing tempos; but rather, involve specific meaningful steps for determining characteristics of a golf swing such as swing tempo. Swing data, comprising a combination of both gyroscope and accelerometer data streams may be analyzed with respect to time (over a predetermined period of time in which a swing is likely to have occurred) and be utilized to identify time intervals associated with an end of a back swing, an impact point of the swing (where the club makes contact with the ball), and the start of the swing. In particular, the impact point of the swing (the first time interval) may be identified first which may in some embodiments involve monitoring the accelerometer data for steep gradients with respect to rate of change of the accelerometer data (within the predetermined period of time). Next, analyzing the swing data at time periods before the first time interval, a second time interval may be identified and associated with the end of the backswing where the gyroscope data reveals a measurement that falls below a predefined threshold, before the first time interval. The gyroscope data may include resultant angular rate values computed from raw gyroscope streams. The beginning or start of the swing may also be determined using the gyroscope data by identifying a third time interval at a point in time before the second interval where the gyroscope data reveals a measurement that falls below a predetermined threshold (but within the predefined period of time). As such, a unique blend of gyroscope data and accelerometer data in addition to specific steps may be utilized such that the described steps as a whole provide a novel and non-conventional method for determining swing tempo. The above steps may be implemented using an application executed by a processor of the wearable device 5000 and/or other devices.

It should be understood that time "interval," as utilized herein, may refer to a period or range of time (e.g. 3:50 pm to 3:52 pm), or may define a specific point in time (e.g. 3:52 p.m.) including seconds or millisecond (or other temporal measurements).

The functionality described herein with respect to the wearable device 5000 of the swing aid apparatus 5001 may be implemented using one or more processors or processing devices similar to the processing device 1110 and may further involve a plurality of sensors similar to the plurality of sensors 1112, a GUI similar to the graphical user interface 1114, and/or a storage device or other memory device similar to the storage device 1116 of FIG. 13. All or a portion of the above components may be embodied within the wearable device 5000, or implemented at least in part by different devices.

A processor, coupled to the wearable device 5000 (or implemented using a different computing device in communication with the wearable device 5000) may be utilized to execute one or more applications in order to implement the functions and methods described herein. Specifically, the processor may be configured, via an application, to analyze access the swing data generated from the gyroscope and accelerometer of the wearable device 5000, and identify key data signatures within the swing data including the accelerometer gradient threshold (associated with the impact of the swing against a golf ball), the minimum value of the angular rate of the gyroscope data before the accelerometer gradient threshold (associated with the backswing end), and the data signatures of the gyroscope data used to determine the start swing data point (a maximum value of the angular rate before the backswing and value of the angular rate that falls below or meets a predefined minimum threshold). Using the aforementioned data signatures, the processor may identify the first, second, and third time intervals discussed herein (in real time) which may further be used to compute a swing tempo.

It should be further understood that a plurality of wearable devices similar to wearable device 5000 may be communicably linked via Wi-Fi, Bluetooth, cellular communication radios, or the like such that the devices may allow users of the respective devices to communicate with another and share information in some form.

Although a particular order of actions is described above with respect to each of the processes, these actions may be performed in other temporal sequences. For example, two or more actions described above may be performed sequentially, concurrently, or simultaneously. Alternatively, two or more actions may be performed in reversed order. Further, one or more actions described above may not be performed at all. The apparatus, methods, and articles of manufacture described herein are not limited in this regard.

As the rules to golf may change from time to time (e.g., new regulations may be adopted or old rules may be eliminated or modified by golf standard organizations and/or governing bodies), golf equipment related to the methods and articles of manufacture described herein may be conforming or non-conforming to the rules of golf at any particular time. Accordingly, golf equipment related to the systems, methods, and articles of manufacture described herein may be advertised, offered for sale, and/or sold as conforming or non-conforming golf equipment. The systems, methods, and articles of manufacture described herein are not limited in this regard.

While the above examples may be described in connection with a putter-type golf club, the systems, methods, and articles of manufacture described herein may be applicable to other types of golf club such as a driver-type golf club, a fairway wood-type golf club, a hybrid-type golf club, an iron-type golf club, or a wedge-type golf club. Alternatively, the systems, methods, and articles of manufacture described herein may be applicable other type of sports equipment such as a hockey stick, a tennis racket, a fishing pole, a ski pole, etc.

Although certain example systems, methods, and articles of manufacture have been described herein, the scope of coverage of this disclosure is not limited thereto. On the contrary, this disclosure covers all systems, methods, and articles of manufacture fairly falling within the scope of the appended claims either literally or under the doctrine of equivalents.

What is claimed is:

1. A method, comprising:
   generating swing data by a wearable device as the wearable device moves during a predetermined period of time associated with a swing of a golf club, the swing data comprising accelerometer data generated from an accelerometer component of the wearable device and gyroscope data generated from a gyroscope component of the wearable device;
   utilizing a processor for:
      determining an impact data point of the swing data as an acceleration rate of change of the accelerometer data that exceeds a predetermined maximum threshold within the predetermined period of time, the impact data point associated with a first time interval;
      determining a backswing-end data point of the swing data as a minimum value of the gyroscope data associated with a second time interval before the first time interval;
      determining a swing-start data point of the swing data associated with a third time interval before the second time interval, by identifying a maximum value of the gyroscope data before the second time interval, and
      selecting the swing-start data point of the swing data as a value of the gyroscope data that drops below a predetermined minimum threshold before the second time interval;
      generating a backswing time and a downswing time associated with the swing of the golf club by analyzing time differences between the first time interval, the second time interval, and the third time interval;
      generating a swing tempo using the backswing time and the downswing time; and
      integrating individual acceleration values associated with the swing data including each of the swing-start data point, the backswing-end data point, and the impact data point with respect to time to generate velocity vectors for each of a plurality of axes.

2. The method of claim 1, further comprising:
generating the downswing time associated with the swing of the golf club by determining a first time difference between the first time interval associated with the impact data point and the second time interval associated with the backswing-end data point; and
generating the backswing time associated with the swing of the golf club by determining a second time difference between the second time interval associated with the backswing-end data point and the third time interval associated with the swing-start data point; and
wherein the impact data point is associated with a strike of a golf ball by the swing of the golf club, the backswing-end data point is associated with an end of the backswing of the swing of the golf club, and the swing-start data point is associated with a beginning motion of the swing of the golf club.

3. The method of claim 1, further comprising:
wherein the wearable device comprises at least one of an electronic watch, an electronic wristband, an electronic ring, or an electronic glove; and
wherein at least one of the gyroscope component or the accelerometer component are embodied by at least one of a microelectromechanical system-based sensor, the microelectromechanical system-based sensor being operable for measuring acceleration and an extent and rate of rotation for movement along at least three axes.

4. The method of claim 1, wherein the gyroscope data comprises a set of resultant angular rate values calculated from raw gyroscope streams generated from the gyroscope component.

5. The method of claim 4, further comprising:
passing the swing data including the set of resultant angular rate values through a filter to remove noise, the noise comprising predetermined undesired features of the swing data.

6. The method of claim 1, further comprising:
engaging a strap of the wearable device to a wrist of an individual.

7. The method of claim 1, further comprising:
engaging a strap of the wearable device to a shaft of the golf club.

8. The method of claim 7, further comprising:
coupling the wearable device to a section of the shaft of the golf club proximate a butt end of the golf club with a first end portion of the wearable device oriented towards a tip end of the golf club.

9. The method of claim 1, further comprising:
combining velocity vectors with quaternion data generated by the wearable device to calculate X,Y,Z position coordinates for the wearable device for a plurality of data points defined by the swing data including each of the swing-start data point, the backswing-end data point, and the impact data point.

10. The method of claim 9, further comprising:
generating a three dimensional swing path using the X,Y,Z position coordinates for the wearable device for the plurality of data points defined by the swing data including each of the swing-start data point, the backswing-end data point, and the impact data point.

11. The method of claim 10, further comprising:
estimating a movement of a wrist of an individual associated with the swing of a golf club using the X,Y,Z position coordinates for the wearable device for the plurality of data points defined by the swing data including the swing-start data point, the backswing-end data point, and the impact data point.

12. The method of claim 10, further comprising:
estimating a wrist path angle of an individual associated with the swing of a golf club using the X,Y,Z position coordinates for the wearable device for the plurality of data points defined by the swing data including the swing-start data point, the backswing-end data point, and the impact data point.

13. The method of claim 1, further comprising:
generating a two-dimensional (2-D) graph to determine the first time interval, the second time interval, and the third time interval, the 2-D graph defining an X-axis associated with time and a Y-axis associated with movement measurements defined by the acceleration data and the gyroscope data of the swing data; and
plotting data points associated with the accelerometer data and the gyroscope data on the 2-D graph, the data points comprising the impact data point of the swing data, the backswing-end data point of the swing data, and the swing-start data point of the swing data in addition to other data points associated with different positions of the golf club during the swing of the golf club.

14. A method, comprising:
determining a first time interval associated with a swing of a golf club when the golf club impacts a golf ball using an accelerometer of a wearable device;
determining a second time interval by working backwards in time from the first time interval until the resultant angular rate is half the rate at the point of impact of the first time interval, and continuing to work backwards until the gradient of the resultant angular rate changes direction, the second time interval associated with a backswing of the swing of the golf club using a gyroscope of the wearable device;
determining a third time interval by working backwards in time from the second time interval, the third time interval associated with a start of the swing of the golf club using the gyroscope of the wearable device; and
generating a tempo of the swing of the golf club by a calculating a difference between at least two of the first time interval, the second time interval or the third time interval.

15. The method of claim 14, further comprising:
generating additional swing data by a wearable device as the wearable device moves during an additional predetermined period of time associated with an additional swing of the golf club;
determining a first time interval associated with the additional swing of the golf club when the golf club impacts a golf ball using the accelerometer of the wearable device;
determining a second time interval associated with a backswing of the additional swing of the golf club using the gyroscope of the wearable device;
determining a third time interval associated with a start of the additional swing of the golf club using the gyroscope of the wearable device;
generating an additional tempo of the additional swing of the golf club by calculating a difference between at least two of the first time interval, the second time interval or the third time interval associated with the additional swing of the golf club; and
calculating a difference between the tempo and the additional tempo to generate a golf swing consistency value.

16. The method of claim 14, further comprising:
utilizing at least one global positioning system of the wearable device to determine a location of the wearable device on a golf course; and
outputting the location to a display of the wearable device.

17. A golf swing aid apparatus, comprising:
a golf club; and
a wearable device that assists with computation of a swing tempo from a swing of the golf club by detecting a first time interval associated with an impact of the golf club against a golf ball using an accelerometer of the wearable device, determining a second time interval by working backwards in time from the first time interval until a resultant angular rate is half a rate at the point of impact of the first time interval, and continuing to work backwards until a gradient of the resultant angular rate changes direction, the second time interval associated with a backswing of the swing of the golf club using a gyroscope of the wearable device, and determining a third time interval by working backwards in time from the second time interval, the third time interval associated with a start of the swing of the golf club using the gyroscope of the wearable device.

18. The golf swing aid apparatus of claim 17, further comprising:
a processor for computing the swing tempo; and
a display device for displaying the swing of the golf club.

19. The golf swing aid apparatus of claim 17, wherein an adjustable band of the wearable device is coupled to a wrist of an individual such that a display of the wearable device is oriented over a predetermined portion of the wrist, and the adjustable band is tightened against skin of the wrist to reduce movement of the display away from the predetermined portion of the wrist.

* * * * *